(12) United States Patent
Desai

(10) Patent No.: US 11,497,737 B2
(45) Date of Patent: Nov. 15, 2022

(54) PHARMACEUTICAL COMPOSITIONS OF ALBUMIN AND RAPAMYCIN

(71) Applicant: Abraxis BioScience, LLC, Summit, NJ (US)

(72) Inventor: Neil P. Desai, Pacific Palisades, CA (US)

(73) Assignee: Abraxis BioScience, LLC, Summit, NJ (US)

( * ) Notice: Subject to any disclaimer, the term of this patent is extended or adjusted under 35 U.S.C. 154(b) by 0 days.

(21) Appl. No.: 17/082,698

(22) Filed: Oct. 28, 2020

(65) Prior Publication Data

US 2021/0121446 A1 Apr. 29, 2021

Related U.S. Application Data

(60) Provisional application No. 62/936,212, filed on Nov. 15, 2019, provisional application No. 62/927,047, filed on Oct. 28, 2019.

(51) Int. Cl.
| | | |
|---|---|---|
| *A61K 31/436* | (2006.01) | |
| *A61K 47/22* | (2006.01) | |
| *A61K 9/16* | (2006.01) | |
| *A61K 47/42* | (2017.01) | |
| *A61K 47/12* | (2006.01) | |

(52) U.S. Cl.
CPC .......... *A61K 31/436* (2013.01); *A61K 9/1658* (2013.01); *A61K 47/12* (2013.01); *A61K 47/22* (2013.01); *A61K 47/42* (2013.01)

(58) Field of Classification Search
None
See application file for complete search history.

(56) References Cited

U.S. PATENT DOCUMENTS

| | | |
|---|---|---|
| 5,362,478 A | 11/1994 | Desai |
| 5,439,686 A | 8/1995 | Desai |
| 5,498,421 A | 3/1996 | Grinstaff |
| 5,505,932 A | 4/1996 | Grinstaff |
| 5,508,021 A | 4/1996 | Grinstaff |
| 5,512,268 A | 4/1996 | Grinstaff |
| 5,560,933 A | 10/1996 | Soon-shiong |
| 5,635,207 A | 6/1997 | Grinstaff |
| 5,639,473 A | 6/1997 | Grinstaff |
| 5,650,156 A | 7/1997 | Grinstaff |
| 5,665,382 A | 9/1997 | Grinstaff |
| 5,665,383 A | 9/1997 | Grinstaff |
| 5,916,596 A | 6/1999 | Desai |
| 5,997,904 A | 12/1999 | Magdassi |
| 6,096,331 A | 8/2000 | Desai |
| 6,506,405 B1 | 1/2003 | Desai |
| 6,528,067 B1 | 3/2003 | Magdassi |
| 6,537,579 B1 | 3/2003 | Desai |
| 6,565,842 B1 | 5/2003 | Sojomihardjo |
| 6,652,884 B2 | 11/2003 | Falciani |
| 6,749,868 B1 | 6/2004 | Desai |
| 6,753,006 B1 | 6/2004 | Desai |
| 7,001,885 B2 | 2/2006 | Machi |
| 7,223,561 B2 | 5/2007 | Goodey |
| 7,758,891 B2 | 7/2010 | Desai |
| 7,771,751 B2 | 8/2010 | Desai |
| 7,780,984 B2 | 8/2010 | Desai |
| 7,820,788 B2 | 10/2010 | Desai |
| 7,923,536 B2 | 4/2011 | Desai |
| 7,981,445 B2 | 7/2011 | De |
| 8,034,375 B2 | 10/2011 | Desai |
| 8,034,765 B2 | 10/2011 | De |
| 8,137,684 B2 | 3/2012 | Desai |
| 8,138,229 B2 | 3/2012 | Desai |
| 8,257,733 B2 | 9/2012 | Desai |
| 8,268,348 B2 | 9/2012 | Desai |
| 8,314,156 B2 | 11/2012 | Desai |
| 8,318,190 B2 | 11/2012 | Burke |
| 8,735,394 B2 | 5/2014 | Desai |
| 8,846,771 B2 | 9/2014 | Desai |
| 8,853,260 B2 | 10/2014 | Desai |
| 8,911,786 B2 | 12/2014 | Desai |
| 8,927,019 B2 | 1/2015 | Desai |
| 8,999,396 B2 | 4/2015 | Desai |
| 9,012,518 B2 | 4/2015 | Desai |
| 9,012,519 B2 | 4/2015 | Desai |

(Continued)

FOREIGN PATENT DOCUMENTS

| | | |
|---|---|---|
| CA | 2395589 A1 | 5/2002 |
| CN | 1406245 A | 3/2003 |

(Continued)

OTHER PUBLICATIONS

US 8,968,752 B2, 03/2015, Desai (withdrawn)
ABRAXANE™ (Dec. 2011). "Abraxane™ Product, FDA Product Label," pp. 1-13.
ABRAXANE®. (Dec. 2014). "Prescribing Insert for Injectable Suspension (Paclitaxel Protein-Bound Particles for Injectable Suspension) (Albumin-Bound)," 24 pages.
Ahn, H.K. et al. (2014). "A Phase II Trial of Cremorphor EL-Free Paclitaxel (Genexol-PM) and Gemcitabine in Patients With Advanced Non-Small Cell Lung Cancer," Cancer Chemother Pharmacol 74:277-282.
American Society of Health-System Pharmacists. (Jun. 15, 2006). "ASHP Guidelines on Handling Hazardous Drugs. Developed by the ASHP Council on Professional Affairs and Approved by the ASHP Board of Directors on Jan. 12, 2006," Am. J. Health-Syst. Pharm. 63(12):1172-1193.
Amgen Inc. (Jun. 11, 2012). "Reply to Communication Pursuant to Article 94(3) EPC dated Dec. 2, 2011," 7 pages.

(Continued)

*Primary Examiner* — Robert T. Crow
*Assistant Examiner* — John P Nguyen
(74) *Attorney, Agent, or Firm* — Morrison & Foerster LLP

(57) ABSTRACT

The present invention provides compositions (such as pharmaceutical compositions), and commercial batches of such compositions, comprising nanoparticles comprising albumin and rapamycin. The compositions (such as pharmaceutical compositions) have specific physicochemical characteristics and are particularly suitable for use in treating diseases such as cancer. Also provided are methods of making and methods of using the compositions (such as pharmaceutical compositions).

30 Claims, 11 Drawing Sheets

(56) References Cited

U.S. PATENT DOCUMENTS

| | | |
|---|---|---|
| 9,061,014 B2 | 6/2015 | Seward |
| 9,101,543 B2 | 8/2015 | Desai |
| 9,149,455 B2 | 10/2015 | Desai |
| 9,308,180 B2 | 4/2016 | De |
| 9,370,494 B2 | 6/2016 | Yeo |
| 9,393,318 B2 | 7/2016 | Desai |
| 9,399,071 B2 | 7/2016 | Desai |
| 9,399,072 B2 | 7/2016 | Desai |
| 9,446,003 B2 | 9/2016 | Desai |
| 9,511,046 B2 | 12/2016 | Desai |
| 9,561,288 B2 | 2/2017 | Desai |
| 9,585,960 B2 | 3/2017 | Foss |
| 9,597,409 B2 | 3/2017 | Desai |
| 9,675,578 B2 | 6/2017 | Desai |
| 9,724,323 B2 | 8/2017 | Desai |
| 9,820,949 B2 | 11/2017 | Desai |
| 9,855,220 B2 | 1/2018 | Desai |
| 9,884,013 B2 | 2/2018 | Seward |
| 9,962,373 B2 | 5/2018 | Desai et al. |
| 10,076,501 B2 | 9/2018 | Foss et al. |
| 10,206,887 B2 | 2/2019 | Desai |
| 10,258,565 B2 | 4/2019 | Seward |
| 10,328,031 B2 | 6/2019 | Desai |
| 10,413,531 B2 | 9/2019 | Desai |
| 10,527,604 B1 | 1/2020 | Peykov |
| 10,555,912 B2 | 2/2020 | Foss |
| 10,660,965 B2 | 5/2020 | Desai |
| 10,682,420 B2 | 6/2020 | Desai |
| 10,705,070 B1 * | 7/2020 | Peykov .............. G01N 21/21 |
| 10,744,110 B2 | 8/2020 | Desai |
| 10,900,951 B1 | 1/2021 | Peykov |
| 10,973,806 B2 | 4/2021 | Desai |
| 2003/0185894 A1 | 10/2003 | Zenoni |
| 2003/0187062 A1 | 10/2003 | Zenoni |
| 2003/0199425 A1 | 10/2003 | Desai |
| 2005/0004002 A1 | 1/2005 | Desai |
| 2005/0152979 A1 | 7/2005 | Besman |
| 2006/0263434 A1 | 11/2006 | Desai |
| 2007/0082838 A1 | 4/2007 | De |
| 2007/0087022 A1 | 4/2007 | Desai |
| 2007/0093547 A1 | 4/2007 | Desai |
| 2007/0116761 A1 | 5/2007 | Desai |
| 2007/0116774 A1 | 5/2007 | Desai |
| 2007/0117744 A1 | 5/2007 | Desai |
| 2007/0128290 A1 | 6/2007 | Desai |
| 2008/0063724 A1 | 3/2008 | Desai |
| 2008/0160095 A1 | 7/2008 | Desai |
| 2008/0161382 A1 | 7/2008 | Desai |
| 2008/0280987 A1 | 11/2008 | Desai |
| 2009/0098210 A1 | 4/2009 | Desai |
| 2009/0130163 A1 | 5/2009 | Desai |
| 2009/0196933 A1 | 8/2009 | De |
| 2009/0263483 A1 | 10/2009 | Desai |
| 2009/0304805 A1 | 12/2009 | Desai |
| 2010/0035800 A1 | 2/2010 | Desai |
| 2010/0048499 A1 | 2/2010 | Desai |
| 2010/0112077 A1 | 5/2010 | Desai |
| 2010/0166869 A1 | 7/2010 | Desai |
| 2010/0183728 A1 | 7/2010 | Desai |
| 2010/0196490 A1 | 8/2010 | Desai |
| 2010/0215751 A1 | 8/2010 | Desai |
| 2010/0226996 A1 | 9/2010 | Desai |
| 2010/0297243 A1 * | 11/2010 | Desai .............. A61P 35/00 424/489 |
| 2011/0052708 A1 | 3/2011 | Soon-shiong |
| 2011/0118342 A1 | 5/2011 | De |
| 2011/0151012 A1 | 6/2011 | Desai |
| 2011/0165256 A1 | 7/2011 | Desai |
| 2011/0196026 A1 | 8/2011 | De |
| 2011/0301248 A1 | 12/2011 | Desai |
| 2012/0004177 A1 | 1/2012 | Desai |
| 2012/0070502 A1 | 3/2012 | Desai |
| 2012/0076862 A1 | 3/2012 | Desai |
| 2012/0128732 A1 | 5/2012 | Tried |
| 2012/0177743 A1 | 7/2012 | Desai |
| 2012/0189701 A1 | 7/2012 | Desai |
| 2012/0231082 A1 | 9/2012 | Desai |
| 2012/0283205 A1 | 11/2012 | Desai |
| 2012/0308612 A1 | 12/2012 | De |
| 2013/0045240 A1 | 2/2013 | Tao |
| 2013/0071438 A1 | 3/2013 | Desai |
| 2013/0115296 A1 | 5/2013 | Yeo |
| 2013/0177598 A1 | 7/2013 | Desimone |
| 2013/0195922 A1 | 8/2013 | Desai |
| 2013/0195983 A1 | 8/2013 | Desai |
| 2013/0195984 A1 | 8/2013 | Desai |
| 2013/0202709 A1 | 8/2013 | Desai |
| 2013/0209518 A1 | 8/2013 | Desai |
| 2013/0244952 A1 | 9/2013 | Desai |
| 2013/0266659 A1 | 10/2013 | Desai |
| 2013/0280336 A1 | 10/2013 | Desai |
| 2013/0280337 A1 | 10/2013 | Desai |
| 2014/0017315 A1 | 1/2014 | Desai |
| 2014/0017316 A1 | 1/2014 | Desai |
| 2014/0017323 A1 | 1/2014 | Desai |
| 2014/0023717 A1 | 1/2014 | Desai |
| 2014/0039069 A1 | 2/2014 | Desai |
| 2014/0039070 A1 | 2/2014 | Desai |
| 2014/0056986 A1 | 2/2014 | Desai |
| 2014/0072630 A1 | 3/2014 | Tao |
| 2014/0072631 A1 | 3/2014 | Trieu |
| 2014/0072643 A1 | 3/2014 | Desai |
| 2014/0079787 A1 | 3/2014 | Yeo |
| 2014/0079788 A1 | 3/2014 | Desai |
| 2014/0079793 A1 | 3/2014 | Desai |
| 2014/0080901 A1 | 3/2014 | Desai |
| 2014/0134257 A1 | 5/2014 | Desai |
| 2014/0155344 A1 | 6/2014 | Desai |
| 2014/0170228 A1 | 6/2014 | Desai |
| 2014/0186447 A1 * | 7/2014 | Desai .............. A61P 35/00 424/491 |
| 2014/0199403 A1 | 7/2014 | Desai |
| 2014/0199404 A1 | 7/2014 | Heise |
| 2014/0199405 A1 | 7/2014 | Pierce |
| 2014/0271871 A1 | 9/2014 | Desai |
| 2014/0296279 A1 | 10/2014 | Seward |
| 2014/0296353 A1 | 10/2014 | Desai |
| 2014/0302157 A1 | 10/2014 | Desai |
| 2015/0050356 A1 | 2/2015 | Desai |
| 2015/0079177 A1 | 3/2015 | Desai |
| 2015/0079181 A1 | 3/2015 | Desai |
| 2015/0104521 A1 | 4/2015 | Desai |
| 2015/0111960 A1 | 4/2015 | Desai |
| 2015/0157722 A1 | 6/2015 | Foss |
| 2015/0165047 A1 | 6/2015 | Desai |
| 2015/0190519 A1 | 7/2015 | Desai |
| 2015/0190556 A1 | 7/2015 | Desai |
| 2015/0313866 A1 | 11/2015 | Desai |
| 2016/0000726 A1 | 1/2016 | Li |
| 2016/0008330 A1 | 1/2016 | Desai |
| 2016/0015681 A1 | 1/2016 | Desai |
| 2016/0015817 A1 | 1/2016 | Benettaib |
| 2016/0151325 A1 | 6/2016 | Desai |
| 2016/0228401 A1 | 8/2016 | Desai |
| 2016/0374952 A1 | 12/2016 | Yeo |
| 2017/0014373 A1 | 1/2017 | Desai |
| 2017/0020824 A1 | 1/2017 | Desai |
| 2017/0049711 A1 | 2/2017 | Desai |
| 2017/0100344 A1 | 4/2017 | Desai |
| 2017/0105951 A1 | 4/2017 | Desai |
| 2017/0157035 A1 | 6/2017 | Seward |
| 2017/0172975 A1 | 6/2017 | Desai |
| 2017/0181988 A1 | 6/2017 | Malhotra |
| 2017/0202782 A1 | 7/2017 | Pierce |
| 2017/0203012 A1 | 7/2017 | Desai |
| 2017/0224627 A1 | 8/2017 | Foss |
| 2017/0333384 A1 | 11/2017 | Desai |
| 2017/0340599 A1 | 11/2017 | Desai |
| 2018/0015181 A1 | 1/2018 | Desai |
| 2018/0064679 A1 | 3/2018 | Pierce |
| 2018/0133157 A1 | 5/2018 | Desai |
| 2018/0147139 A1 | 5/2018 | Seward |
| 2018/0153820 A1 | 6/2018 | Desai |
| 2018/0153863 A1 | 6/2018 | Desai |

(56) References Cited

U.S. PATENT DOCUMENTS

| | | |
|---|---|---|
| 2018/0169017 A1 | 6/2018 | Desai |
| 2018/0177770 A1 | 6/2018 | Desai |
| 2018/0177771 A1 | 6/2018 | Desai |
| 2018/0214425 A1 | 8/2018 | Desai |
| 2018/0256551 A1 | 9/2018 | Desai et al. |
| 2018/0289620 A1 | 10/2018 | Desai et al. |
| 2018/0374583 A1 | 12/2018 | Goldstein |
| 2019/0022020 A1 | 1/2019 | Desai |
| 2019/0054033 A1 | 2/2019 | Foss |
| 2019/0147986 A1 | 5/2019 | Luo |
| 2019/0167629 A1 | 6/2019 | Desai |
| 2019/0175564 A1 | 6/2019 | Desai |
| 2019/0183789 A1 | 6/2019 | Seward |
| 2019/0184031 A1 | 6/2019 | Desai |
| 2019/0192477 A1 | 6/2019 | Desai |
| 2019/0247357 A1 | 8/2019 | Foss |
| 2019/0307732 A1 | 10/2019 | Desai |
| 2019/0343789 A1 | 11/2019 | Desai |
| 2020/0040398 A1 | 2/2020 | Desai |
| 2020/0129469 A1 | 4/2020 | Renschler |
| 2020/0138793 A1 | 5/2020 | Desai |
| 2020/0246275 A1 | 8/2020 | Pierce |
| 2020/0316216 A1 | 10/2020 | Desai |
| 2021/0000752 A1 | 1/2021 | Desai |
| 2021/0085621 A1 | 3/2021 | Desai et al. |
| 2021/0137848 A1 | 5/2021 | Desai et al. |
| 2021/0315823 A1 | 10/2021 | Desai et al. |
| 2021/0322335 A1 | 10/2021 | Desai et al. |
| 2021/0322391 A1 | 10/2021 | Desai |

FOREIGN PATENT DOCUMENTS

| | | |
|---|---|---|
| CN | 101670112 A | 3/2010 |
| CN | 102078306 A | 6/2011 |
| WO | 199418954 A1 | 9/1994 |
| WO | 199814174 A1 | 4/1998 |
| WO | 199814175 A1 | 4/1998 |
| WO | 199900113 A1 | 1/1999 |
| WO | 200064437 A1 | 11/2000 |
| WO | 200071079 A2 | 11/2000 |
| WO | 200189522 A1 | 11/2001 |
| WO | 2002087545 A1 | 11/2002 |
| WO | 2003096944 A1 | 11/2003 |
| WO | 2004052401 A2 | 6/2004 |
| WO | 2004052401 A3 | 2/2005 |
| WO | 2006089290 A1 | 8/2006 |
| WO | 2007027819 A2 | 3/2007 |
| WO | 2007027941 A2 | 3/2007 |
| WO | 2007027819 A3 | 4/2007 |
| WO | 2007027941 A3 | 4/2007 |
| WO | 200071079 A3 | 3/2008 |
| WO | 2008027055 A1 | 3/2008 |
| WO | 2008057562 A1 | 5/2008 |
| WO | 2008076373 A1 | 6/2008 |
| WO | 2008109163 A1 | 9/2008 |
| WO | 2008137148 A2 | 11/2008 |
| WO | 2008150532 A1 | 12/2008 |
| WO | 2008137148 A3 | 2/2009 |
| WO | 2009126175 A1 | 10/2009 |
| WO | 2009126401 A1 | 10/2009 |
| WO | 2009126938 A1 | 10/2009 |
| WO | 2010068925 A1 | 6/2010 |
| WO | 2010105172 A1 | 9/2010 |
| WO | 2010118365 A1 | 10/2010 |
| WO | 2010121000 A1 | 10/2010 |
| WO | 2011025838 A1 | 3/2011 |
| WO | 2011119988 A1 | 9/2011 |
| WO | 2011123393 A1 | 10/2011 |
| WO | 2011123395 | 10/2011 |
| WO | 2011153009 A1 | 12/2011 |
| WO | 2011153010 A1 | 12/2011 |
| WO | 2011156119 A1 | 12/2011 |
| WO | 2012092712 A1 | 7/2012 |
| WO | 2012149451 A1 | 11/2012 |
| WO | 2013090634 A1 | 6/2013 |
| WO | 2013144554 A1 | 10/2013 |
| WO | 2014105644 A1 | 7/2014 |
| WO | 2014110345 A1 | 7/2014 |
| WO | 2014110408 A1 | 7/2014 |
| WO | 2014110443 A1 | 7/2014 |
| WO | 2014123612 A1 | 8/2014 |
| WO | 2014143613 A1 | 9/2014 |
| WO | 2014151853 A1 | 9/2014 |
| WO | 2014159171 A1 | 10/2014 |
| WO | 2015157120 A1 | 10/2015 |
| WO | 2016141365 A1 | 9/2016 |
| WO | 2017004249 A1 | 1/2017 |
| WO | 2017004264 A1 | 1/2017 |
| WO | 2017004266 A1 | 1/2017 |
| WO | 2017004267 A1 | 1/2017 |
| WO | 2017201189 A1 | 11/2017 |
| WO | 2018064405 A1 | 4/2018 |
| WO | 2018067943 A1 | 4/2018 |
| WO | 2018071399 A1 | 4/2018 |
| WO | 2019033028 A1 | 2/2019 |
| WO | 2019126223 A1 | 6/2019 |
| WO | 2019183146 A1 | 9/2019 |
| WO | 2019226685 A1 | 11/2019 |
| WO | 2020191053 A1 | 9/2020 |

OTHER PUBLICATIONS

Anderson, C.L. et al. (Jul. 2006, e-pub. May 30, 2006) "Perspective—FcRn Transports Albumin: Relevance to Immunology and Medicine," Trends in Immunology 27(7):343-348.

Authier, N. et al. (2000) "Description of a Short-term Taxol®-Induced Nociceptive Neuropathy in Rats," Brain Research 887:239-249.

Blum, J.L. (Dec. 2007). "Phase II Study of Weekly Albumin-Bound Paclitaxel for Patients With Metastatic Breast Dancer Heavily Pretreated with Taxanes," Clinical Breast Cancer 7(11):850-856.

Bristol-Myers Squibb Company. (Apr. 2011). "Prescribing Insert for Taxol® (paclitaxel) Injection (Patient Information Included)," 53 pages.

CDC Workplace Health and Safety. (Sep. 2004). "NIOSH Alert. Preventing Occupational Exposures to Antineoplastic and Other Hazardous Drugs in Health Care Settings," CDC Workplace Health and Safety 58 pages.

Celegene Corporation et al. (Mar. 6, 2015). "Citizen Petition," 116 pages.

Chen, N. et al. (2014). "Pharmacokinetics and Pharmacodynamics of nab-Paclitaxel in Patients With Solid Tumors Disposition Kinetics and Pharmacology Distinct From Solvent-Based Paclitaxel," The Journal of Clinical Pharmacology 54(10):1097-1107.

Chen, N. et al. (2015). "Albumin-Bound nanoparticle (nab) paclitaxel exhibits enhanced paclitaxel tissue distribution and tumor penetration," Cancer Chemother Pharmacol. 76:699-712.

Chen, N. et al. (2014). "Population Pharmacokinetics (PK) and Exposure—Neutropenia Relationship of nab-Paclitaxel (nab-P) in Patients (pts) with Solid Tumors," J. Clin. Oncol. 32(15):Abstract 2559, 3 pages.

Commisso, C. et al. (May 20, 2013). "Macropinocytosis of Protein is an Amino Acid Supply Route in Ras-Transformed Cells," Nature 497(7451):1-13.

Cortes, J. et al. (2010). "Nanoparticle Albumin-Bound (nab™)-Paclitaxel: Improving Efficacy and Tolerability by Targeted Drug Delivery in Metastatic Breast Cancer," EJC Supplements 8:1-10.

Dada, O.O. et al. (2017, e-pub. Jun. 17, 2017). "Comparison of SEC and CE-SDS Methods for Monitoring Hinge Fragmentation in IgG1 Monoclonal Antibodies," Journal of Pharmaceutical and Biomedical Analysis 145:91-97.

Desai, N. et al. (Feb. 15, 2006). "Increased Antitumor Activity, Intratumor Paclitaxel Concentrations, and Endothelial Cell Transport of Cremophor-Free, Albumin-Bound Paclitaxel, ABI-007, Compared With Cremophor-Based Paclitaxel," Clin. Cancer Res. 12(4):1317-1324.

Elzoghby, A.O. et al. (2012, e-pub. Aug. 1, 2011). "Albumin-Based Nanoparticles as Potential Controlled Release Drug Delivery Systems," Journal of Controlled Release 157(2):168-182.

(56) References Cited

OTHER PUBLICATIONS

EMA. (Mar. 26, 2015). "Reflection Paper on the Data Requirements for Intravenous Iron-Based Nano-Colloidal Products developed With Reference to an Innovator Medicinal Product," 11 pages.

EMA. (May 22, 2013). "Reflection Paper on Surface Coatings: General Issues for Consideration Regarding Parenthera Administration of Coated Nanomedicine Products," 5 pages.

European Search Report and European Search Opinion dated Jul. 6, 2016, for European Patent Application No. 13868481.6, filed on Dec. 19, 2013, 9 pages.

FDA. (2017). "FDA's Approach to Regulation of Nanotechnology Products," 4 pages.

FDA. (Jun. 2014). "Guidance for Industry Considering Whether an FDA-Regulated Product Involves the Application of Nanotechnology," 14 pages.

FDA. (Mar. 7, 2004). Center for Drug Evaluation and Reseach. Pharmacology/Toxicology Review and Evaluation. NDA No. 21-660, Product ABI-007, American Bioscience, Inc., 49 pages.

FDA. (May 16, 2014). "Generic Drug User Fee Amendments of 2012 Regulatory Science Initiatives: Request for Public Input for FY 2015 Generic Drug Research. Part 15 Public Hearing," 4 pages.

FDA. (Oct. 13, 2010). Petition Response, Docket No. FDA-2007-P-0182, 12 pages.

FDA. (Oct. 2011). "Draft Guidance on Enoxaparin Sodium," 1 page.

FDA. (Oct. 2011). "Draft Guidance on Zolpidem," 2 pages.

FDA. (Sep. 2012). "Draft Guidance on Methylphenidate Hydrochloride," 6 pages.

FDA. (Sep. 2012). "Draft Guidance on Paclitaxel," 2 pages.

FDANEWS. (2017). "Phase III Trial of Tocosol Paclitaxel Does Not Meet Primary Endpoint," 1 page.

Federal Register. (2014). "Generic Drug User Fee Amendments of 2012; Regulatory Science Initiatives; Public Hearing; Request for Comments," FDA 5 pages.

Final Office Action dated May 20, 2014, for U.S. Appl. No. 13/073,824, filed Mar. 28, 2011, 11 pages.

Final Office Action dated May 31, 2018, for U.S. Appl. No. 15/183,636, filed Jun. 15, 2016, 37 pages.

Freese, K.K. et al. (Mar. 2012, e-pub. Feb. 28, 2012). "nab-Paclitaxel Potentiates Gemcitabine Activity by Reducing Cytidine Deaminase Levels in a Mouse Model of Pancreatic Cancer," Cancer Discovery 261-269.

Frei, E. et al. (2011). "Albumin Binding Ligands and Albumin Conjugate Uptake by Cancer Cells," BioMed Central 3 (11):1-4.

Fujita, A. et al. (2007). "Anaphylactiod Shock in a Patient Following 5% Human Serum Albumin Infusin During Off-Pump Coronary Artery Bypass Grafting," Journal of Anesthesia 21:396-398.

Gabizon, A. et al. (Feb. 15, 1994). "Prolonged Circulation Time and Enhanced Accumulation in Malignant Exudates of Doxorubicin Encapsulated in Polyethylene-glycol Coated Liposomes," Cancer Research 54:987-992.

Gales, B.J. et al. (1993). "Adverse Reaction to Human Serum Albumin," Ann. Pharmacother. 27:87-94.

Galli, C. (2006, e-pub. Mar. 9, 2016). "Experimental Determination of the Diffusion Boundary Layer Width of Micron and Submicron Particles," International Journal of Pharmaceutics 313:114-122.

Gardner, E.R. et al. (Jul. 1, 2008). "Randomized crossover pharmacokinetic study of solvent-based paclitaxel and nab-paclitaxel," Clin Cancer Res. 14(13):4200-4205.

Garro, A.G. et al. (Jun. 10, 2011). "Reversible Exposure of Hydrophobic Residues on Albumin as a Novel Strategy for Formulation of Nanodelivery Vehicles for Taxanes," Int. J. Nanomedicine 6:1193-1200.

GDUFA. (2015). "Regulatory Science Priorities for Fiscal year 2015," 3 pages.

GGPS. (Jan. 6, 2015). "Guidance Agenda: New & Revised Draft Guidances CDER is Planning to Publish During Calendar Year 2015," 5 pages.

Goetz, H. et al. (2004). "Comparison of Selected Analytical Techniques for Protein Sizing, Quantitation and Molecular Weight Determination," J. Biochem. Biophys. Methods 60:281-293.

Gonzalez-Angulo, A.M. et al. (Oct. 1, 2013). "Weekly nab-Rapamycin in Patients With Advanced Nonhematologic Malignancies: Final Resultsofa Phase I Trial," Clinical Cancer Research 19(19):5474-5484.

Gradishar, W. J. et al. (Nov. 1, 2005). "Phase III Trial of Nanoparticle Albumin-Bound Paclitaxel Compared with Polyethylated Castor Oil-Based Paclitaxel in Women With Breast Cancer," J. Clin Oncol. 23(31):7794-7803.

Green, M.R. et al. (2006, e-pub. Jun. 1, 2006). "Abraxane®, a novel Cremophor@-free, albumin-bound particle form of paclitaxel for the treatment of advanced non-small-cell lung cancer," Annuals of Oncology 17:1263-1268.

Hanauske, A.R. et al. (2005). "Pharmacokinetics (PK) of Free and Total Paclitaxel After Equal Doses of Paclitaxel njectable Emulsion and Paclitaxel Injection," J Clin Oncol 23:Abstract No. 2045, 1 page.

Herr, I. et al. (Jun. 15, 2003). "Glucocorticoid Cotreatment Induces Apoptosis Resistance toward Cancer Therapy in Carcinomas," Cancer Research 63:3112-3120.

Holloway, C. et al. (2012). "Scientific Considerations for Complex Drugs in Light of Established and Emerging Regulatory Guidance," Ann. N.Y. Acad Sci. 1276:26-36.

Ibrahim, N.K. et al. (Sep. 1, 2006). "Multicenter Phase II Trail of ABI-007, an Albumin-Bound Paclitaxel, in Women With Metastatic Breast Cancer," Journal of Clinical Oncology 23(25):6019-6026.

Infante, J.R. et al. (Jan. 20, 2007). "Peritumoral Fibroblast SPARC Expression and Patient Outcome With Resectable Pancreatic Adenocarcinoma," Journal of Clinical Oncology 25(3):319-325.

International Search Report and Written Opinion dated Jan. 7, 2021, filed on Oct. 28, 2020, 26 pages.

Irizarry, L.D. et al. (Mar. 2009). "Cremophor EL-Containing Paclitaxel-Induced Anaphylaxis: A Call to Action," Community Oncology 6:132-134.

Jain, R.K. et al. (Jan. 7, 2005). "Normalization of Tumor Vasculature: An Emerging Concept in Antiangiogenic Therapy," Science 307:58-62.

Josić, DJ. et al. (1984). "Size-Exclusion High-Performance Liquid Chromatography and Sodium Dodecyl Sulfate-Polyacrylamide Gel Electrophoresis of Protein: A Comparison," Analytical Biochemistry 142:473-479.

Khan, S. et al. (2013). "Activation of NFkB is a Novel Mechanism of Pro-Survival Activity of Glucocorticoids in Breast Dancer Cells," Cancer Letters 337:90-95.

Kranenburg, O. et al. (Nov. 27, 2001). "Regulating c-Ras Function: Cholesterol Depletion Affects Caveolin Association, GTP Loading, and Signaling," Current Biology 11:1880-1884.

Langer, C.J. et al. (2008). "Phase III Trial Comparing Paclitaxel Poliglumex (CT-2103, PPX) in Combination with Carboplatin Versus Standard Paclitaxel and Carboplatin in the Treatment of PS 2 Patients with Chemotherapy-Naive Advanced Non-small Cell Lung Cancer," Journal of Thoracic Oncology 3(6):623-630.

Langer, K. et al. (2008, e-pub. Jun. 23, 2007). "Human Serum Albumin (HSA) Nanoparticles: Reproducibility of Preparation Process and Kinetics of Enzymatic Degradation", International Journal of Pharmaceutics 347 (1-2):109-117.

Lee, K.S. et al. (Mar. 2008, e-pub. May 3, 2007). "Multicenter Phase II Trial of Genexol-PM (Cynviloq), a Cremophor-Free, Polymeric Micelle Formulation of Paclitaxel, in Patients With Metastatic Breast Cancer," Breast Cancer Res Treat. 108:241-250.

Li, Y. et al. (Feb. 25, 2015). "Pharmacologic Sensitivity of Paclitaxel to Its Delivery Vehicles Drives Distinct Clinical Dutcome of Paclitaxel Formulations Molecular Pharmaceutics," Molecular Pharmaceutics 12:1308-1317.

Liggins, R.T. et al. (Dec. 1997). "Solid-State Characterization of Paclitaxel," Journal of Pharmaceutical Sciences 86(12):1458-1463.

Lim, W.T. et al. (Feb. 2010, e-pub. Jul. 24, 2009). "Phase I Pharmacokinetic Study of a Weekly Liposomal Paclitaxel Formulation (Genexol®-PM) in Patients with Solid Tumors," Annals of Oncology 21(2):382-388.

(56) References Cited

OTHER PUBLICATIONS

Lindfors, L. et al. (Jan. 31, 2006). "Amorphous Drug Nanosuspensions. 1. Inhibition of Ostwald Ripening," Langmuir 22(3):906-910.

Lindfors, L. et al. (Sep. 11, 2007). "Amorphous Drug Nanosuspensions. 3. Particle Dissolution and Crystal Growth," Langmuir 33(19):9866-9874.

Löhr, J.M. et al. (2012, e-pub. Sep. 6, 2011). "Cationic liposomal paclitaxel plus gemcitabine orgemcitabine alone in patients with advanced pancreatic cancer: a randomized controlled phase II trial," Annals of Oncology 23:1214-1222.

Maeda, S. et al. (2011, e-pub. Apr. 1, 2011). "Paclitaxel as Second-Line Chemotherapy in Patients With Gemcitabine-Refractory Pancreatic Cancer: A Retrospective Study," Int. J Clin. Oncol. 16:539-545.

Makriyannis, A. et al. (2005). "Albumin Enhances the Diffusion of Lipophilic Drugs Into the Membrane Bilayer," Life Sciences 77:1605-1611.

Merisko-Liversidge, E. et al. (1996). "Formulation and Antitumor Activity Evaluation of Nanocrystalline Supensions of Poorly Soluble Anticancer Drugs," Pharmaceutical Research 13(2):272-278.

Merisko-Liversidge, E. et al. (2003). "Nanosizing: A Formulation Approach for Poorly-Water-Soluble Compounds," European Journal of Pharmaceutical Sciences 18:113-120.

Micili, A.J. et al. (Dec. 1987). "Transcytosis of Albumin in Capillary Endothelium," The Journal of Cell Biology 105(Part 6)(Part 1):2603-2612.

Mielke, S. et al. (2006, epub. Nov. 15, 2005). "Peripheral Neuropathy: A Persisting Challenge in Paclitaxel-Based Regimes," European Journal Of Cancer 42:24-30.

Minshall, R.D. et al. (2002, epub. Jan. 22, 2002). "Vesicle Formation and Trafficking in Endotherlial Cells and Regulation of Endotherlial Barrier Function," Histochem Cell Biol. 117:105-112.

Müller, B.G. et al. (1996). "Albumin Nanospheres as Carriers for Passive Drug Targeting: An Optimized Manufacturing Technique," Pharmaceutical Research 13(1):32-37.

National Cancer Institute. (2017). "Learn About Nanotechnology in Cancer," published at http://www.nano.cancer.gov/learn/understanding/, last visited on Jul. 24, 2017, 2 pages.

National Cancer Institute. (2017). "Nanotechnology Animation: Cantilevers," published at http://www.nano.cancer.gov/learn/understanding/nanotech_cantilevers.asp, last visited on Jul. 24, 2017, 2 pages.

National Cancer Institute. (2017). "Nanotechnology Animations: Nanoshells," published at http://www.nano.cancer.gov/learn/understanding/nanotech_nanoshells.asp, last visited on Jul. 24, 2017, 2 pages.

National Cancer Institute. (2017). "Nanotechnology Animations: Nanowires," published at http://www.nano.cancer.gov/learn/understanding/nanotech_nanowires.asp, last visited on Jul. 24, 2017, 1 page.

National Cancer Institute. (2017). "Nanotechnology Glossary," published at http://www.nano.cancer.gov/learn/Linderstanding/nanotech_glossary.asp, last visited on Jul. 24, 2017, 5 pages.

National Cancer Institute. (2017). "Tools for Education," published at http://www.nano.cancer.gov/learn/understanding/tools.asp, last visited on Jul. 24, 2017, 2 pages.

National Cancer Institute. (2017). "Understanding Nanotechnology" published at http://www.nano.cancer.gov/learn/understanding/, last visited on Jul. 24, 2017, 2 pages.

National Cancer Institute. (2017). "Video Journey Into Nanotechnology," published at http://www.nano.cancer.gov/learn/understanding/video_journey.asp, last visited on Jul. 24, 2017, 1 page.

National Cancer Institute. (2017). "Where it Stands Now" published at http://www.nano.cancer.gov/learn/now/, last visited on Jul. 24, 2017, 1 page.

National Cancer Institute. (Nov. 2013). "Frequently Asked Questions," published at http://www.nano.cancer.gov/learn/understanding/faq.asp, last visited on Jul. 24, 2017, 5 pages.

NCI. (2017). "Impacts on Cancer," http://www.nano.cancer.gov/learn/impact, last visited on Jul. 24, 2017, 1 page.

Non-Final Office Action dated Dec. 5, 2017, for U.S. Appl. No. 15/183,636, filed Jun. 15, 2016, 31 pages.

Non-Final Office Action dated Jan. 10, 2020, for U.S. Appl. No. 16/517,967, filed Jul. 22, 2019, 10 pages.

Non-Final Office Action dated Nov. 1, 2017, for U.S. Appl. No. 15/062,046, filed Mar. 5, 2016, 16 pages.

Non-Final Office Action dated Sep. 11, 2015, for U.S. Appl. No. 13/782,990, filed Mar. 2, 2013, 26 pages.

OSHA. (2017). "Section VI: Chapter 2: Controlling Occupational Exposure to Hazardous Drugs," located at https://vww.osha.gov/dts/osta/otm/otm_vi/otm_vi_2.html, last visited on Jul. 25, 2017, 20 pages.

Pang, D. et al. (Aug. 2006, e-pub. May 26, 2006). "Dexamethasone Decreases Xenograft Response to Paclitaxel Through Inhibition of Tumor Cell Apoptosis," Cancer Biology & Therapy 5(8):933-940.

Paál, K. et al. (2001). "High Affinity Binding of Paclitaxel to Human Serum Albumin," Eur. J. Biochem. 268 (7):2187-2191.

Paál, K. et al. (2007, e-pub. Sep. 12, 2007). "Paclitaxel Binding to the Fatty Acid-Induced Conformation of Human Serum Albumin-Automated Docking Studies," Boorganic & Medicinal Chemistry 15:7568-7575.

Quilliet, C. et al. (2008). "Anisotropic Colloids Through Non-Trivial Buckling," The European Physical Journal E 27:13-20.

Richly, H. et al. (2009). "Plasma and Cellular Pharmacokinetics of Doxorubicin After Intravenous Infusion of Caelyx™/Doxil® in Patients With Hematological Tumors," International Journal of Clinical Pharmacology and Therapeutics 47:55-57.

Ring, J. et al. (1979). "Anaphylactiod Reactions to Infusions of Plasma Protein and Human Serum Albumin," Clinical Allergy 9:89-97.

Rizvi, N.A. et al. (Feb. 1, 2008). "Phase I/II Trial of Weekly Intravenous 130-nm Albumin-Bound Paclitaxel as Initial Chemotherapy in Patients with Stage IV Non-Small-Cell Lung Cancer," J. Clin. Oncol 26(4):639-643.

Schnitzer, J.E. et al. (1992). "Antibodies to SPARC Inhibit Albumin Binding to SPARC, gp60, and Microvascular Endothelium," Am J Physiol 263: H1872-H1879.

Schnitzer, J.E. et al. (Apr. 5, 1993). "High Affinity Binding, Endocytosis, and Degradation of Conformationally Modified Albumins," The Journal of Biological Chemistry 268(10):7562-7570.

Schnitzer, J.E. et al. (Dec. 5, 1992). "Preferential Interactiono f Albumin-binding Proteins,g p30 and gp18, with Conformationally Modified Albumins," The Journal of Biological Chemistry 267(34):24544 24553.

Schnitzer, J.E. et al. (Feb. 25, 1994). "Albondin-mediated Capillary Permeability to Albumin. Differential Role of Receptors in Endothelial Transcytosis and Endocytosis of Native and Modified Albumins," The Journal of Biological Chemistry 269(3):6072-6082.

Sheffield, W.P. et al. (Sep. 15, 2000). "Modulation of Clearance of Recombinant Serum Albumin by Either Glycosylation or Truncation," Thromb Res 99(6):613-621.

Skoczen, S. et al. (Dec. 28, 2015). "Stable Isotope Method to Measure Drug Release From Nanomedicines," J. Control Release 220(A):169-174, 17 pages.

Socinski, M.A. et al. (Apr. 30, 2012). "Weekly nab-Paclitaxel in Combination With Carboplatin Versus Solvent-Based Paclitaxel Plus Carboplatin as First-Line Therapy in Patients With Advanced Non-Small-Cell Lung Cancer: Final Results of a Phase III Trial," Journal Of Clinical Oncology 30(17):2055-2062.

Socinski, M.A. et al. (Jun. 2010). "A Dose Finding Study of Weekly and Every-3-Week nab-Paclitaxel Followed by Carboplatin as First-Line Therapy in Patients with Advanced Non-Small Cell Lung Cancer," J. Thorac. Oncol. 5 (6):852-861.

Sorrento Therapeutics, Inc. (Mar. 31, 2014). "Sorrento Announces First Patient Dosed in Registration to Evaluate Bioequivalence Between Cynviloq and Abraxane," published at http://sorrentotherapeutics.com/sorrento-announces-firstpatient-dosed-in-registration-trial-to-evaluate-bioequivalence-between-cynviloq-and-abraxane/, last visited Aug. 8, 2017, 4 pages.

Sparreboom, A. et al. (1998). "Preclinical Pharmacokinetics of Paclitaxel and Docetaxel," Anti-Cancer Drugs 9:1-17.

Sparreboom, A. et al. (Jun. 1, 2005). "Comparative Preclinical and Clinical Pharmacokinetics of a Cremophor-Free, Nanoparticle Albumin-

(56) References Cited

OTHER PUBLICATIONS

Bound Paclitaxel (ABI-007) and Paclitaxel Formulated in Cremophor (Taxol)," Clin. Cancer Res. 11(11)4136-4143.

Sui, M. et al. (2006, e-pub. Feb. 22, 2006). "Glucocorticoids interfere with therapeutic efficacy of paclitaxel against human breast and ovarian xenograft tumors," Int. J. Cancer 119:712-717.

Surati, M. et al. (2011). "Role of MetMAb (OA-5D5) in C-MET Active Lung Maligiancies," Expert Opinion Bio. Ther. 11(12):1655-1662.

Tacal, O. et al. (2002). "A Comparison Between SDS-PAGE and Size Exclusion Chromatography as Analytical Methods for Determining Product Composition in Protein Conjugation Reactions," J. Biochem. Biophys. Methods 52:161-168.

Tanaka, K. et al. (Nov. 1998). "Purification of Human Albumin by the Combination of the Method of Cohn With Liquid Chromatography," Braz. J. Med. Biol. Res. 31(11):1383-1388.

Tang, L.C. et al. (2013). "Higher rate of skin rash in a phase II trial with weekly nanoparticle albumin-bound paclitaxel and cisplatin combination in Chinese breast cancer patients," BMC Cancer 13(232):1-6.

TAXOL®. (Apr. 2011). "Prescribing Insert for Taxol®(paclitaxel) Injection (Patient Information Included)," 53 pages.

Ten Tije, A.J. et al. (2003). "Pharmacological Effects of Formulation Vehicles Implications for Cancer Chemotherapy," Clin. Pharmacokinet 42(7): 665-685.

Tinkle, S. et al. (2014). "Nanomedicines: addressing the scientific and regulatory gap," Ann. N.Y. Acad. Sci. 1313:35-36.

Trynda-Lemiesz, L. (2004, e-pub. May 8, 2004). "Paclitaxel-HSA Interaction. Binding Sites on HSA Molecule," Bioorg. Med. Chem. 12:3269-3275.

U.S. Department of Health and Human Services. (Feb. 2012). "Guidance for Industry Quality Considerations in Demonstrating Biosimilarity to a Reference Protein Product," 20 pages.

U.S. FDA (Jun. 2014). "Considering Whether an FDA-Regulated Product Involves the Application of Nanotechnology-Guidance for Industry," FDA-2010-D-0530, 14 pages.

U.S. FDA. (Dec. 2017). "Drug Products, Including Biological Products, that Contain Nanomaterials—Guidance for Industry," FDA-2013-S-0610, 29 pages.

U.S. Food & Drug Administration. (2017). "Questions and Answers Regarding Methylphenidate Hydrochloride Extended Release Tablets (Generic Concerta) Made by Mallinckrodt and UCB/Kremers Urban (Formerly Kudco," published at https://www.fda.gov/Drugs/DrugSafety/ucm422569.htm, last visited on Jul. 24, 2017, 5 pages.

U.S. Food & Drug Administration. (Jun. 2014). "Considering Whether an FDA-Regulated Product Involves the Application of Nanotechnology. Guidance for Industry," published at https://www.fda.gov/regulatoryinformation/guidances/ucm257698.htm, last visited on Jul. 24, 2017, 13 pages.

U.S. Appl. No. 15/399,366, filed Jan. 5, 2017, for Pierce et al. (U.S. Patent Application is not submitted herewith pursuant to the waiver of 37 C.F.R. § 1.98(a)(2)(iii) issued by the Office on Sep. 21, 2004.).

U.S. Appl. No. 15/462,361, filed Mar. 17, 2017, for Tao et al. (U.S. Patent Application is not submitted herewith pursuant to the waiver of 37 C.F.R. § 1.98(a)(2)(iii) issued by the Office on Sep. 21, 2004.).

U.S. Appl. No. 15/663,351, filed Jul. 28, 2017, for Desai et al. (U.S. Patent Application is not submitted herewith pursuant to the waiver of 37 C.F.R. § 1.98(a)(2)(iii) issued by the Office on Sep. 21, 2004.).

U.S. Appl. No. 15/782,630, filed Oct. 12, 2017, for Foss et al. (U.S. Patent Application is not submitted herewith pursuant to the waiver of 37 C.F.R. § 1.98(a)(2)(iii) issued by the Office on Sep. 21, 2004.).

Venkataramanan, R. et al. (1986). "Leaching of Diethylhexyl phthalate From Polyvinyl chloride Bags Into Intravenous Cyclosporine Solution," Am J Hosp Pharm, 43:2800-2802.

Vllegenthart, G.A. et al. (Apr. 28, 2011). "Compression, Crumpling and Collapse of Spherical Shells and Capsules," New Journal of Physics 13:1-24.

Von Hoff, D.D. et al. (2013). "Randomized Phase III Study of Weekly nab-Paclitaxel Plus Gemcitabine Versus Gemcitabine Alone in Patients With Metastatic Adenocarcinoma of the Pancreas (MPACT)," J. Clin. Oncol. 31 (4) Abstract LBA148, 4 pages.

Von Hoff, D.D. et al. (Dec. 1, 2011, e-pub: Oct. 3, 2011). "Gemcitabine Plus nab-Paclitaxel Is an Active Regimen in Patients With Advanced Pancreatic Cancer: A Phase I/II Trial," J. Clin. Oncol. 29(34):4548-4554.

Weiss, R. B. et al. (Jul. 1990). "Hypersensitivity Reactions from Taxol," J. Clin. Oncol. 8(7):1263-1268.

Whitehead, R.P. et al. (Jun. 1997). "Phase II Trial of Paclitaxel and Granulocyte Colony-Stimulating Factor in Patients With Pancreatic Carcinoma: A Southwest Oncology Group Study," J. Clin Oncol. 15(6):2414-2419.

Woodcock, J. (Feb. 4, 2013). Letter to FDA Sandra Rattray Concerning Docket No. FDA-2009-P-0216, 16 pages.

Written Opinion dated Mar. 18, 2014, for PCT Application No. PCT/US2013/076630, filed on Dec. 19, 2013, 4 pages.

Zavodovskaya, M. et al. (Apr. 2015). "Abstract 5469: Dexamethasone Interrupts Paclitaxel-Induced Apoptosis in Solid Tumor Cells," Proceedings AACR 106 the Annual Meeting 2015, Apr. 18-22, 2015, Philadelphia, PA, 4 pages.

International Search Report dated Mar. 18, 2014, for PCT Application No. PCT/US2013/076630, filed on Dec. 19, 2013, 9 pages.

International Preliminary Report on Patentability, dated May 3, 2022, for PCT Application No. PCT/JS2020/057710, filed on Oct. 28, 2020, 16 pages.

\* cited by examiner

PHARMACEUTICAL COMPOSITIONS OF ALBUMIN AND RAPAMYCIN

CROSS-REFERENCE TO RELATED APPLICATIONS

This application claims priority to U.S. Provisional Application No. 62/927,047, filed on Oct. 28, 2019; and U.S. Provisional Application No. 62/936,212, filed on Nov. 15, 2019; each of which is incorporated herein by reference for all purposes.

FIELD OF THE INVENTION

Compositions containing nanoparticles having albumin and rapamycin, and emulsions containing albumin and rapamycin, are described herein. Further described are methods of making and/or controlling the quality of such compositions and emulsions.

BACKGROUND OF THE INVENTION

The mammalian target of rapamycin (mTOR) is a conserved serine/threonine kinase that serves as a central hub of signaling in the cell to integrate intracellular and extracellular signals and to regulate cellular growth and homeostasis. Activation of the mTOR pathway is associated with cell proliferation and survival, while inhibition of mTOR signaling leads to inflammation and cell death. Dysregulation of the mTOR signaling pathway has been implicated in an increasing number of human diseases, including cancer and autoimmune disorders. Consequently, mTOR inhibitors have found wide applications in treating diverse pathological conditions such as solid tumors, hematological malignancies, organ transplantation, restenosis, and rheumatoid arthritis.

Rapamycin, also known as sirolimus (INN/USAN), is an immunosuppressant drug used to prevent rejection in organ transplantation; it is especially useful in kidney transplants. Rapamycin-eluting stents were approved in the United States to treat coronary restenosis. Additionally, rapamycin has been demonstrated as an effective inhibitor of tumor growth in various cell lines and animal models. Other limus drugs, such as analogs of rapamycin, have been designed to improve the pharmacokinetic and pharmacodynamic properties of rapamycin. For example, temsirolimus was approved in the United States and Europe for the treatment of renal cell carcinoma. Everolimus was approved in the U.S. for treatment of advanced breast cancer, pancreatic neuroendocrine tumors, advanced renal cell carcinoma, and subependymal giant cell astrocytoma (SEGA) associated with Tuberous Sclerosis. The mode of action of rapamycin is to bind the cytosolic protein FK-binding protein 12 (FKBP12), and the rapamycin-FKBP12 complex in turn inhibits the mTOR pathway by directly binding to the mTOR Complex 1 (mTORC1).

Albumin-based nanoparticle compositions have been developed as a drug delivery system for delivering substantially water insoluble drugs. See, for example, U.S. Pat. Nos. 5,916,596, 6,506,405, 6,749,868, 6,537,579, 7,820,788, and 7,923,536. Nab-paclitaxel, sold under the trade name ABRAXANE®, an albumin stabilized nanoparticle formulation of paclitaxel, was approved in the United States and various other countries for treating metastatic breast cancer, pancreatic cancer, and lung cancer.

The disclosures of all publications, patents, patent applications and published patent applications referred to herein are hereby incorporated herein by reference in their entirety.

BRIEF SUMMARY OF THE INVENTION

Described herein are nanoparticle compositions, pharmaceutical compositions, and emulsions containing rapamycin and albumin, along with commercial batches of such nanoparticle compositions, pharmaceutical compositions, and emulsions. Also described are methods of making such nanoparticle compositions, pharmaceutical compositions, and emulsions, as well as methods of using such nanoparticle compositions, pharmaceutical compositions (including, for example, for the treatment of cancer), and emulsions. Additionally, described herein are methods for assessing the suitability of the pharmaceutical compositions for use in a human individual, as well as methods for processing pharmaceutical compositions (and commercial batches of such pharmaceutical compositions) identified as suitable for use in a human individual.

Parameters of the nanoparticle composition, such as those as described here, can be used to ensure consistency during manufacturing of the composition. The nanoparticles contain rapamycin, a drug known to have efficacy in cancer therapy, and predictable release of the drug is important for reliable treatment. Consistently manufactured nanoparticles are expected to have a consistent drug release profile. Changes to the manufacturing protocol, such as scale up during commercial batch production, can result in changes in the physical and functional parameters of the nanoparticle composition. Described herein are commercial batches of nanoparticle compositions and commercial batches of emulsions used to manufacture commercial batches of the nanoparticle compositions, with physical and functional parameters that have been determined for such commercial batches.

A nanoparticle composition described herein can include (a) nanoparticles comprising rapamycin and albumin, and (b) a non-nanoparticle portion comprising albumin and rapamycin. In some embodiments, the nanoparticles comprise a core comprising rapamycin and a coating comprising albumin.

In a nanoparticle composition, or a commercial batch of such a nanoparticle composition, about 80% to about 95% of the albumin in the composition is in the form of monomeric albumin, about 4% to about 15% of the albumin in the composition is in the form of dimeric albumin, and about 0.5% to about 5% of the albumin in the composition is in the form of polymeric albumin when the percentage of albumin in the composition that is in the form of monomeric albumin, dimeric albumin, or polymeric albumin is determined by subjecting the composition to size-exclusion chromatography (SEC) using a saline mobile phase coupled with a multiple angle light scattering (MALS) detector. In the nanoparticle portion of the composition, about 70% to about 85% of the albumin in the nanoparticle portion is in the form of monomeric albumin, about 9% to about 20% of the albumin in the nanoparticle portion is in the form of dimeric albumin, and about 5% to about 15% of the albumin in the nanoparticle portion is in the form of polymeric albumin when the percentage of albumin in the nanoparticle portion that is in the form of monomeric albumin, dimeric albumin, or polymeric albumin is determined by separating the nanoparticles from the non-nanoparticle portion, re-suspending the nanoparticles in saline, and subjecting the re-suspended nanoparticles to size-exclusion chromatography (SEC)

using a saline mobile phase coupled with a multiple angle light scattering (MALS) detector. In the non-nanoparticle portion of the composition, about 80% to about 95% of the albumin in the non-nanoparticle portion is in the form of monomeric albumin, about 4% to about 14% of the albumin in the non-nanoparticle portion is in the form of dimeric albumin, and about 0.5% to about 5% of the albumin in the non-nanoparticle portion is in the form of polymeric albumin when the percentage of albumin in the non-nanoparticle portion that is in the form of monomeric albumin, dimeric albumin, or polymeric albumin is determined by separating the nanoparticles from the non-nanoparticle portion, and subjecting the non-nanoparticle portion to size-exclusion chromatography (SEC) using a saline mobile phase coupled with a multiple angle light scattering (MALS) detector. The nanoparticle composition may be further characterized in having less than 3% by weight of the sum of seco-rapamycin and rapamycin in the composition being in the form of seco-rapamycin.

In another characterization of the nanoparticle composition or a commercial batch of the nanoparticle composition, about 42% to about 60% of the albumin in the nanoparticle portion is in the form of polymeric albumin other than oligomeric albumin when the percentage of albumin in the nanoparticle portion that is in the form of polymeric albumin other than oligomeric albumin is determined by separating the nanoparticles from the non-nanoparticle portion, dissolving the nanoparticles, and subjecting the dissolved nanoparticles to size-exclusion chromatography. About 1% to about 4.5% of the albumin in the nanoparticle portion is in the form of oligomeric albumin when the percentage of albumin in the nanoparticle portion that is in the form of oligomeric albumin is determined by separating the nanoparticles from the non-nanoparticle portion, dissolving the nanoparticles, and subjecting the dissolved nanoparticles to size-exclusion chromatography. About 25% to about 50% of the albumin in the nanoparticle portion is in the form of monomeric albumin or about 5% to about 16% of the albumin in the nanoparticle portion is in the form of dimeric albumin when the percentage of albumin in the nanoparticle portion that is in the form of monomeric albumin or dimeric albumin is determined by separating the nanoparticles from the non-nanoparticle portion, dissolving the nanoparticles, and subjecting the dissolved nanoparticles to size-exclusion chromatography. For the non-nanoparticle portion, about 80% to about 95% of the albumin in the non-nanoparticle portion is in the form of monomeric albumin, about 4% to about 14% of the albumin in the non-nanoparticle portion is in the form of dimeric albumin, about 0.5% to about 4% of the albumin in the non-nanoparticle portion is in the form of oligomeric albumin, and/or about 0.5% to about 3% of the albumin in the non-nanoparticle portion is in the form of polymeric albumin other than oligomeric albumin when the percentage of albumin in the non-nanoparticle portion that is in the form of monomeric albumin, dimeric albumin, oligomeric albumin, and/or polymeric albumin other than oligomeric albumin is determined by separating the nanoparticles from the non-nanoparticle portion, and subjecting the non-nanoparticle portion to size-exclusion chromatography. In the composition as a whole, about 80% to about 95% of the total albumin composition is in the form of monomeric albumin, about 4% to about 15% of the total albumin in the composition is in the form of dimeric albumin, about 0.3% to about 3% of the total albumin in the composition is in the form of oligomeric albumin, and/or about 2% to about 7% of the total albumin in the composition is in the form of polymeric albumin other than oligomeric albumin when the percentage of monomeric albumin, dimeric albumin, oligomeric albumin, and/or polymeric albumin other than oligomeric albumin in the composition is determined by subjecting the composition to size-exclusion chromatography. The nanoparticle composition may be further characterized in having less than 3% by weight of the sum of seco-rapamycin and rapamycin in the composition being in the form of seco-rapamycin.

In some embodiments of the nanoparticle composition, about 70% to about 85% of the albumin in the nanoparticle portion is in the form of monomeric albumin. In some embodiments, about 5% to about 15% of the albumin in the nanoparticle portion is in the form of polymeric albumin. In some embodiments, about 9% to about 20% of the albumin in the nanoparticle portion is in the form of dimeric albumin. In some embodiments, about 0.5% to about 5% of the albumin in the non-nanoparticle portion is in the form of polymeric albumin. In some embodiments, about 80% to about 95% of the albumin in the non-nanoparticle portion is in the form of monomeric albumin. In some embodiments, about 4% to about 14% of the albumin in the non-nanoparticle portion is in the form of dimeric albumin. In some embodiments, about 0.5% to about 5% of total albumin in the composition is in the form of polymeric albumin. In some embodiments, about 80% to about 95% of total albumin in the composition is in the form of monomeric albumin. In some embodiments, about 4% to about 15% of total albumin in the composition is in the form of dimeric albumin. In some embodiments, the percentage of polymeric albumin, dimeric albumin, or monomeric albumin is determined using size-exclusion chromatography.

In some embodiments of the nanoparticle composition, the volume-weighted mean particle size of the nanoparticles is about 200 nm or less. In some embodiments, the volume-weighted mean particle size of the nanoparticles is about 50 nm to about 200 nm. In some embodiments, the Z-average particle size of the nanoparticles is about 200 nm or less. In some embodiments, the Z-average particle size of the nanoparticles is about 50 nm to about 200 nm.

In some embodiments of the nanoparticle composition, the polydispersity index of the nanoparticles is less than 0.2. In some embodiments, the polydispersity index of the nanoparticles is about 0.03 to about 0.2. In some embodiments, the span of particle size distribution $((D_v 95 - D_v 5)/D_v 50)$ of the nanoparticles is about 0.8 to about 1.2.

In some embodiments of the nanoparticle composition, the weight percentage of the albumin in the nanoparticle portion is about 25% to about 45%. In some embodiments, the weight percentage of rapamycin in the nanoparticle portion is about 55% to about 75%. In some embodiments, the weight ratio of the albumin to the rapamycin in the nanoparticle portion is about 1:1 to about 1:4.

In some embodiments of the nanoparticle composition, the weight ratio of the albumin to the rapamycin in the composition is about 1:1 to about 10:1.

In some embodiments, about 90% or more of the albumin in the composition is in the non-nanoparticle portion. In some embodiments, about 90% or more of the rapamycin in the composition is in the nanoparticles.

In some embodiments of the nanoparticle composition, the nanoparticle composition is a nanoparticle suspension. In some embodiments, the nanoparticle composition is a dried composition, such as a powder. In some embodiments, the nanoparticles had been resuspended from the dried composition.

In some embodiments of the nanoparticle composition, the concentration of albumin in the composition is about 30 mg/mL to about 100 mg/mL. In some embodiments, the concentration of albumin in the composition that is in the non-nanoparticle portion is about 30 mg/mL to about 100 mg/mL. In some embodiments, the concentration of albumin in the nanoparticle composition that is in the nanoparticle portion is about 1 mg/mL to about 5 mg/mL. In some embodiments, the concentration of rapamycin in the nanoparticle composition is about 1 mg/mL to about 100 mg/mL. In some embodiments, the concentration of rapamycin in the composition that is in the non-nanoparticle portion is about 20 µg/mL to about 55 µg/mL. In some embodiments, the concentration of rapamycin in the composition that is in the nanoparticle portion is about 1 mg/mL to about 15 mg/mL.

In some embodiments of the nanoparticle composition, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5.

In some embodiments of the nanoparticle composition, the composition is stable at 25° C. for at least 24 hours. In some embodiments, the composition is stable at 4° C. for at least 24 hours.

In some embodiments of the nanoparticle composition, the composition comprises less than 10 µg/mL tert-butanol. In some embodiments, the composition comprises tert-butanol. In some embodiments, the composition comprises less than 5 µg/mL chloroform. In some embodiments, the composition comprises chloroform.

In some embodiments of the nanoparticle composition, the zeta potential of the nanoparticles is about −25 mV to about −50 mV.

In some embodiments of the nanoparticle composition, the composition has an amorphous morphology as determined by measuring crystallinity of a lyophilized form of the composition by X-ray diffraction. In some embodiments, the nanoparticles have an amorphous morphology as determined by separating the nanoparticles from the composition, lyophilizing the separated nanoparticles, and measuring crystallinity of the separated and lyophilized nanoparticles by X-ray diffraction.

In some embodiments of the nanoparticle composition, the rapamycin in nanoparticles has an amorphous morphology as determined by Raman spectroscopy, polarized light microscopy, differential scanning calorimetry (DSC), modulated differential scanning calorimetry (mDSC), Fourier transform infrared (FTIR) spectroscopy, or nuclear magnetic resonance (NMR) spectroscopy.

In some embodiments of the nanoparticle composition, the vinyl chain of the rapamycin in the nanoparticle portion interacts with the albumin in the nanoparticles.

In some embodiments of the nanoparticle composition, at least a portion of the nanoparticles are non-spherical. In some embodiments, at least 20% of the nanoparticles in the composition are non-spherical.

In some embodiments of the nanoparticle composition, the nanoparticle composition comprises less than about 3% seco-rapamycin in the nanoparticles compared to the sum of seco-rapamycin and rapamycin in the nanoparticles, by weight. In some embodiments, the nanoparticle composition comprises more than about 0.2% seco-rapamycin in the nanoparticles compared to the sum of seco-rapamycin and rapamycin in the nanoparticles, by weight.

In some embodiments of the nanoparticle composition, about 3% or less of the rapamycin in the nanoparticle composition is free rapamycin.

In some embodiments of the nanoparticle composition, the albumin is human albumin.

In some embodiments of the nanoparticle composition, the nanoparticle composition is sterile.

In some embodiments of the nanoparticle composition, the nanoparticle composition has been sterilized by filtration.

In some embodiments of the nanoparticle composition, the nanoparticle composition is contained within a sealed container. In some embodiments, the sealed container is a sealed vial or a sealed bag.

In some embodiments of the nanoparticle composition, the nanoparticle composition is a pharmaceutical composition.

Also described herein is an emulsion (for example, an emulsion in a commercial batch), comprising: a dispersed organic phase comprising nanodroplets comprising rapamycin dissolved in an organic solvent comprising chloroform and tert-butanol, and a continuous aqueous phase comprising albumin.

In some embodiments of the emulsion, the organic solvent comprises about 10% to about 50% tert-butanol by volume. In some embodiments, the organic solvent comprises about 50% to about 90% chloroform by volume. In some embodiments, the organic solvent comprises chloroform and tert-butanol at a volumetric ratio of about 1:1 to about 9:1.

In some embodiments of the emulsion, the concentration of rapamycin in the organic phase is about 20 mg/mL to about 500 mg/mL. In some embodiments, the concentration of rapamycin in the emulsion is about 2 mg/mL to about 50 mg/mL. In some embodiments, the concentration of albumin in the aqueous phase is about 10 mg/mL to about 200 mg/mL. In some embodiments, the concentration of albumin in the emulsion is about 8 mg/mL to about 200 mg/mL.

In some embodiments of the emulsion, the phase fraction of the organic phase in the emulsion is about 1% to about 20%.

In some embodiments of the emulsion, the nanodroplets have a Z-average particle size of about 200 nm or less. In some embodiments, the nanodroplets have a Z-average particle size of about 50 nm to about 200 nm.

In some embodiments of the emulsion, the Z-average particle size of the nanodroplets does not increase by more than 30% after storing the emulsion for about 4 hours at 4° C.

In some embodiments of the emulsion, the albumin is human albumin.

Also described herein is a method of making a nanoparticle suspension. The method may include removing organic solvent from an emulsion to make the nanoparticle suspension, the emulsion comprising: a dispersed organic phase comprising nanodroplets comprising rapamycin dissolved in an organic solvent comprising chloroform and tert-butanol, and a continuous aqueous phase comprising albumin. In some embodiments, the organic solvent is removed using a wiped film evaporator or a rotary evaporator. The evaporator can be a continuous evaporator or a batch evaporator. A continuous evaporator is an evaporator in which the feed and product streams are continuous and their concentrations remain generally constant with a consistent input to the feed stream. A batch evaporator is an evaporator in which the feed and product streams are discontinuous. In some embodiments, the organic solvent is removed with a continuous evaporator. In some embodiments, the organic solvent is removed with a batch evaporator. In some embodiments, the method further comprises forming the emulsion by homogenizing the organic phase and the aqueous phase.

In some embodiments of making the nanoparticle suspension, the organic solvent comprises about 10% to about 50% tert-butanol by volume. In some embodiments, the organic solvent comprises about 50% to about 90% chloroform by volume. In some embodiments, the organic solvent comprises chloroform and tert-butanol at a volumetric ratio of about 1:1 to about 9:1. In some embodiments, the concentration of rapamycin in the organic phase is about 20 mg/mL to about 500 mg/mL. In some embodiments, the concentration of rapamycin in the emulsion is about 2 mg/mL to about 50 mg/mL. In some embodiments, the concentration of albumin in the aqueous phase is about 10 mg/mL to about 200 mg/mL. In some embodiments, the concentration of albumin in the emulsion is about 8 mg/mL to about 200 mg/mL. In some embodiments, the phase fraction of the organic phase in the emulsion is about 1% to about 20%. In some embodiments, the nanodroplets have a Z-average particle size of about 200 nm or less. In some embodiments, the nanodroplets have a Z-average particle size of about 50 nm to about 200 nm. In some embodiments, the albumin is human albumin.

In some embodiments of making the nanoparticle suspension, the emulsion is stored between about 2° C. and about 8° C. before removing the organic solvent. In some embodiments, the emulsion is stored for about 4 hours or for about 24 hours.

In some embodiments of making the nanoparticle suspension, the method further comprises filtering the organic phase, the aqueous phase, or both, prior to forming the emulsion.

In some embodiments of making the nanoparticle suspension, the organic phase and the aqueous phase are homogenized using a high pressure homogenizer.

In some embodiments of making the nanoparticle suspension, the method further comprises adding a solution comprising albumin to the nanoparticle suspension. In some embodiments, adding the solution comprising albumin adjusts the weight ratio of albumin to rapamycin in the nanoparticle suspension to between about 1:1 and about 10:1.

In some embodiments of making the nanoparticle suspension, the method further comprises filtering the nanoparticle suspension.

In some embodiments of making the nanoparticle suspension, the method further comprises lyophilizing the nanoparticle suspension. In some embodiments of making the nanoparticle suspension, the method further adding the nanoparticle suspension into one or more vials. In some embodiments, the method comprises lyophilizing the nanoparticle suspension after adding the nanoparticle suspension into the one or more vials.

Also described herein is a method of assessing suitability of a pharmaceutical composition for medical use in a human individual, wherein the pharmaceutical composition comprises (a) nanoparticles comprising rapamycin and albumin, and (b) a non-nanoparticle portion comprising albumin and rapamycin, the method comprising measuring a quality control parameter for the pharmaceutical composition; and assessing the suitability of the pharmaceutical composition for medical use in a human individual, wherein a measured quality control parameter within a quality control threshold is indicative of suitability of the pharmaceutical composition for medical use. In some embodiments, the method further comprises separating the nanoparticles from the non-nanoparticle portion, wherein the quality control parameter comprises a quality control parameter for the nanoparticles or the non-nanoparticle portion. In some embodiments, the nanoparticles comprise a core comprising rapamycin and a coating comprising albumin. The quality control parameter can be any or a combination of the multiple parameters described herein for the nanoparticle compositions, for example, as assessed by corresponding methods described herein.

In some embodiments of assessing the suitability of the pharmaceutical composition, the quality control parameter comprises a weight percentage of albumin in the form of monomeric albumin in the nanoparticle portion of the total albumin in the nanoparticle portion; and a weight percentage of albumin in the form of monomeric albumin in the nanoparticle portion of the total albumin in the nanoparticle portion being about 70% to about 85% is indicative of suitability of the pharmaceutical composition for medical use.

In some embodiments of assessing the suitability of the pharmaceutical composition, the quality control parameter comprises a weight percentage of albumin in the form of polymeric albumin in the nanoparticle portion of the total albumin in the nanoparticle portion; and a weight percentage of albumin in the form of polymeric albumin in the nanoparticle portion of the total albumin in the nanoparticle portion being about 5% to about 15% is indicative of suitability of the pharmaceutical composition for medical use.

In some embodiments of assessing the suitability of the pharmaceutical composition, the quality control parameter comprises a weight percentage of albumin in the form of dimeric albumin in the nanoparticle portion of the total albumin in the nanoparticle portion; and a weight percentage of albumin in the form of dimeric albumin in the nanoparticle portion of the total albumin in the nanoparticle portion being about 9% to about 20% is indicative of suitability of the pharmaceutical composition for medical use.

In some embodiments of assessing the suitability of the pharmaceutical composition, the quality control parameter comprises a weight percentage of albumin in the form of polymeric albumin in the non-nanoparticle portion of the total albumin in the non-nanoparticle portion; and a weight percentage of albumin in the form of polymeric albumin in the non-nanoparticle portion of the total albumin in the non-nanoparticle portion being about 0.5% to about 5% is indicative of suitability of the pharmaceutical composition for medical use.

In some embodiments of assessing the suitability of the pharmaceutical composition, the quality control parameter comprises a weight percentage of albumin in the form of monomeric albumin in the non-nanoparticle portion of the total albumin in the non-nanoparticle portion; and a weight percentage of albumin in the form of monomeric albumin in the non-nanoparticle portion of the total albumin in the non-nanoparticle portion being about 80% to about 95% is indicative of suitability of the pharmaceutical composition for medical use.

In some embodiments of assessing the suitability of the pharmaceutical composition, the quality control parameter comprises a weight percentage of albumin in the form of dimeric albumin in the non-nanoparticle portion of the total albumin in the non-nanoparticle portion; and a weight percentage of albumin in the form of dimeric albumin in the non-nanoparticle portion of the total albumin in the non-nanoparticle portion being about 4% to about 15% is indicative of suitability of the pharmaceutical composition for medical use.

In some embodiments of assessing the suitability of the pharmaceutical composition, the quality control parameter comprises a weight percentage of albumin in the form of polymeric albumin in the composition of the total albumin in the composition; and a weight percentage of albumin in the form of polymeric albumin in the composition of the total albumin in the composition being about 0.5% to about 5% is indicative of suitability of the pharmaceutical composition for medical use.

In some embodiments of assessing the suitability of the pharmaceutical composition, the quality control parameter comprises a weight percentage of albumin in the form of monomeric albumin in the composition of the total albumin in the composition; and a weight percentage of albumin in the form of monomeric albumin in the composition of the total albumin in the composition being about 80% to about 95% is indicative of suitability of the pharmaceutical composition for medical use.

In some embodiments of assessing the suitability of the pharmaceutical composition, the quality control parameter comprises a weight percentage of albumin in the form of dimeric albumin in the composition of the total albumin in the composition; and a weight percentage of albumin in the form of dimeric albumin in the composition of the total albumin in the composition being about 4% to about 15% is indicative of suitability of the pharmaceutical composition for medical use.

In some embodiments of assessing the suitability of the pharmaceutical composition, the percentage of polymeric albumin, dimeric albumin, or monomeric albumin is determined using size-exclusion chromatography.

In some embodiments of assessing the suitability of the pharmaceutical composition, the quality control parameter comprises a volume weighted mean particle size of the nanoparticles; and a volume weighted mean particle size of the nanoparticles being about 200 nm or less is indicative of suitability of the pharmaceutical composition for medical use.

In some embodiments of assessing the suitability of the pharmaceutical composition, the quality control parameter comprises a volume-weighted mean particle size of the nanoparticles; and a volume weighted mean particle size of the nanoparticles being about 50 nm to about 200 nm is indicative of suitability of the pharmaceutical composition for medical use.

In some embodiments of assessing the suitability of the pharmaceutical composition, the quality control parameter comprises a Z-average particle size of the nanoparticles; and a Z-average particle size of the nanoparticles being about 200 nm or less is indicative of suitability of the pharmaceutical composition for medical use.

In some embodiments of assessing the suitability of the pharmaceutical composition, the quality control parameter comprises a Z-average particle size of the nanoparticles; and a Z-average particle size being about 50 nm to about 200 nm is indicative of suitability of the pharmaceutical composition for medical use.

In some embodiments of assessing the suitability of the pharmaceutical composition, the quality control parameter comprises a polydispersity index of the nanoparticles; and a polydispersity index of the nanoparticles being less than 0.3 is indicative of suitability of the pharmaceutical composition for medical use.

In some embodiments of assessing the suitability of the pharmaceutical composition, the quality control parameter comprises a polydispersity index of the nanoparticles; and a polydispersity index of the nanoparticles being about 0.03 to about 0.3 is indicative of suitability of the pharmaceutical composition for medical use.

In some embodiments of assessing the suitability of the pharmaceutical composition, the quality control parameter comprises a span of particle size distribution $((D_v95-D_v5)/D_v50)$ of the nanoparticles; and a span of particle size distribution of the nanoparticles being about 1.2 or less is indicative of suitability of the pharmaceutical composition for medical use.

In some embodiments of assessing the suitability of the pharmaceutical composition, the quality control parameter comprises a weight percentage of the albumin in the nanoparticle portion; and a weight percentage of the albumin in the nanoparticle portion being about 25% to about 45% is indicative of the suitability of the pharmaceutical composition for medical use.

In some embodiments of assessing the suitability of the pharmaceutical composition, the quality control parameter comprises a weight percentage of the rapamycin in the nanoparticle portion; and a weight percentage of the rapamycin in the nanoparticle portion being about 55% to about 75% is indicative of the suitability of the pharmaceutical composition for medical use.

In some embodiments of assessing the suitability of the pharmaceutical composition, the quality control parameter comprises a weight ratio of the albumin to the rapamycin in the nanoparticle portion; and a weight ratio of the albumin to the rapamycin in the nanoparticle portion being about 1:1 to about 1:4 is indicative of the suitability of the pharmaceutical composition for medical use.

In some embodiments of assessing the suitability of the pharmaceutical composition, the quality control parameter comprises a weight ratio of the albumin to the rapamycin in the composition; and a weight ratio of the albumin to the rapamycin in the composition being about 1:1 to about 10:1 is indicative of the suitability of the pharmaceutical composition for medical use.

In some embodiments of assessing the suitability of the pharmaceutical composition, the quality control parameter comprises a percentage of albumin in the composition that is in the non-nanoparticle portion; and a percentage of albumin in the composition that is in the non-nanoparticle portion being about 95% or more is indicative of the suitability of the pharmaceutical composition for medical use.

In some embodiments of assessing the suitability of the pharmaceutical composition, the quality control parameter comprises a percentage of rapamycin in the composition that is in the nanoparticle portion; and a percentage of rapamycin in the composition that is in the nanoparticle portion being about 98% or more is indicative of the suitability of the pharmaceutical composition for medical use.

In some embodiments of assessing the suitability of the pharmaceutical composition, the pharmaceutical composition is a nanoparticle suspension.

In some embodiments of assessing the suitability of the pharmaceutical composition, the pharmaceutical composition is reconstituted from a dried nanoparticle composition, such as a powder.

In some embodiments of assessing the suitability of the pharmaceutical composition, the quality control parameter comprises a concentration of albumin in the composition; and a concentration of albumin in the composition being about 30 mg/mL to about 100 mg/mL is indicative of the suitability of the pharmaceutical composition for medical use.

In some embodiments of assessing the suitability of the pharmaceutical composition, the quality control parameter comprises a concentration of albumin in the composition that is in the non-nanoparticle portion; and a concentration of albumin in the composition that is in the non-nanoparticle portion being about 30 mg/mL to about 100 mg/mL is indicative of the suitability of the pharmaceutical composition for medical use.

In some embodiments of assessing the suitability of the pharmaceutical composition, the quality control parameter comprises a concentration of albumin in the composition that is in the nanoparticle portion; and a concentration of albumin in the composition that is in the nanoparticle portion being about 1.8 mg/mL to about 15 mg/mL is indicative of the suitability of the pharmaceutical composition for medical use.

In some embodiments of assessing the suitability of the pharmaceutical composition, the quality control parameter comprises a concentration of rapamycin in the composition; and a concentration of rapamycin in the composition being about 1 mg/mL to about 15 mg/mL is indicative of the suitability of the pharmaceutical composition for medical use.

In some embodiments of assessing the suitability of the pharmaceutical composition, the quality control parameter comprises a concentration of rapamycin in the composition that is in the non-nanoparticle portion; and a concentration of rapamycin in the composition that is in the non-nanoparticle portion being about 20 µg/mL to about 55 µg/mL is indicative of the suitability of the pharmaceutical composition for medical use.

In some embodiments of assessing the suitability of the pharmaceutical composition, the quality control parameter comprises a concentration of rapamycin in the composition that is in the nanoparticle portion; and a concentration of rapamycin in the composition that is in the nanoparticle portion being about 1 mg/mL to about 15 mg/mL is indicative of the suitability of the pharmaceutical composition for medical use.

In some embodiments of assessing the suitability of the pharmaceutical composition, the quality control parameter comprises an osmolality of the composition; and an osmolality of the composition being about 300 mOSm/kg to about 350 mOSm/kg is indicative of the suitability of the pharmaceutical composition for medical use.

In some embodiments of assessing the suitability of the pharmaceutical composition, the quality control parameter comprises a viscosity of the composition; and a viscosity of the composition being about 1.2 cP to about 1.5 cP is indicative of the suitability of the pharmaceutical composition for medical use.

In some embodiments of assessing the suitability of the pharmaceutical composition, the quality control parameter comprises a stability of the composition; and the composition being stable at 25° C. for at least 24 hours is indicative of the suitability of the pharmaceutical composition for medical use.

In some embodiments of assessing the suitability of the pharmaceutical composition, the quality control parameter comprises a stability of the composition; and the composition being stable at 4° C. for at least 24 hours is indicative of the suitability of the pharmaceutical composition for medical use.

In some embodiments of assessing the suitability of the pharmaceutical composition, the quality control parameter comprises a pH of the composition; and a pH of the composition being about 6.0 to about 7.5 is indicative of the suitability of the pharmaceutical composition for medical use.

In some embodiments of assessing the suitability of the pharmaceutical composition, the composition is made using tert-butanol, and wherein the quality control parameter comprises a concentration of tert-butanol; and a concentration of tert-butanol being less than 10 µg/mL tert-butanol is indicative of the suitability of the pharmaceutical composition for medical use.

In some embodiments of assessing the suitability of the pharmaceutical composition, the composition is made using chloroform, and wherein: the quality control parameter comprises a concentration of chloroform; and a concentration of tert-butanol being less than 5 µg/mL chloroform is indicative of the suitability of the pharmaceutical composition for medical use.

In some embodiments of assessing the suitability of the pharmaceutical composition, the quality control parameter comprises a zeta potential of the nanoparticles; and a zeta potential of the nanoparticles being about −25 mV to about −50 mV is indicative of the suitability of the pharmaceutical composition for medical use.

In some embodiments of assessing the suitability of the pharmaceutical composition, the quality control parameter comprises a morphology of the composition, wherein the morphology is measured by measuring crystallinity of a lyophilized form of the composition by X-ray diffraction; and an amorphous morphology of the composition is indicative of the suitability of the pharmaceutical composition for medical use.

In some embodiments of assessing the suitability of the pharmaceutical composition, the quality control parameter comprises a morphology of the composition, wherein the morphology is measured by separating the nanoparticles from the composition, lyophilizing the separated nanoparticles, and measuring crystallinity of the separated and lyophilized nanoparticles by X-ray diffraction; and an amorphous morphology of the composition is indicative of the suitability of the pharmaceutical composition for medical use.

In some embodiments of assessing the suitability of the pharmaceutical composition, the quality control parameter comprises a morphology of the composition, wherein the morphology is measured by Raman spectroscopy differential scanning calorimetry (DSC), modulated differential scanning calorimetry (mDSC), Fourier transform infrared (FTIR) spectroscopy, or nuclear magnetic resonance (NMR) spectroscopy; and an amorphous morphology of the composition is indicative of the suitability of the pharmaceutical composition for medical use.

In some embodiments of assessing the suitability of the pharmaceutical composition, the quality control parameter comprises an interaction of the vinyl chain of the rapamycin in the nanoparticle portion with the albumin in the nanoparticle portion; and an identified interaction between the vinyl chain of the rapamycin in the nanoparticle portion with the albumin in the nanoparticle portion is indicative of the suitability of the pharmaceutical composition for medical use.

In some embodiments of assessing the suitability of the pharmaceutical composition, the quality control parameter comprises a portion of the nanoparticles that are non-spherical; and identification of at least a portion of the nanoparticles as non-spherical is indicative of the suitability of the pharmaceutical composition for medical use.

In some embodiments of assessing the suitability of the pharmaceutical composition, the quality control parameter comprises a portion of the nanoparticles that are non-spherical; and identification of at least 20% of the nanoparticles as non-spherical is indicative of the suitability of the pharmaceutical composition for medical use.

In some embodiments of assessing the suitability of the pharmaceutical composition, the quality control parameter comprises a percentage of seco-rapamycin compared to the sum of seco-rapamycin and rapamycin, by weight, in the nanoparticle portion; and a percentage of seco-rapamycin compared to the sum of seco-rapamycin and rapamycin, by weight, in the nanoparticle portion being less than 2.5% seco-rapamycin is indicative of the suitability of the pharmaceutical composition for medical use.

In some embodiments of assessing the suitability of the pharmaceutical composition, the quality control parameter comprises a percentage of rapamycin in the pharmaceutical composition that is free rapamycin; and a percentage of rapamycin in the pharmaceutical composition that is free rapamycin being less than 3% is indicative of the suitability of the pharmaceutical composition for medical use.

In some embodiments of assessing the suitability of the pharmaceutical composition, the albumin is human albumin.

Also provided herein is a method of releasing a commercial batch of a pharmaceutical composition comprising (a) nanoparticles comprising rapamycin and albumin, and (b) a non-nanoparticle portion comprising albumin and rapamycin, the method comprising: assessing the suitability of the pharmaceutical composition for medical use in a human individual using a sample of the commercial batch, and releasing the commercial batch if the pharmaceutical composition is suitable for medical use.

Further provided herein is a method of processing a sample of a pharmaceutical composition to validate the sample as suitable for medical use in a human individual, the pharmaceutical composition comprising (a) nanoparticles comprising rapamycin and albumin, and (b) a non-nanoparticle portion comprising albumin and rapamycin, the method comprising: obtaining the sample from a commercial batch; and assessing the suitability of the pharmaceutical composition for medical use in a human individual using a sample of the commercial batch.

Also described is a method of preparing a pharmaceutical composition comprising (a) nanoparticles comprising rapamycin and albumin, and (b) a non-nanoparticle portion comprising albumin and rapamycin for release, the method comprising: assessing the suitability of the pharmaceutical composition for medical use in a human individual; identifying the pharmaceutical composition as suitable for medical use in a human individual; and packaging the pharmaceutical composition for release. In some embodiments, packaging the pharmaceutical composition comprises lyophilizing the pharmaceutical composition. In some embodiments, packaging the pharmaceutical composition comprises filling the pharmaceutical composition in a container. In some embodiments, the method comprises sealing the container.

DETAILED DESCRIPTION

Figure 1:
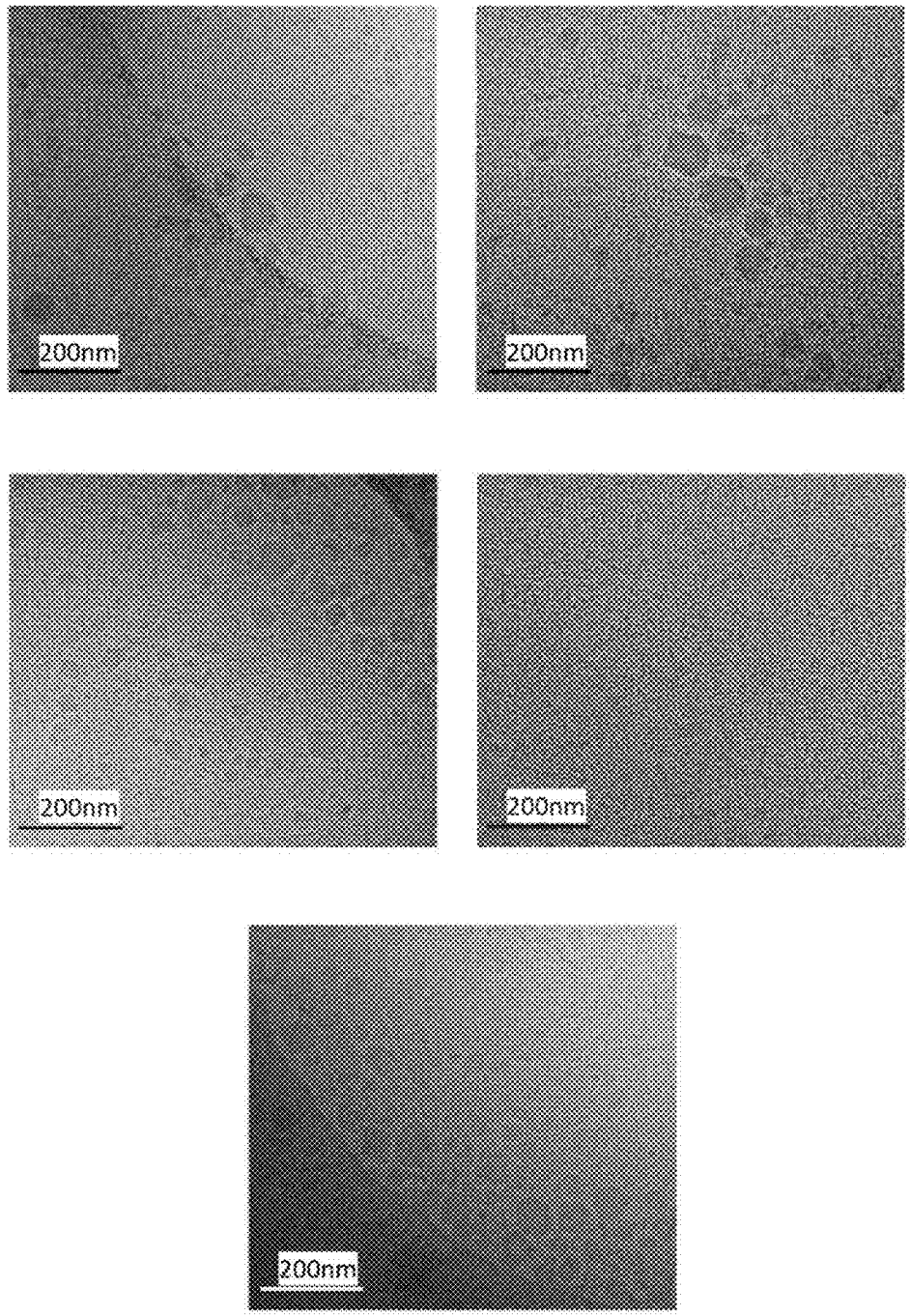
FIG. 1 depicts Cryo-TEM images at 52,000× magnification (0.21 nm/pixel) of lot #11 (top left), lot #1 (top right), lot #3 (middle left), human albumin alone (middle right), or lot #2 (bottom).

Described herein are nanoparticle compositions (such as pharmaceutical compositions) that include albumin and rapamycin, or commercial batches of the nanoparticle compositions. The nanoparticles include albumin and rapamycin associated with each other in the nanoparticle. For example, the nanoparticles may include a coating comprising the albumin, and a core comprising the rapamycin. The composition may further include a non-nanoparticle portion that includes albumin and rapamycin that is not included within the nanoparticle portion. That is, the composition may include nanoparticle-bound albumin and nanoparticle-bound rapamycin in the nanoparticle portion of the composition, and non-nanoparticle albumin and non-nanoparticle rapamycin in the non-nanoparticle portion of the composition. As used herein, "in the nanoparticles" is used synonymously with "in the nanoparticle portion."

Further described herein are stable emulsions, which include organic phase nanodroplets containing an organic solvent and rapamycin dispersed in a continuous aqueous phase containing albumin. The emulsion may be used, for example, to manufacture the nanoparticle composition by removing organic solvent from the emulsion according to the manufacturing methods described herein.

Additionally, described herein is a quality control process for a pharmaceutical formulation, which can be used to ensure the pharmaceutical composition is suitable for medical use in a human individual. For example, the pharmaceutical composition may be subjected to the quality control process before a commercial batch of the pharmaceutical composition is released, which helps ensure the safety and efficacy of the pharmaceutical composition. The process can include measuring a quality control parameter of the composition (i.e., distinct characteristic of the composition that indicates its suitability for medical use), and comparing the measured quality control parameter to a quality control threshold. If the measured parameter is within the threshold, the comparison indicates that the pharmaceutical composition is suitable for medical use in a human individual.

The nanoparticle compositions described herein (such as pharmaceutical compositions), or commercial batches of the nanoparticle compositions (such as pharmaceutical compositions), may have distinct characteristics for any one or more (in any combination) of the following: (1) the oligomeric status of the albumin associated with (such as in) the nanoparticles, such as the percentage of albumin monomers, dimers, oligomers, and/or polymers (or polymers other than oligomers) of the albumin associated with (such as in) the nanoparticles; (2) the oligomeric status of the albumin associated with (such as in) the non-nanoparticle portion of the composition, such as the percentage of albumin monomers, dimers, oligomers, and/or polymers (or polymers other than oligomers) of the albumin associated with (such as in) the non-nanoparticle portion of the composition; (3) the oligomeric status of the total albumin in the composition, such as the percentage of albumin monomers, dimers, oligomers, and/or polymers (or polymers other than oligomers) of the total albumin in the composition; (4) the particle size profile of the nanoparticles, such as the average particle size, polydispersity index, and/or size distribution; (5) the portion (e.g., weight percentage) of the nanoparticles that is albumin and/or the portion (e.g., weight percentage) of the nanoparticles that is rapamycin; (6) the weight ratio of the albumin to the rapamycin in the nanoparticles; (7) the weight ratio of the albumin to the rapamycin in the non-nanoparticle portion of the composition; (8) the weight ratio of the albumin to the rapamycin in the non-nanoparticle portion of the composition (9) the weight ratio of the total albumin to the total rapamycin in the composition; (10) the portion (e.g., weight percentage) of rapamycin that is in the nanoparticles (or the non-nanoparticle portion of the composition) compared to the total rapamycin in the composition; (11) the portion (e.g., weight percentage) of albumin that is in the non-nanoparticle portion (or in the nanoparticles) compared to the total albumin in the composition; (12) the concentration of albumin in the composition; (13) the concentration of albumin in the non-nanoparticle portion of the composition; (14) the concentration of albumin in the composition that is associated with (such as in) the nanoparticles; (15) the concentration of rapamycin in the composition; (16) the concentration of rapamycin in the non-nanoparticle portion of the composition; (17) the concentration of rapamycin in the composition that is associated with (such as in) the nanoparticles; (18) the osmolality of the composition; (19) the viscosity of the composition; (20) the pH of the composition; (21) the stability of the nanoparticles in the composition; (22) the amount of residual solvent in the composition; (23) the zeta potential of the nanoparticles in the composition; (24) the crystalline status of the rapamycin in the nanoparticles; (25) the particle morphology of the nanoparticles, such as the shape, sphericity, thickness of the coating, and/or surface-to-volume ratio; (26) the weight percentage of seco-rapamycin in the nanoparticles, as compared to the sum of seco-rapamycin and rapamycin, by weight; (27) the presence, percentage, or concentration of albumin stabilizer (such as a caprylic acid derivative e.g., sodium caprylate and/or a tryptophan derivative e.g., N-acetyltryptophanate) in the composition; (28) the recovery of rapamycin following filtration; (29) in vitro release kinetics of the nanoparticles; and/or (30) the portion of total rapamycin in the composition that is both in the non-nanoparticle portion of the composition and not bound to albumin. The physicochemical parameters discussed above can affect drug release and delivery of the albumin-based rapamycin nanoparticle compositions (such as pharmaceutical compositions), and thus constitute unique properties to the compositions.

The nanoparticle compositions described herein (such as pharmaceutical compositions), or commercial batches of the nanoparticle compositions (such as pharmaceutical compositions), may have distinct characteristics for any one or more (in any combination) of the following: (1) the oligomeric status of the albumin associated with (such as in) the nanoparticles, such as the percentage of albumin monomers, dimers, and/or polymers (e.g., trimers) of the albumin associated with (such as in) the nanoparticles; (2) the oligomeric status of the albumin associated with (such as in) the non-nanoparticle portion of the composition, such as the percentage of albumin monomers, dimers, and/or trimers of the albumin associated with (such as in) the non-nanoparticle portion of the composition; (3) the oligomeric status of the total albumin in the composition, such as the percentage of albumin monomers, dimers, and/or trimers of the total albumin in the composition; (4) the particle size profile of the nanoparticles, such as the average particle size, polydispersity index, and/or size distribution; (5) the portion (e.g., weight percentage) of the nanoparticles that is albumin and/or the portion (e.g., weight percentage) of the nanoparticles that is rapamycin; (6) the weight ratio of the albumin to the rapamycin in the nanoparticles; (7) the weight ratio of the albumin to the rapamycin in the non-nanoparticle portion of the composition; (8) the weight ratio of the albumin to the rapamycin in the non-nanoparticle portion of the composition (9) the weight ratio of the total albumin to the total rapamycin in the composition; (10) the portion (e.g., weight percentage) of rapamycin that is in the nanoparticles (or the non-nanoparticle portion of the composition) compared to the total rapamycin in the composition; (11) the portion (e.g., weight percentage) of albumin that is in the non-nanoparticle portion (or in the nanoparticles) compared to the total albumin in the composition; (12) the concentration of albumin in the composition; (13) the concentration of albumin in the non-nanoparticle portion of the composition; (14) the concentration of albumin in the composition that is associated with (such as in) the nanoparticles; (15) the concentration of rapamycin in the composition; (16) the concentration of rapamycin in the non-nanoparticle portion of the composition; (17) the concentration of rapamycin in the composition that is associated with (such as in) the nanoparticles; (18) the osmolality of the composition; (19) the viscosity of the composition; (20) the pH of the composition; (21) the stability of the nanoparticles in the composition; (22) the amount of residual solvent in the composition; (23) the zeta potential of the nanoparticles in the composition; (24) the crystalline status of the rapamycin in the nanoparticles; (25) the particle morphology of the nanoparticles, such as the shape, sphericity, thickness of the coating, and/or surface-to-volume ratio; (26) the weight percentage of seco-rapamycin in the nanoparticles, as compared to the sum of seco-rapamycin and rapamycin, by weight; (27) the presence, percentage, or concentration of albumin stabilizer (such as a caprylic acid derivative e.g., sodium caprylate and/or a tryptophan derivative e.g., N-acetyltryptophanate) in the composition; (28) the recovery of rapamycin following filtration; (29) in vitro release kinetics of the nanoparticles; and/or (30) the portion of total rapamycin in the composition that is both in the non-nanoparticle portion of the composition and not bound to albumin. The physicochemical parameters discussed above can affect drug release and delivery of the albumin-based rapamycin nanoparticle compositions (such as pharmaceutical compositions), and thus constitute unique properties to the compositions.

The emulsions (such as emulsions in a commercial batch) described herein include organic phase nanodroplets containing an organic solvent (such as chloroform and/or tert-butanol, or others) and rapamycin dispersed in a continuous aqueous phase containing albumin. Such emulsions may have distinct characteristics for any one or more (in any combination) of the following: (1) a percentage (e.g., volume percentage) of a given solvent in an organic solvent mixture in the organic phase; (2) a relative ratio of two or more solvents in an organic solvent mixture in the organic phase; (3) a concentration of rapamycin in the organic phase; (4) a concentration of rapamycin in the emulsion; (5) a concentration of albumin in the aqueous phase of the emulsion; (6) a concentration of albumin in the emulsion; (7) a phase fraction of the organic phase in the emulsion; and/or (8) the particle size profile of the nanodroplets, such as the average particle size, polydispersity index, and/or size distribution.

The compositions (such as pharmaceutical compositions), or commercial batches of the nanoparticle compositions (such as pharmaceutical compositions), disclosed herein are useful for treating various diseases, such as cancer. Accordingly, further provided herein are methods of using such compositions (such as pharmaceutical compositions) for the treatment of diseases, including cancer. Also provided are kits, commercial batches, medicines, and dosage forms comprising the compositions (such as pharmaceutical compositions) described herein and for use in methods described herein.

Certain exemplary embodiments provided herein disclose pharmaceutical compositions. It is to be understood that these are exemplary compositions and that these descriptions apply equally to and describe other compositions of the invention as provided herein, such as compositions having any of the characteristics defined in these exemplary embodiments.

Throughout this application characteristics and properties of albumin-based rapamycin nanoparticle compositions are described and defined. These characteristics and properties are also described as quality control parameters in certain embodiments. Throughout these descriptions, the compositions may be in the form of manufactured lots of the composition. It is understood that assessment of a sample of the lot (such as, for example, a single vial of a lot comprising a plurality of vials) may be used to assess a characteristic or property of the composition throughout the manufactured lot. Alternatively, in some embodiments, a plurality of samples of a manufactured lot may be assessed and the results averaged to assess the particular characteristic or property of the entire lot. Unless otherwise specified, reference to a "composition," a "pharmaceutical composition," and/or a "commercial batch," or the like, includes reference to a manufactured lot of the composition, pharmaceutical composition, commercial batch, or the like.

Definitions

As used herein and in the appended claims, the singular forms "a," "or," and "the" include plural referents unless the context clearly dictates otherwise.

Reference to "about" a value or parameter herein includes (and describes) variations that are directed to that value or parameter per se. For example, description referring to "about X" includes description of "X." Further, the term "about X-Y" used herein has the same meaning as "about X to about Y." Additionally, use of "about" preceding any series of numbers includes "about" each of the recited numbers in that series. For example, description referring to "about X, Y, or Z" is intended to describe "about X, about Y, or about Z."

"Albumin dimers" or "dimeric albumin" refers to an albumin species having two, and only two, albumin units.

"Albumin monomers" or "monomeric albumin" refers to an albumin species having one, and only one, albumin unit.

"Albumin polymers" or "polymeric albumin" refers to albumin species having a higher molecular weight than albumin monomers and albumin dimers.

"Albumin trimers" or "trimeric albumin" refers to albumin species having three, and only three albumin units.

Figure 9:
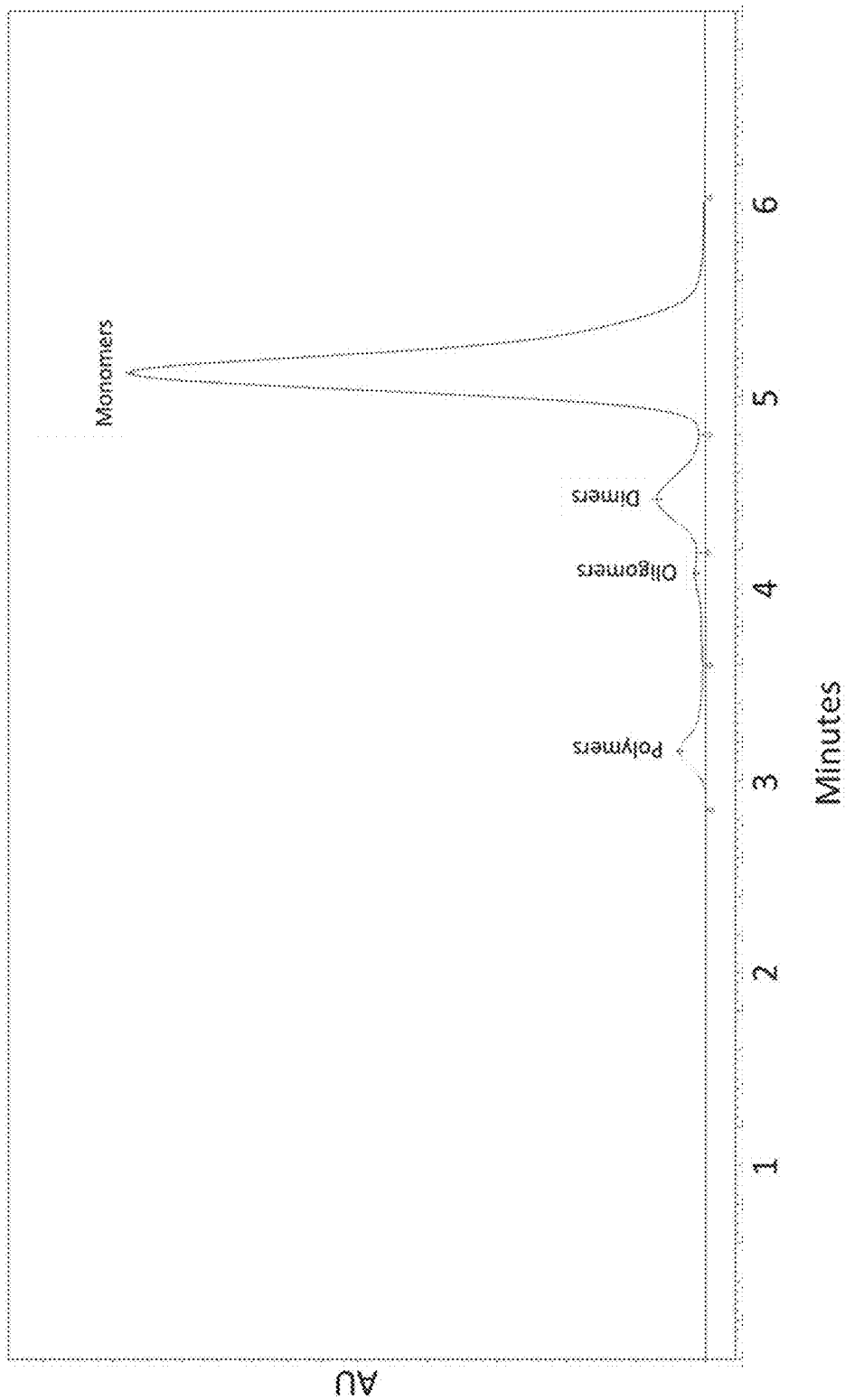
FIG. 9 depicts an SEC-UV chromatogram of the oligomeric profile of the total human albumin in a rapamycin nanoparticle drug product. The peak labeled "polymers" corresponds to albumin polymers other than oligomers.
Figure 10:
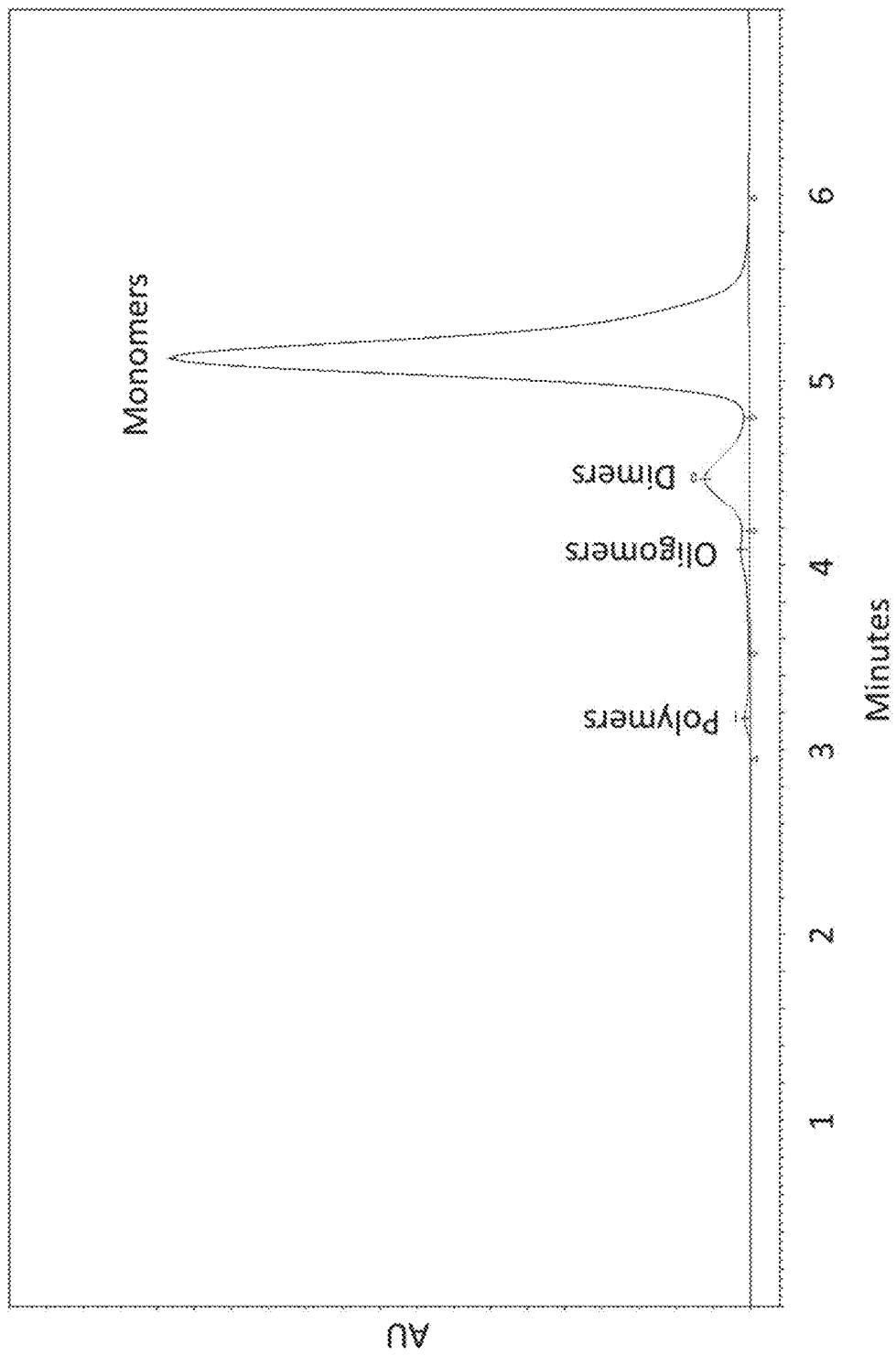
FIG. 10 depicts an SEC-UV chromatogram of the oligomeric profile of the non-nanoparticle portion of the human albumin in a rapamycin nanoparticle drug product. The peak labeled "polymers" corresponds to albumin polymers other than oligomers.
Figure 11:
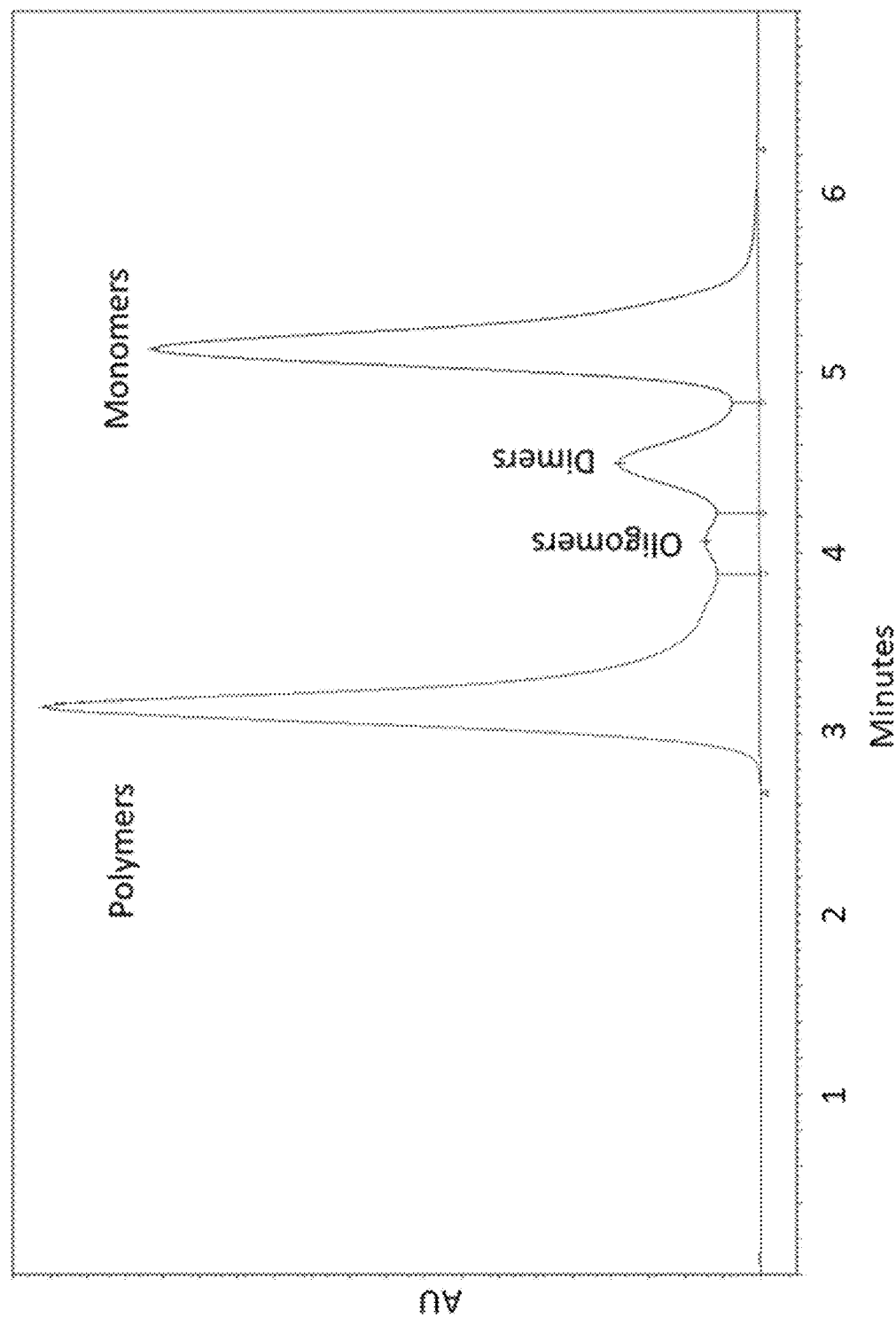
FIG. 11 depicts an SEC-UV chromatogram of the oligomeric profile of the nanoparticle portion of the human albumin in a rapamycin nanoparticle drug product. The peak labeled "polymers" corresponds to albumin polymers other than oligomers.

"Albumin oligomers" refers to lower molecular weight polymeric albumin species associated with a UV-absorbance-based size-exclusion chromatography peak observed between a peak associated with albumin dimers and higher molecular weight polymeric albumin species. FIGS. 9-11 illustrate exemplary size-exclusion chromatograms with peaks labeled for monomers, dimers, oligomers, and polymers (other than oligomers).

"Free rapamycin" is used to describe rapamycin in the composition that is not in the nanoparticles and not bound to albumin in the non-nanoparticle portion of the composition.

A material described as "in the nanoparticles" refers to the material being part of the nanoparticles in any configuration. The material may therefore be coated on the surface of the nanoparticle, within a core of the nanoparticle, or embedded within the nanoparticle, or a mixture thereof. A material described as being "in the non-nanoparticle portion" of the composition refers to a material in the composition that is not "in the nanoparticles."

The term "individual" refers to a mammal and includes, but is not limited to, human, bovine, horse, feline, canine, rodent, or primate.

The term "nanoparticles" is used herein to refer to solid particles. The term "nanodroplets" is used to refer to liquid particles, for example in the context of an oil-in-water or other emulsion.

It is understood that aspects and embodiments described herein include "consisting" and/or "consisting essentially of" aspects and embodiments.

It is understood that reference to relative percentages in a composition assumes that the combined total percentages of all components in the composition add up to 100. It is further understood that relative percentages of one or more components may be adjusted upwards or downwards such that the percent of the components in the composition combine to a total of 100, provided that the percent of any particular component does not fall outside the limits of the range specified for that component.

Albumin-Based Nanoparticle Compositions

The nanoparticle composition, or a commercial batch of the nanoparticle composition, described herein includes (a) nanoparticles that include rapamycin and albumin, and (b) a non-nanoparticle portion that includes rapamycin and albumin. The rapamycin and the albumin of the nanoparticles are associated with each other in the nanoparticles. For example, the nanoparticles may include a coating having the albumin, which surrounds a core comprising the rapamycin. In the non-nanoparticle portion of the composition, the rapamycin and the albumin may or may not associated with each other (i.e., the rapamycin may be in a reversible binding equilibrium with the albumin), but do not associate with each other in a manner that forms nanoparticles. The albumin of the nanoparticles may be further distinguishable from the albumin in the non-nanoparticle portion of the composition; for example, the oligomeric profile of the albumin in the nanoparticles may differ from the oligomeric profile of the albumin in the non-nanoparticle portion of the composition.

The albumin of the nanoparticles associates with the rapamycin of the nanoparticles so that a nanoparticle suspension has a high concentration of rapamycin, which allows the composition to be used as a pharmaceutical composition for treating certain diseases, such as cancer. Manufactured nanoparticles (which may be made, for example, using the methods described herein) may be formulated, filtered, or otherwise processed to obtain the pharmaceutical composition, which may be suitable for medical use in a human individual.

The nanoparticle compositions described herein (such a pharmaceutical composition), or commercial batches of the nanoparticle compositions (such as pharmaceutical compositions), may have distinct characteristics for any one or more (in any combination) of the following: (1) the oligomeric status of the albumin associated with (such as in) the nanoparticles, such as the percentage of albumin monomers, dimers, oligomers, and/or polymers (or polymers other than oligomers) of the albumin associated with (such as in) the nanoparticles; (2) the oligomeric status of the albumin associated with (such as in) the non-nanoparticle portion of the composition, such as the percentage of albumin monomers, dimers, oligomers, and/or polymers (or polymers other than oligomers) of the albumin associated with (such as in) the non-nanoparticle portion of the composition; (3) the oligomeric status of the total albumin in the composition, such as the percentage of albumin monomers, dimers, oligomers, and/or polymers (or polymers other than oligomers) of the total albumin in the composition; (4) the particle size profile of the nanoparticles, such as the average particle size, polydispersity index, and/or size distribution; (5) the portion (e.g., weight percentage) of the nanoparticles that is albumin and/or the portion (e.g., weight percentage) of the nanoparticles that is rapamycin; (6) the weight ratio of the albumin to the rapamycin in the nanoparticles; (7) the weight ratio of the albumin to the rapamycin in the non-nanoparticle portion of the composition; (8) the weight ratio of the albumin to the rapamycin in the non-nanoparticle portion of the composition (9) the weight ratio of the total albumin to the total rapamycin in the composition; (10) the portion (e.g., weight percentage) of rapamycin that is in the nanoparticles (or the non-nanoparticle portion of the composition) compared to the total rapamycin in the composition; (11) the portion (e.g., weight percentage) of albumin that is in the non-nanoparticle portion (or in the nanoparticles) compared to the total albumin in the composition; (12) the concentration of albumin in the composition; (13) the concentration of albumin in the non-nanoparticle portion of the composition; (14) the concentration of albumin in the composition that is associated with (such as in) the nanoparticles; (15) the concentration of rapamycin in the composition; (16) the concentration of rapamycin in the non-nanoparticle portion of the composition; (17) the concentration of rapamycin in the composition that is associated with (such as in) the nanoparticles; (18) the osmolality of the composition; (19) the viscosity of the composition; (20) the pH of the composition; (21) the stability of the nanoparticles in the composition; (22) the amount of residual solvent in the composition; (23) the zeta potential of the nanoparticles in the composition; (24) the crystalline status of the rapamycin in the nanoparticles; (25) the particle morphology of the nanoparticles, such as the shape, sphericity, thickness of the coating, and/or surface-to-volume ratio; (26) the weight percentage of seco-rapamycin in the nanoparticles, as compared to the sum of seco-rapamycin and rapamycin, by weight; (27) the presence, percentage, or concentration of albumin stabilizer (such as sodium caprylate and/or N-acetyltryptophanate) in the composition; (28) the recovery of rapamycin following filtration; (29) in vitro release kinetics of the nanoparticles; and/or (30) the portion of total rapamycin in the composition that is both in the non-nanoparticle portion of the composition and not bound to albumin.

The nanoparticle compositions described herein (such as a pharmaceutical composition), or commercial batches of the nanoparticle compositions (such as pharmaceutical compositions), may have distinct characteristics for any one or more (in any combination) of the following: (1) the oligomeric status of the albumin associated with (such as in) the nanoparticles, such as the percentage of albumin monomers, dimers, and/or trimers of the albumin associated with (such as in) the nanoparticles; (2) the oligomeric status of the albumin associated with (such as in) the non-nanoparticle portion of the composition, such as the percentage of albumin monomers, dimers, and/or trimers of the albumin associated with (such as in) the non-nanoparticle portion of the composition; (3) the oligomeric status of the total albumin in the composition, such as the percentage of albumin monomers, dimers, and/or trimers of the total albumin in the composition; (4) the particle size profile of the nanoparticles, such as the average particle size, polydispersity index, and/or size distribution; (5) the portion (e.g., weight percentage) of the nanoparticles that is albumin and/or the portion (e.g., weight percentage) of the nanoparticles that is rapamycin; (6) the weight ratio of the albumin to the rapamycin in the nanoparticles; (7) the weight ratio of the albumin to the rapamycin in the non-nanoparticle portion of the composition; (8) the weight ratio of the albumin to the rapamycin in the non-nanoparticle portion of the composition (9) the weight ratio of the total albumin to the total rapamycin in the composition; (10) the portion (e.g., weight percentage) of rapamycin that is in the nanoparticles (or the non-nanoparticle portion of the composition) compared to the total rapamycin in the composition; (11) the portion (e.g., weight percentage) of albumin that is in the non-nanoparticle portion (or in the nanoparticles) compared to the total albumin in the composition; (12) the concentration of albumin in the composition; (13) the concentration of albumin in the non-nanoparticle portion of the composition; (14) the concentration of albumin in the composition that is associated with (such as in) the nanoparticles; (15) the concentration of rapamycin in the composition; (16) the concentration of rapamycin in the non-nanoparticle portion of the composition; (17) the concentration of rapamycin in the composition that is associated with (such as in) the nanoparticles; (18) the osmolality of the composition; (19) the viscosity of the composition; (20) the pH of the composition; (21) the stability of the nanoparticles in the composition; (22) the amount of residual solvent in the composition; (23) the zeta potential of the nanoparticles in the composition; (24) the crystalline status of the rapamycin in the nanoparticles; (25) the particle morphology of the nanoparticles, such as the shape, sphericity, thickness of the coating, and/or surface-to-volume ratio; (26) the weight percentage of seco-rapamycin in the nanoparticles, as compared to the sum of seco-rapamycin and rapamycin, by weight; (27) the presence, percentage, or concentration of albumin stabilizer (such as a caprylic acid derivative e.g., sodium caprylate and/or a tryptophan derivative e.g., N-acetyltryptophanate) in the composition; (28) the recovery of rapamycin following filtration; (29) in vitro release kinetics of the nanoparticles; and/or (30) the portion of total rapamycin in the composition that is both in the non-nanoparticle portion of the composition and not bound to albumin.

In some embodiments, the nanoparticle composition, or the commercial batch of the nanoparticle composition, has one or more of the following distinct characteristics: (1) about 80% to about 95% (or as further provided herein) of the total albumin in the composition is in the form of monomeric albumin; (2) about 4% to about 15% (or as further provided herein) of the total albumin in the composition is in the form of dimeric albumin; (3) about 0.5% to about 5% (or as further provided herein) of the total albumin in the composition is in the form of polymeric albumin (or trimeric albumin); (4) the weight ratio of the total albumin to the total rapamycin in the composition is about 1:1 to about 10:1 (or as further provided herein); (5) about 90% or more (or as further provided herein) of the total rapamycin in the composition is in the nanoparticles; (6) about 90% or more (or as further provided herein) of the total albumin in the composition is in the non-nanoparticle portion of the nanoparticles; (7) the composition comprises tert-butanol at a concentration of less than about 10 µg/mL or less than about 10 ppm (or as further provided herein); (8) the composition comprises chloroform at a concentration of less than about 5 µg/mL or less than about 5 ppm (or as further provided herein); (9) the composition comprises an albumin stabilizer (such as a caprylic acid derivative e.g., sodium caprylate and/or a tryptophan derivative e.g., N-acetyltryptophanate); (10) at least about 80% or more (or as further provided herein) of the rapamycin in the composition is recoverable after filtering the composition with a 0.2 micron filter; (11) the composition is stable for at least 24 hours; and/or (12) less than about 5% of the total rapamycin in the composition is both in the non-nanoparticle portion of the composition and unbound to albumin in the non-nanoparticle portion of the composition. In some embodiments, the nanoparticle composition may be a nanoparticle suspension, and the nanoparticle composition may have one or more of the following distinct characteristics (in addition to or in alternative to any one of the previously described district characteristics): (1) the concentration of albumin in the composition is about 30 mg/mL to about 100 mg/mL (or as further provided herein); (2) the concentration of rapamycin in the composition is about 1 mg/mL to about 15 mg/mL (or as further provided herein, such as about 1 mg/mL to about 7 mg/mL); (3) the osmolality of the composition is about 300 mOsm/kg to about 350 mOsm/kg (or as otherwise provided herein); (4) the viscosity of the composition is about 1.2 cP to about 1.5 cP (or as otherwise provided herein); and/or (5) the pH of the composition is about 6.0 to about 7.5 (or as otherwise provided herein).

In some embodiments, the nanoparticle composition, or the commercial batch of the nanoparticle composition, has one or more of the following distinct characteristics: (1) about 80% to about 95% (or as further provided herein) of the total albumin in the composition is in the form of monomeric albumin; (2) about 4% to about 15% (or as further provided herein) of the total albumin in the composition is in the form of dimeric albumin; (3) about 0.3% to about 3% of the total albumin in the composition is in the form of oligomeric albumin; (4) about 2% to about 7% (or as further provided herein) of the total albumin in the composition is in the form of polymeric albumin (other than oligomeric albumin); (5) the weight ratio of the total albumin to the total rapamycin in the composition is about 1:1 to about 10:1 (or as further provided herein); (6) about 90% or more (or as further provided herein) of the total rapamycin in the composition is in the nanoparticles; (7) about 90% or more (or as further provided herein) of the total albumin in the composition is in the non-nanoparticle portion of the nanoparticles; (8) the composition comprises tert-butanol at a concentration of less than about 10 µg/mL or less than about 10 ppm (or as further provided herein); (9) the composition comprises chloroform at a concentration of less than about 5 µg/mL or less than about 5 ppm (or as further provided herein); (10) the composition comprises an albumin stabilizer (such as a caprylic acid derivative e.g., sodium caprylate and/or a tryptophan derivative e.g., N-acetyltryptophanate); (11) at least about 80% or more (or as further provided herein) of the rapamycin in the composition is recoverable after filtering the composition with a 0.2 micron filter; (12) the composition is stable for at least 24 hours; and/or (13) less than about 5% of the total rapamycin in the composition is both in the non-nanoparticle portion of the composition and unbound to albumin in the non-nanoparticle portion of the composition. In some embodiments, the nanoparticle composition may be a nanoparticle suspension, and the nanoparticle composition may have one or more of the following distinct characteristics (in addition to or in alternative to any one of the previously described district characteristics): (1) the concentration of albumin in the composition is about 30 mg/mL to about 100 mg/mL (or as further provided herein); (2) the concentration of rapamycin in the composition is about 1 mg/mL to about 15 mg/mL (or as further provided herein, such as about 1 mg/mL to about 7 mg/mL); (3) the osmolality of the composition is about 300 mOsm/kg to about 350 mOsm/kg (or as otherwise provided herein); (4) the viscosity of the composition is about 1.2 cP to about 1.5 cP (or as otherwise provided herein); and/or (5) the pH of the composition is about 6.0 to about 7.5 (or as otherwise provided herein)

In some embodiments, the nanoparticles of the composition, or the nanoparticles of the composition of the commercial batch, have one or more of the following distinct characteristics: (1) about 70% to about 85% (or as otherwise provided herein) of the albumin in the nanoparticles is in the form of albumin monomers; (2) about 9% to about 20% (or as otherwise provided herein) of the albumin in the nanoparticles is in the form of albumin dimers; (3) about 5% to about 15% (or as otherwise provided herein) of the albumin in the nanoparticles is in the form of albumin polymers (or albumin trimers); (4) the nanoparticles have a volume weighted mean particle size and/or Z-average particle size of about 200 nm or less (or as otherwise provided herein, such as between about 50 nm and about 200 nm); (5) the nanoparticles have a polydispersity index of less than about 0.2 (or as otherwise provided herein, such as between about 0.03 and about 0.2); (6) the span of the particle size distribution (($Dv_{95}-Dv_5$)/$Dv_{50}$) is about 0.8 to about 1.2 (or as otherwise provided herein); (7) the nanoparticles are about 25% to about 45% albumin by weight (or as otherwise provided herein); (8) the nanoparticles are about 55% to about 75% rapamycin by weight (or as otherwise provided herein); (9) the weight ratio of albumin to rapamycin in the nanoparticles is about 1:1 to about 1:4 (or as otherwise provided herein); (10) the zeta potential of the nanoparticles in the composition is about −25 mV to about −50 mV (or as otherwise provided herein); (11) the nanoparticles have an amorphous morphology; (12) the rapamycin in the nanoparticles has an amorphous morphology; (13) the vinyl chain of the rapamycin in the nanoparticles interacts with the albumin in the nanoparticles; (14) at least a portion (such as at least 20%, or as otherwise provided herein) of the nanoparticles in the composition are non-spherical; and/or (15) the nanoparticles comprise less than about 2.5% seco-rapamycin (or as otherwise provided herein, such as between about 0.2% and about 2.5%) compared to the sum of seco-rapamycin and rapamycin by weight. In some embodiments, the nanoparticle composition may be a nanoparticle suspension, and in some embodiments the concentration of the albumin in the nanoparticle suspension that is in the nanoparticles is about 1.8 mg/mL to about 3 mg/mL (or as otherwise provided herein).

In some embodiments, the nanoparticles of the composition, or the nanoparticles of the composition of the commercial batch, have one or more of the following distinct characteristics: (1) about 25% to about 50% (or as otherwise provided herein) of the albumin in the nanoparticles is in the form of albumin monomers; (2) about 5% to about 16% (or as otherwise provided herein) of the albumin in the nanoparticles is in the form of albumin dimers; (3) about 1% to about 4.5% (or as otherwise provided herein) of the albumin in the nanoparticles is in the form of albumin oligomers; (4) about 42% to about 60% (or as otherwise provided herein) of the albumin in the nanoparticles is in the form of albumin polymers (other than albumin oligomers); (5) the nanoparticles have a volume weighted mean particle size and/or Z-average particle size of about 200 nm or less (or as otherwise provided herein, such as between about 50 nm and about 200 nm); (6) the nanoparticles have a polydispersity index of less than about 0.2 (or as otherwise provided herein, such as between about 0.03 and about 0.2); (7) the span of the particle size distribution (($Dv_{95}-Dv_5$)/$Dv_{50}$) is about 0.8 to about 1.2 (or as otherwise provided herein); (8) the nanoparticles are about 25% to about 45% albumin by weight (or as otherwise provided herein); (9) the nanoparticles are about 55% to about 75% rapamycin by weight (or as otherwise provided herein); (10) the weight ratio of albumin to rapamycin in the nanoparticles is about 1:1 to about 1:4 (or as otherwise provided herein); (11) the zeta potential of the nanoparticles in the composition is about −25 mV to about −50 mV (or as otherwise provided herein); (12) the nanoparticles have an amorphous morphology; (13) the rapamycin in the nanoparticles has an amorphous morphology; (14) the vinyl chain of the rapamycin in the nanoparticles interacts with the albumin in the nanoparticles; (15) at least a portion (such as at least 20%, or as otherwise provided herein) of the nanoparticles in the composition are non-spherical; and/or (16) the nanoparticles comprise less than about 2.5% seco-rapamycin (or as otherwise provided herein, such as between about 0.2% and about 2.5%) compared to the sum of seco-rapamycin and rapamycin by weight. In some embodiments, the nanoparticle composition may be a nanoparticle suspension, and in some embodiments the concentration of the albumin in the nanoparticle suspension that is in the nanoparticles is about 1.8 mg/mL to about 3 mg/mL (or as otherwise provided herein).

In some embodiments, the non-nanoparticle portion of the composition, or the non-nanoparticle portion of the composition of the commercial batch, has one or more of the following distinct characteristics: (1) about 80% to about 95% (or as otherwise provided herein) of the albumin in the non-nanoparticle portion of the composition is in the form of albumin monomers; (2) about 5% to about 14% (or as otherwise provided herein) of the albumin in the non-nanoparticle portion of the composition is in the form of albumin dimers; and/or (3) about 1% to about 5% (or as otherwise provided herein) of the albumin in the non-nanoparticle portion of the composition is in the form of albumin polymers (or albumin trimers). In some embodiments, the nanoparticle composition may be a nanoparticle suspension, and the non-nanoparticle portion of the nanoparticle suspension may have one or more of the following distinct characteristics (in addition to or in alternative to any one of the previously described district characteristics): (1) the concentration of albumin in the non-nanoparticle portion of the composition is between about 30 mg/mL and about 100 mg/mL (or as otherwise provided herein); and/or (2) the concentration of rapamycin in the non-nanoparticle portion is about 20 µg/mL to about 55 µg/mL (or as otherwise provided herein).

In some embodiments, the non-nanoparticle portion of the composition, or the non-nanoparticle portion of the composition of the commercial batch, has one or more of the following distinct characteristics: (1) about 80% to about 95% (or as otherwise provided herein) of the albumin in the non-nanoparticle portion of the composition is in the form of albumin monomers; (2) about 4% to about 14% (or as otherwise provided herein) of the albumin in the non-nanoparticle portion of the composition is in the form of albumin dimers; and/or (3) about 0.5% to about 4% (or as otherwise provided herein) of the albumin in the non-nanoparticle portion of the composition is in the form oligomers; (4) about 0.5% to about 3% (or as otherwise provided herein) of the albumin in the non-nanoparticle portion of the composition is in the form of albumin polymers (other than albumin oligomers). In some embodiments, the nanoparticle composition may be a nanoparticle suspension, and the non-nanoparticle portion of the nanoparticle suspension may have one or more of the following distinct characteristics (in addition to or in alternative to any one of the previously described district characteristics): (1) the concentration of albumin in the non-nanoparticle portion of the composition is between about 30 mg/mL and about 100 mg/mL (or as otherwise provided herein); and/or (2) the concentration of rapamycin in the non-nanoparticle portion is about 20 μg/mL to about 55 μg/mL (or as otherwise provided herein).

The compositions (such as pharmaceutical compositions), or the compositions (such as pharmaceutical compositions) of the commercial batches, described herein can be in liquid (e.g., as a nanoparticle suspension) or powder forms. For example, in some embodiments, the composition is a liquid nanoparticle suspension (for example prior to lyophilization). In some embodiments, the composition is a reconstituted suspension (e.g., in an aqueous solution such as a saline solution). In some embodiments, the composition is dried, such as lyophilized. Lyophilized compositions are generally a white or slightly yellow lyophilized cake, which may be broken into a loose powder and/or reconstituted to into an aqueous suspension. In some embodiments, the composition is sterile. In some embodiments, the composition is contained in a sealed container, such as a sealed vial (e.g., a glass vial) or sealed bag.

In some embodiments, a nanoparticle composition, or the commercial batch of the nanoparticle composition, comprises (a) nanoparticles comprising rapamycin and albumin (such as human albumin), and (b) a non-nanoparticle portion comprising albumin (such as human albumin) and rapamycin. In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles comprising rapamycin and albumin (such as human albumin), and (b) a non-nanoparticle portion comprising albumin (such as human albumin) and rapamycin. In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles comprising a coating comprising albumin (such as human albumin) and a core comprising rapamycin, and (b) a non-nanoparticle portion comprising albumin (such as human albumin) and rapamycin. In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles comprising a coating comprising albumin (such as human albumin) and a core comprising rapamycin, and (b) a non-nanoparticle portion comprising albumin (such as human albumin) and rapamycin. In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles comprising rapamycin and albumin (such as human albumin), wherein about 70% to about 85% of the albumin in the nanoparticles is in the form of monomeric albumin; and (b) a non-nanoparticle portion comprising albumin (such as human albumin) and rapamycin. In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles comprising rapamycin and albumin (such as human albumin), wherein about 25% to about 50% of the albumin in the nanoparticles is in the form of monomeric albumin; and (b) a non-nanoparticle portion comprising albumin (such as human albumin) and rapamycin. In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL.

In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles comprising a coating comprising albumin (such as human albumin) and a core comprising rapamycin, wherein about 70% to about 85% of the albumin in the nanoparticles is in the form of monomeric albumin; and (b) a non-nanoparticle portion comprising albumin (such as human albumin) and rapamycin. In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles comprising a coating comprising albumin (such as human albumin) and a core comprising rapamycin, wherein about 25% to about 50% of the albumin in the nanoparticles is in the form of monomeric albumin; and (b) a non-nanoparticle portion comprising albumin (such as human albumin) and rapamycin. In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles comprising rapamycin and albumin (such as human albumin), wherein about 5% to about 15% of the albumin in the nanoparticles is in the form of polymeric albumin (or trimeric albumin); and (b) a non-nanoparticle portion comprising albumin (such as human albumin) and rapamycin. In some embodiments, the nanoparticle composition comprises less than 10 μg/mL tert-butanol and/or comprises less than 5 μg/mL chloroform. In some embodiments, about 0.5% to about 5% of the albumin in the non-nanoparticle portion or the total albumin in the nanoparticle composition is in the form of polymeric albumin. In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles comprising rapamycin and albumin (such as human albumin), wherein about 42% to about 62% of the albumin in the nanoparticles is in the form of polymeric albumin (other than oligomeric albumin); and (b) a non-nanoparticle portion comprising albumin (such as human albumin) and rapamycin. In some embodiments, the nanoparticle composition comprises less than 10 µg/mL tert-butanol and/or comprises less than 5 µg/mL chloroform. In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles comprising a coating comprising albumin (such as human albumin) and a core comprising rapamycin, wherein about 5% to about 15% of the albumin in the nanoparticles is in the form of polymeric albumin (or trimeric albumin); and (b) a non-nanoparticle portion comprising albumin (such as human albumin) and rapamycin. In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles comprising a coating comprising albumin (such as human albumin) and a core comprising rapamycin, wherein about 42% to about 60% of the albumin in the nanoparticles is in the form of polymeric albumin (other than oligomeric albumin); and (b) a non-nanoparticle portion comprising albumin (such as human albumin) and rapamycin. In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles comprising rapamycin and albumin (such as human albumin), wherein about 9% to about 20% of the albumin in the nanoparticles is in the form of dimeric albumin; and (b) a non-nanoparticle portion comprising albumin (such as human albumin) and rapamycin. In some embodiments, the nanoparticle composition comprises less than 10 μg/mL tert-butanol and/or comprises less than 5 μg/mL chloroform. In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles comprising rapamycin and albumin (such as human albumin), wherein about 5% to about 16% of the albumin in the nanoparticles is in the form of dimeric albumin; and (b) a non-nanoparticle portion comprising albumin (such as human albumin) and rapamycin. In some embodiments, the nanoparticle composition comprises less than 10 μg/mL tert-butanol and/or comprises less than 5 μg/mL chloroform. In some embodiments, about 0.5% to about 7% of the albumin in the non-nanoparticle portion or the total albumin in the nanoparticle composition is in the form of polymeric albumin. In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles comprising a coating comprising albumin (such as human albumin) and a core comprising rapamycin, wherein about 9% to about 20% of the albumin in the nanoparticles is in the form of dimeric albumin; and (b) a non-nanoparticle portion comprising albumin (such as human albumin) and rapamycin. In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles comprising a coating comprising albumin (such as human albumin) and a core comprising rapamycin, wherein about 5% to about 16% of the albumin in the nanoparticles is in the form of dimeric albumin; and (b) a non-nanoparticle portion comprising albumin (such as human albumin) and rapamycin. In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles comprising rapamycin and albumin (such as human albumin), wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin. In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles comprising rapamycin and albumin (such as human albumin), wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 60% of the albumin in the nanoparticles is in the form of polymeric albumin (other than oligomeric albumin); and (b) a non-nanoparticle portion comprising albumin (such as human albumin) and rapamycin. In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles comprising a coating comprising albumin (such as human albumin) and a core comprising rapamycin, wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin. In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles comprising a coating comprising albumin (such as human albumin) and a core comprising rapamycin, wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 60% of the albumin in the nanoparticles is in the form of polymeric albumin (other than oligomeric albumin); and (b) a non-nanoparticle portion comprising albumin (such as human albumin) and rapamycin. In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm), comprising rapamycin and albumin (such as human albumin), wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin. In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm), comprising rapamycin and albumin (such as human albumin), wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 60% of the albumin in the nanoparticles is in the form of polymeric albumin (other than oligomeric albumin); and (b) a non-nanoparticle portion comprising albumin (such as human albumin) and rapamycin. In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm), comprising a coating comprising albumin (such as human albumin) and a core comprising rapamycin, wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin. In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm), comprising a coating comprising albumin (such as human albumin) and a core comprising rapamycin, wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 60% of the albumin in the nanoparticles is in the form of polymeric albumin (other than oligomeric albumin); and (b) a non-nanoparticle portion comprising albumin (such as human albumin) and rapamycin. In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm), comprising about 55% to about 65% (by weight) rapamycin and about 25% to about 45% (by weight) albumin (such as human albumin), wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin. In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm), comprising about 55% to about 65% (by weight) rapamycin and about 25% to about 45% (by weight) albumin (such as human albumin), wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 60% of the albumin in the nanoparticles is in the form of polymeric albumin (other than oligomeric albumin); and (b) a non-nanoparticle portion comprising albumin (such as human albumin) and rapamycin. In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm), comprising a coating comprising albumin (such as human albumin) and a core comprising rapamycin, wherein the albumin comprises about 25% to about 45% of the nanoparticles by weight and the rapamycin comprises about 55% to about 75% of the nanoparticles by weight, wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin. In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm), comprising a coating comprising albumin (such as human albumin) and a core comprising rapamycin, wherein the albumin comprises about 25% to about 45% of the nanoparticles by weight and the rapamycin comprises about 55% to about 75% of the nanoparticles by weight, wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 60% of the albumin in the nanoparticles is in the form of polymeric albumin (other than oligomeric albumin); and (b) a non-nanoparticle portion comprising albumin (such as human albumin) and rapamycin. In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm), comprising about 55% to about 75% (by weight) rapamycin and about 25% to about 45% (by weight) albumin (such as human albumin), wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL). In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm), comprising about 55% to about 75% (by weight) rapamycin and about 25% to about 45% (by weight) albumin (such as human albumin), wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 60% of the albumin in the nanoparticles is in the form of polymeric albumin (other than oligomeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL). In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm), comprising a coating comprising albumin (such as human albumin) and a core comprising rapamycin, wherein the albumin comprises about 25% to about 45% of the nanoparticles by weight and the rapamycin comprises about 55% to about 75% of the nanoparticles by weight, wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL). In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm), comprising a coating comprising albumin (such as human albumin) and a core comprising rapamycin, wherein the albumin comprises about 25% to about 45% of the nanoparticles by weight and the rapamycin comprises about 55% to about 75% of the nanoparticles by weight, wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 60% of the albumin in the nanoparticles is in the form of polymeric albumin (other than oligomeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL). In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm) and a zeta potential of about −25 mV to about −50 mV, comprising about 55% to about 75% (by weight) rapamycin and about 25% to about 45% (by weight) albumin (such as human albumin), wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL). In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm) and a zeta potential of about −25 mV to about −50 mV, comprising about 55% to about 75% (by weight) rapamycin and about 25% to about 45% (by weight) albumin (such as human albumin), wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 60% of the albumin in the nanoparticles is in the form of polymeric albumin (other than oligomeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL). In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm) and a zeta potential of about −25 mV to about −50 mV, comprising a coating comprising albumin (such as human albumin) and a core comprising rapamycin, wherein the albumin comprises about 25% to about 45% of the nanoparticles by weight and the rapamycin comprises about 55% to about 75% of the nanoparticles by weight, wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL). In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm) and a zeta potential of about −25 mV to about −50 mV, comprising a coating comprising albumin (such as human albumin) and a core comprising rapamycin, wherein the albumin comprises about 25% to about 45% of the nanoparticles by weight and the rapamycin comprises about 55% to about 75% of the nanoparticles by weight, wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 60% of the albumin in the nanoparticles is in the form of polymeric albumin (other than oligomeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL). In some embodiments, about 0.5% to about 7% of the albumin in the non-nanoparticle portion or the total albumin in the nanoparticle composition is in the form of polymeric albumin (other than oligomeric albumin). In some embodiments, about 1% to about 4.5% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm) and a zeta potential of about −25 mV to about −50 mV, comprising about 55% to about 75% (by weight) rapamycin and about 25% to about 45% (by weight) albumin (such as human albumin), wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL); and wherein about 3% or less of the rapamycin in the nanoparticle composition is free rapamycin. In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm) and a zeta potential of about −25 mV to about −50 mV, comprising about 55% to about 75% (by weight) rapamycin and about 25% to about 45% (by weight) albumin (such as human albumin), wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 60% of the albumin in the nanoparticles is in the form of polymeric albumin (other than oligomeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL); and wherein about 3% or less of the rapamycin in the nanoparticle composition is free rapamycin. In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm) and a zeta potential of about −25 mV to about −50 mV, comprising a coating comprising albumin (such as human albumin) and a core comprising rapamycin, wherein the albumin comprises about 25% to about 45% of the nanoparticles by weight and the rapamycin comprises about 55% to about 75% of the nanoparticles by weight, wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL); and wherein about 3% or less of the rapamycin in the nanoparticle composition is free rapamycin. In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm) and a zeta potential of about −25 mV to about −50 mV, comprising a coating comprising albumin (such as human albumin) and a core comprising rapamycin, wherein the albumin comprises about 25% to about 45% of the nanoparticles by weight and the rapamycin comprises about 55% to about 75% of the nanoparticles by weight, wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 60% of the albumin in the nanoparticles is in the form of polymeric albumin (other than oligomeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL); and wherein about 3% or less of the rapamycin in the nanoparticle composition is free rapamycin. In some embodiments, about 0.5% to about 7% of the albumin in the non-nanoparticle portion or the total albumin in the nanoparticle composition is in the form of polymeric albumin (other than oligomeric albumin). In some embodiments, about 1% to about 4.5% of the albumin in the non-particle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm) and a zeta potential of about −25 mV to about −50 mV, comprising about 55% to about 75% (by weight) rapamycin and about 25% to about 45% (by weight) albumin (such as human albumin), wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL); and wherein the sum of seco-rapamycin and rapamycin in the nanoparticles is less than 3% (such as about 0.2% to about 3%) seco-rapamycin, by weight. In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm) and a zeta potential of about −25 mV to about −50 mV, comprising about 55% to about 75% (by weight) rapamycin and about 25% to about 45% (by weight) albumin (such as human albumin), wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 60% of the albumin in the nanoparticles is in the form of polymeric albumin (other than oligomeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL); and wherein the sum of seco-rapamycin and rapamycin in the nanoparticles is less than 3% (such as about 0.2% to about 3%) seco-rapamycin, by weight. In some embodiments, about 0.5% to about 7% of the albumin in the non-nanoparticle portion or the total albumin in the nanoparticle composition is in the form of polymeric albumin (other than oligomeric albumin). In some embodiments, about 1% to about 4.5% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm) and a zeta potential of about −25 mV to about −50 mV, comprising a coating comprising albumin (such as human albumin) and a core comprising rapamycin, wherein the albumin comprises about 25% to about 45% of the nanoparticles by weight and the rapamycin comprises about 55% to about 75% of the nanoparticles by weight, wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL); and wherein the sum of seco-rapamycin and rapamycin in the nanoparticles is less than 3% (such as about 0.2% to about 3%) seco-rapamycin, by weight. In some embodiments, about 0.5% to about 5% of the albumin in the non-nanoparticle portion or the total albumin in the nanoparticle composition is in the form of polymeric albumin (or trimeric albumin). In some embodiments, about 4% to about 14% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 200 nm or less (such as about 50 nm to about 200 nm) and a zeta potential of about −25 mV to about −50 mV, comprising a coating comprising albumin (such as human albumin) and a core comprising rapamycin, wherein the albumin comprises about 25% to about 45% of the nanoparticles by weight and the rapamycin comprises about 55% to about 75% of the nanoparticles by weight, wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 60% of the albumin in the nanoparticles is in the form of polymeric albumin (other than oligomeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL); and wherein the sum of seco-rapamycin and rapamycin in the nanoparticles is less than 3% (such as about 0.2% to about 3%) seco-rapamycin, by weight. In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of polymeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the nanoparticle composition that is in the non-nanoparticle portion or the concentration of total albumin in the nanoparticle composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles comprising rapamycin and albumin (such as human albumin), wherein about 74% to about 80% of the albumin in the nanoparticles is in the form of monomeric albumin; and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles comprising rapamycin and albumin (such as human albumin), wherein about 25% to about 50% of the albumin in the nanoparticles is in the form of monomeric albumin; and (b) a non-nanoparticle portion comprising albumin (such as human albumin) and rapamycin. In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 14% of the albumin in the non-nanoparticle portion in the nanoparticle composition is in the form of dimeric albumin. In some embodiments, about 4% to about 15% of the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles comprising a coating comprising albumin (such as human albumin) and a core comprising rapamycin, wherein about 74% to about 80% of the albumin in the nanoparticles is in the form of monomeric albumin; and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles comprising a coating comprising albumin (such as human albumin) and a core comprising rapamycin, wherein about 25% to about 50% of the albumin in the nanoparticles is in the form of monomeric albumin; and (b) a non-nanoparticle portion comprising albumin (such as human albumin) and rapamycin. In some embodiments, about 0.5% to about 7% of the albumin in the non-nanoparticle portion or the total albumin in the nanoparticle composition is in the form of polymeric albumin (other than oligomeric albumin). In some embodiments, about 1% to about 4.5% of the albumin in the non-nanoparticle portion or the total albumin in the nanoparticle composition is in the form of oligomeric albumin. In some embodiments, about 4% to about 14% of the albumin in the non-nanoparticle portion in the nanoparticle composition is in the form of dimeric albumin. In some embodiments, about 4% to about 15% of the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles comprising rapamycin and albumin (such as human albumin), wherein about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles comprising a coating comprising albumin (such as human albumin) and a core comprising rapamycin, wherein about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles comprising rapamycin and albumin (such as human albumin), wherein about 12% to about 17% of the albumin in the nanoparticles is in the form of dimeric albumin; and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles comprising a coating comprising albumin (such as human albumin) and a core comprising rapamycin, wherein about 12% to about 17% of the albumin in the nanoparticles is in the form of dimeric albumin; and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles comprising rapamycin and albumin (such as human albumin), wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles comprising a coating comprising albumin (such as human albumin) and a core comprising rapamycin, wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 85 nm to about 95 nm, comprising rapamycin and albumin (such as human albumin); and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 85 nm to about 95 nm, comprising a coating comprising albumin (such as human albumin) and a core comprising rapamycin; and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 85 nm to about 95 nm, comprising rapamycin and albumin (such as human albumin), wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 85 nm to about 95 nm, comprising rapamycin and albumin (such as human albumin), wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 60% of the albumin in the nanoparticles is in the form of polymeric albumin (other than oligomeric albumin); and (b) a non-nanoparticle portion comprising albumin (such as human albumin) and rapamycin. In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 85 nm to about 95 nm, comprising a coating comprising albumin (such as human albumin) and a core comprising rapamycin, wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a zeta potential of about −33 mV to about −39 mV, comprising rapamycin and albumin (such as human albumin); and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a zeta potential of about −33 mV to about −39 mV, comprising a coating comprising albumin (such as human albumin) and a core comprising rapamycin; and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a zeta potential of about −33 mV to about −39 mV, comprising rapamycin and albumin (such as human albumin), wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a zeta potential of about −33 mV to about −39 mV, comprising rapamycin and albumin (such as human albumin), wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 60% of the albumin in the nanoparticles is in the form of polymeric albumin (other than oligomeric albumin); and (b) a non-nanoparticle portion comprising albumin (such as human albumin) and rapamycin. In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension.

In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a zeta potential of about −33 mV to about −39 mV, comprising a coating comprising albumin (such as human albumin) and a core comprising rapamycin, wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a Z-average particle size of about 85 nm to about 95 nm and a zeta potential of about −33 mV to about −39 mV, comprising rapamycin and albumin (such as human albumin); and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a Z-average particle size of about 85 nm to about 95 nm and a zeta potential of about −33 mV to about −39 mV, comprising a coating comprising albumin (such as human albumin) and a core comprising rapamycin; and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 85 nm to about 95 nm and a zeta potential of about −33 mV to about −39 mV, comprising rapamycin and albumin (such as human albumin), wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 85 nm to about 95 nm and a zeta potential of about −33 mV to about −39 mV, comprising rapamycin and albumin (such as human albumin), wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 60% of the albumin in the nanoparticles is in the form of polymeric albumin (other than oligomeric albumin); and (b) a non-nanoparticle portion comprising albumin (such as human albumin) and rapamycin. In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

In some embodiments, a nanoparticle composition, or the commercial batch of the nanoparticle composition, comprises (a) nanoparticles having a Z-average particle size of about 85 nm to about 95 nm and a zeta potential of about −33 mV to about −39 mV, comprising a coating comprising albumin (such as human albumin) and a core comprising rapamycin, wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a Z-average particle size of about 85 nm to about 95 nm, comprising about 62% to about 68% (by weight) rapamycin and about 32% to about 38% (by weight) albumin (such as human albumin), wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a Z-average particle size of about 85 nm to about 95 nm, comprising about 62% to about 68% (by weight) rapamycin and about 32% to about 38% (by weight) albumin (such as human albumin), wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 60% of the albumin in the nanoparticles is in the form of polymeric albumin (other than oligomeric albumin); and (b) a non-nanoparticle portion comprising albumin (such as human albumin) and rapamycin. In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a Z-average particle size of about 85 nm to about 95 nm, comprising a coating comprising albumin (such as human albumin) and a core comprising rapamycin, wherein the albumin comprises about 32% to about 38% of the nanoparticles by weight and the rapamycin comprises about 62% to about 68% of the nanoparticles by weight, wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a Z-average particle size of about 85 nm to about 95 nm, comprising about 62% to about 68% (by weight) rapamycin and about 32% to about 38% (by weight) albumin (such as human albumin), wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL). In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a Z-average particle size of about 85 nm to about 95 nm, comprising a coating comprising albumin (such as human albumin) and a core comprising rapamycin, wherein the albumin comprises about 32% to about 38% of the nanoparticles by weight and the rapamycin comprises about 62% to about 68% of the nanoparticles by weight, wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL). In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a Z-average particle size of about 85 nm to about 95 nm and a zeta potential of about −33 mV to about −39 mV, comprising about 62% to about 68% (by weight) rapamycin and about 32% to about 38% (by weight) albumin (such as human albumin), wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL). In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a Z-average particle size of about 85 nm to about 95 nm and a zeta potential of about −33 mV to about −39 mV, comprising about 62% to about 68% (by weight) rapamycin and about 32% to about 38% (by weight) albumin (such as human albumin), wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 60% of the albumin in the nanoparticles is in the form of polymeric albumin (other than oligomeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL). In some embodiments, about 0.5% to about 7% of the albumin in the non-nanoparticle portion or the total albumin in the nanoparticle composition is in the form of polymeric albumin (other than oligomeric albumin). In some embodiments, about 0.3% to about 4% of the albumin in the non-nanoparticle portion or the total albumin in the nanoparticle composition is in the form of oligomeric albumin. In some embodiments, about 4% to about 15% of the albumin in the non-nanoparticle portion or the total albumin in the nanoparticle composition is in the form of dimeric albumin. In some embodiments, about 80% to about 95% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a Z-average particle size of about 85 nm to about 95 nm and a zeta potential of about −33 mV to about −39 mV, comprising a coating comprising albumin (such as human albumin) and a core comprising rapamycin, wherein the albumin comprises about 32% to about 38% of the nanoparticles by weight and the rapamycin comprises about 62% to about 68% of the nanoparticles by weight, wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL). In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a Z-average particle size of about 85 nm to about 95 nm and a zeta potential of about −33 mV to about −39 mV, comprising about 62% to about 68% (by weight) rapamycin and about 32% to about 38% (by weight) albumin (such as human albumin), wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL); and wherein about 1% or less of the rapamycin in the nanoparticle composition is free rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a Z-average particle size of about 85 nm to about 95 nm and a zeta potential of about −33 mV to about −39 mV, comprising a coating comprising albumin (such as human albumin) and a core comprising rapamycin, wherein the albumin comprises about 32% to about 38% of the nanoparticles by weight and the rapamycin comprises about 62% to about 68% of the nanoparticles by weight, wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL); and wherein about 1% or less of the rapamycin in the nanoparticle composition is free rapamycin. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a Z-average particle size of about 85 nm to about 95 nm and a zeta potential of about of about −33 mV to about −39 mV, comprising about 62% to about 68% (by weight) rapamycin and about 32% to about 38% (by weight) albumin (such as human albumin), wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL); and wherein the sum of seco-rapamycin and rapamycin in the nanoparticles is less than 1% (such as about 0.5% to about 1%) seco-rapamycin, by weight. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin in the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 μg/mL tert-butanol and/or comprises less than 5 μg/mL chloroform.

In some embodiments, a nanoparticle composition, or the commercial batch of the nanoparticle composition, comprises (a) nanoparticles having a Z-average particle size of about 85 nm to about 95 nm and a zeta potential of about −33 mV to about −39 mV, comprising a coating comprising albumin (such as human albumin) and a core comprising rapamycin, wherein the albumin comprises about 32% to about 38% of the nanoparticles by weight and the rapamycin comprises about 62% to about 68% of the nanoparticles by weight, wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL); and wherein the sum of seco-rapamycin and rapamycin in the nanoparticles is less than 1% (such as about 0.5% to about 1%) seco-rapamycin, by weight. In some embodiments, about 1.5% to about 3% of the albumin in the non-nanoparticle portion or the total albumin in the nanoparticle composition is in the form of polymeric albumin (or trimeric albumin). In some embodiments, about 7% to about 11% of the albumin in the non-nanoparticle portion in the nanoparticle composition is in the form of dimeric albumin. In some embodiments, about 7% to about 11% of the total albumin in the nanoparticle composition is in the form of dimeric albumin. In some embodiments, about 83% to about 92% of the albumin of the non-nanoparticle portion or the total albumin in the nanoparticle composition is in the form of monomeric albumin. In some embodiments, the weight ratio of the albumin to the rapamycin in the composition is about 7:1 to about 9:1. In some embodiments, about 95% or more of the albumin in the composition is in the non-nanoparticle portion. In some embodiments, about 98% to about 99.5% of the rapamycin in the composition is in the nanoparticles. In some embodiments, the concentration of albumin in the nanoparticle composition that is in the non-nanoparticle portion or the concentration of total albumin in the nanoparticle composition is about 35 mg/mL to about 45 mg/mL. In some embodiments, the osmolality of the composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the composition is stable at 4° C. and/or 25° C. for at least 24 hours. In some embodiments, the rapamycin in the nanoparticles has an amorphous morphology. In some embodiment, the nanoparticle composition is a nanoparticle suspension. In some embodiments, the nanoparticle composition is a dried composition. In some embodiments, the nanoparticle composition is sterile, for example by filtration. In some embodiments, the nanoparticle composition is contained within a sealed container, such as a sealed vial or a sealed bag. In some embodiments, the nanoparticle composition comprises less than 10 µg/mL tert-butanol and/or comprises less than 5 µg/mL chloroform.

Oligomeric Status of Albumin in the Compositions

The albumin in the compositions (such as pharmaceutical compositions), or in the commercial batches of the nanoparticle compositions (such as pharmaceutical compositions), described herein can have a range of oligomeric forms and profiles. As used herein, an oligomeric profile refers to the relative proportions of albumin monomers, dimers, and/or polymers (including trimers and/or oligomers of albumin) in the total composition, the nanoparticles of the composition, and/or the non-nanoparticle portion of the composition. Any given albumin species may be in the form of albumin monomers, albumin dimers, or albumin polymers (including trimers and/or oligomers of albumin). Albumin in the composition, the nanoparticles, or the non-nanoparticle portion of the composition may be in one of these oligomeric states. The oligomer profile of the albumin associated with the nanoparticles (such as within the nanoparticles or coating the nanoparticles) may impact the particle stability, solubility, dissolution rate, and in vivo distribution, and thus affects the suitability of the composition for pharmaceutical applications. Further, because albumin-rapamycin binding is greater for cross-linked albumin (e.g., albumin dimers, trimers, oligomers, polymers and polymers other than oligomers) than albumin monomers, the oligomeric status of the albumin on the nanoparticles may also affect in vivo behavior of an albumin-based rapamycin nanoparticle composition.

The oligomeric profile of the albumin in the nanoparticles may differ from the oligomeric profile of the albumin in the non-nanoparticle portion of the composition. For example, the portion of monomeric albumin may be greater in the non-nanoparticle portion of the composition compared to the nanoparticles, the portion of dimeric albumin may be greater in the nanoparticles than the non-nanoparticle portion of the composition, and/or the portion of polymeric (including trimeric and/or oligomeric albumin) albumin may be greater in the nanoparticles than the non-nanoparticle portion of the composition.

The oligomeric profile of the nanoparticle composition (or nanoparticle composition components, such as the nanoparticles or the non-nanoparticle portion of the composition) can be determined using size exclusion chromatography. A detector (such as a UV-absorption detector or a multi-angled light scattering (MALS) detector) can be coupled to the size exclusion column to detect albumin species eluting from the size exclusion column. MALS can effectively distinguish between monomer, dimer, and trimer species as they are eluted from the size exclusion column. For example, a nanoparticle composition may be subjected to analysis by size exclusion chromatography using a mobile phase (e.g., a saline mobile phase), and the MALS detector can be used to determine the percentage of albumin in the composition that is in the form of monomeric albumin, dimeric albumin, and trimeric albumin (i.e., as a proportion of the sum of monomeric, dimeric, and trimeric albumin species). The albumin profile of the separate components of the nanoparticle composition (i.e., the nanoparticles or the non-nanoparticle portion) can be similarly determined by separating the nanoparticles from the non-nanoparticle portion (e.g., by centrifugation). The non-nanoparticle portion can be decanted from the separated nanoparticles and subjected to size exclusion chromatography using a mobile phase (e.g., a saline mobile phase) and the MALS detector can be used to determine the percentage of albumin in the non-nanoparticle portion of the composition that is in the form of monomeric albumin, dimeric albumin, and trimeric albumin (i.e., as a proportion of the sum of monomeric, dimeric, and trimeric albumin species). The nanoparticles may be re-suspended (for example, in saline) and the re-suspended nanoparticles subjected to size exclusion chromatography using a mobile phase (e.g., a saline mobile phase) and the MALS detector can be used to determine the percentage of albumin in the nanoparticles that is in the form of monomeric albumin, dimeric albumin, and trimeric albumin (i.e., as a proportion of the sum of monomeric, dimeric, and trimeric albumin species). A portion of the albumin in the nanoparticles dissociates from the re-suspended nanoparticles and is take as a proxy for the oligomeric profile of the albumin in the nanoparticles when re-suspended nanoparticles are subjected to size exclusion chromatography; intact nanoparticles and non-dissociated albumin may flow through the size exclusion column in the void volume of the mobile phase and are not considered as part of the albumin profile analysis.

The albumin oligomeric profile of the nanoparticle composition (or components, such as the non-nanoparticle portion or the nanoparticles) can also or alternatively be determined using size exclusion chromatography (for example, using a mobile phase, which may contain an aqueous buffer with a miscible organic solvent, such as 7.5% methanol) coupled to a UV-absorption detector to determine the percentage of albumin that is in the form of monomeric albumin, dimeric albumin, oligomeric albumin, or polymeric albumin (other than oligomeric albumin). For example, the nanoparticle composition can be subjected to size exclusion chromatography using a mobile phase (e.g., 7.5% methanol in an aqueous buffer), and the UV-abs portion detector can be used to determine the percentage of albumin in the composition that is in the form of monomeric albumin, dimeric albumin, oligomeric albumin, or polymeric albumin other than oligomeric albumin. The albumin profile of the separate components of the nanoparticle composition (i.e., the nanoparticles or the non-nanoparticle portion) can be similarly determined by separating the nanoparticles from the non-nanoparticle portion (e.g., by centrifugation). The non-nanoparticle portion can be decanted from the separated nanoparticles and subjected to size exclusion chromatography using a mobile phase (e.g., 7.5% methanol in an aqueous buffer) and the UV-absorption detector can be used to determine the percentage of albumin in the non-nanoparticle portion of the composition that is in the form of monomeric albumin, dimeric albumin, oligomeric albumin, and polymeric albumin other than oligomeric albumin. The nanoparticles may be dissolved (for example, in large volume of saline or a mixture of methanol and saline) and the dissolved nanoparticles subjected to size exclusion chromatography using a mobile phase (e.g., 7.5% methanol in an aqueous buffer) and the UV-absorption detector can be use d to determine the percentage of albumin in the nanoparticles portion of the composition that is in the form of monomeric albumin, dimeric albumin, oligomeric albumin, and polymeric albumin other than oligomeric albumin.

In some embodiments, about 80% to about 95% (such about 80-83%, about 83-86%, about 86-89%, about 89-92%, or about 92-95%, or a combination of such ranges) of the total albumin in the composition is in the form of albumin monomers. In some embodiments, about any of about 80%, 81%, 82%, 83%, 84%, 85%, 86%, 87%, 88%, 89%, 90%, 91%, 92%, 93%, 94% or 95% of the total albumin in the composition is in the form of albumin monomers. In some embodiments, about 4% to about 15% (such as about 4-6%, about 6-8%, about 8-10%, about 10-12%, or about 12-15%, or a combination of such ranges) of the total albumin in the composition is in the form of albumin dimers. In some embodiments, about 4%, 5%, 6%, 7%, 8%, 9%, 10%, 11%, 12%, 13%, 14%, or 15% of the total albumin in the composition is in the form of albumin dimers. In some embodiments, about 0.5% to about 5% (such as about 0.5-1%, about 1-1.5%, about 1.5-2%, about 2-2.5%, about 2.5-3%, about 3-3.5%, about 3.5-4%, about 4-4.5%, or about 4.5-5%, or a combination of such ranges) of the total albumin in the composition is in the form of albumin polymers (or albumin trimers). In some embodiments, about 0.5%, 1%, 1.5%, 2%, 2.5%, 3%, 3.5%, 4%, 4.5%, or 5% of the total albumin in the composition is in the form of albumin polymers (or albumin trimers). In some embodiments, about 80% to about 95% of the total albumin in the composition is in the form of albumin monomers, and about 4% to about 15% of the total albumin in the composition is in the form of albumin dimers. In some embodiments, about 80% to about 95% of the total albumin in the composition is in the form of albumin monomers, and about 0.5% to about 5% of the total albumin in the composition is in the form of albumin polymers (or albumin trimers). In some embodiments, about 4% to about 15% of the total albumin in the composition is in the form of albumin dimers, and about 0.5% to about 5% of the total albumin in the composition is in the form of albumin polymers (or albumin trimers). In some embodiments, about 80% to about 95% of the total albumin in the composition is in the form of albumin monomers, about 4% to about 15% of the total albumin in the composition is in the form of albumin dimers, and about 0.5% to about 5% of the total albumin in the composition is in the form of albumin polymers (or albumin trimers). The percentage of the monomeric albumin, the dimeric albumin, or the polymeric albumin (or trimeric albumin) compared to the total albumin in the composition may be determined as a percentage of the sum of the total monomeric albumin, dimeric albumin, and polymeric (or trimeric) albumin in the composition. The percentage of the monomeric albumin, the dimeric albumin, or the polymeric albumin (or trimeric albumin) in the composition can be measured by subjecting the composition to size-exclusion chromatography (SEC) using an aqueous mobile phase (such as saline) coupled with multiple angle light scattering (MALS) detector.

In some embodiments, about 83% to about 92% of the total albumin in the nanoparticle composition is in the form of monomeric albumin. In some embodiments, about 7% to about 11% of the total albumin in the nanoparticle composition is in the form of dimeric albumin. In some embodiments, about 1.5% to about 3% of the total albumin in the nanoparticle composition is in the form of polymeric albumin (or trimeric albumin). In some embodiments, about 83% to about 92% of the total albumin in the nanoparticle composition is in the form of monomeric albumin; about 7% to about 11% of the total albumin in the nanoparticle composition is in the form of dimeric albumin; and about 1.5% to about 3% of the total albumin in the nanoparticle composition is in the form of polymeric albumin (or trimeric albumin).

In some embodiments, about 80% to about 95% (such about 80-83%, about 83-86%, about 86-89%, about 89-92%, or about 92-95%, or a combination of such ranges) of the total albumin in the composition is in the form of albumin monomers. In some embodiments, about any of about 80%, 81%, 82%, 83%, 84%, 85%, 86%, 87%, 88%, 89%, 90%, 91%, 92%, 93%, 94% or 95% of the total albumin in the composition is in the form of albumin monomers. In some embodiments, about 4% to about 15% (such as about 4-6%, about 6-8%, about 8-10%, about 10-12%, or about 12-15%, or a combination of such ranges) of the total albumin in the composition is in the form of albumin dimers. In some embodiments, about 4%, 5%, 6%, 7%, 8%, 9%, 10%, 11%, 12%, 13%, 14%, or 15% of the total albumin in the composition is in the form of albumin dimers. In some embodiments, about 0.3% to about 3% (such as 0.3-1%, 1-2%, or about 2-3%, or a combination of such ranges) of the total albumin in the composition is in the form of albumin oligomers. In some embodiments, about 0.3%, 1%, 2%, or 3% of the total albumin in the composition is in the form of albumin oligomers. In some embodiments, about 2% to about 7% (such as about 2-2.5%, about 2.5-3%, about 3-3.5%, about 3.5-4%, about 4-4.5%, about 4.5-5%, about 5-5.5%, about 5.5-6%, about 6-6.5%, or about 6.5-7%, or a combination of such ranges) of the total albumin in the composition is in the form of albumin polymers (other than albumin oligomers). In some embodiments, about 2%, 2.5%, 3%, 3.5%, 4%, 4.5%, 5%, 5.5%, 6%, 6.5%, or 7% of the total albumin in the composition is in the form of albumin polymers (other than albumin oligomers). In some embodiments, about 80% to about 95% of the total albumin in the composition is in the form of albumin monomers, and about 4% to about 15% of the total albumin in the composition is in the form of albumin dimers. In some embodiments, about 80% to about 95% of the total albumin in the composition is in the form of albumin monomers, and about 2% to about 7% of the total albumin in the composition is in the form of albumin polymers (other than albumin oligomers). In some embodiments, about 4% to about 15% of the total albumin in the composition is in the form of albumin dimers, and about 2% to about 7% of the total albumin in the composition is in the form of albumin polymers (other than albumin oligomers). In some embodiments, about 80% to about 95% of the total albumin in the composition is in the form of albumin monomers, about 4% to about 15% of the total albumin in the composition is in the form of albumin dimers, and about 2% to about 7% of the total albumin in the composition is in the form of albumin polymers (other than albumin oligomers). In some embodiments, about 80% to about 95% of the total albumin in the composition is in the form of albumin monomers, about 4% to about 15% of the total albumin in the composition is in the form of albumin dimers, about 0.3% to about 3% of the total albumin in the composition is in the form of albumin oligomers, and about 2% to about 7% of the total albumin in the composition is in the form of albumin polymers (other than albumin oligomers). The percentage of monomeric albumin, dimeric albumin, oligomeric albumin, or polymeric albumin (other than oligomeric albumin) compared to the total albumin in the composition may be determined as a percentage of the sum of total monomeric albumin, dimeric albumin, oligomeric albumin, and polymeric albumin (other than oligomeric albumin) in the composition. The percentage of the monomeric albumin, the dimeric albumin, the oligomeric albumin, or the polymeric albumin (other than oligomeric albumin) in the composition can be measured by dissolving the nanoparticles and subjecting the composition to size exclusion chromatography (SEC) using a mobile phase containing an aqueous portion and a miscible organic portion (such as an aqueous buffer containing 7.5% methanol) coupled with a UV detector.

In some embodiments, about 70% to about 85% (such as any of about 70-72%, about 72-74%, about 74-76%, about 76-78%, about 78-80%, about 80-82%, or about 82-85%, or any combination of such ranges) of the albumin in the nanoparticles of the composition is in the form of albumin monomers. In some embodiments, about 70%, 71%, 72%, 73%, 74%, 75%, 76%, 77%, 78%, 79%, 80%, 81%, 82%, 83%, 84%, or 85% of the albumin in the nanoparticles of the composition is in the form of albumin monomers. In some embodiments, about 9% to about 20% (such as about 9-11%, about 11-13%, about 13-15%, about 15-17%, or about 17-20%, or any combination of such ranges) of the albumin in the nanoparticle portion of the composition is in the form of dimers. In some embodiments, about 9%, 10%, 11%, 12%, 13%, 14%, 15%, 16%, 17%, 18%, 19%, or 20% of the albumin in the nanoparticles of the composition is in the form of albumin dimers. In some embodiments, about 5% to about 15% (such as any of about 5-7%, about 7-9%, about 9-11%, about 11-13%, or about 13-15%, or any combination of such ranges) of the albumin in the nanoparticles of the composition is in the form of albumin polymers (or albumin trimers). In some embodiments, about 5%, 6%, 7%, 8%, 9%, 10%, 11%, 12%, 13%, 14%, or 15% of the albumin in the nanoparticles of the composition is in the form of albumin polymers (or albumin trimers). In some embodiments, about 70% to about 85% of the albumin in the nanoparticles of the composition is in the form of albumin monomers, and about 9% to about 20% of the albumin in the nanoparticles of the composition is in the form of albumin dimers. In some embodiments, about 70% to about 85% of the albumin in the nanoparticles of the composition is in the form of albumin monomers, and about 5% to about 15% of the albumin in the nanoparticles of the composition is in the form of albumin polymers (or albumin trimers). In some embodiments, about 9% to about 20% of the albumin in the nanoparticles of the composition is in the form of albumin dimers, and about 5% to about 15% of the albumin in the nanoparticles of the composition is in the form of albumin polymers (or albumin trimers). In some embodiments, about 70% to about 85% of the albumin in the nanoparticles of the composition is in the form of albumin monomers, about 9% to about 20% of the albumin in the nanoparticles of the composition is in the form of albumin dimers, and about 5% to about 15% of the albumin in the nanoparticles of the composition is in the form of albumin polymers (or albumin trimers). The percentage of the monomeric albumin, the dimeric albumin, or the polymeric albumin (or trimeric albumin) in the nanoparticles may be determined as a percentage of the sum of monomeric albumin, dimeric albumin, and polymeric albumin (or trimeric albumin) in the nanoparticles. The percentage of the monomeric albumin, the dimeric albumin, or the polymeric albumin (or the trimeric albumin) in the nanoparticles can be measured by separating the nanoparticles from the non-nanoparticle portion (e.g., by centrifugation), re-suspending the nanoparticles (for example, in an aqueous solution, such as saline), and subjecting the re-suspended nanoparticles to size-exclusion chromatography (SEC) using an aqueous mobile phase (such as saline) coupled with multiple angle light scattering (MALS) detector.

In some embodiments, about 74% to about 80% of the albumin in the nanoparticles is in the form of monomeric albumin. In some embodiments, about 12% to about 17% of the albumin in the nanoparticles is in the form of dimeric albumin. In some embodiments, about 7% to about 11% of the albumin in the nanoparticles is in the form of polymeric albumin (or trimeric albumin). In some embodiments, about 74% to about 80% of the albumin in the nanoparticles is in the form of monomeric albumin; about 12% to about 17% of the albumin in the nanoparticles is in the form of dimeric albumin; and about 7% to about 11% of the albumin in the nanoparticles is in the form of polymeric albumin (or trimeric albumin).

In some embodiments, about 25% to about 50% (such as any of about 25-30%, about 30-35%, about 35-40%, about 40-45%, or about 45-50%, or any combination of such ranges) of the albumin in the nanoparticles is in the form of albumin monomers. In some embodiments, about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% of the albumin in the nanoparticles of the composition is in the form of albumin monomers. In some embodiments, about 5% to about 16% (such as about 5-7%, about 7-9%, about 9-11%, about 11-13%, about 13-15%, or about 15-16%, or any combination of such ranges) of the albumin in the nanoparticle portion of the composition is in the form of dimers. In some embodiments, about 5%, 6%, 7%, 8%, 9%, 10%, 11%, 12%, 13%, 14%, or 15% of the albumin in the nanoparticles of the composition is in the form of albumin dimers. In some embodiments, about 1% to about 4.5% (such as about 1-2%, about 2-3%, about 3-4%, or about 4-4.5%, or any combination of such ranges) of the albumin in the nanoparticle portion of the composition is in the form of oligomers. In some embodiments, about 1%, about 1.5%, about 2%, about 2.5%, about 3%, about 3.5%, about 4%, or about 4.5% of the albumin in the nanoparticles of the composition is in the form of albumin oligomers. In some embodiments, about 42% to about 60% (such as any of about 42-45%, about 45-48%, about 48-51%, about 51-54%, about 54-57%, or about 57-60%, or any combination of such ranges) of the albumin in the nanoparticles is in the form of albumin polymers (other than albumin oligomers). In some embodiments, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% of the albumin in the nanoparticles of the composition is in the form of albumin polymers (other than albumin oligomers). In some embodiments, about 25-50% of the albumin in the nanoparticles of the composition is in the form of albumin monomers, and about 5% to about 16% of the albumin in the nanoparticles of the composition is in the form of albumin dimers. In some embodiments, about 25% to about 50% of the albumin in the nanoparticles of the composition is in the form of albumin monomers, and about 42% to about 60% of the albumin in the nanoparticles of the composition is in the form of albumin polymers (other than albumin oligomers). In some embodiments, about 5% to about 16% of the albumin in the nanoparticles of the composition is in the form of albumin dimers, and about 42% to about 60% of the albumin in the nanoparticles of the composition is in the form of albumin polymers (other than albumin oligomers). In some embodiments, about 25% to about 50% of the albumin in the nanoparticles of the composition is in the form of albumin monomers, about 5% to about 16% of the albumin in the nanoparticles of the composition is in the form of albumin dimers, and about 42% to about 60% of the albumin in the nanoparticles of the composition is in the form of albumin polymers (other than albumin oligomers). In some embodiments, about 25% to about 50% of the albumin in the nanoparticles of the composition is in the form of albumin monomers, about 5% to about 16% of the albumin in the nanoparticles of the composition is in the form of albumin dimers, about 1% to about 4.5% of the albumin in the nanoparticles of the composition is in the form of albumin oligomers, and about 42% to about 60% of the albumin in the nanoparticles of the composition is in the form of albumin polymers (other than albumin oligomers). The percentage of the monomeric albumin, the dimeric albumin, the oligomeric albumin, or the polymeric albumin (other than oligomeric albumin) in the nanoparticles may be determined as a percentage of the sum of monomeric albumin, dimeric albumin, oligomeric albumin, and polymeric albumin (other than oligomeric albumin) in the nanoparticles. The percentage of the monomeric albumin, the dimeric albumin, the oligomeric albumin, or the polymeric albumin (other than the oligomeric albumin) in the nanoparticles can be measured by separating the nanoparticles from the non-nanoparticle portion (e.g., by centrifugation), dissolving the nanoparticles, and subjecting the re-suspended nanoparticles to size-exclusion chromatography (SEC) using a mobile phase containing an aqueous portion and a miscible organic portion (such as an aqueous buffer containing 7.5% methanol) coupled with a UV detector.

In some embodiments, about 80% to about 95% (such as any of about 80% to about 82%, about 82% to about 84%, about 84% to about 86%, about 86% to about 88%, about 88% to about 90%, about 90% to about 92%, or about 90% to about 93%, or a combination of such ranges) of the albumin in the non-nanoparticle portion of the composition is in the form of albumin monomers. In some embodiments, about any of 80%, 81%, 82%, 83%, 84%, 85%, 86%, 87%, 88%, 89%, 90%, 91%, 92%, 93%, 94%, or 95% of the albumin in the non-nanoparticle portion of the composition is in the form of albumin monomers. In some embodiments, about 4% to about 14% (such as about 4-6%, about 6-8%, about 8-10%, about 10-12%, or about 12-15%, or a combination of such ranges) of the albumin in the non-nanoparticle portion of the composition is in the form of albumin dimers. In some embodiments, about 4%, 5%, 6%, 7%, 8%, 9%, 10%, 11%, 12%, 13%, or 14% of the albumin in the non-nanoparticle portion of the composition is in the form of albumin dimers. In some embodiments, about 0.5% to about 5% (such about 0.5-1%, about 1-1.5%, about 1.5-2%, about 2-2.5%, about 2.5-3%, about 3-3.5%, about 3.5-4%, about 4-4.5%, or about 4.5-5%, or a combination of such ranges) of the albumin in the non-nanoparticle portion of the composition is in the form of albumin polymers (or albumin trimers). In some embodiments, about 0.5%, 1%, 1.5%, 2%, 2.5%, 3%, 3.5%, 4%, 4.5%, or 5% of the albumin in the non-nanoparticle portion of the composition is in the form of albumin polymers (or albumin trimers). In some embodiments, about 80% to about 95% of the albumin in the non-nanoparticle portion of the composition is in the form of albumin monomers, and about 4% to about 14% of the albumin in the non-nanoparticle portion of the composition is in the form of albumin dimers. In some embodiments, about 80% to about 95% of the albumin in the non-nanoparticle portion of the composition is in the form of albumin monomers, and about 0.5% to about 5% of the albumin in the non-nanoparticle portion of the composition is in the form of albumin polymers (or albumin trimers). In some embodiments, about 4% to about 14% of the albumin in the non-nanoparticle portion of the composition is in the form of albumin dimers, and about 0.5% to about 5% of the albumin in the non-nanoparticle portion of the composition is in the form of albumin polymers (or albumin trimers). In some embodiments, about 80% to about 95% of the albumin in the non-nanoparticle portion of the composition is in the form of albumin monomers, about 4% to about 14% of the albumin in the non-nanoparticle portion of the composition is in the form of albumin dimers, and about 0.5% to about 5% of the albumin in the non-nanoparticle portion of the composition is in the form of albumin polymers (or albumin trimers). The percentage of the monomeric albumin, the dimeric albumin, or the polymeric albumin (or the trimeric albumin) in the non-nanoparticle portion may be determined as a percentage of the sum of monomeric albumin, dimeric albumin, and polymeric albumin (or trimeric albumin) in the non-nanoparticle portion. The percentage of the monomeric albumin, the dimeric albumin, or the polymeric albumin (or the trimeric albumin) in the non-nanoparticle portion can be measured by separating the nanoparticles from the non-particle portion (e.g., by centrifugation), and subjecting the non-nanoparticle portion to size-exclusion chromatography (SEC) using an aqueous mobile phase (such as saline) coupled with a multiple angle light scattering (MALS) detector.

In some embodiments, about 83% to about 92% of the albumin in the non-nanoparticle portion of the nanoparticle composition is in the form of monomeric albumin. In some embodiments, about 7% to about 11% of the albumin in the non-nanoparticle portion of the nanoparticle composition is in the form of dimeric albumin. In some embodiments, about 1.5% to about 3% of the albumin in the non-nanoparticle portion of the nanoparticle composition is in the form of polymeric albumin (or trimeric albumin). In some embodiments, about 83% to about 92% of the albumin in the non-nanoparticle portion of the nanoparticle composition is in the form of monomeric albumin; about 7% to about 11% of the albumin in the non-nanoparticle portion of the nanoparticle composition is in the form of dimeric albumin; and about 1.5% to about 3% of the albumin in the non-nanoparticle portion of the nanoparticle composition is in the form of polymeric albumin (or trimeric albumin).

In some embodiments, about 80% to about 95% (such as any of about 80% to about 82%, about 82% to about 84%, about 84% to about 86%, about 86% to about 88%, about 88% to about 90%, about 90% to about 92%, or about 90% to about 93%, or a combination of such ranges) of the albumin in the non-nanoparticle portion of the composition is in the form of albumin monomers. In some embodiments, about any of 80%, 81%, 82%, 83%, 84%, 85%, 86%, 87%, 88%, 89%, 90%, 91%, 92%, 93%, 94%, or 95% of the albumin in the non-nanoparticle portion of the composition is in the form of albumin monomers. In some embodiments, about 4% to about 14% (such as about 4-6%, about 6-8%, about 8-10%, about 10-12%, or about 12-15%, or a combination of such ranges) of the albumin in the non-nanoparticle portion of the composition is in the form of albumin dimers. In some embodiments, about 4%, 5%, 6%, 7%, 8%, 9%, 10%, 11%, 12%, 13%, or 14% of the albumin in the non-nanoparticle portion of the composition is in the form of albumin dimers. In some embodiments, about 0.5% to about 4% (such as about 0.5-1%, about 1-2%, about 2-3%, or about 3-4%, or a combination of such ranges) of the albumin in the non-nanoparticle portion of the composition is in the form of albumin oligomers. In some embodiments, about 0.5%, 1%, 1.5%, 2%, 2.5%, 3%, 3.5%, or 4% of the albumin in the non-nanoparticle portion of the composition is in the form of albumin oligomers. In some embodiments, about 0.5% to about 3% (such about 0.5-1%, about 1-1.5%, about 1.5-2%, about 2-2.5%, or about 2.5-3%, or a combination of such ranges) of the albumin in the non-nanoparticle portion of the composition is in the form of albumin polymers (other than albumin oligomers). In some embodiments, about 0.5%, 1%, 1.5%, 2%, 2.5%, or 3% of the albumin in the non-nanoparticle portion of the composition is in the form of albumin polymers (other than albumin oligomers). In some embodiments, about 80% to about 95% of the albumin in the non-nanoparticle portion of the composition is in the form of albumin monomers, and about 4% to about 14% of the albumin in the non-nanoparticle portion of the composition is in the form of albumin dimers. In some embodiments, about 80% to about 95% of the albumin in the non-nanoparticle portion of the composition is in the form of albumin monomers, and about 0.5% to about 3% of the albumin in the non-nanoparticle portion of the composition is in the form of albumin polymers (other than albumin oligomers). In some embodiments, about 4% to about 14% of the albumin in the non-nanoparticle portion of the composition is in the form of albumin dimers, and about 0.5% to about 3% of the albumin in the non-nanoparticle portion of the composition is in the form of albumin polymers (other than albumin oligomers). In some embodiments, about 80% to about 95% of the albumin in the non-nanoparticle portion of the composition is in the form of albumin monomers, about 4% to about 14% of the albumin in the non-nanoparticle portion of the composition is in the form of albumin dimers, and about 0.5% to about 3% of the albumin in the non-nanoparticle portion of the composition is in the form of albumin polymers (other than albumin oligomers). In some embodiments, about 80% to about 95% of the albumin in the non-nanoparticle portion of the composition is in the form of albumin monomers, about 4% to about 14% of the albumin in the non-nanoparticle portion of the composition is in the form of albumin dimers, about 0.5% to about 4% of the albumin in the non-nanoparticle portion of the composition is in the form of albumin oligomers, and about 0.5% to about 3% of the albumin in the non-nanoparticle portion of the composition is in the form of albumin polymers (other than albumin oligomers). The percentage of the monomeric albumin, the dimeric albumin, the oligomeric albumin, or the polymeric albumin (other than oligomeric albumin) in the non-nanoparticle portion may be determined as a percentage of the sum of monomeric albumin, dimeric albumin, oligomeric albumin, and polymeric albumin (other than oligomeric albumin) in the non-nanoparticle portion. The percentage of the monomeric albumin, the dimeric albumin, the oligomeric albumin, or the polymeric albumin (other than oligomeric albumin) can be measured by separating the nanoparticles from the non-nanoparticle portion (e.g., by centrifugation), and subjecting the supernatant (i.e., the non-nanoparticle portion) to size-exclusion chromatography (SEC) using a mobile phase containing an aqueous portion and a miscible organic portion (such as an aqueous buffer containing 7.5% methanol) coupled with a UV detector.

In some embodiments, less than about 85% (such as less than about 85%, 84%, 83%, 82%, 81%, 80%, 79%, 78%, 77%, 76%, 75%, 74%, 73%, 72%, or 71%) of the albumin in the nanoparticles of the composition is in the form of monomers. In some embodiments, less than about 20% (such as less than about any of 20%, 19%, 18%, 17%, 16%, 15%, 14%, 13%, 12%, 11%, 10%, or 9%) of the albumin in the nanoparticles of the composition is in the form of dimers. In some embodiments, less than about 15% (such as less than about any of 15%, 14%, 13%, 12%, 11%, 10%, 9%, 8%, 7%, or 6%) of the albumin in the nanoparticles of the composition is in the form of polymers (or trimers). In some embodiments, less than about 85% of the albumin in the nanoparticles of the composition is in the form of monomers, less than about 20% of the albumin in the nanoparticles of the composition is in the form of dimers, and less than about 15% of the albumin in the nanoparticles of the composition is in the form of polymers.

In some embodiments, less than about 50% (such as less than about 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, or 25%) of the albumin in the nanoparticles of the composition is in the form of monomers. In some embodiments, less than about 16% (such as less than about any of 16%, 15%, 14%, 13%, 12%, 11%, 10%, 9%, or 8%) of the albumin in the nanoparticles is in the form of dimers. In some embodiments, less than 4.5% (such as less than about any of 4.5%, 4%, 3.5%, 3%, 2.5%, 2%, 1.5%, or 1%) of the albumin in the nanoparticles is in the form of oligomers. In some embodiments, less than about 60% (such as less than about any of 60%, 59%, 58%, 57%, 56%, 55%, 54%, 53%, 52%, 51%, 50%, 49%, 48%, 47%, 46%, or 45%) of the albumin in the nanoparticles is in the form of polymers (other than oligomers). In some embodiments, less than about 50% of the albumin in the nanoparticles of the composition is in the form of monomers, less than about 16% of the albumin in the nanoparticles of the composition is in the form of dimers, less than about 4.5% of the albumin in the nanoparticles of the composition is in the form of oligomers, and less than about 60% of the albumin in the nanoparticles of the composition is in the form of polymers (other than oligomers).

In some embodiments, the oligomeric status of the total albumin in the composition, albumin in the nanoparticles of composition, and/or albumin in the non-nanoparticle portion of the composition described herein does not change substantially upon storage (such as after storage at about 25° C. for about any of 1 month, 3 months, 6 months, 9 months, 12 months, 18 months, 24 months, or 36 months). In some embodiments, the percentage of albumin monomers in the composition, the nanoparticles of the composition, and/or the non-nanoparticle portion of the composition does not increase by more than about any of 1%, 5%, 10%, 15%, 20%, or 25% after a period of storage. In some embodiments, the percentage of albumin dimers in the composition, the nanoparticles of the composition, and/or the non-nanoparticle portion of the composition does not increase by more than about any of 1%, 5%, 10%, 15%, 20%, 25%, 30%, 35%, 40%, 45%, or 50% after a period of storage. In some embodiments, the percentage of albumin polymers in the composition, the nanoparticles of the composition, and/or the non-nanoparticle portion of the composition does not increase by more than about any of 1%, 5%, 10%, 15%, 20%, 25%, 30%, 35%, 40%, 45%, or 50% after a period of storage. In some embodiments, the percentage of albumin monomers in the composition, the nanoparticles of the composition, and/or the non-nanoparticle portion of the composition does not decrease by more than about any of 1%, 5%, 10%, 15%, 20%, or 25% after a period of storage. In some embodiments, the percentage of albumin dimers in the composition, the nanoparticles of the composition, and/or the non-nanoparticle portion of the composition does not decrease by more than about any of 1%, 5%, 10%, 15%, 20%, 25%, 30%, 35%, 40%, 45%, or 50% after a period of storage. In some embodiments, the percentage of albumin polymers in the composition, the nanoparticles of the composition, and/or the non-nanoparticle portion of the composition does not decrease by more than about any of 1%, 5%, 10%, 15%, 20%, 25%, 30%, 35%, 40%, 45%, or 50% after a period of storage. In some embodiments, the period of storage is about any of 1 month, 3 months, 6 months, 9 months, 12 months, 18 months, 24 months, or 36 months. In some embodiments, the period of storage is at a temperature of about any of about 2° C. to about 8° C., about 15° C. to about 25°, or about 25° C. to about 40° C., or about 2° C., about 4° C., about 8° C., about 15° C., about 25° C., about 30° C., or about 40° C. In some embodiments, the composition is stored in a dried form, such as a lyophilized form. In some embodiments, the stability of the oligomeric profile is determined by assessing the composition before lyophilization and after reconstitution, wherein the period of storage is after lyophilization but before reconstitution.

Oligomeric status of the albumin in the composition can be determined by any suitable means, including by size exclusion chromatography, such as gel permeation chromatography, polyacrylamide gel electrophoresis (such as sodium dodecyl sulfate polyacrylamide gel electrophoresis, SDS-PAGE), or other methods known in the art. For example, the oligomeric status of the nanoparticles and/or the non-nanoparticle portion can be determined by isolating the albumin in the nanoparticles in the composition from the free albumin not associated with the nanoparticles (i.e., albumin in the non-nanoparticle portion) by, for example, ultracentrifugation or gel filtration chromatography. Subsequent methods of analysis of the albumin by, for example, size exclusion chromatography can be used to determine the amount of albumin on the nanoparticles that is in the form of monomers, dimers, and/or polymers (including trimers). The different classes of albumins can be determined based on differing retention time of albumin when subject to a chromatography (such as size exclusion chromatography). The distribution of the components can be confirmed, for example by permeation chromatography.

In some embodiments, the separation range for the size exclusion chromatography is about 10,000 to about 500,000 Daltons. In some embodiments, the size exclusion chromatography is run with a TSKgel G3000 SWXL column. In some embodiments, the size exclusion chromatography is run with a column of TOSOH TSKgel G3000 SWXL, 7.8×300 mm, 5 μm or equivalent. In some embodiments, the size exclusion chromatography is run with a column of BioSep-S3000. In some embodiments, the size exclusion chromatography is run with a flow rate of about 1 mL/min. In some embodiments, the size exclusion chromatography is run at ambient temperature. In some embodiments, the size exclusion chromatography is run with a column of TOSOH TSKgel G3000 SWXL, 7.8×300 mm, 5 μm or equivalent, at a flow rate of about 1 mL/min at room temperature.

In some embodiments, the percentage of the albumin in the nanoparticles that is in the form of a monomer can be determined by comparing the amount of monomeric albumin in the nanoparticles with the total amount of the albumin in the nanoparticles. In some embodiments, the percentage of the albumin in the nanoparticles that is in the form of albumin dimers can be determined by comparing the amount of dimeric albumin in the nanoparticles with the total amount of the albumin in the nanoparticles. In some embodiments, the percentage of the albumin in the nanoparticles that is in the form of albumin polymers can be determined by comparing the amount of polymeric albumin in the nanoparticles with the total amount of the albumin in the nanoparticles.

In an exemplary method, the percentage of the monomeric, the dimeric, and the trimeric albumin in the total composition, the nanoparticles, and the non-nanoparticle portion is determined as the percentage of the sum of the monomeric, the dimeric, and the trimeric albumin in the total composition, the nanoparticles, and the non-particle portion, respectively. The percentage of the monomeric, the dimeric, and the trimeric albumin in the total composition is measured by subjecting the composition to size-exclusion chromatography (SEC) using an aqueous mobile phase (such as saline) coupled with a multiple angle light scattering (MALS) detector. To determine the percentage of the monomeric, the dimeric, and the trimeric albumin in the nanoparticle and non-nanoparticle portion, the nanoparticles are first separated from the non-nanoparticle portion by centrifugation to form the nanoparticle portion (i.e., the pellet) and the non-nanoparticle portion (i.e., the supernatant). To determine the percentage of the monomeric, the dimeric, and the trimeric albumin in the nanoparticle portion, the pellet is resuspended in an aqueous solution, such as saline, and subjected to SEC using an aqueous mobile phase (such as saline) coupled with a MALS detector. To determine the percentage of the monomeric, the dimeric, and the trimeric albumin in the non-nanoparticle portion, the supernatant is subjected to SEC using an aqueous mobile phase (such as saline) coupled with a MALS detector.

In an exemplary method, the percentage of the monomeric, the dimeric, and the polymeric albumin (or trimeric albumin) in the total composition, the nanoparticles, and the non-nanoparticle portion is determined as the percentage of the sum of the monomeric, the dimeric, and the polymeric albumin (or trimeric albumin) in the total composition, the nanoparticles, and the non-particle portion, respectively. The percentage of the monomeric, the dimeric, and the polymeric albumin (or trimeric albumin) in the total composition is measured by subjecting the composition to size-exclusion chromatography (SEC) using an aqueous mobile phase (such as saline) coupled with a multiple angle light scattering (MALS) detector. To determine the percentage of the monomeric, the dimeric, and the trimeric albumin (or trimeric albumin) in the nanoparticle and non-nanoparticle portion, the nanoparticles are first separated from the non-nanoparticle portion by centrifugation to form the nanoparticle portion (i.e., the pellet) and the non-nanoparticle portion (i.e., the supernatant). To determine the percentage of the monomeric, the dimeric, and the polymeric albumin (or trimeric albumin) in the nanoparticle portion, the pellet is resuspended in an aqueous solution, such as saline, and subjected to SEC using an aqueous mobile phase (such as saline) coupled with a MALS detector. To determine the percentage of the monomeric, the dimeric, and the polymeric albumin (or trimeric albumin) in the non-nanoparticle portion, the supernatant is subjected to SEC using an aqueous mobile phase (such as saline) coupled with a MALS detector.

In an exemplary method, the percentage of the monomeric, the dimeric, the oligomeric, and the polymeric albumin (other than oligomeric albumin) in the total composition, the nanoparticles, and the non-nanoparticle portion is determined as the percentage of the sum of the monomeric, the dimeric, the oligomeric, and the polymeric albumin (other than oligomeric albumin) in the total composition, the nanoparticles, and the non-nanoparticle portion, respectively. The percentage of the monomeric, the dimeric, the oligomeric, and the polymeric albumin (other than oligomeric albumin) in the total composition is measured by subjecting the composition to size-exclusion chromatography (SEC) using a mobile phase containing an aqueous portion and a miscible organic portion (such as an aqueous buffer containing 7.5% methanol) coupled with a UV detector. To determine the percentage of the monomeric, the dimeric, the oligomeric, and the polymeric albumin (other than oligomeric albumin) in the nanoparticles and the non-nanoparticle portion, the nanoparticles are first separated from the non-nanoparticle portion by centrifugation to form the nanoparticle portion (i.e., the pellet) and the non-nanoparticle portion (i.e., the supernatant). To determine the percentage of the monomeric, the dimeric, the oligomeric, and the polymeric albumin (other than oligomeric albumin) in the nanoparticles, the nanoparticles in the pellet are dissolved and then subjected to SEC using a mobile phase containing an aqueous portion and miscible organic portion (such as an aqueous buffer containing 7.5% methanol) coupled with a UV detector. To determine the percentage of the monomeric, the dimeric, the oligomeric, and the polymeric albumin (other than oligomeric albumin) in the non-nanoparticle portion, the supernatant is subjected to SEC using a mobile phase containing an aqueous portion and a miscible organic portion (such as an aqueous buffer containing 7.5% methanol) coupled with a UV detector.

Particle Size

The nanoparticles in the albumin-based rapamycin compositions described herein (such as pharmaceutical compositions) may have particular particle size ranges. Particle size impacts the dissolution rate of nanoparticles, controls the solubility of nanoparticles, and contributes to the functional behavior of the nanoparticles. The compositions described herein may have a defined particle size distribution for the nanoparticle. Particle size and/or particle size distribution may be determined according to known methods in the art. The particle size and/or distribution may be based on, for example a volume-weighted mean particle size or particle size distribution, or a Z-average mean particle size or particle size distribution.

The volume distribution can result in a larger proportion of the volume of nanoparticles in the composition being encompassed by nanoparticles having a higher diameter even if the quantity of particles in a particular size range (i.e., a particular "bin") is similar. To ensure that only drug-containing albumin-rapamycin nanoparticles are included in the analysis, the volume encompassed by small, round particles and/or large albumin aggregates may be excluded when determining volume-weighted particle sizes or distributions. For example, in some embodiments, the assessment of particle size, such as the average volume-weighted particle size of the nanoparticles in the composition, excludes those particles that are less than 20 nm in diameter in their longest dimension. In some embodiments, the assessment of particle size, such as the average volume-weighted particle size of the nanoparticles in the composition, excludes particles that are greater than 200 nm in diameter in their longest dimension.

In some embodiments, the volume-weighted mean particle size of the nanoparticles in the composition (such as a pharmaceutical composition) is less than about 200 nm, such as between about 50 nm and about 200 nm. In some embodiments, the volume-weighted mean particle size of the nanoparticles in the composition may be about 200 nm or less, about 190 nm or less, about 180 nm or less, about 170 nm or less, about 160 nm or less, about 150 nm or less, about 140 nm or less, about 130 nm or less, about 120 nm or less, about 110 nm or less, about 100 nm or less, about 90 nm or less, about 80 nm or less, about 70 nm or less, or about 60 nm. In some embodiments, the average volume-weighted particle size of the nanoparticles in the composition is about 60-70 nm, about 70-80 nm, about 80-90 nm, about 90-100 nm, about 100-110 nm, about 110-120 nm, about 120-130 nm, about 130-140 nm, about 140-150 nm, about 150-160 nm, about 160-180 nm, about 180-190 nm, about 190-200 nm, about 200-210 nm, about 210-220 nm, or about 220-230 nm.

In some embodiments, the volume-weighted average particle size of the nanoparticles is about 90-100 nm.

In some embodiments, the Z-average particle size of the nanoparticles in the composition (such as a pharmaceutical composition) is less than about 200 nm, such as between about 50 nm and about 200 nm. In some embodiments, the Z-average particle size of the nanoparticles in the composition may be about 200 nm or less, about 190 nm or less, about 180 nm or less, about 170 nm or less, about 160 nm or less, about 150 nm or less, about 140 nm or less, about 130 nm or less, about 120 nm or less, about 110 nm or less, about 100 nm or less, about 90 nm or less, about 80 nm or less, about 70 nm or less, or about 60 nm. In some embodiments, the Z-average particle size of the nanoparticles in the composition is about 60-70 nm, about 70-80 nm, about 80-90 nm, about 90-100 nm, about 100-110 nm, about 110-120 nm, about 120-130 nm, about 130-140 nm, about 140-150 nm, about 150-160 nm, about 160-180 nm, about 180-190 nm, about 190-200 nm, about 200-210 nm, about 210-220 nm, or about 220-230 nm.

In some embodiments, the Z-average particle size of the nanoparticles is about 85 nm to about 95 nm.

In some embodiments, 5% of the volume of the nanoparticles in the composition is encompassed by nanoparticles having a particle size less than about 65 nm, such as less than any of about 60 nm, 55 nm, 50 nm, or 45 nm. In some embodiments, 95% of the volume of the nanoparticles in the composition is encompassed by nanoparticles having a particle size less than about 180 nm, such as less than any of about 175 nm, 170 nm, 165 nm, 160 nm, 155 nm, 150 nm, 145 nm, 140 nm, 135 nm, or 130 nm. In some embodiments, 95% of the volume of the nanoparticles in the composition is encompassed by nanoparticles having a particle size greater than 45 nm, such as greater than about any of 50 nm, 55 nm, 60 nm, or 65 nm.

The physiochemical characteristics of a nanoparticle composition (such as a pharmaceutical composition) depends, in part, on the span of particle sizes. The distribution of a particle size distribution can be further defined by the polydispersity index (also termed the "dispersity"). The polydispersity index (PDI) describes the degree of non-uniformity of a size distribution of nanoparticles. In some embodiments, the nanoparticles in the composition have a polydispersity index of less than about 0.3. In some embodiments, the nanoparticles in the composition have a polydispersity index of less than about any of 0.3, 0.25, 0.2, 0.15, 0.1, or 0.05. In some embodiments, the nanoparticles in the composition have a polydispersity index of about any of 0.03-0.05, 0.05-0.07, 0.07-0.09, 0.09-0.11, 0.11-0.13, 0.13-0.15, 0.15-0.17, 0.17-0.2, 0.2-0.25, 0.25-0.3, 0.05-0.09, 0.09-0.13, 0.13-0.17, 0.17-0.25, 0.06-0.08, 0.08-0.12, 0.12-0.16, 0.16-0.18, 0.18-0.22, 0.22-0.28, 0.28-0.3, 0.06-0.12, 0.12-0.18, 0.18-0.3, 0.05-0.1, 0.1-0.15, 0.15-0.2, or 0.2-0.3. In some embodiments, the polydispersity index of the nanoparticles is about 0.14 to about 0.16.

The parameter $((Dv_{95}-Dv_5)/Dv_{50})$ describes the span of distribution of the particle sizes of the nanoparticles. $Dv_{50}$ refers to the volume-weighted median particle diameter. $Dv_{95}$ refers to the particle diameter where 95% of the volume of all nanoparticles is contained in nanoparticles with smaller diameters. $Dv_5$ refers to the particle diameter where 5% of the volume of all nanoparticles is contained in nanoparticles with smaller diameters. In some embodiments, the nanoparticles in the composition have a span of size distribution $((Dv_{95}-Dv_5)/Dv_{50})$ of about 0.8 to about 1.5. In some embodiments, the nanoparticles in the composition have a span of size distribution $((Dv_{95}-Dv_5)/Dv_{50})$ of about any of 0.7, 0.8, 0.9, 1, 1.1, 1.2, 1.3, 1.4, 1.5, 1.6, 1.7, or 1.8. In some embodiments, the nanoparticles in the composition have a span of size distribution $((Dv_{95}-Dv_5)/Dv_{50})$ of about any of 0.7-0.8. 0.8-0.9, 0.9-1, 1-1.1, 1.1-1.2, 1.2-1.3, 1.3-1.4, 0.8-1.0, 0.9-1.1, 1.0-1.2, 1.1-1.3, 1.2-1.4, 1.3-1.5, 0.7-1.0, 0.8-1.1, 0.9-1.2, 1.0-1.3, 1.1-1.4, 1.2-1.5, 0.7-1.1, 0.8-1.2, 0.9-1.3, 1.0-1.4, 1.1-1.5, 0.7-1.2, 0.8-1.3, 0.9-1.4, 0.9-1.5, 0.7-1.3, 0.8-1.4, 0.9-1.5, or 1.0-1.6. In some embodiments, the calculation of Dv95, Dv5, and/or Dv50 excludes particles having a diameter less than 20 nm in their longest dimension. In some embodiments, the calculation of Dv95, Dv5, and/or Dv50 excludes particles having a diameter greater than 200 nm in their longest dimension. In some embodiments, the nanoparticles in the composition have a span of size distribution $((Dv_{95}-Dv_5)/Dv_{50})$ of about 0.8 to about 1.2.

It is understood that the shape of a perfect sphere can be described by a single value, i.e., the radius or diameter. In some embodiments, the radius or diameter of a nanoparticle is expressed as the radius or diameter in the longest dimension of the nanoparticle. In some embodiments, the radius or diameter of a nanoparticle is expressed as the mean of a plurality of dimensions of the nanoparticle.

In some embodiments, the particle size is determined by a dynamic light scattering method. In some embodiments, the particle size is determined by volume weighted arithmetic mean particle diameter (D4,3) using a laser diffraction technique. In some embodiments, the particle size is determined by disc centrifugation methods. In some embodiments, the particle size is determined by tunable resistive pulse sensing (TRPS). In some embodiments, the particle size is determined by laser diffraction polarizing intensity differential scattering (LD-PIDS). LD-PIDS is particularly suitable for determining the size of nanoparticles that are in the submicron size range. In some embodiments, the particle size is determined by sucrose gradient centrifugation. In some embodiments, the particle size is determined by analytical centrifugation.

Weight Percentage of Albumin in the Nanoparticles

The nanoparticles of the compositions described herein include albumin in the nanoparticles (such as in a coating of the nanoparticles). In some embodiments, the nanoparticles in the composition are about 25% to about 45% albumin by weight. In some embodiments, the nanoparticles of the composition are about 25-26%, about 26-27%, about 27-28%, about 28-29%, about 29-30%, about 30-31%, about 31-32%, about 32-33%, about 33-34%, about 34-35%, about 35-36%, about 36-37%, about 37-38%, about 38-39%, about 39-40%, about 40-41%, about 41-42%, about 42-43%, about 43-44%, or about 44-45% (or any combination of such ranges) albumin by weight. In some embodiments, the nanoparticles of the composition comprise about 25%, 26%, 27%, 28%, 29%, 30%, 31%, 32%, 33%, 34%, 35%, 36%, 37%, 38%, 39%, 40%, 41%, 42%, 43%, 44%, or 45% albumin by weight.

In some embodiments, the nanoparticles comprises about 32% to about 38% albumin, by weight.

The weight percentage of albumin in the nanoparticles (that is the weight percentage of the nanoparticles that is albumin) refers to the weight of the albumin compared to the dry weight of the nanoparticles. Generally, to determine the weight percentage of the albumin in the nanoparticles, the amount of albumin in the nanoparticles and the total dry weight of the nanoparticles are determined. Amount of the albumin in the nanoparticles can be determined by, for example, chromatography, such as size exclusion chromatography, or spectrophotometric measurements. In some embodiments, the amount of the albumin in the nanoparticles is determined by isolating the nanoparticles in the composition from free albumin not associated in the nanoparticles (i.e., free of albumin in the non-nanoparticle portion of the composition) by, for example, ultracentrifugation or gel filtration chromatography. Subsequent methods of analysis of the albumin in the nanoparticles by, for example, reversed-phase chromatography or size exclusion chromatography followed by spectrophotometric measurements can be used to determine the amount of the albumin in the nanoparticles.

In some embodiments, the total dry weight of the nanoparticle portion is determined by addition of the amount of the albumin in the nanoparticles and the amount of the rapamycin in the nanoparticles. Amount of the rapamycin in the nanoparticle portion can be determined by, for example, chromatography, such as reversed-phase high performance liquid chromatography (RP-HPLC), spectrophotometric measurements, or mass spectrometric measurements. In some embodiments, the amount of the rapamycin in the nanoparticles is determined by isolating the nanoparticles of the composition by, for example, ultracentrifugation or gel filtration chromatography. Subsequent methods of analysis of the rapamycin in the nanoparticles by, for example, RP-HPLC followed by spectrophotometric measurement or mass spectrometric measurements can be used to determine the amount of the rapamycin in the nanoparticles.

In some embodiments, the amount of the albumin in the nanoparticle portion and amount of rapamycin in the nanoparticle portion are used to determine the total weight of the nanoparticle. Thus, in some embodiments, the dry weight of the nanoparticles is understood to exclude any substances that are not rapamycin or albumin. The weight percentage of the albumin in the nanoparticle portion can be calculated from the amount of the albumin in the nanoparticles and the total dry weight of the nanoparticle portion.

Weight Percentage of Rapamycin in the Nanoparticles

The nanoparticles of the compositions described herein include rapamycin in the nanoparticles (such as in a core of the nanoparticles). In some embodiments, the nanoparticles in the composition are about 50% to about 80% (such as about 50-52%, about 52-54%, about 54-56%, about 56-58%, about 58-60%, about 60-62%, about 62-64%, about 64-66%, about 66-68%, about 68-70%, about 70-72%, about 72-74%, about 74-76%, about 76-78%, or about 78-80%) rapamycin by weight. In some embodiments, the nanoparticles in the composition are about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 59%, or 80% rapamycin by weight.

In some embodiments, the nanoparticles comprise about 62% to about 68% rapamycin, by weight.

The weight percentage of rapamycin in the nanoparticles (that is the weight percentage of the nanoparticles that is rapamycin) refers to the weight of the rapamycin compared to the dry weight of the nanoparticles. Generally, to determine the weight percentage of the rapamycin in the nanoparticles, the amount of rapamycin in the nanoparticles and the total dry weight of the nanoparticles are determined. Amount of the rapamycin in the nanoparticles can be determined by any of the techniques described herein or known in the art, such as HPLC (e.g., reverse-phase HPLC).

In some embodiments, the amount of the albumin in the nanoparticle portion and amount of rapamycin in the nanoparticles are used to determine the total weight of the nanoparticles. Thus, in some embodiments, the dry weight of the nanoparticles is understood to exclude any substances that are not rapamycin or albumin. The weight percentage of the rapamycin in the nanoparticles can be calculated from the amount of the rapamycin in the nanoparticles and the total dry weight of the nanoparticles.

Weight Ratio of Albumin to Rapamycin

The nanoparticles of the composition described herein include rapamycin and albumin, which may be present in the nanoparticles at a weight ratio. The weight ratio of the albumin to rapamycin in the nanoparticles is determined by comparing the weight of albumin in the nanoparticles to the amount of rapamycin in the nanoparticles. The amount of albumin in the nanoparticles and the amount of rapamycin in the nanoparticles can be determined as discussed herein, and such methods may include separating the nanoparticles from the non-nanoparticle portion of the composition. In some embodiments, the weight ratio of the albumin to the rapamycin in the nanoparticles of the composition is about 1:1 to about 1:4 (such as about 1:1 to about 1:1.5, about 1:1.5 to about 1:2, about 1:2 to about 1:2.5, about 1.25 to about 1:3, about 1:3 to about 1:3.5, or about 1:3.5 to about 1:4, or any combination of such ranges). In some embodiments, the weight ratio of the albumin to the rapamycin in the nanoparticles is about 1:1, about 1:1.5, about 1:2, about 1:2.5, about 1:3, about 1:3.5, or about 1:4.

In some embodiments, the weight ratio of the albumin to the rapamycin in the nanoparticles is about 32:68 to about 38:62.

In some embodiments, the weight ratio of the albumin to the rapamycin in the nanoparticles of the composition does not change substantially upon storage (such as after a storage at about 25° C. for about any of 1 month, 3 months, 6 months, 9 months, 12 months, 18 months, 24 months, or 36 months). In some embodiments, the weight ratio of the albumin to the rapamycin in the nanoparticles of the composition does not increase by more than about any of 1%, 5%, 10%, 15%, 20%, 25%, 30%, 35%, 40%, 45%, or 50% after a period of storage. In some embodiments, the weight ratio of the albumin to the rapamycin in the nanoparticles of the composition does not decrease by more than about any of 1%, 5%, 10%, 15%, 20%, 25%, 30%, 35%, 40%, 45%, or 50%. In some embodiments, the period of storage is about any of 1 month, 3 months, 6 months, 9 months, 12 months, 18 months, 24 months, or 36 months. In some embodiments, the period of storage is at a temperature of about any of about 2° C. to about 8° C., about 15° C. to about 25° C., or about 25° C. to about 40° C., or about 2° C., about 4° C., about 8° C., about 15° C., about 25° C., about 30° C., or about 40° C. In some embodiments, the composition is stored in a dried form, such as a lyophilized form. In some embodiments, the stability is determined by assessing the composition before lyophilization and after reconstitution, wherein the period of storage is after lyophilization but before reconstitution.

The weight ratio of albumin to rapamycin in the compositions described herein (such as pharmaceutical compositions) may also be determined. In some embodiments, the weight ratio of the total albumin to the total rapamycin in the composition is about 1:1 to about 12:1 (such as about 1:1 to about 2:1, about 2:1 to about 3:1, about 3:1 to about 4:1, about 4:1 to about 5:1, about 5:1 to about 6:1, about 6:1 to about 7:1, about 7:1 to about 8:1, about 8:1 to about 9:1, or about 9:1 to about 10:1, or any combination of such ranges). In some embodiments, the weight ratio of the total albumin to the total rapamycin in the composition is about 1:1, about 2:1, about 3:1, about 4:1, about 5:1, about 6:1, about 7:1, about 8:1, about 9:1, about 10:1, about 11:1, or about 12:1.

In some embodiments, to determine the weight ratio of the total albumin to the total rapamycin in the composition, the amount albumin in the nanoparticles, the amount of albumin in the non-nanoparticle portion, the amount of rapamycin in the nanoparticles, and the amount of rapamycin in the non-nanoparticle portion of the composition are determined. As discussed herein, the amount of albumin in the nanoparticle portion can be determined by, for example, chromatography, such as size exclusion chromatography, or spectrophotometric measurements following isolation of the nanoparticles in the composition. In some embodiments, for example, following separation of the nanoparticles form the non-nanoparticle portion of the composition (such as by ultracentrifugation to pellet the nanoparticles or gel filtration chromatography), the amount of albumin in the resulting supernatant can be determined by similar methods discussed herein for determining the amount of albumin not in the nanoparticle portion. The amount of rapamycin in the nanoparticle portion can be determined by, for example, chromatography, such as RP-HPLC, spectrophotometric measurements, or mass spectrometric measurements. In some embodiments, for example, following separation of the nanoparticles from the non-nanoparticle portion (for example, by ultracentrifugation to pellet the nanoparticles or gel filtration chromatography), the amount of rapamycin in the resulting supernatant can be determined by similar methods discussed above for determining the amount of rapamycin not in the nanoparticle portion.

Albumin Concentration

The composition (such as the pharmaceutical composition) includes albumin that may be present in both the nanoparticles of the composition and the non-nanoparticle portion of the composition. It is possible to determine the concentration of albumin in the composition, the concentration of albumin in the in the non-nanoparticle portion of the composition, and/or the concentration of albumin in the composition that is in the nanoparticles.

The concentration of albumin in the composition that is in the nanoparticle refers to the amount of albumin that is in the nanoparticles of the composition given the volume of the entire composition. That is, the concentration of albumin in the composition that is in the nanoparticles is determined by excluding the albumin in the non-nanoparticle portion of the composition and calculating the concentration using the volume of the composition being assessed. For example, in a pharmaceutical composition comprising 100 mg rapamycin and 800 mg albumin in a 20 mL injection, the nanoparticles are separated from the composition and the mg quantity of albumin in the nanoparticles is assessed. The concentration of albumin in the composition that is in the nanoparticles is then understood to be the assessed mg value of the albumin in the nanoparticle portion in a 20 mL volume. In some embodiments, the composition is in a dried form, such as a lyophilized form. In the case of a dried (such as lyophilized) form, the concentration is assessed by the volume that the dried composition is to be reconstituted in.

In some embodiments, the concentration of albumin in the composition (such as a pharmaceutical composition) is about 30 mg/mL to about 100 mg/mL (for example, about 30-35 mg/mL, about 35-40 mg/mL, about 40-45 mg/mL, about 45-50 mg/mL, about 50-55 mg/mL, about 55-60 mg/mL, about 60-65 mg/mL, about 65-70 mg/mL, about 70-75 mg/mL, about 75-80 mg/mL, about 80-85 mg/mL, about 85-90 mg/mL, about 90-95 mg/mL, about or about 95-100 mg/mL, or any combination of such ranges). In some embodiments, the concentration of albumin in the composition is about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL. In some embodiments, the concentration of albumin in the composition is about 1 mg/mL to about 100 mg/mL (e.g., about 1 mg/mL to about 5 mg/mL, about 5 mg/mL to about 10 mg/mL, about 10 mg/mL to about 20 mg/mL, about 20 mg/mL to about 30 mg/mL, about 30-35 mg/mL, about 35-40 mg/mL, about 40-45 mg/mL, about 45-50 mg/mL, about 50-55 mg/mL, about 55-60 mg/mL, about 60-65 mg/mL, about 65-70 mg/mL, about 70-75 mg/mL, about 75-80 mg/mL, about 80-85 mg/mL, about 85-90 mg/mL, about 90-95 mg/mL, about or about 95-100 mg/mL, or any combination of such ranges). In some embodiments, the composition is in a dried form, such as a lyophilized form. In the case of a dried (such as lyophilized) form, the concentration is assessed by the volume that the dried composition is to be reconstituted in.

In some embodiments, the concentration of albumin in the composition is about 35 mg/mL to about 45 mg/mL.

In some embodiments, the concentration of albumin in the non-nanoparticle portion of the composition (such as a pharmaceutical composition) is about 30 mg/mL to about 100 mg/mL (for example, about 30-35 mg/mL, about 35-40 mg/mL, about 40-45 mg/mL, about 45-50 mg/mL, about 50-55 mg/mL, about 55-60 mg/mL, about 60-65 mg/mL, about 65-70 mg/mL, about 70-75 mg/mL, about 75-80 mg/mL, about 80-85 mg/mL, about 85-90 mg/mL, about 90-95 mg/mL, about or about 95-100 mg/mL, or any combination of such ranges). In some embodiments, the concentration of albumin in the non-nanoparticle portion of the composition is about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL. In some embodiments, the composition is in a dried form, such as a lyophilized form. In the case of a dried (such as lyophilized) form, the concentration is assessed by the volume that the dried composition is to be reconstituted in.

In some embodiments, the concentration of albumin in the non-nanoparticle portion of the nanoparticle composition is about 35 mg/mL to about 45 mg/mL.

In some embodiments, the concentration of albumin in the composition (such as a pharmaceutical composition) that is in the nanoparticles of the composition is about 1 mg/mL to about 10 mg/mL (such as about 1-1.2 mg/mL, about 1.2-1.5 mg/mL, about 1.5-1.8 mg/mL, about 1.8-2 mg/L, about 2-2.5 mg/mL, about 2.5-3 mg/mL, about 3-3.5 mg/mL, about 3.5-4 mg/mL, about 4-4.5 mg/mL, or about 4.5-5 mg/mL, about 5-6 mg/mL, about 6-7 mg/mL, about 7-8 mg/mL, about 8-9 mg/mL, or about 9-10 mg/mL, or any combination of such ranges). In some embodiments, the concentration of albumin in the composition (such as a pharmaceutical composition) that is in the nanoparticles of the composition is about 1 mg/mL, about 1.2 mg/mL, about 1.5 mg/mL, about 1.8 mg/mL, about 2 mg/mL, about 2.5 mg/mL, about 3 mg/mL, about 3.5 mg/mL, about 4 mg/mL, about 4.5 mg/mL, or about 5 mg/mL.

In some embodiments, the concentration of albumin in the composition that is in the nanoparticles of the composition is about 2.2 mg/mL to about 2.6 mg/mL.

In any of the described embodiments, the concentration of albumin in the composition, whether the total composition, the nanoparticles of the composition, or the non-nanoparticle portion, may be assessed by any suitable methodology. In some embodiments, the concentration is assessed after separating the nanoparticle portion from the non-nanoparticle portion. In some embodiments, the concentration of albumin is determined by size exclusion chromatography.

Rapamycin Concentration

The composition (such as the pharmaceutical composition) includes rapamycin that may be present in both the nanoparticles of the composition and the non-nanoparticle portion of the composition. It is possible to determine the concentration of rapamycin in the composition, the concentration of rapamycin in the in the non-nanoparticle portion of the composition, and/or the concentration of rapamycin in the composition that is in the nanoparticles.

Rapamycin may take the form of trans-rapamycin or cis-rapamycin. As one skilled in the art would understand, the rapamycin concentrations discussed herein refer to the total of the cis and trans form of rapamycin.

In some embodiments, the concentration of rapamycin in the composition is about 1 mg/mL to about 100 mg/mL (such as about 1-5 mg/mL, about 5-10 mg/mL, about 10-15 mg/mL, about 15-20 mg/mL, about 20-25 mg/mL, about 25-30 mg/mL, about 30-40 mg/mL, about 40-50 mg/mL, about, about 50-60 mg/mL, about 60-70 mg/mL, about 70-80 mg/mL, about 80-90 mg/mL, or about 90-100 mg/mL, or any combination of these ranges). In some embodiments, the concentration of rapamycin in the composition is about 1 mg/mL to about 15 mg/mL (such as about 1-2 mg/mL, about 2-3 mg/mL, about 3-4 mg/mL, about 4-5 mg/mL, about 5-6 mg/mL, about 6-7 mg/mL, about 7-8 mg/mL, about 8-9 mg/mL, about, about 9-10 mg/mL, about 10-11 mg/mL, about 11-12 mg/mL, about 13-14 mg/mL, or about 14-15 mg/mL, or any combination of these ranges). In some embodiments, the concentration of rapamycin in the composition is about 1 mg/ml, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, or about 15 mg/mL.

In some embodiments, the concentration of rapamycin in the composition is about 4 mg/mL to about 6 mg/mL, such as about 5 mg/mL. In some embodiments, the concentration of rapamycin in the composition is about 9 mg/mL to about 11 mg/mL, such as about 10 mg/mL.

In some embodiments, the concentration of rapamycin in the composition that is in the nanoparticles is about 1 mg/mL to about 100 mg/mL (such as about 1-5 mg/mL, about 5-10 mg/mL, about 10-15 mg/mL, about 15-20 mg/mL, about 20-25 mg/mL, about 25-30 mg/mL, about 30-40 mg/mL, about 40-50 mg/mL, about, about 50-60 mg/mL, about 60-70 mg/mL, about 70-80 mg/mL, about 80-90 mg/mL, or about 90-100 mg/mL, or any combination of these ranges). In some embodiments, the concentration of rapamycin in the composition that is in the nanoparticles of the composition is about 1 mg/mL to about 15 mg/mL (such as about 1-2 mg/mL, about 2-3 mg/mL, about 3-4 mg/mL, about 4-5 mg/mL, about 5-6 mg/mL, about 6-7 mg/mL, about 7-8 mg/mL, about 8-9 mg/mL, about, about 9-10 mg/mL, about 10-11 mg/mL, about 11-12 mg/mL, about 13-14 mg/mL, or about 14-15 mg/mL, or any combination of these ranges). In some embodiments, the concentration of rapamycin in the composition that is in the nanoparticles of the composition is about 1 mg/ml, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, or about 15 mg/mL.

In some embodiments, the concentration of rapamycin in the composition that is in the nanoparticles of the composition is about 4 mg/mL to about 6 mg/mL, such as about 5 mg/mL. In some embodiments, the concentration of rapamycin in the composition that is in the nanoparticles of the composition is about 9 mg/mL to about 11 mg/mL, such as about 10 mg/mL.

In some embodiments, the concentration of rapamycin in the non-nanoparticle portion of the composition is less than about 55 µg/mL, such as about 1-5 µg/mL, about 5-10 µg/mL, about 10-15 µg/mL, about 15-20 µg/mL, about 20-25 µg/mL, about 25-30 µg/mL, about 30-35 µg/mL, about 35-40 µg/mL, about 40-45 µg/mL, about 45-50 µg/mL, or about 50-55 µg/mL.

In some embodiments, the concentration of rapamycin in the non-nanoparticle portion of the composition is about 33 µg/mL to about 39 µg/mL.

In some embodiments, the rapamycin concentration in the nanoparticles of the composition is determined by an HPLC assay. Briefly, the nanoparticle portion of the composition (such as a pharmaceutical composition) is separated from the non-nanoparticle portion of the composition, for example by ultracentrifugation, for example, at 50,000 rpm for about 40 minutes at 25° C., or gel filtration chromatography. The supernatant is removed and the pellet is gently washed with water twice. The pellet is then dispersed in a volume of 50:50 acetonitrile:water solution, for example 3.0 ml, by sonication. The sample is further diluted to ensure a homogenous solution is formed. The sample is analyzed on an HPLC system equipped with, for example, a UV absorbance detector and data acquisition system set up with a Phenomenex, Curosil PFP guard column (4.6 mm×30 mm, 5 µm particle size) and a Phenomenex, Curosil PFP analytical column (4.6 mm×250 mm, 5 µm particle size). Chromatograms are generated with the UV absorbance detector set at 228 nm. Comparison to analysis of rapamycin standards is used to determine the concentration of rapamycin in the nanoparticle portion of the composition.

The rapamycin concentration in the nanoparticles is determined by the amount of rapamycin in the nanoparticle portion of the composition in the same volume of the original sample. In the case of a dried (such as lyophilized) composition, the rapamycin concentration in the nanoparticle portion (such as in the nanoparticles) is determined by the volume that the composition is to be reconstituted in.

Distribution of Albumin and Rapamycin in the Nanoparticles and the Non-Nanoparticle Portion The nanoparticle compositions (such as a pharmaceutical composition) described herein contain albumin in both the nanoparticle portion and the non-nanoparticle portion. Similarly, the nanoparticle compositions comprises rapamycin in both the nanoparticle portion and the non-nanoparticle portion. The distribution of the total albumin and the total rapamycin in the nanoparticles and the non-nanoparticle portions can be a distinguishing characteristic of the nanoparticle composition.

In some embodiments, about 85% or more (such as about 90% or more, about 95% or more, about 97% or more, about 97.5% or more, about 98% or more, about 98.5% or more, about 99% or more, or about 99.5% or more) of the total rapamycin in the composition is in the nanoparticles. For example, in some embodiments, about 85-90%, about 90-95%, about 95-97%, about 97-97.5%, about 97.5-98%, about 98-98.5%, about 98.5-99%, about 99-99.5%, or about 99.5-99.9% (or any combination of such ranges) of the total rapamycin (by weight) in the composition is in the nanoparticles. In some embodiments, about 85% to about 95% of the total rapamycin (by weight) in the composition is in the nanoparticles. In some embodiments, less than about 95% of the total rapamycin (by weight) in the composition is in the nanoparticles. The balance of rapamycin in the composition that is not in the nanoparticles is in the non-nanoparticle portion of the composition.

In some embodiments, more than about 98% of the total rapamycin (by weight) in the composition is in the nanoparticles.

The percentage of the total rapamycin in the composition in the nanoparticles can be determined by reversed-phase high performance liquid chromatography (RP-HPLC) or other suitable methods. For example, the nanoparticles can first be separated from the non-nanoparticle portion, for example by ultracentrifugation or gel filtration chromatography. Subsequently, the amount of the rapamycin in the nanoparticles can then be determined by assaying with quantitative RP-HPLC methods. The amount of the rapamycin measured from the isolated nanoparticles can then be compared with the amount of the total rapamycin in the composition to calculate the percentage of the total rapamycin in the composition that is in the nanoparticles. In some embodiments, the amount of the rapamycin in the nanoparticles can be determined by measuring the amount of the rapamycin not associated with the nanoparticles. For example, following ultracentrifugation to pellet the nanoparticles, the amount of rapamycin in the resulting supernatant can be assayed by RP-HPLC methods to determine the amount of rapamycin in solution (i.e., not associated with nanoparticles, such as the non-nanoparticle portion). The amount of the rapamycin measured from the supernatant and the amount of the total rapamycin in the composition can be used to calculate the percentage of the total rapamycin in the composition that is in the nanoparticles.

In some embodiments, about 80% or more (such as about 85% or more, about 90% or more, about 95% or more, about 97% or more, about 97.5% or more, about 98% or more, about 98.5% or more, about 99% or more, or about 99.5% or more) of the total albumin (by weight) in the composition is in the non-nanoparticle portion of the composition. For example, in some embodiments, about 80-90%, about 85-90%, about 90-95%, about 95-97%, about 97-97.5%, about 97.5-98%, about 98-98.5%, about 98.5-99%, about 99-99.5%, or about 99.5-99.9% (or any combination of such ranges) of the total albumin (by weight) in the composition is in the non-nanoparticle portion of the composition. The balance of total albumin in the composition that is not in the non-nanoparticle portion of the composition is in the nanoparticles of the composition.

In some embodiments, about 95% or more of the total albumin (by weight) in the composition is in the non-nanoparticle portion of the composition.

The quantity of the albumin in the nanoparticles can be determined from nanoparticles separated from the nanoparticle portion by assaying for albumin content by size exclusion chromatography or other suitable methods. The albumin in the non-nanoparticle portion can be determined by assaying the supernatant using a similar size exclusion chromatography method or other suitable methods.

Portion of Unbound Rapamycin

Rapamycin in the non-nanoparticle portion of the composition may reversibly bind albumin in the non-nanoparticle portion of the composition. Thus, the rapamycin in the non-nanoparticle portion may be considered in two states: bound rapamycin (which is bound to albumin in the non-nanoparticle portion) and free rapamycin (which is not bound to albumin). These rapamycin states are in addition to the rapamycin that is in the nanoparticles, but not in the non-nanoparticle portion. The compositions (such as pharmaceutical compositions) provided herein may have low percentages of free rapamycin (i.e., unbound to albumin) in the non-nanoparticle portion. In some embodiments, the amount of free albumin in the non-nanoparticle portion of the composition is stable after a period of storage or after lyophilization and subsequent reconstitution of the composition.

In some embodiments, about 5% or less (such as about 4% or less, about 3% or less, about 2.5% or less, about 2% or less, about 1.5% or less, about 1% or less, about 0.5% or less, about 0.2% or less, about 0.1% or less, about 0.05% or less, about 0.01% or less, or about 0.005% or less) of the total rapamycin in the composition (such as a pharmaceutical composition) is free rapamycin. In some embodiments, about 0.001% to about 5% (such as about 0.001-0.01%, about 0.01-0.05%, about 0.05-0.1% about 0.1-0.2%, about 0.2-0.5%, about 0.5-1%, about 1-1.5%, about 1.5-2%, about 2-2.5%, about 2.5-3%, about 3-4%, or about 4-5%) of the total rapamycin in the composition is free rapamycin.

In some embodiments, less than about 1% of the rapamycin in the composition is free rapamycin.

In some embodiments, the percentage of free rapamycin in the composition (such as a pharmaceutical composition) does not increase by more than about 5%, 10%, 15%, 20%, 25%, 30%, 35%, 40%, 45%, 50%, 55%, 60%, 65%, 70%, 75%, 80%, 85%, 90%, 95%, 100%, or more than about 100% after a period of storage. In some embodiments, the period of storage is about any of 1 month, 3 months, 6 months, 9 months, 12 months, 18 months, 24 months, or 36 months. In some embodiments, the period of storage is at a temperature of about 2° C. to about 8° C., about 15° C. to about 25°, or about 25° C. to about 40° C., or about 2° C., about 4° C., about 8° C., about 15° C., about 25° C., about 30° C., or about 40° C. In some embodiments, the compositions is stored in a dried form, such as a lyophilized form. In some embodiments, the change in percentage of free rapamycin in the composition (such as a pharmaceutical composition) is determined by assessing the composition before lyophilization and after reconstitution, wherein the period of storage is after lyophilization but before reconstitution.

Concentrations of rapamycin in the composition may be assessed as described throughout this application. To determine the percentage of free rapamycin in the composition, in some embodiments, the nanoparticles of the composition may first be separated from the non-nanoparticle portion of the composition. The separated non-nanoparticle portion may include both free (not albumin-bound) rapamycin and bound rapamycin (albumin-bound rapamycin). In some embodiments, size exclusion chromatography may be used to separate free rapamycin from bound rapamycin in the non-nanoparticle portion. In some embodiments, the free rapamycin is separated from the bound rapamycin in the supernatant by a centrifugal filter unit, such as a MICROCON®, AMICON®, or similar device. In some embodiments, the free rapamycin is separated from the bound rapamycin in the supernatant by a centrifugal filter unit with a 10 kDa filter. In some embodiments, the proportion of free rapamycin as compared to bound rapamycin in the composition is determined by assessing the amount of rapamycin in the flow-through of the centrifugal filter unit as compared to the rapamycin in the retentate of the centrifugal filter unit and the rapamycin in the nanoparticle portion of the composition.

Nanoparticle Morphology

In some embodiments, the nanoparticles of the composition have certain morphological attributes. The morphology of nanoparticles in an albumin-based rapamycin nanoparticle composition (such as a pharmaceutical composition) can affect particle solubility, dissolution rate, and disintegration kinetics. The rate of dissolution of nanoparticles relates to the availability of drug in humans. Conventional lab-scale processes would provide largely spherical particles due to slower rates of evaporation and less aggressive conditions. The nanoparticles of the composition have reduced sphericity, and are more irregularly shaped than what was previously observed. The increased irregularity and reduced sphericity of the nanoparticle compositions described herein are due in part to faster evaporation conditions. Nanoparticles having irregular shape have greater surface area-to-volume ratios compared to those nanoparticles that are spherical. The increased surface area would change the dissolution profile, allowing nanoparticles to rapidly dissolve under appropriate conditions.

In some embodiments, the composition comprises nanoparticles that are of irregular shape (i.e., are non-spherical shape). In some embodiments, the composition comprises nanoparticles that have a non-smooth surface. In some embodiments, the composition comprises nanoparticles that are of irregular shape and have a non-smooth surface. In some embodiments, the composition comprises nanoparticles that have a high degree of rugosity. In some embodiments, the composition comprises nanoparticles that are of irregular shape and have a high degree of rugosity. In some embodiments, the composition comprises nanoparticles wherein the thickness of the albumin coating on said nanoparticles is about 3 nanometers to about 7 nanometers as measured by cryogenic transmission electron microscopy (cryo-TEM). In some embodiments, the composition comprises nanoparticles that are of irregular shape and have an albumin coating with a thickness of about 5 to about 7 nanometers as measured by cryo-TEM. In some embodiments, the composition comprises nanoparticles having an albumin coating with a thickness of about any of 3 nm, 4 nm, 5 nm, 5.5 nm, 6 nm, 6.5 nm, 7 nm, 8 nm, or 9 nm as measured by cryo-TEM. In some embodiments, the composition comprises nanoparticles having an albumin coating with a thickness of about any of 3-4 nm, 4-5 nm, 5-6 nm, 6-7 nm, 7-8 nm, 8-9 nm, 3-5 nm, 5-7 nm, 7-9 nm, 5-5.5 nm, 5.5-6 nm, 6-6.5 nm, 6.5-7 nm, 4.5-5.5 nm, 5.5-6.5 nm, 6.5-7.5 nm, 5-6.5 nm, or 5.5-7 nm nanometers as measured by cryo-TEM.

In some embodiments, the composition comprises nanoparticles of irregular shape and comprises nanoparticles that are spherical. In some embodiments, about 20% or more (such as about 20% or more, about 25% or more, about 30% or more, about 35% or more, about 40% or more, about 45% or more, about 50% or more, about 55% or more, or about 60% or more) of the nanoparticles in the composition are non-spherical (such as irregularly shaped). The assessment of nanoparticles as spherical or non-spherical (such as irregularly shaped) is understood in the art and can be determined by inspection of a sample population of the nanoparticle composition by suitable techniques such as cryo-TEM.

The morphology of the nanoparticles may additionally or alternatively be defined based on the variance of the radius passing through the nanoparticles. For example, if the radius of nanoparticle varies by about 10% or more (such as about 15% or more, about 20% or more, or about 25% or more), the nanoparticle can be considered irregularly shaped. It is understood that sample populations of a nanoparticle composition will comprise small, regularly shaped particles of, for example, albumin. These particles are not included in the assessment of nanoparticle samples for sphericity or morphology. Thus, in some embodiments, the percentage of non-spherical (such as irregularly shaped) and spherical nanoparticles is determined by observing only those particles between about 20 nm and about 200 nm.

Figure 3:
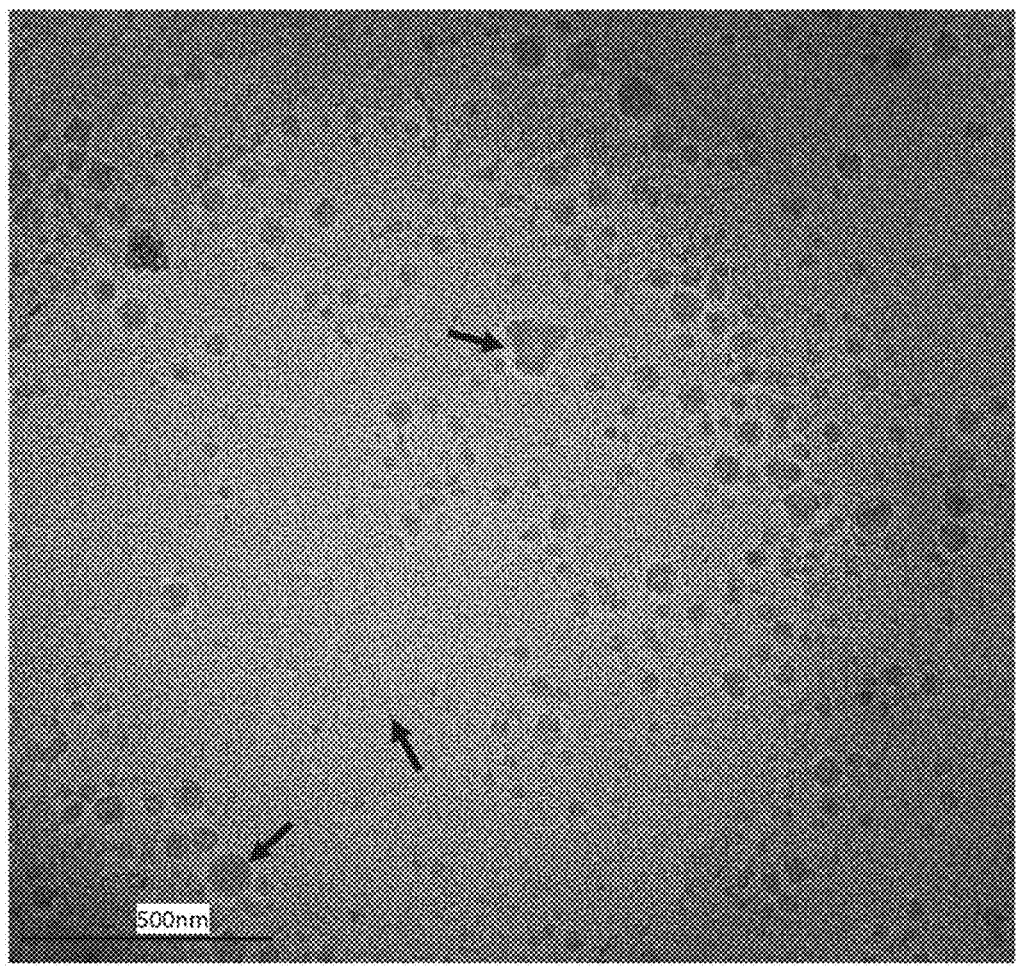
FIG. 3 depicts a Cryo-TEM image at 21,000× magnification of lot #1 with an observed irregularly shaped particle with nonuniform internal density (top arrow), a spherical particle (bottom arrow) with uniform density, and a small round particle (middle arrow).

The shape (such as morphology) of the nanoparticles in the composition can be determined by microscopy methods, such as, cryogenic transmission electron microscopy (cryo-TEM). Thickness of the albumin coating on the nanoparticles can be measured by suitable microscopy methods, such as, cryo-TEM. For example, the composition can be rapidly cooled to cryogenic temperatures following reconstitution of the composition to form a vitreous form of the reconstituted composition which can then be analyzed. The nanoparticles of the composition remain in their native structure during cryo-TEM sample preparation and image recording. In some embodiments, cryo-TEM records the native structure of the nanoparticles of the composition. The shape of nanoparticles can be assessed, for example, by observing the cryo-TEM image of the nanoparticle composition. In FIG. 3, for example, the bottom arrow points to a spherical particle, and the top arrow points to a non-spherical (or irregularly shaped) particle. In some embodiments, a nanoparticle may be assessed as non-spherical (such as irregularly shaped) by drawing a line through the nanoparticle on a cryo-TEM image along the longest dimension that intersects the center of the nanoparticle, and drawing a line through the same nanoparticle on the cryo-TEM image along the shortest dimension that intersects the center of the nanoparticle. If the line along the longer dimension is significantly longer than the line along the shorter dimension, the nanoparticle is assessed as non-spherical (such as irregularly shaped). The nanoparticle is considered non-spherical if the ratio of the shortest particle dimension to the longest particle dimension is less than 0.9.

In an exemplary method, cryo-TEM images are analyzed by an image analysis software, such as MIPAR. First, the image is loaded into the system and the scale is calibrated per the cryo-TEM scale. The image is rendered with a median and StDev filter for course particle identification. After the filters are applied, the nanoparticle outlines are identified. The application is adjusted for the resolution, thickness of the particle outlines, and separation between particles to optimize particle identification. After an acceptable image of separate particles is generated, the area, caliper diameter (maximum diameter of nanoparticles) and minimum diameter are calculated. The ratio of the minimum and maximum diameters is calculated to generate the percentage of how spherical the particles are. A ratio of 1 would indicate a perfect sphere or circle cross section, and a ratio of less than 1 indicates an increasingly non-spherical nanoparticle. Nanoparticles with a ratio of the shortest diameter to the longest diameter of less than 0.9 are assessed as non-spherical (such as irregularly shaped). In some embodiments, greater than about 10% (such as greater than 10%, about 15%, about 20%, or about 25%, about 30%) of the nanoparticles in the composition are irregularly shaped or non-spherical, wherein a nanoparticle is irregularly shaped or non-spherical when the ratio of the maximum diameter and the minimum diameter of the particular nanoparticle is less than 0.9. In some embodiments, greater than about 20% of the nanoparticles in the composition are non-spherical, wherein a nanoparticle non-spherical when the ratio of the maximum diameter and the minimum diameter of the particular nanoparticle is less than 0.9. In some embodiments, the average ratio of the maximum diameter and the minimum diameter of the nanoparticles in the nanoparticle composition is less than 0.9 (such as less than about 0.9, less than about 0.85, or less than about 0.80).

In some embodiments, the thickness of the albumin coating on the nanoparticles can be calculated based on measured parameters of the nanoparticles, including, the albumin-to-rapamycin ratio of the nanoparticles.

In some embodiments, the average surface-area-to-volume ratio of the nanoparticles in the composition is more than about $6/\bar{d}$ wherein $\bar{d}$ is the average diameter of the nanoparticles (i.e. the surface-to-volume ratio of a perfect sphere having the same particle size as the nanoparticles). In some embodiments, the surface-to-volume ratio of the nanoparticles is more than about any of 1.1, 1.2, 1.3, 1.4, 1.5, 1.6, 1.7, 1.8, 1.9, 2, 2.1, 2.2, 2.3, 2.4, 2.5, 3, 4, or 5 times $6/\bar{d}$. The surface-to-volume ratio of the nanoparticles is related to the average diameter (and thus radius) of the nanoparticles. As used herein, "diameter of the nanoparticle"

refers to the diameter of the sphere that has the same volume or weight as the nanoparticle. "Average diameter of the nanoparticles" is the average of the diameters of all nanoparticles in the composition. Surface-to-volume ratios of the nanoparticles can be determined, for example, by microscopy methods, such as, cryogenic transmission electron microscopy (cryo-TEM), atomic force microscopy, or Fourier transform infrared spectroscopy.

In some embodiments, the nanoparticles of the composition have an amorphous (i.e., non-crystalline morphology). The amorphous morphology of the nanoparticles of the composition can be determined in dry nanoparticles. For example, the nanoparticles may be separated from the non-nanoparticle portion of the composition, and drying the separated nanoparticles. In some embodiments, the composition itself may have an amorphous morphology. For example, the composition as a whole may be dried (for example, by lyophilizing the composition) and the morphology of the composition is determined to be amorphous (i.e., non-crystalline). Crystallinity of the nanoparticles and/or the composition may be determined, for example, by X-ray diffraction.

Rapamycin and Albumin Interaction in Nanoparticles

The albumin associated with the rapamycin in the nanoparticles of the composition can exhibit certain through-space interactions. In some embodiments, the vinyl chain of the rapamycin interacts with the albumin in the nanoparticles (for example through aromatic rings of the albumin). This interaction may be determined, for example, by a change in the chemical environment of the rapamycin vinyl chain compared to free rapamycin. For example, a chemical shift of the rapamycin vinyl chain protons may be detected by NMR spectroscopy.

Surface Potential

Particle surface potential such, as zeta-potential, can play an important role in preventing the particles from aggregating when suspended in a liquid. For example, populations of nanoparticles having higher magnitude zeta potential can have improved stability due to increased electrostatic repulsion between particles, and therefore reduced aggregation.

In some embodiments, the nanoparticles in the composition (such as the pharmaceutical composition) have a zeta-potential of about −25 mV to about −50 mV. In some embodiments, the nanoparticles in the composition have a zeta-potential of about −36 mV. In some embodiments, the nanoparticles in the composition have a zeta-potential of about any of −50 mV, −49 mV, −48 mV, −47 mV, −46 mV, −45 mV, −44 mV, −43 mV, −42 mV, −41 mV, −40 mV, −39 mV, −38 mV, −37 mV, −36 mV, −35 mV, −34 mV, −33 mV, −32 mV, −31 mV, −30 mV, −29 mV, −28 mV, −27 mV, −26 mV, or −25 mV. In some embodiments, the nanoparticles in the composition have a zeta-potential of any of about −50 mV to about −45 mV, about −40 mV to about −35 mV, about −35 mV to about −30 mV, about −30 mV to about −25 mV, about −44 mV to about −42 mV, about −42 mV to about −40 mV, about −40 mV to about −38 mV, about −38 mV to about −36 mV, about −36 mV to about −34 mV, about −34 mV to about −32 mV, about −32 mV to about −30 mV, about −30 mV to about −28 mV, about −45 mV to about −42 mV, about −42 mV to about −39 mV, about −39 mV to about −36 mV, about −36 mV to about −33 mV, about −33 mV to about −30 mV, about −30 mV to about −27 mV, about −44 mV to about −40 mV, about −40 mV to about −36 mV, about −36 mV to about −32 mV, about −32 mV to about −28 mV, about −45 mV to about −35 mV, about −35 mV to about −25 mV, about −45 mV to about −25 mV, or about −40 mV to about −30 mV, or any combination of such ranges.

In some embodiments, the nanoparticles have a zeta potential of about −33 mV to about −39 mV.

In some embodiments, the zeta potential of the nanoparticles does not change substantially upon storage (such as after a storage at about 25° C. for about any of 1 month, 3 months, 6 months, 9 months, 12 months, 18 months, 24 months, or 36 months). In some embodiments, the magnitude of the zeta potential of the nanoparticles does not increase by more than about any of about 1 mV, 2 mV, 3 mV, 4 mV, 5 mV, 6 mV, 7 mV, 8 mV, 9 mV, or 10 mV after a period of storage. In some embodiments, the magnitude of the zeta potential of the nanoparticles does not decrease by more than about any of about 1 mV, 2 mV, 3 mV, 4 mV, 5 mV, 6 mV, 7 mV, 8 mV, 9 mV, or 10 mV. In some embodiments, the absolute magnitude of the zeta potential of the nanoparticles is within any of about 1%, 2%, 3%, 4%, 5%, 6%, 7%, 8%, 9%, 10%, 11%, 12%, 13%, 14%, 15%, 16%, 17%, 18%, 19%, or 20% after a period of storage. In some embodiments, the period of storage is about any of 1 month, 3 months, 6 months, 9 months, 12 months, 18 months, 24 months, or 36 months. In some embodiments, the period of storage is at a temperature of about any of about 2° C. to about 8° C., about 15° C. to about 25°, or about 25° C. to about 40° C., or about 2° C., about 4° C., about 8° C., about 15° C., about 25° C., about 30° C., or about 40° C. In some embodiments, the composition is stored in a dried form, such as a lyophilized form. In some embodiments, the change in zeta potential is determined by assessing the composition before lyophilization and after reconstitution, wherein the period of storage is after lyophilization but before reconstitution.

Zeta-potential of the nanoparticles can be determined by techniques, such as, for example, microelectrophoresis, electrophoretic light scattering, or dynamic electrophoretic mobility. In some embodiments, the zeta-potential of the nanoparticles can be determined by tunable resistive pulse sensing (TRPS).

Rapamycin Crystallinity

Rapamycin in the nanoparticles of the composition (such as the pharmaceutical composition) may be amorphous (i.e., non-crystalline). Methods for determining the crystalline status of the rapamycin in the nanoparticles may be determined for example by Raman spectroscopy, polarized light microscopy, differential scanning calorimetry (DSC), modulated differential scanning calorimetry (mDSC), Fourier transform infrared (FTIR) spectroscopy, or nuclear magnetic resonance (NMR) spectroscopy. In some embodiments, the nanoparticles are separated from the non-nanoparticle portion of the composition to measure the rapamycin in the nanoparticles.

In some embodiments, the rapamycin in the nanoparticles of the composition is non-crystalline or amorphous after a period of storage (such as after a storage at about 25° C. for about any of 1 month, 3 months, 6 months, 9 months, 12 months, 18 months, 24 months, or 36 months). In some embodiments, the rapamycin is non-crystalline immediately after reconstitution. In some embodiments, the rapamycin is non-crystalline immediately after reconstitution after a period of storage in a lyophilized form. In some embodiments, the period of storage is about any of 1 month, 3 months, 6 months, 9 months, 12 months, 18 months, 24 months, or 36 months. In some embodiments, the period of storage is at a temperature of about any of about 2° C. to about 8° C., about 15° C. to about 25°, or about 25° C. to about 40° C., or about 2° C., about 4° C., about 8° C., about 15° C., about 25° C., about 30° C., or about 40° C. In some embodiments, the composition is stored in a dried form, such as a lyophilized form.

The crystalline state of the rapamycin in the nanoparticles can be determined by techniques, such as, x-ray diffraction and/or polarized light microscopy. In some embodiments, Raman spectroscopy is used to determine the crystalline state of the rapamycin. In some embodiments, the nanoparticles are separated from the non-nanoparticle portion by, for example, ultracentrifugation or gel permeation chromatography. The isolated nanoparticles may then dried by, for example, lyophilization. Subsequent analysis of the nanoparticles by x-ray diffraction can determine the crystalline state of the rapamycin in the nanoparticles. Non-crystalline or amorphous rapamycin in the nanoparticles will exhibit broad scattering halos, indicative of an amorphous material (e.g., non-crystalline). Crystalline rapamycin in the nanoparticles will exhibit numerous well-defined scattering peaks.

Polarized light microscopy of a suspension of nanoparticles can also be used to determine the crystalline state of the rapamycin in the nanoparticles. A birefringence test can be performed with an optical microscope to determine if the rapamycin in the nanoparticles is crystalline or non-crystalline. Absence of birefringence indicates that the rapamycin remained amorphous. In some embodiments, the crystalline state of the rapamycin in the nanoparticles can be assessed by both x-ray diffraction and polarized light microscopy tests.

In some embodiments, the crystalline state of the rapamycin in the nanoparticles is assessed by Raman spectroscopy. In some embodiments, the crystalline state of the rapamycin in the nanoparticles is assessed by second harmonic generation microscopy. In some embodiments, the crystalline state of the rapamycin in the nanoparticles is assessed by X-ray powder diffraction. In some embodiments, the crystalline state of the rapamycin in the nanoparticles is assessed by differential scanning calorimetry. In some embodiments, the crystalline state of the rapamycin in the nanoparticles is assessed by thermal gravimetric analysis. In some embodiments, the crystalline state of the rapamycin in the nanoparticles is assessed by one or more techniques selected from the group consisting of X-ray diffraction, X-ray powder diffraction, light microscopy, polarized light microscopy, Raman spectroscopy, second harmonic generation microscopy, differential scanning calorimetry, and thermal gravimetric analysis. Any of the described methods of assessing the crystalline state of the rapamycin in the nanoparticles have a limit of detection. For example, if the limit of detection of a method is about 1%, then if less than 1% of the rapamycin is crystalline the assay will not detect crystalline rapamycin and the composition will be assessed as amorphous. In some embodiments, the crystalline state of the rapamycin in the nanoparticles is assessed by a method with a limit of detection of about 1% crystalline rapamycin or less. In some embodiments, if the crystalline state of the rapamycin in the nanoparticles is assessed by a method with a limit of detection of about 1% crystalline rapamycin or less, and the method detects no crystalline rapamycin, then the rapamycin is assessed to be amorphous.

In some embodiments, the crystalline state of the rapamycin in the nanoparticles is assessed by qualitatively determining the presence of one or more crystalline forms of rapamycin. In some embodiments, the crystalline state of the rapamycin in the nanoparticles is assessed by qualitatively determining two crystalline forms of rapamycin. In some embodiments, the crystalline state of the rapamycin in the nanoparticles is assessed by quantitatively determining the presence of one or more crystalline forms of rapamycin. In some embodiments the crystalline state of the rapamycin in the nanoparticles is assessed by quantitatively determining two crystalline forms of rapamycin. In some embodiments, the crystalline state of the rapamycin in the nanoparticles is assessed by qualitatively and quantitatively determining one or more crystalline forms of rapamycin. In some embodiments, the crystalline state of the rapamycin in the nanoparticles is assessed by qualitatively and quantitatively determining two crystalline forms of rapamycin.

Impurities and Degradation Products of the Nanoparticle Compositions

Rapamycin contains a macrocyclic lactone ring that can spontaneously yield a ring-opened degradant. A common ring-opened degradant of rapamycin is seco-rapamycin. Ring-opened derivatives of rapamycin may exhibit substantially changed or reduced physiological effect, for example, reduced immunosuppressive activity and loss of mTOR binding. The concentration of rapamycin degradant, such as the concentration of seco-rapamycin, or the rate of formation of rapamycin degradant, such as the rate of formation of seco-rapamycin, may affect the shelf life of the compositions and/or their suitability as pharmaceutical compositions. Commercial batches of the compositions (such as pharmaceutical compositions) described herein may be especially prone to the formation of rapamycin degradation products. The production of commercial batches involves longer production times, which may result in the formation of additional rapamycin degradation products.

In some embodiments, about 3% or less (such as about 2.5% or less, about 2% or less, about 1.5% or less, about 1% or less, or about 0.5% or less) of the sum of rapamycin degradant and rapamycin in the composition (such as the pharmaceutical composition) is the rapamycin degradant. In some embodiments, about 3% or less (such as about 2.5% or less, about 2% or less, about 1.5% or less, about 1% or less, or about 0.5% or less) of the sum of seco-rapamycin and rapamycin in the composition is seco-rapamycin. In some embodiments, about 0.1-3% (such as about 0.1-0.2%, about 0.2-0.3%, about 0.3-0.4%, about 0.4-0.5%, about 0.5-0.7%, about 0.7-1%, about 1-1.5%, about 1.5-2%, about 2-2.5%, or 2.5-3%, or any combination of such ranges) of the sum of rapamycin degradant and rapamycin in the composition is the rapamycin degradant. In some embodiments, the composition is substantially free of rapamycin degradants. In some embodiments, about 0.1-3% (such as about 0.1-0.2%, about 0.2-0.3%, about 0.3-0.4%, about 0.4-0.5%, about 0.5-0.7%, about 0.7-1%, about 1-1.5%, about 1.5-2%, about 2-2.5%, or 2.5-3%, or any combination of such ranges) of the sum of seco-rapamycin and rapamycin in the composition is seco-rapamycin. In some embodiments, the composition is substantially free of seco-rapamycin. In some embodiments, the concentration of seco-rapamycin is substantially unchanged from a time point before lyophilization of the composition to immediately after reconstitution of the composition.

In some embodiments, the sum of seco-rapamycin and rapamycin in the nanoparticles is less than 1% seco-rapamycin, by weight.

In some embodiments, the sum of seco-rapamycin and rapamycin in the nanoparticles is about 0.5% to about 1% seco-rapamycin, by weight.

In some embodiments, the concentration of seco-rapamycin as compared to the sum of seco-rapamycin and rapamycin in the composition does not change substantially upon storage (such as after a storage at about 25° C. for about any of 1 month, 3 months, 6 months, 9 months, 12 months, 18 months, 24 months, or 36 months). In some embodiments, the concentration of seco-rapamycin as compared to the sum of seco-rapamycin and rapamycin in the composition does not increase by more than about any of about 1%, 5%, 10%, 15%, 20%, 25%, 30%, 35%, 40%, 45%, 50%, 55%, 60%, 65%, 70%, 75%, 80%, 85%, 90%, 95%, or 100% after a period of storage. In some embodiments, the period of storage is about any of 1 month, 3 months, 6 months, 9 months, 12 months, 18 months, 24 months, or 36 months. In some embodiments, the period of storage is at a temperature of about any of about 2° C. to about 8° C., about 15° C. to about 25°, or about 25° C. to about 40° C., or about 2° C., about 4° C., about 8° C., about 15° C., about 25° C., about 30° C., or about 40° C. In some embodiments, the composition is stored in a dried form, such as a lyophilized form. In some embodiments, the change in seco-rapamycin concentration as compared to the sum of seco-rapamycin and rapamycin in the composition is determined by assessing the composition before lyophilization and after reconstitution, wherein the period of storage is after lyophilization but before reconstitution.

The amount of rapamycin can be determined by methods described above. The amount of seco-rapamycin can be determined by known methods, including, for example, chromatography, such as reversed-phase high performance liquid chromatography (RP-HPLC), spectrophotometric measurements, or mass spectrometric measurements.

The nanoparticle composition may include other impurities, such as prolylrapamycin, 14-epi-rapamycin, rapamycin aldehyde, or other individual hydrophobic small-molecule impurities. These impurities may be detected, and optionally quantified, using RP-HPLC. Preferably (with the exception of seco-rapamycin discussed above), no single impurity makes up more than 1%, more than 0.8%, more than 0.6%, more than 0.4%, more than 0.3%, or more than 0.2% of the weight of rapamycin in the composition. In some embodiments, the sum of rapamycin impurities (including seco-rapamycin), makes up less than 5%, less than 4%, less than 3%, less than 2%, or less than 1% of the total amount of rapamycin in the composition.

Recovery of Rapamycin Following Filtration

Loss of rapamycin following filtration, such as after 0.2 micron filtration, is a measure of the fraction of rapamycin mass associated with larger nanoparticles, such as nanoparticles larger than 200 nm of the individual nanoparticle. This measure can be more sensitive to the large nanoparticle fraction than particle sizing techniques. The albumin-based rapamycin nanoparticle composition described herein in some embodiments has a high rapamycin recovery following filtration with a 0.2 micron filter.

In some embodiments, the composition (such as the pharmaceutical composition) has a rapamycin recovery of about 80% or more, about 81% or more, about 82% or more, about 83% or more, about 84% or more, about 85% or more, about 86% or more, about 87% or more, about 88% or more, about 89% or more, about 90% or more, about 91% or more, about 92% or more, about 93% or more, about 94% or more, about 95% or more, about 96% or more, about 97% or more, about 98% or more, about 99% or more, about 99.5% or more, about or more following a 0.2 micron filtration (for example, after formation of the nanoparticles or immediately after reconstitution). In some embodiments, the composition has a rapamycin recovery of about 80-85%, about 85-90%, about 90-95%, about 95-98%, about 98-99%, about 99%-99.5%, or about 99.5%-100% following a 0.2 micron filtration (for example, after formation of the nanoparticles or immediately after reconstitution).

In some embodiments, the composition has a rapamycin recovery of at least about any of 80%, 85%, 90%, 95%, 98%, 99%, 99.5%, or more following a 0.2 micron filtration after a period of storage (for example, under storage at about 25° C. for 1 month, or under accelerated storage conditions such as 40° C. for 1 month). In some embodiments, the composition has a rapamycin recovery of about any of 80-85%, 85-90%, 90-95%, 95-98%, 80-90%, 90-98%, 85-95%, 85-98%, 80-95%, 80-98%, 98-99%, 99%-99.5%, or 99.5%-100% following a 0.2 micron filtration after a period of storage. In some embodiments, the period of storage is about any of 1 month, 3 months, 6 months, 9 months, 12 months, 18 months, 24 months, or 36 months. In some embodiments, the period of storage is at a temperature of about any of about 2° C. to about 8° C., about 15° C. to about 25°, or about 25° C. to about 40° C., or about 2° C., about 4° C., about 8° C., about 15° C., about 25° C., about 30° C., or about 40° C. In some embodiments, the composition is stored in a dried form, such as a lyophilized form.

The recovery of the rapamycin in the composition following 0.2 micron filtration can be determined by measuring the amount of rapamycin in the composition that passes through a 0.2 micron filter. In some embodiments, the amount of rapamycin can be measured by RP-HPLC techniques as described herein, or any other suitable method. In some embodiments, to determine the recovery, the amount of rapamycin that remains in the composition following 0.2 micron filtration is compared with the total amount of rapamycin in the composition prior to filtration. In some embodiments, the recovery is assessed following storage of the composition at elevated temperatures, for example, for at least about 24 hours at about 40° C.

In Vitro Release Kinetics

The albumin-based rapamycin nanoparticle compositions described herein in some embodiments have a particular in vitro release kinetic behavior. The release rate of rapamycin from the albumin-based rapamycin nanoparticle compositions may be estimated using an in vitro release kinetic assay. In this assay, the particle size and intensity of light scattered by the particles are measured by DLS over time following a reduction in particle concentration. In some embodiments, the release kinetics are determined by diluting the pharmaceutical composition in a 0.9% saline solution. In some embodiments, the release kinetics are determined by diluting the pharmaceutical composition in a 5% human albumin solution.

In some embodiments, the in vitro release kinetics is determined by using the UV absorption dissolution method. In some embodiments, an in vitro release kinetics assay measures the absorbance of the composition over a period of time immediately following a reduction in particle concentration. In some embodiments, the absorbance of the composition is measured using a UV-Vis spectrophotometer. In some embodiments, the absorbance of the composition is measured using a UV-Vis spectrophotometer equipped with a 295 nm cut-off filter. In some embodiments, the absorbance of the composition is measured at 340 nm. In some embodiments, the composition is diluted to 25 µg/ml, as measured by the concentration of rapamycin. In some embodiments, the composition is diluted to 5 µg/ml, as measured by the concentration of rapamycin.

In some embodiments, the in vitro release is determined using the dynamic light scattering method. In some embodiments, the in vitro release kinetics assay measures the intensity of light scattered by the composition over a period of time immediately following a reduction in particle concentration. In some embodiments, the light scattering intensity of the composition is measured using a dynamic light scattering apparatus, where the concentration of rapamycin released from the nanoparticles is calculated from the intensity of scattered light. In some embodiments, the intensity of light scattered is measured at a scattering angle of 173°.

In some embodiments, the mean value of percent released rapamycin from a nanoparticle composition (such as a pharmaceutical composition) at 5 μg/ml in 0.9% sodium chloride solution, as measured by the rapamycin concentration, after about 1 minute is about 100%. In some embodiments, the mean value of percent released rapamycin from a nanoparticle composition (such as a pharmaceutical composition) at 25 μg/ml in 0.9% sodium chloride solution, as measured by the rapamycin concentration, after about 1 minute is about 30%. In some embodiments, the solubility of rapamycin is about 10-20 μg/ml after reconstitution in a 0.9% sodium chloride solution. In some embodiments, the solubility of rapamycin is about 16.1 μg/ml after reconstitution in a 0.9% sodium chloride solution.

Physical Stability

In some embodiments, the nanoparticle compositions described herein (such as pharmaceutical compositions) are physically stable. In some embodiments, the nanoparticles are physically stable immediately after reconstitution. In some embodiments, the nanoparticles are physically stable for at least about any of 6 hours, 12 hours, 24 hours, 36 hours, 48 hours, 72 hours or more hours upon storage (for example under storage at room temperature, under refrigerated conditions, or under accelerated storage condition (for example at about 40° C.)). In some embodiments, the nanoparticles are physically stable for at least about any of 1 month, 3 months, 6 months, 9 months, 12 months, 18 months, 24 months, or 36 months upon storage. In some embodiments, stability is determined by the magnitude of change in the measurement of one or more characteristics or properties of the composition, such as any of the characteristics or properties of the compositions described throughout this application.

Stability of nanoparticles in the pharmaceutical composition can be assayed by a number of techniques, including, but not limited to, visual inspection (such as visual appearance, visible shape, visible sphericity, visual color, visible particulate matter), microscopy imaging, and loss of potency. In some embodiments, sedimentation is indicative of a loss of stability. Sedimentation can be assessed by visual inspection and/or microscopy (such as cross-polarization microscopy). Microscopy can be used to determine the size of aggregated sediment particles. In some embodiments, the stability of the pharmaceutical composition can be assessed by the crystalline state of the rapamycin in the nanoparticles. In some embodiments, increased presence of nanoparticles with crystalline rapamycin is indicative of a loss of stability. In some embodiments, stability of the pharmaceutical composition can be assessed by a loss of potency following 0.2 μm filtration of the composition. In some embodiments, loss of potency is indicative of a loss of stability. In some embodiments, loss of in vitro potency is assessed for a composition (such as a pharmaceutical composition) following 0.2 μm filtration of the composition. In some embodiments, loss of in vivo potency is assessed for a composition (such as a pharmaceutical composition) following 0.2 μm filtration of the composition. In some embodiments, stability measurements are assessed following a period of accelerated storage, for example, after about 24 hours at about 40° C. In some embodiments, stability measurements are assessed following a period of storage. In some embodiments, the period of storage is about any of 1 month, 3 months, 6 months, 9 months, 12 months, 18 months, 24 months, or 36 months. In some embodiments, the period of storage is at a temperature of about any of about 2° C. to about 8° C., about 15° C. to about 25°, or about 25° C. to about 40° C., or about 2° C., about 4° C., about 8° C., about 15° C., about 25° C., about 30° C., or about 40° C. In some embodiments, the composition is stored in a dried form, such as a lyophilized form. In some embodiments, the stability is determined by assessing the composition before lyophilization and after reconstitution, wherein the period of storage is after lyophilization but before reconstitution.

In some embodiments, the pharmaceutical composition shows no visible particulate matter (for example immediately after reconstitution). In some embodiments, the pharmaceutical composition shows no visible particulate matter for at least about any of 6 hours, 12 hours, 24 hours, 36 hours, 48 hours, 72 hours or more hours upon storage (for example under storage at room temperature, under refrigerated conditions, or under accelerated storage condition (for example at 40° C.)). In some embodiments, the pharmaceutical composition shows no visible particulate matter after storage for 8 hours at about 5° C. followed by storage for 8 hours at about 25° C., or after storage for about 24 hours at about 25° C.

In some embodiments, the pharmaceutical composition shows no sedimentation (for example immediately after reconstitution). In some embodiments, the pharmaceutical composition shows no sedimentation for at least about any of 6 hours, 12 hours, 24 hours, 36 hours, 48 hours, 72 hours or more hours upon storage (for example under storage at room temperature, under refrigerated conditions, or under accelerated storage condition (for example at about 40° C.)). In some embodiments, the pharmaceutical composition shows no sedimentation after storage for 8 hours at about 5° C. followed by storage for 8 hours at about 25° C., or after storage for about 24 hours at about 25° C.

In some embodiments, the pharmaceutical composition shows no crystallinity of the rapamycin in the nanoparticles (e.g., by polarized light microscopy) (for example immediately after reconstitution). In some embodiments, the pharmaceutical composition shows no crystallinity of the rapamycin in the nanoparticles (e.g., by polarized light microscopy) for at least about any of 6 hours, 12 hours, 24 hours, 36 hours, 48 hours, 72 hours or more hours upon storage (for example under storage at room temperature, under refrigerated conditions, or under accelerated storage condition (for example at about 40° C.)). In some embodiments, the pharmaceutical composition shows no crystallinity of the rapamycin in the nanoparticles (e.g., by polarized light microscopy) after storage for 8 hours at about 5° C. followed by storage for 8 hours at about 25° C., or after storage for about 24 hours at about 25° C.

In some embodiments, the pharmaceutical composition shows no loss of potency (e.g., by in vitro or in vivo testing) following a 0.2 micron filtration (for example immediately after reconstitution). In some embodiments, the pharmaceutical composition shows no loss of potency (e.g., by in vitro or in vivo testing) for at least about any of 6 hours, 12 hours, 24 hours, 36 hours, 48 hours, 72 hours or more hours upon storage (for example under storage at room temperature, under refrigerated conditions, or under accelerated storage condition (for example at about 40° C.)). In some embodiments, the pharmaceutical composition shows no loss of potency (e.g., by in vitro or in vivo testing) after storage for 8 hours at about 5° C. followed by storage for 8 hours at about 25° C., or after storage for about 24 hours at about 25° C.

In some embodiments, the pharmaceutical composition is stable for a period of storage and stability is assessed by the lack of a statistically significant change in any of one or more measured properties of the composition, such as the oligomeric profile of the total composition, the oligomeric profile of the nanoparticle portion of the composition, the volume-weighted particle size of the nanoparticles in the composition, the weight ratio of albumin to rapamycin in the nanoparticle portion of the composition, the morphology of the nanoparticles, such as the sphericity of the nanoparticles, the percentage of seco-rapamycin as compared to the sum of seco-rapamycin and rapamycin by weight, the surface potential of the nanoparticles such as the zeta potential, or the distribution of albumin and/or rapamycin in the nanoparticle and/or non-nanoparticle portion of the composition. In some embodiments, the period of storage is about any of 1 month, 3 months, 6 months, 9 months, 12 months, 18 months, 24 months, or 36 months. In some embodiments, the period of storage is at a temperature of about any of about 2° C. to about 8° C., about 15° C. to about 25°, or about 25° C. to about 40° C., or about 2° C., about 4° C., about 8° C., about 15° C., about 25° C., about 30° C., or about 40° C. In some embodiments, the composition is stored in a dried form, such as a lyophilized form. In some embodiments, the stability is determined by assessing the composition before lyophilization and after reconstitution, wherein the period of storage is after lyophilization but before reconstitution.

Osmolality

The isotonicity or, alternatively, the degree of hyperosmolality of an injection as compared to blood or tissue osmolality can affect the pharmaceutical properties of a composition upon injection. In some embodiments, the nanoparticle compositions described herein (such as the pharmaceutical composition) has an osmolality of about 280 mOsm/kg to about 400 mOSm/kg, about 280 mOsm/kg to about 300 mOsm/kg, about 300 mOsm/kg to about 350 mOsm/kg (such as about 300-310 mOsm/kg, about 310-320 mOsm/kg, about 320-330 mOsm/kg, about 330-340 mOsm/kg, or about 340-350 mOsm/kg, or any combination of such ranges), or about 350 mOsm/kg to about 400 mOsm/kg. In some embodiments, the osmolality of the pharmaceutical composition is between about 280 mOsm/kg to about 400 mOSm/kg, about 280 mOsm/kg to about 300 mOsm/kg, about 300 mOsm/kg to about 350 mOsm/kg (such as about 300-310 mOsm/kg, about 310-320 mOsm/kg, about 320-330 mOsm/kg, about 330-340 mOsm/kg, or about 340-350 mOsm/kg, or any combination of such ranges), or about 350 mOsm/kg to about 400 mOsm/kg immediately after reconstitution. In some embodiments, the composition (such as a pharmaceutical composition) has an osmolality of about 325 mOsm/kg, 326 mOsm/kg, 327 mOsm/kg, 328 mOsm/kg, 329 mOsm/kg, 330 mOsm/kg, 331 mOsm/kg, 332 mOsm/kg, 333 mOsm/kg, 334 mOsm/kg, 335 mOsm/kg, 336 mOsm/kg, 337 mOsm/kg, 338 mOsm/kg, 339 mOsm/kg, 340 mOsm/kg, 341 mOsm/kg, 342 mOsm/kg, 343 mOsm/kg, 344 mOsm/kg, 345 mOsm/kg, 346 mOsm/kg, 347 mOsm/kg or 348 mOsm/kg.

In some embodiments, the osmolality of the composition is about 280 mOsm/kg to about 400 mOsm/kg. In some embodiments, the osmolality of the composition is about 325 mOsm/kg to about 340 mOsm/kg.

Osmolality of a composition (such as a pharmaceutical composition) can be assayed by a number of methods, including, for example, by use of a vapor pressure depression osmometer, a membrane osmometer, or a freezing point depression osmometer.

In some embodiments, the osmolality of the composition does not change substantially upon storage (such as after a storage at about 25° C. for about any of 1 month, 3 months, 6 months, 9 months, 12 months, 18 months, 24 months, or 36 months). In some embodiments, the osmolality of the composition does not change by more than any of about 5 mOsm/kg, 10 mOsm/kg, 15 mOsm/kg, 20 mOsm/kg, 25 mOsm/kg, 30 mOsm/kg, 35 mOsm/kg, 40 mOsm/kg, 45 mOsm/kg, or 50 mOsm/kg during a period of storage. In some embodiments, the change in osmolality of the composition is less than about any of 50 mOsm/kg, 45 mOsm/kg, 40 mOsm/kg, 35 mOsm/kg, 30 mOsm/kg, 25 mOsm/kg, 20 mOsm/kg, 15 mOsm/kg, 10 mOsm/kg, or 5 mOsm/kg after a period of storage. In some embodiments, the period of storage is about any of 1 month, 3 months, 6 months, 9 months, 12 months, 18 months, 24 months, or 36 months. In some embodiments, the period of storage is at a temperature of about any of about 2° C. to about 8° C., about 15° C. to about 25°, or about 25° C. to about 40° C., or about 2° C., about 4° C., about 8° C., about 15° C., about 25° C., about 30° C., or about 40° C. In some embodiments, the composition is stored in a dried form, such as a lyophilized form. In some embodiments, change in osmolality is determined by assessing the composition before lyophilization and after reconstitution, wherein the period of storage is after lyophilization but before reconstitution.

Viscosity

High concentration compositions, such as pharmaceutical compositions, can exhibit high viscosities which may not be desirable for pharmaceutical purposes. High viscosity can affect administration, syringe draw, and injection properties. In some embodiments, the nanoparticle composition (such as the pharmaceutical composition) described herein has a viscosity of between about 1.20 centipoise (cP) to about 1.50 cP (such as about 1.20-1.25 cP, about 1.25-1.30 cP, about 1.30-1.35 cP, about 1.35-1.40 cP, about 1.40-1.45 cP, or about 1.45-1.50 cP, or any combination of such ranges). In some embodiments, the viscosity of the composition is about 1.20 cP to about 1.50 cP (such as about 1.20-1.25 cP, about 1.25-1.30 cP, about 1.30-1.35 cP, about 1.35-1.40 cP, about 1.40-1.45 cP, or about 1.45-1.50 cP, or any combination of such ranges) for at least about any of 1 month, 2 months, 3 months, 4 months, 5 months, 6 months, or more months upon storage (for example under storage at room temperature, under refrigerated conditions, or under accelerated storage condition (for example at about 40° C.)). In some embodiments, the composition has a viscosity of about 1.25 cP, 1.26 cP, 1.27 cP, 1.28 cP, 1.29 cP, 1.30 cP, 1.31 cP, 1.32 cP, 1.33 cP, 1.34 cP, 1.35 cP, 1.36 cP, 1.37 cP, 1.38 cP, 1.39 cP, 1.40 cP, 1.41 cP, 1.42 cP, 1.43 cP, 1.44 cP, or 1.45 centipoise. In some embodiments, the viscosity is assessed after reconstitution of a dried form (such as a lyophilized form) of the composition. In some embodiments, the viscosity is assessed in the volume of the composition that is for injection in a subject. In some embodiments, the viscosity is assessed at room temperature, such as between about 20° C. and about 27° C. In some embodiments, the viscosity is assessed at room temperature, such as about 20° C., about 22° C., about 25° C., or about 27° C.

In some embodiments, the viscosity of the composition is about 1.3 cP to about 1.35 cP. In some embodiments, the viscosity is assessed at room temperature, such as about 20° C., about 22° C., about 25° C., or about 27° C.

Viscosity (such as dynamic viscosity) of a composition (such as a pharmaceutical composition) can be assayed by a number of suitable methods, including, for example, by use of a viscometers and/or rheometers.

In some embodiments, the composition (such as a pharmaceutical composition) is made to be isotonic with blood by the addition of a suitable tonicity modifier, such as glycerol.

Composition pH

In some embodiments, the composition (such as a pharmaceutical composition) is formulated to have a pH in the range of about 4.5 to about 9.0, for example pH ranges of any one of about 4.5-5.0, about 5.0-5.5, about 5.5-6.0, about 6.0-6.5, about 6.5-7.0, about 7.0-7.5, about 7.5-8.0, about 8.0-8.5, or about 8.5-9.0, or any combination of such ranges. In some embodiments, the pH of the composition (such as a pharmaceutical composition) is formulated to no less than about 6, including for example no less than about any one of 6.5, 7, or 8. In some embodiments, the pH of the composition is formulated to about 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0.

In some embodiments, the pH of the composition is about 6.7 to about 6.8.

Pharmaceutically acceptable buffers, acids, or bases may be added to the composition to obtain the desired pH.

Dried Composition and Reconstitution

A liquid composition or pharmaceutical composition containing the nanoparticles can be dried, for example by lyophilization. The dried powder or cake can then be reconstituted by adding an aqueous liquid (such as a saline solution) to the dried composition, and mixing the composition to re-suspend the nanoparticles. The dried composition generally has a white or yellow appearance, and becomes a white or yellow translucent suspension upon reconstitution.

The dried composition preferably has about 5% or less water content by weight, such as about 4% or less, about 3% or less, about 2% or less, or about 1% or less water content by weight.

The morphology of the nanoparticles in the composition, among other properties including particle size, can influence the reconstitution time of the dried (such as lyophilized) composition. Reconstitution time is determined from the time an aqueous solution (such as a sodium chloride solution) is added to the dried/lyophilized composition until no remaining dried material remains, wherein the material is gently mixed if not fully dissolved after 5 minutes. In some embodiments, the nanoparticle compositions (such as pharmaceutical compositions) have particular reconstitution times. In some embodiments, the compositions reconstitute after addition of a suitable solution in less than 20 minutes, less than 18 minutes, less than 16 minutes, less than 14 minutes, less than 12 minutes, less than 10 minutes, less than 9 minutes, less than 8 minutes, less than 7 minutes, or less than 6 minutes. In some embodiments, the compositions reconstitute after addition of a suitable solution between about 5 minutes and about 20 minutes, or between about 5 minutes and about 14 minutes, such as about 5-7 minutes, about 7-9 minutes, about 9-12 minutes, or about 12-14 minutes, or about any of 5, 6, 7, 8, 9, 10, 11, 12, 13, or 14 minutes. In some embodiments, the reconstitution time is assessed by adding a solution of saline, such as 0.9% saline, to the lyophilized cake and measuring the time with gentle agitation for the composition to reconstitute.

The reconstituted composition should be free or essentially free from visible particulates upon observation by the unaided eye (i.e., without a microscope or other device for magnified examination). The reconstituted composition may optionally be inspected by microscopy, which can be used to determine the number of non-nanoparticle particles (for example, a number of particles about 10 μm in diameter or more, or a number of particles about 25 μm in diameter or more) in the composition. In some embodiments, the composition has a density of particles having a diameter of about 10 μm or more of no more than about 5000, no more than about 4000, no more than about 3000, no more than about 2000, or no more than about 1000, about 100 to about 6000, about 100 to about 500, about 500 to about 1000, about 1000 to about 2000, about 2000 to about 3000, about 3000 to about 4000, or about 4000 to about 5000 particles per 20 mL sample of the composition. In some embodiments, the composition has a density of particles having a diameter of about 25 μm or more of no more than about 500, no more than about 400, no more than about 300, no more than about 200, or no more than about 100, about 10 to about 600, about 10 to about 50, about 50 to about 100, about 100 to about 200, about 200 to about 300, about 300 to about 400, or about 400 to about 500 particles per 20 mL sample of the composition.

Albumin Stabilizers in the Composition

The compositions (such as pharmaceutical compositions) described herein in various embodiments comprise stabilizers for the carrier protein (i.e., albumin, such as human albumin). The presence of albumin stabilizer can improve shelf life, stability (such as maintaining the oligomeric profile of the albumin in the composition, for example, by preventing polymerization of the albumin), can act as a preservative, and other properties of the composition desirable for pharmaceutical applications. The presence of albumin stabilizer, such as a caprylic acid derivative (e.g., sodium caprylate), can also help form the rapamycin-nanoparticle complex. In some embodiments, the albumin stabilizer is selected from one or more of amino acids, salts of amino acids, derivatives of amino acids, fatty acids, salts of fatty acids, derivatives of fatty acids, sugars, polyols, and osmolytes. In some embodiments, the albumin stabilizer comprises caprylate or caprylic acid derivative, for example sodium caprylate. In some embodiments, the albumin stabilizer comprises sodium acetyltryptophanate or tryptophan. In some embodiments, the albumin stabilizer comprises sodium caprylate and sodium acetyltryptophanate. In some embodiments, the composition comprises about 0.05 mM to about 500 mM albumin stabilizer, such as about 0.05-0.1 mM, about 0.1-0.2 mM, about 0.2-0.5 mM, about 0.5-1 mM, about 1-2.5 mM, about 2.5-5 mM, about 5-10 mM, about 10-25 mM, about 25-50 mM, about 50-100 mM, about 100-150 mM, about 150-200 mM, about 200-250 mM, about 250 mM-300 mM, about 300-400 mM, or about 400-500 mM, or any combination of such ranges, of the albumin stabilizer. In some embodiments, the composition comprises between about 0.05 mM and about 500 mM of a caprylic acid derivative, eg., sodium caprylate (such as about 0.05-0.1 mM, about 0.1-0.2 mM, about 0.2-0.5 mM, about 0.5-1 mM, about 1-2.5 mM, about 2.5-5 mM, about 5-10 mM, about 10-25 mM, about 25-50 mM, about 50-100 mM, about 100-150 mM, about 150-200 mM, about 200-250 mM, about 250 mM-300 mM, about 300-400 mM, or about 400-500 mM caprylic acid derivative, e.g., sodium caprylate). In some embodiments, the composition comprises between about 0.05 mM and about 500 mM tryptophan derivative, e.g., N-acetyltryptophanate (such as about 0.05-0.1 mM, about 0.1-0.2 mM, about 0.2-0.5 mM, about 0.5-1 mM, about 1-2.5 mM, about 2.5-5 mM, about 5-10 mM, about 10-25 mM, about 25-50 mM, about 50-100 mM, about 100-150 mM, about 150-200 mM, about 200-250 mM, about 250 mM-300 mM, about 300-400 mM, or about 400-500 mM tryptophan derivative, e.g., N-acetyltryptophanate).

Concentrations of Organic Solvents in the Nanoparticle Compositions

The nanoparticle compositions (such as pharmaceutical compositions) described herein may be prepared using one or more organic solvents, which are generally removed from an emulsion during the manufacturing process. Because organic solvents may be toxic, the suitability of a composition for pharmaceutical application can depend, in part, on sufficient removal of organic solvents from the final composition. The compositions (such as pharmaceutical compositions) may exhibit different properties and characteristics (including those described throughout this application) depending upon the method of removing and the extent of removal of the one or more organic solvents from the emulsion. For example, removal of one or more organic solvents from an emulsion by evaporation may affect the properties and characteristics of the resulting nanoparticle composition (such as a pharmaceutical composition) depending upon the stringency of the evaporation step (i.e., the extent of remaining organic solvent(s)). Thus, in some embodiments, described herein are compositions (such as pharmaceutical compositions) that comprise concentrations of organic solvents, such as ethanol, methanol, isopropanol, butanol, tert-butanol, chloroform, or others, and any combinations thereof. For example, in some embodiments, the composition (such as a pharmaceutical composition) comprises chloroform/ethanol, chloroform/tert-butanol, or chloroform/isopropanol.

In some embodiments, the nanoparticle composition (such as the pharmaceutical composition) comprises less than about 400 µg/ml total organic solvent, such as any of less than about 400 µg/ml, 380 µg/ml, 360 µg/ml, 340 µg/ml, 320 µg/ml, 300 µg/ml, 280 µg/ml, 260 µg/ml, 240 µg/ml, 220 µg/ml, 200 µg/ml, 180 µg/ml, 160 µg/ml, 140 µg/ml, 120 µg/ml, 100 µg/ml, 80 µg/ml, 60 µg/ml, 40 µg/ml, or 20 µg/ml total organic solvent. In some embodiments, the composition (such as a pharmaceutical composition) comprises about 20-100 µg/ml, about 100-200 µg/ml, about 200-300 µg/ml, or about 300-400 µg/ml (or a combination of such ranges) of total organic solvent. In some embodiments, the nanoparticle composition (such as the pharmaceutical composition) comprises less than about 400 ppm total organic solvent, such as any of less than about 400 ppm, 380 ppm, 360 ppm, 340 ppm, 320 ppm, 300 ppm, 280 ppm, 260 ppm, 240 ppm, 220 ppm, 200 ppm, 180 ppm, 160 ppm, 140 ppm, 120 ppm, 100 ppm, 80 ppm, 60 ppm, 40 ppm, 20 ppm, 10 ppm, 5 ppm, or 1 ppm total organic solvent. In some embodiments, the composition (such as a pharmaceutical composition) comprises about 0.1-1 ppm, about 1-5 ppm, about 5-10 ppm, about 10-20 ppm, about 20-100 ppm, about 100-200 ppm, about 200-300 ppm, or about 300-400 ppm (or a combination of such ranges) of total organic solvent. In some embodiments, the composition is substantially free of organic solvent. In some embodiments, the nanoparticle composition (such as the pharmaceutical composition) comprises less than about 20 µg/ml total organic solvent, such as any of less than about 20 µg/ml, 19 µg/ml, 18 µg/ml, 17 µg/ml, 16 µg/ml, 15 µg/ml, 14 µg/ml, 13 µg/ml, 12 µg/ml, 11 µg/ml, 10 µg/ml, 9 µg/ml, 8 µg/ml, 7 µg/ml, 6 µg/ml, 5 µg/ml, 4 µg/ml, 3 µg/ml, 2 µg/ml, or 1 µg/ml total organic solvent. In some embodiments, the composition (such as a pharmaceutical composition) comprises about 1-5 µg/ml, about 5-10 µg/ml, about 10-15 µg/ml, about 15-20 µg/ml (or a combination of such ranges) of total organic solvent. In some embodiments, the nanoparticle composition (such as the pharmaceutical composition) comprises less than about 20 ppm total organic solvent, such as any of less than about 20 ppm, 19 ppm, 18 ppm, 17 ppm, 16 ppm, 15 ppm, 14 ppm, 13 ppm, 12 ppm, 11 ppm, 10 ppm, 9 ppm, 8 ppm, 7 ppm, 6 ppm, 5 ppm, 4 ppm, 3 ppm, 2 ppm, or 1 ppm total organic solvent. In some embodiments, the composition (such as a pharmaceutical composition) comprises about 0.1-1 ppm, about 1-5 ppm, about 5-10 ppm, about 10-15 ppm, about 15-20 ppm (or a combination of such ranges) of total organic solvent. In some embodiments, the composition is substantially free of organic solvent.

In some embodiments, the nanoparticle composition (such as a pharmaceutical composition) comprises less than about 60 µg/ml chloroform, such as less than about any of 60 µg/ml, 55 µg/ml, 50 µg/ml, 45 µg/ml, 40 µg/ml, 35 µg/ml, 30 µg/ml, 25 µg/ml, 20 µg/ml, or 15 µg/ml chloroform. In some embodiments, the composition (such as a pharmaceutical composition) comprises any of about 15-30 µg/ml, about 30-45 µg/ml, or about 45-60 µg/ml chloroform. In some embodiments, the composition comprises less than about 60 ppm chloroform, such as any of less than about 60 ppm, 55 ppm, 50 ppm, 45 ppm, 40 ppm, 35 ppm, 30 ppm, 25 ppm, 20 ppm, 15 ppm, 10 ppm, 5 pp, or 1 ppm chloroform. In some embodiments, the composition comprises any of about 0.1-1 ppm, about 1-5 ppm, about 5-10 ppm, about 1-15 ppm, about 15-30 ppm, about 30-45 ppm, or about 45-60 ppm chloroform. In some embodiments, the nanoparticle composition (such as the pharmaceutical composition) is substantially free of chloroform. In some embodiments, the nanoparticle composition (such as a pharmaceutical composition) comprises less than about 10 µg/ml chloroform, such as less than about any of 10 µg/ml, 9 µg/ml, 8 µg/ml, 7 µg/ml, 6 µg/ml, 5 µg/ml, 4 µg/ml, 3 µg/ml, 2 µg/ml, or 1 µg/ml chloroform. In some embodiments, the composition (such as a pharmaceutical composition) comprises any of about 1-2 µg/ml, about 2-5 µg/ml, or about 5-10 µg/ml chloroform. In some embodiments, the composition comprises less than about 10 ppm chloroform, such as any of less than about 10 ppm, 9 ppm, 8 ppm, 7 ppm, 6 ppm, 5 ppm, 4 ppm, 3 ppm, 2 ppm, or 1 ppm chloroform. In some embodiments, the composition comprises any of about 1-2 ppm, about 2-5 ppm, or about 5-10 ppm chloroform. In some embodiments, the nanoparticle composition (such as the pharmaceutical composition) is substantially free of chloroform.

In some embodiments, the nanoparticle composition comprises less than 60 µg/mL or less than 60 ppm chloroform. In some embodiments, the nanoparticle composition comprises less than 5 µg/mL or less than 5 ppm chloroform.

In some embodiments, the nanoparticle composition (such as a pharmaceutical composition) comprises less than about 60 µg/ml ethanol, such as less than about any of 60 µg/ml, 55 µg/ml, 50 µg/ml, 45 µg/ml, 40 µg/ml, 35 µg/ml, 30 µg/ml, 25 µg/ml, 20 µg/ml, or 15 µg/ml ethanol. In some embodiments, the composition (such as a pharmaceutical composition) comprises any of about 15-30 µg/ml, about 30-45 µg/ml, or about 45-60 µg/ml ethanol. In some embodiments, the composition comprises less than about 60 ppm ethanol, such as any of less than about 60 ppm, 55 ppm, 50 ppm, 45 ppm, 40 ppm, 35 ppm, 30 ppm, 25 ppm, 20 ppm, or 15 ppm ethanol. In some embodiments, the composition comprises any of about 15-30 ppm, about 30-45 ppm, or about 45-60 ppm ethanol. In some embodiments, the nanoparticle composition (such as the pharmaceutical composition) is substantially free of ethanol. In some embodiments, the nanoparticle composition (such as a pharmaceutical composition) comprises less than about 10 μg/ml ethanol, such as less than about any of 10 μg/ml, 9 μg/ml, 8 μg/ml, 7 μg/ml, 6 μg/ml, 5 μg/ml, 4 μg/ml, 3 μg/ml, 2 μg/ml, or 1 μg/ml ethanol. In some embodiments, the composition (such as a pharmaceutical composition) comprises any of about 1-2 μg/ml, about 2-5 μg/ml, or about 5-10 μg/ml ethanol. In some embodiments, the composition comprises less than about 10 ppm ethanol, such as any of less than about 10 ppm, 9 ppm, 8 ppm, 7 ppm, 6 ppm, 5 ppm, 4 ppm, 3 ppm, 2 ppm, or 1 ppm ethanol. In some embodiments, the composition comprises any of about 1-2 ppm, about 2-5 ppm, or about 5-10 ppm ethanol. In some embodiments, the nanoparticle composition (such as the pharmaceutical composition) is substantially free of ethanol.

In some embodiments, the nanoparticle composition comprises less than 60 μg/mL ethanol or less than 60 ppm ethanol. In some embodiments, the nanoparticle composition comprises less than 5 μg/mL or less than 5 ppm ethanol.

In some embodiments, the nanoparticle composition (such as a pharmaceutical composition) comprises less than about 60 μg/ml isopropanol, such as less than about any of 60 μg/ml, 55 μg/ml, 50 μg/ml, 45 μg/ml, 40 μg/ml, 35 μg/ml, 30 μg/ml, 25 μg/ml, 20 μg/ml, or 15 μg/ml isopropanol. In some embodiments, the composition (such as a pharmaceutical composition) comprises any of about 15-30 μg/ml, about 30-45 μg/ml, or about 45-60 μg/ml isopropanol. In some embodiments, the composition comprises less than about 60 ppm isopropanol, such as any of less than about 60 ppm, 55 ppm, 50 ppm, 45 ppm, 40 ppm, 35 ppm, 30 ppm, 25 ppm, 20 ppm, or 15 ppm isopropanol. In some embodiments, the composition comprises any of about 15-30 ppm, about 30-45 ppm, or about 45-60 ppm isopropanol. In some embodiments, the nanoparticle composition (such as the pharmaceutical composition) is substantially free of isopropanol. In some embodiments, the nanoparticle composition (such as a pharmaceutical composition) comprises less than about 10 μg/ml isopropanol, such as less than about any of 10 μg/ml, 9 μg/ml, 8 μg/ml, 7 μg/ml, 6 μg/ml, 5 μg/ml, 4 μg/ml, 3 μg/ml, 2 μg/ml, or 1 μg/ml isopropanol. In some embodiments, the composition (such as a pharmaceutical composition) comprises any of about 1-2 μg/ml, about 2-5 μg/ml, or about 5-10 μg/ml isopropanol. In some embodiments, the composition comprises less than about 10 ppm isopropanol, such as any of less than about 10 ppm, 9 ppm, 8 ppm, 7 ppm, 6 ppm, 5 ppm, 4 ppm, 3 ppm, 2 ppm, or 1 ppm isopropanol. In some embodiments, the composition comprises any of about 1-2 ppm, about 2-5 ppm, or about 5-10 ppm isopropanol. In some embodiments, the nanoparticle composition (such as the pharmaceutical composition) is substantially free of isopropanol.

In some embodiments, the nanoparticle composition comprises less than 60 μg/mL or less than 60 ppm isopropanol. In some embodiments, the nanoparticle composition comprises less than 5 μg/mL or less than 5 ppm isopropanol.

In some embodiments, the nanoparticle composition (such as a pharmaceutical composition) comprises less than about 250 μg/ml tert-butanol, such as less than about any of 250 μg/ml, 225 μg/ml, 200 μg/ml, 175 μg/ml, 150 μg/ml, 125 μg/ml, 100 μg/ml, 75 μg/ml, 50 μg/ml, or 25 μg/ml tert-butanol. In some embodiments, the composition (such as a pharmaceutical composition) comprises any of about 25-50 μg/ml, about 50-150 μg/ml, or about 150-250 μg/ml tert-butanol. In some embodiments, the composition comprises less than about 250 ppm tert-butanol, such as any of less than about 250 ppm, 225 ppm, 200 ppm, 175 ppm, 150 ppm, 125 ppm, 100 ppm, 75 ppm, 50 ppm, or 25 ppm tert-butanol. In some embodiments, the composition comprises any of about 25-50 ppm, about 50-150 ppm, or about 150-300 ppm tert-butanol. In some embodiments, the nanoparticle composition (such as the pharmaceutical composition) is substantially free of tert-butanol. In some embodiments, the nanoparticle composition (such as a pharmaceutical composition) comprises less than about 10 μg/ml tert-butanol, such as less than about any of 10 μg/ml, 9 μg/ml, 8 μg/ml, 7 μg/ml, 6 μg/ml, 5 μg/ml, 4 μg/ml, 3 μg/ml, 2 μg/ml, or 1 μg/ml tert-butanol. In some embodiments, the composition (such as a pharmaceutical composition) comprises any of about 1-2 μg/ml, about 2-5 μg/ml, or about 5-10 μg/ml tert-butanol. In some embodiments, the composition comprises less than about 10 ppm tert-butanol, such as any of less than about 10 ppm, 9 ppm, 8 ppm, 7 ppm, 6 ppm, 5 ppm, 4 ppm, 3 ppm, 2 ppm, or 1 ppm tert-butanol. In some embodiments, the composition comprises any of about 1-2 ppm, about 2-5 ppm, or about 5-10 ppm tert-butanol. In some embodiments, the nanoparticle composition (such as the pharmaceutical composition) is substantially free of tert-butanol.

In some embodiments, the nanoparticle composition comprises less than 250 μg/mL or less than 250 ppm tert-butanol. In some embodiments, the nanoparticle composition comprises less than 10 μg/mL or less than 10 ppm tert-butanol.

Other Components in the Composition

In some embodiments, the compositions (such as pharmaceutical compositions) described herein also includes an antimicrobial agent (e.g., an agent in addition to the rapamycin) in an amount sufficient to significantly inhibit (e.g., delay, reduce, slow, and/or prevent) microbial growth in the composition (such as a pharmaceutical composition) for use in the methods of treatment, methods of administration, and dosage regimens described herein. Exemplary microbial agents and variations for the use of microbial agents are disclosed in US 2007/0117744 A1 (such as those described in paragraphs [0036] to [0058] therein), the content of which is hereby incorporated by reference in its entirety. In some embodiments, the antimicrobial agent is a chelating agent, such as EDTA, edetate, citrate, pentetate, tromethamine, sorbate, ascorbate, derivatives thereof, or mixtures thereof. In some embodiments, the antimicrobial agent is a polydentate chelating agent. In some embodiments, the antimicrobial agent is a non-chelating agent, such as any of sulfites, benzoic acid, benzyl alcohol, chlorobutanol, and paraben. In some embodiments, an antimicrobial other than the taxane discussed above is not contained or used in the methods of treatment, methods of administration, and dosage regimens described herein.

In some embodiments, the compositions (such as pharmaceutical compositions) described herein include a sugar. Exemplary sugars and variations for the use of sugars are disclosed in US 2007/0117744 A1 (such as those described in paragraphs [0084] to [0090] therein), the content of which is hereby incorporated by reference in its entirety. In some embodiments, the sugar serves as a reconstitution enhancer which causes a lyophilized composition to dissolve or suspend in water and/or aqueous solution more quickly than the lyophilized composition would dissolve without the sugar. In some embodiments, the composition (such as a pharmaceutical composition) is a liquid (e.g., aqueous) composition obtained by reconstituting or resuspending a dry composition. In some embodiments, the concentration of sugar in the composition (such as a pharmaceutical composition) is greater than about 50 mg/ml. In some embodiments, the sugar is in an amount that is effective to increase the stability of the rapamycin in the pharmaceutical composition as compared to a composition (such as a pharmaceutical composition) without the sugar. In some embodiments, the sugar is in an amount that is effective to improve filterability of the composition (such as a pharmaceutical composition) as compared to a composition (such as a pharmaceutical composition) without the sugar.

The sugar-containing compositions (such as pharmaceutical compositions) described herein may further comprise one or more antimicrobial agents, such as the antimicrobial agents described herein or in US 2007/0117744 A1. In addition to one or more sugars, other reconstitution enhancers (such as those described in US 2005/0152979 A1, which is hereby incorporated by reference in its entirety) can also be added to the compositions (such as pharmaceutical compositions).

Pharmaceutical Compositions

The compositions described herein may be used as a pharmaceutical compositions, or may be formulated into a pharmaceutical composition. For example, a precursor nanoparticle composition described herein may be formulated into a pharmaceutical composition by combining the nanoparticle composition with a pharmaceutically acceptable carrier, excipients, stabilizing agents and/or other agents, which are known in the art, for use in the methods of treatment, methods of administration, and dosage regimens described herein.

To increase stability by increasing the negative zeta-potential of nanoparticles, certain negatively charged components may be added. Such negatively charged components include, but are not limited to bile salts, bile acids, glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid, and others; phospholipids including lecithin (egg yolk) based phospholipids which include the following phosphatidylcholines: palmitoyloleoylphosphatidylcholine, palmitoyllinoleoylphosphatidylcholine, stearoyllinoleoylphosphatidylcholine, stearoyloleoylphosphatidylcholine, stearoylarachidoylphosphatidylcholine, and dipalmitoylphosphatidylcholine. Other phospholipids including L-α-dimyristoylphosphatidylcholine (DMPC), dioleoylphosphatidylcholine (DOPC), distearoylphosphatidylcholine (DSPC), hydrogenated soy phosphatidylcholine (HSPC), and other related compounds. Negatively charged surfactants or emulsifiers are also suitable as additives, e.g., sodium cholesteryl sulfate and the like.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer. The final form may be sterile and may also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

The pharmaceutical compositions described herein may include other agents, excipients, or stabilizers to improve properties of the composition. Examples of suitable excipients and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. Examples of emulsifying agents include tocopherol esters such as tocopheryl polyethylene glycol succinate and the like, PLURONIC®, emulsifiers based on polyoxy ethylene compounds, Span 80 and related compounds and other emulsifiers known in the art and approved for use in animals or human dosage forms. The compositions (such as pharmaceutical compositions) can be formulated so as to provide rapid, sustained or delayed release of the active ingredient after administration to the patient by employing procedures well known in the art.

In some embodiments, about 80% to about 95% (such about 80-83%, about 83-86%, about 86-89%, about 89-92%, or about 92-95%, or a combination of such ranges) of the total albumin in the pharmaceutical composition is in the form of albumin monomers. In some embodiments, about any of about 80%, 81%, 82%, 83%, 84%, 85%, 86%, 87%, 88%, 89%, 90%, 91%, 92%, 93%, 94% or 95% of the total albumin in the composition is in the form of albumin monomers. In some embodiments, about 4% to about 15% (such as about 4-6%, about 6-8%, about 8-10%, about 10-12%, or about 12-15%, or a combination of such ranges) of the total albumin in the pharmaceutical composition is in the form of albumin dimers. In some embodiments, about 4%, 5%, 6%, 7%, 8%, 9%, 10%, 11%, 12%, 13%, 14%, or 15% of the total albumin in the pharmaceutical composition is in the form of albumin dimers. In some embodiments, about 0.5% to about 5% (such about 0.5-1%, about 1-1.5%, about 1.5-2%, about 2-2.5%, about 2.5-3%, about 3-3.5%, about 3.5-4%, about 4-4.5%, or about 4.5-5%, or a combination of such ranges) of the total albumin in the pharmaceutical composition is in the form of albumin polymers (or albumin trimers). In some embodiments, about 0.5%, 1%, 1.5%, 2%, 2.5%, 3%, 3.5%, 4%, 4.5%, or 5% of the total albumin in the pharmaceutical composition is in the form of albumin polymers (or albumin trimers). In some embodiments, about 80% to about 95% of the total albumin in the pharmaceutical composition is in the form of albumin monomers, and about 4% to about 15% of the total albumin in the pharmaceutical composition is in the form of albumin dimers. In some embodiments, about 80% to about 95% of the total albumin in the pharmaceutical composition is in the form of albumin monomers, and about 0.5% to about 5% of the total albumin in the pharmaceutical composition is in the form of albumin polymers (or albumin trimers). In some embodiments, about 4% to about 15% of the total albumin in the pharmaceutical composition is in the form of albumin dimers, and about 0.5% to about 5% of the total albumin in the pharmaceutical composition is in the form of albumin polymers (or albumin trimers). In some embodiments, about 80% to about 95% of the total albumin in the pharmaceutical composition is in the form of albumin monomers, about 4% to about 15% of the total albumin in the pharmaceutical composition is in the form of albumin dimers, and about 0.5% to about 5% of the total albumin in the pharmaceutical composition is in the form of albumin polymers (or albumin trimers). The percentage of the monomeric albumin, the dimeric albumin, or the polymeric albumin (or trimeric albumin) compared to the total albumin in the pharmaceutical composition may be determined as a percentage of the sum of the total monomeric albumin, dimeric albumin, and polymeric (or trimeric) albumin in the pharmaceutical composition. The percentage of the monomeric albumin, the dimeric albumin, or the polymeric albumin (or trimeric albumin) in the pharmaceutical composition can be measured by subjecting the pharmaceutical composition to size-exclusion chromatography (SEC) using an aqueous mobile phase (such as saline) coupled with multiple angle light scattering (MALS) detector.

In some embodiments, about 83% to about 92% of the total albumin in the pharmaceutical composition is in the form of monomeric albumin. In some embodiments, about 7% to about 11% of the total albumin in the pharmaceutical composition is in the form of dimeric albumin. In some embodiments, about 1.5% to about 3% of the total albumin in the pharmaceutical composition is in the form of polymeric albumin (or trimeric albumin). In some embodiments, about 83% to about 92% of the total albumin in the pharmaceutical composition is in the form of monomeric albumin; about 7% to about 11% of the total albumin in the pharmaceutical composition is in the form of dimeric albumin; and about 1.5% to about 3% of the total albumin in the pharmaceutical composition is in the form of polymeric albumin (or trimeric albumin).

In some embodiments, about 80% to about 95% (such about 80-83%, about 83-86%, about 86-89%, about 89-92%, or about 92-95%, or a combination of such ranges) of the total albumin in the pharmaceutical composition is in the form of albumin monomers. In some embodiments, about any of about 80%, 81%, 82%, 83%, 84%, 85%, 86%, 87%, 88%, 89%, 90%, 91%, 92%, 93%, 94% or 95% of the total albumin in the composition is in the form of albumin monomers. In some embodiments, about 4% to about 15% (such as about 4-6%, about 6-8%, about 8-10%, about 10-12%, or about 12-15%, or a combination of such ranges) of the total albumin in the pharmaceutical composition is in the form of albumin dimers. In some embodiments, about 4%, 5%, 6%, 7%, 8%, 9%, 10%, 11%, 12%, 13%, 14%, or 15% of the total albumin in the pharmaceutical composition is in the form of albumin dimers. In some embodiments, about 0.3% to about 3% (such about 0.3-1%, about 1-1.5%, about 1.5-2%, about 2-2.5%, or about 2.5-3%, or a combination of such ranges) of the total albumin in the pharmaceutical composition is in the form of albumin oligomers. In some embodiments, about 0.3%, 0.5%, 1%, 1.5%, 2%, 2.5%, or 3% of the total albumin in the pharmaceutical composition is in the form of albumin oligomers. In some embodiments, about 2% to about 7% of the total albumin in the pharmaceutical composition is in the form of albumin polymers (other than albumin oligomers). In some embodiments, about 2%, 3%, 4%, 5%, 6%, or 7% of the total albumin in the pharmaceutical composition is in the form of albumin polymers (other than albumin oligomers). In some embodiments, about 80% to about 95% of the total albumin in the pharmaceutical composition is in the form of albumin monomers, and about 4% to about 15% of the total albumin in the pharmaceutical composition is in the form of albumin dimers. In some embodiments, about 80% to about 95% of the total albumin in the pharmaceutical composition is in the form of albumin monomers, and about 2% to about 7% of the total albumin in the pharmaceutical composition is in the form of albumin polymers (other than albumin oligomer). In some embodiments, about 4% to about 15% of the total albumin in the pharmaceutical composition is in the form of albumin dimers, and about 2% to about 7% of the total albumin in the pharmaceutical composition is in the form of albumin polymers (other than albumin oligomers). In some embodiments, about 80% to about 95% of the total albumin in the pharmaceutical composition is in the form of albumin monomers, about 4% to about 15% of the total albumin in the pharmaceutical composition is in the form of albumin dimers, and about 2% to about 7% of the total albumin in the pharmaceutical composition is in the form of albumin polymers (other than albumin oligomers). In some embodiments, about 80% to about 95% of the total albumin in the pharmaceutical composition is in the form of albumin monomers, about 4% to about 15% of the total albumin in the pharmaceutical composition is in the form of albumin dimers, about 0.3% to about 3% of the total albumin in the pharmaceutical composition is in the form of albumin oligomers, and about 2% to about 7% of the total albumin in the pharmaceutical composition is in the form of albumin polymers (other than albumin oligomers). The percentage of the monomeric albumin, the dimeric albumin, the oligomeric albumin, or the polymeric albumin (other than oligomeric albumin) in the pharmaceutical composition can be measured by dissolving the nanoparticles and subjecting the composition to size exclusion chromatography (SEC) using a mobile phase containing an aqueous portion and a miscible organic portion (such as an aqueous buffer containing 7.5% methanol) coupled with multiple angle light scattering (MALS) detector.

In some embodiments, about 70% to about 85% (such as any of about 70-72%, about 72-74%, about 74-76%, about 76-78%, about 78-80%, about 80-82%, or about 82-85%, or any combination of such ranges) of the albumin in the nanoparticles of the pharmaceutical composition is in the form of albumin monomers. In some embodiments, about 70%, 71%, 72%, 73%, 74%, 75%, 76%, 77%, 78%, 79%, 80%, 81%, 82%, 83%, 84%, or 85% of the albumin in the nanoparticles of the pharmaceutical composition is in the form of albumin monomers. In some embodiments, about 9% to about 20% (such as about 9-11%, about 11-13%, about 13-15%, about 15-17%, or about 17-20%, or any combination of such ranges) of the albumin in the nanoparticle portion of the pharmaceutical composition is in the form of dimers. In some embodiments, about 9%, 10%, 11%, 12%, 13%, 14%, 15%, 16%, 17%, 18%, 19%, or 20% of the albumin in the nanoparticles of the pharmaceutical composition is in the form of albumin dimers. In some embodiments, about 5% to about 15% (such as any of about 5-7%, about 7-9%, about 9-11%, about 11-13%, or about 13-15%, or any combination of such ranges) of the albumin in the nanoparticles of the pharmaceutical composition is in the form of albumin polymers (or albumin trimers). In some embodiments, about 5%, 6%, 7%, 8%, 9%, 10%, 11%, 12%, 13%, 14%, or 15% of the albumin in the nanoparticles of the pharmaceutical composition is in the form of albumin polymers (or albumin trimers). In some embodiments, about 70% to about 85% of the albumin in the nanoparticles of the pharmaceutical composition is in the form of albumin monomers, and about 9% to about 20% of the albumin in the nanoparticles of the pharmaceutical composition is in the form of albumin dimers. In some embodiments, about 70% to about 85% of the albumin in the nanoparticles of the pharmaceutical composition is in the form of albumin monomers, and about 5% to about 15% of the albumin in the nanoparticles of the pharmaceutical composition is in the form of albumin polymers (or albumin trimers). In some embodiments, about 9% to about 20% of the albumin in the nanoparticles of the pharmaceutical composition is in the form of albumin dimers, and about 5% to about 15% of the albumin in the nanoparticles of the pharmaceutical composition is in the form of albumin polymers (or albumin trimers). In some embodiments, about 70% to about 85% of the albumin in the nanoparticles of the pharmaceutical composition is in the form of albumin monomers, about 9% to about 20% of the albumin in the nanoparticles of the pharmaceutical composition is in the form of albumin dimers, and about 5% to about 15% of the albumin in the nanoparticles of the pharmaceutical composition is in the form of albumin polymers (or albumin trimers). The percentage of the monomeric albumin, the dimeric albumin, or the polymeric albumin (or trimeric albumin) in the nanoparticles of the pharmaceutical composition may be determined as a percentage of the sum of monomeric albumin, dimeric albumin, and polymeric albumin (or trimeric albumin) in the nanoparticles of the pharmaceutical composition. The percentage of the monomeric albumin, the dimeric albumin, or the polymeric albumin (or the trimeric albumin) in the nanoparticles of the pharmaceutical composition can be measured by separating the nanoparticles from the non-nanoparticle portion (e.g., by centrifugation), re-suspending the nanoparticles (for example, in an aqueous solution, such as saline), and subjecting the re-suspended nanoparticles to size-exclusion chromatography (SEC) using an aqueous mobile phase (such as saline) coupled with multiple angle light scattering (MALS) detector.

In some embodiments, about 74% to about 80% of the albumin in the nanoparticles is in the form of monomeric albumin. In some embodiments, about 12% to about 17% of the albumin in the nanoparticles is in the form of dimeric albumin. In some embodiments, about 7% to about 11% of the albumin in the nanoparticles is in the form of polymeric albumin (or trimeric albumin). In some embodiments, about 74% to about 80% of the albumin in the nanoparticles is in the form of monomeric albumin; about 12% to about 17% of the albumin in the nanoparticles is in the form of dimeric albumin; and about 7% to about 11% of the albumin in the nanoparticles is in the form of polymeric albumin (or trimeric albumin).

In some embodiments, about 25% to about 50% (such as any of about 25-28%, about 28-31%, about 31-34%, about 34-37%, about 37-40%, about 40-43%, about 43-46%, about 46-48%, or about 48-50%, or any combination of such ranges) of the albumin in the nanoparticles of the pharmaceutical composition is in the form of albumin monomers. In some embodiments, about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% of the albumin in the nanoparticles of the pharmaceutical composition is in the form of albumin monomers. In some embodiments, about 5% to about 16% (such as about 5-7%, about 7-9%, about 9-11%, about 11-13%, about 13-15%, or about 15-16, or any combination of such ranges) of the albumin in the nanoparticle portion of the pharmaceutical composition is in the form of dimers. In some embodiments, about 5%, 6%, 7%, 8%, 9%, 10%, 11%, 12%, 13%, 14%, 15%, or 16% of the albumin in the nanoparticles of the pharmaceutical composition is in the form of albumin dimers. In some embodiments, about 1% to about 4.5% (such as about 1-1.5%, about 1.5-2%, about 2-2.5%, about 2.5-3%, about 3-3.5%, about 3.5-4%, or about 4-4.5%, or any combination of such ranges) of the albumin in the nanoparticle portion of the pharmaceutical composition is in the form of oligomers. In some embodiments, about 1%, 1.5%, 2%, 2.5%, 3%, 3.5%, 4%, or 4.5% of the albumin in the nanoparticles of the pharmaceutical composition is in the form of albumin oligomers. In some embodiments, about 42% to about 60% (such as any of about 42-45%, about 45-48%, about 48-51%, about 51-54%, about 54-57%, or about 57-60%, or any combination of such ranges) of the albumin in the nanoparticles of the pharmaceutical composition is in the form of albumin polymers (other than albumin oligomers). In some embodiments, about 42%, 43%, 44%, 45%, 46%, 47%, 48%, 49%, 50%, 51%, 52%, 53%, 54%, 55%, 56%, 57%, 58%, 59%, or 60% of the albumin in the nanoparticles of the pharmaceutical composition is in the form of albumin polymers (other than albumin oligomers). In some embodiments, about 25% to about 50% of the albumin in the nanoparticles of the pharmaceutical composition is in the form of albumin monomers, and about 5% to about 16% of the albumin in the nanoparticles of the pharmaceutical composition is in the form of albumin dimers. In some embodiments, about 25% to about 50% of the albumin in the nanoparticles of the pharmaceutical composition is in the form of albumin monomers, and about 42% to about 60% of the albumin in the nanoparticles of the pharmaceutical composition is in the form of albumin polymers (other than albumin oligomers). In some embodiments, about 5% to about 16% of the albumin in the nanoparticles of the pharmaceutical composition is in the form of albumin dimers, and about 42% to about 60% of the albumin in the nanoparticles of the pharmaceutical composition is in the form of albumin polymers (other than oligomeric albumin). In some embodiments, about 25% to about 50% of the albumin in the nanoparticles of the pharmaceutical composition is in the form of albumin monomers, about 5% to about 16% of the albumin in the nanoparticles of the pharmaceutical composition is in the form of albumin dimers, and about 42% to about 60% of the albumin in the nanoparticles of the pharmaceutical composition is in the form of albumin polymers (other than albumin oligomers). In some embodiments, about 25% to about 50% of the albumin in the nanoparticles of the pharmaceutical composition is in the form of albumin monomers, about 5% to about 16% of the albumin in the nanoparticles of the pharmaceutical composition is in the form of albumin dimers, about 1% to about 4.5% of the albumin in the nanoparticles of the pharmaceutical composition is in the form of albumin oligomers, and about 42% to about 60% of the albumin in the nanoparticles of the pharmaceutical composition is in the form of albumin polymers (other than albumin oligomers). The percentage of the monomeric albumin, the dimeric albumin, the oligomeric albumin, or the polymeric albumin (other than oligomeric albumin) in the nanoparticles of the pharmaceutical composition may be determined as a percentage of the sum of monomeric albumin, dimeric albumin, oligomeric albumin, and polymeric albumin (other than oligomeric albumin) in the nanoparticles of the pharmaceutical composition. The percentage of the monomeric albumin, the dimeric albumin, the oligomeric albumin, or the polymeric albumin (other than the oligomeric albumin) in the nanoparticles of the pharmaceutical composition can be measured by separating the nanoparticles from the non-nanoparticle portion (e.g., by centrifugation), dissolving the nanoparticles, and subjecting the re-suspended nanoparticles to size-exclusion chromatography (SEC) using a mobile phase containing an aqueous portion and a miscible organic portion (such as an aqueous buffer containing 7.5% methanol) coupled with a multiple angle light scattering (MALS) detector.

In some embodiments, about 80% to about 95% (such as any of about 80% to about 82%, about 82% to about 84%, about 84% to about 86%, about 86% to about 88%, about 88% to about 90%, about 90% to about 92%, or about 90% to about 93%, or a combination of such ranges) of the albumin in the non-nanoparticle portion of the pharmaceutical composition is in the form of albumin monomers. In some embodiments, about any of 80%, 81%, 82%, 83%, 84%, 85%, 86%, 87%, 88%, 89%, 90%, 91%, 92%, 93%, 94%, or 95% of the albumin in the non-nanoparticle portion of the pharmaceutical composition is in the form of albumin monomers. In some embodiments, about 4% to about 14% (such as about 4-6%, about 6-8%, about 8-10%, about 10-12%, or about 12-15%, or a combination of such ranges) of the albumin in the non-nanoparticle portion of the pharmaceutical composition is in the form of albumin dimers. In some embodiments, about 4%, 5%, 6%, 7%, 8%, 9%, 10%, 11%, 12%, 13%, or 14% of the albumin in the non-nanoparticle portion of the pharmaceutical composition is in the form of albumin dimers. In some embodiments, about 0.5% to about 5% (such about 0.5-1%, about 1-1.5%, about 1.5-2%, about 2-2.5%, about 2.5-3%, about 3-3.5%, about 3.5-4%, about 4-4.5%, or about 4.5-5%, or a combination of such ranges) of the albumin in the non-nanoparticle portion of the pharmaceutical composition is in the form of albumin polymers (or albumin trimers). In some embodiments, about 0.5%, 1%, 1.5%, 2%, 2.5%, 3%, 3.5%, 4%, 4.5%, or 5% of the albumin in the non-nanoparticle portion of the pharmaceutical composition is in the form of albumin polymers (or albumin trimers). In some embodiments, about 80% to about 95% of the albumin in the non-nanoparticle portion of the pharmaceutical composition is in the form of albumin monomers, and about 4% to about 14% of the albumin in the non-nanoparticle portion of the pharmaceutical composition is in the form of albumin dimers. In some embodiments, about 80% to about 95% of the albumin in the non-nanoparticle portion of the pharmaceutical composition is in the form of albumin monomers, and about 0.5% to about 5% of the albumin in the non-nanoparticle portion of the pharmaceutical composition is in the form of albumin polymers (or albumin trimers). In some embodiments, about 4% to about 14% of the albumin in the non-nanoparticle portion of the pharmaceutical composition is in the form of albumin dimers, and about 0.5% to about 5% of the albumin in the non-nanoparticle portion of the pharmaceutical composition is in the form of albumin polymers (or albumin trimers). In some embodiments, about 80% to about 95% of the albumin in the non-nanoparticle portion of the pharmaceutical composition is in the form of albumin monomers, about 4% to about 14% of the albumin in the non-nanoparticle portion of the pharmaceutical composition is in the form of albumin dimers, and about 0.5% to about 5% of the albumin in the non-nanoparticle portion of the pharmaceutical composition is in the form of albumin polymers (or albumin trimers). The percentage of the monomeric albumin, the dimeric albumin, or the polymeric albumin (or the trimeric albumin) in the non-nanoparticle portion of the pharmaceutical composition may be determined as a percentage of the sum of monomeric albumin, dimeric albumin, and polymeric albumin (or trimeric albumin) in the non-nanoparticle portion of the pharmaceutical composition. The percentage of the monomeric albumin, the dimeric albumin, or the polymeric albumin (or the trimeric albumin) in the non-nanoparticle portion of the pharmaceutical composition can be measured by separating the nanoparticles from the non-particle portion (e.g., by centrifugation), and subjecting the non-nanoparticle portion to size-exclusion chromatography (SEC) using an aqueous mobile phase (such as saline) coupled with a multiple angle light scattering (MALS) detector.

In some embodiments, about 83% to about 92% of the albumin in the non-nanoparticle portion of the pharmaceutical composition is in the form of monomeric albumin. In some embodiments, about 7% to about 11% of the albumin in the non-nanoparticle portion of the pharmaceutical composition is in the form of dimeric albumin. In some embodiments, about 1.5% to about 3% of the albumin in the non-nanoparticle portion of the pharmaceutical composition is in the form of polymeric albumin (or trimeric albumin). In some embodiments, about 83% to about 92% of the albumin in the non-nanoparticle portion of the pharmaceutical composition is in the form of monomeric albumin; about 7% to about 11% of the albumin in the non-nanoparticle portion of the pharmaceutical composition is in the form of dimeric albumin; and about 1.5% to about 3% of the albumin in the non-nanoparticle portion of the pharmaceutical composition is in the form of polymeric albumin (or trimeric albumin).

In some embodiments, about 80% to about 95% (such as any of about 80% to about 82%, about 82% to about 84%, about 84% to about 86%, about 86% to about 88%, about 88% to about 90%, about 90% to about 92%, or about 90% to about 93%, or a combination of such ranges) of the albumin in the non-nanoparticle portion of the pharmaceutical composition is in the form of albumin monomers. In some embodiments, about any of 80%, 81%, 82%, 83%, 84%, 85%, 86%, 87%, 88%, 89%, 90%, 91%, 92%, 93%, 94%, or 95% of the albumin in the non-nanoparticle portion of the pharmaceutical composition is in the form of albumin monomers. In some embodiments, about 4% to about 14% (such as about 4-6%, about 6-8%, about 8-10%, about 10-12%, or about 12-15%, or a combination of such ranges) of the albumin in the non-nanoparticle portion of the pharmaceutical composition is in the form of albumin dimers. In some embodiments, about 4%, 5%, 6%, 7%, 8%, 9%, 10%, 11%, 12%, 13%, or 14% of the albumin in the non-nanoparticle portion of the pharmaceutical composition is in the form of albumin dimers. In some embodiments, about 0.5% to about 4% (such about 0.5-1%, about 1-1.5%, about 1.5-2%, about 2-2.5%, about 2.5-3%, about 3-3.5%, or about 3.5-4%, or a combination of such ranges) of the albumin in the non-nanoparticle portion of the pharmaceutical composition is in the form of albumin oligomers. In some embodiments, about 0.5%, 1%, 1.5%, 2%, 2.5%, 3%, 3.5%, or 4% of the albumin in the non-nanoparticle portion of the pharmaceutical composition is in the form of albumin oligomers. In some embodiments, about 0.5% to about 3% (such about 0.5-1%, about 1-1.5%, about 1.5-2%, about 2-2.5%, or about 2.5-3%, or a combination of such ranges) of the albumin in the non-nanoparticle portion of the pharmaceutical composition is in the form of albumin polymers (other than albumin oligomers). In some embodiments, about 0.5%, 1%, 1.5%, 2%, 2.5%, or 3% of the albumin in the non-nanoparticle portion of the pharmaceutical composition is in the form of albumin polymers (other than albumin oligomers). In some embodiments, about 80% to about 95% of the albumin in the non-nanoparticle portion of the pharmaceutical composition is in the form of albumin monomers, and about 4% to about 14% of the albumin in the non-nanoparticle portion of the pharmaceutical composition is in the form of albumin dimers. In some embodiments, about 80% to about 95% of the albumin in the non-nanoparticle portion of the pharmaceutical composition is in the form of albumin monomers, and about 0.5% to about 3% of the albumin in the non-nanoparticle portion of the pharmaceutical composition is in the form of albumin polymers (other than albumin oligomers). In some embodiments, about 4% to about 14% of the albumin in the non-nanoparticle portion of the pharmaceutical composition is in the form of albumin dimers, and about 0.5% to about 3% of the albumin in the non-nanoparticle portion of the pharmaceutical composition is in the form of albumin polymers (other than albumin oligomers). In some embodiments, about 80% to about 95% of the albumin in the non-nanoparticle portion of the pharmaceutical composition is in the form of albumin monomers, about 4% to about 14% of the albumin in the non-nanoparticle portion of the pharmaceutical composition is in the form of albumin dimers, and about 0.5% to about 3% of the albumin in the non-nanoparticle portion of the pharmaceutical composition is in the form of albumin polymers (other than albumin oligomers). In some embodiments, about 80% to about 95% of the albumin in the non-nanoparticle portion of the pharmaceutical composition is in the form of albumin monomers, about 4% to about 14% of the albumin in the non-nanoparticle portion of the pharmaceutical composition is in the form of albumin dimers, about 0.5% to about 4% of the albumin in the non-nanoparticle portion of the pharmaceutical composition is in the form of albumin oligomers, and about 0.5% to about 3% of the albumin in the non-nanoparticle portion of the pharmaceutical composition is in the form of albumin polymers (other than albumin oligomers). The percentage of the monomeric albumin, the dimeric albumin, the oligomeric albumin, or the polymeric albumin (other than oligomeric albumin) in the non-nanoparticle portion of the pharmaceutical composition may be determined as a percentage of the sum of monomeric albumin, dimeric albumin, oligomeric albumin, and polymeric albumin (other than oligomeric albumin) in the non-nanoparticle portion of the pharmaceutical composition. The percentage of the monomeric albumin, the dimeric albumin, the oligomeric albumin, or the polymeric albumin (other than oligomeric albumin) can be measured by separating the nanoparticles from the non-nanoparticle portion (e.g., by centrifugation), and subjecting the supernatant (i.e., the non-nanoparticle portion) to size-exclusion chromatography (SEC) using a mobile phase containing an aqueous portion and a miscible organic portion (such as an aqueous buffer containing 7.5% methanol) coupled with a UV detector.

In some embodiments, the volume-weighted mean particle size of the nanoparticles in the pharmaceutical composition is less than about 200 nm, such as between about 50 nm and about 200 nm. In some embodiments, the volume-weighted mean particle size of the nanoparticles in the pharmaceutical composition may be about 200 nm or less, about 190 nm or less, about 180 nm or less, about 170 nm or less, about 160 nm or less, about 150 nm or less, about 140 nm or less, about 130 nm or less, about 120 nm or less, about 110 nm or less, about 100 nm or less, about 90 nm or less, about 80 nm or less, about 70 nm or less, or about 60 nm. In some embodiments, the average volume-weighted particle size of the nanoparticles in the pharmaceutical composition is about 60-70 nm, about 70-80 nm, about 80-90 nm, about 90-100 nm, about 100-110 nm, about 110-120 nm, about 120-130 nm, about 130-140 nm, about 140-150 nm, about 150-160 nm, about 160-180 nm, about 180-190 nm, about 190-200 nm, about 200-210 nm, about 210-220 nm, or about 220-230 nm.

In some embodiments, the volume-weighted average particle size of the nanoparticles in the pharmaceutical composition is about 90-100 nm.

In some embodiments, the Z-average particle size of the nanoparticles in the pharmaceutical composition is less than about 200 nm, such as between about 50 nm and about 200 nm. In some embodiments, the Z-average particle size of the nanoparticles in the pharmaceutical composition may be about 200 nm or less, about 190 nm or less, about 180 nm or less, about 170 nm or less, about 160 nm or less, about 150 nm or less, about 140 nm or less, about 130 nm or less, about 120 nm or less, about 110 nm or less, about 100 nm or less, about 90 nm or less, about 80 nm or less, about 70 nm or less, or about 60 nm. In some embodiments, the Z-average particle size of the nanoparticles in the pharmaceutical composition is about 60-70 nm, about 70-80 nm, about 80-90 nm, about 90-100 nm, about 100-110 nm, about 110-120 nm, about 120-130 nm, about 130-140 nm, about 140-150 nm, about 150-160 nm, about 160-180 nm, about 180-190 nm, about 190-200 nm, about 200-210 nm, about 210-220 nm, or about 220-230 nm.

In some embodiments, the Z-average particle size of the nanoparticles in the pharmaceutical composition is about 85 nm to about 95 nm.

In some embodiments, the nanoparticles in the pharmaceutical composition have a polydispersity index of less than about 0.3. In some embodiments, the nanoparticles in the pharmaceutical composition have a polydispersity index of less than about any of 0.3, 0.25, 0.2, 0.15, 0.1, or 0.05. In some embodiments, the nanoparticles in the pharmaceutical composition have a polydispersity index of about any of 0.03-0.05, 0.05-0.07, 0.07-0.09, 0.09-0.11, 0.11-0.13, 0.13-0.15, 0.15-0.17, 0.17-0.2, 0.2-0.25, 0.25-0.3, 0.05-0.09, 0.09-0.13, 0.13-0.17, 0.17-0.25, 0.06-0.08, 0.08-0.12, 0.12-0.16, 0.16-0.18, 0.18-0.22, 0.22-0.28, 0.28-0.3, 0.06-0.12, 0.12-0.18, 0.18-0.3, 0.05-0.1, 0.1-0.15, 0.15-0.2, or 0.2-0.3.

In some embodiments, the polydispersity index of the nanoparticles in the pharmaceutical composition is about 0.14 to about 0.16.

In some embodiments, the nanoparticles in the pharmaceutical composition have a span of size distribution (($Dv_{95}$–$Dv_5$)/$Dv_{50}$) of about 1.5 or less, such as about 0.8 to about 1.5. In some embodiments, the nanoparticles in the pharmaceutical composition have a span of size distribution (($Dv_{95}$–$Dv_5$)/$Dv_{50}$) of about any of 0.7, 0.8, 0.9, 1, 1.1, 1.2, 1.3, 1.4, 1.5, 1.6, 1.7, or 1.8. In some embodiments, the nanoparticles in the pharmaceutical composition have a span of size distribution (($Dv_{95}$–$Dv_5$)/$Dv_{50}$) of about any of 0.7-0.8. 0.8-0.9, 0.9-1, 1-1.1, 1.1-1.2, 1.2-1.3, 1.3-1.4, 0.8-1.0, 0.9-1.1, 1.0-1.2, 1.1-1.3, 1.2-1.4, 1.3-1.5, 0.7-1.0, 0.8-1.1, 0.9-1.2, 1.0-1.3, 1.1-1.4, 1.2-1.5, 0.7-1.1, 0.8-1.2, 0.9-1.3, 1.0-1.4, 1.1-1.5, 0.7-1.2, 0.8-1.3, 0.9-1.4, 0.9-1.5, 0.7-1.3, 0.8-1.4, 0.9-1.5, or 1.0-1.6. In some embodiments, the calculation of Dv95, Dv5, and/or Dv50 excludes particles having a diameter less than 20 nm in their longest dimension. In some embodiments, the calculation of $Dv_{95}$, $Dv_5$, and/or $Dv_{50}$ excludes particles having a diameter greater than 200 nm in their longest dimension.

In some embodiments, the nanoparticles in the pharmaceutical composition have a span of size distribution (($Dv_{95}$–$Dv_5$)/$Dv_{50}$) of about 0.8 to about 1.2.

In some embodiments, the nanoparticles in the pharmaceutical composition are about 25% to about 45% albumin by weight. In some embodiments, the nanoparticles of the pharmaceutical composition are about 25-26%, about 26-27%, about 27-28%, about 28-29%, about 29-30%, about 30-31%, about 31-32%, about 32-33%, about 33-34%, about 34-35%, about 35-36%, about 36-37%, about 37-38%, about 38-39%, about 39-40%, about 40-41%, about 41-42%, about 42-43%, about 43-44%, or about 44-45% (or any combination of such ranges) albumin by weight. In some embodiments, the nanoparticles in the pharmaceutical composition comprise about 25%, 26%, 27%, 28%, 29%, 30%, 31%, 32%, 33%, 34%, 35%, 36%, 37%, 38%, 39%, 40%, 41%, 42%, 43%, 44%, or 45% albumin by weight.

In some embodiments, the nanoparticles in the pharmaceutical composition comprises about 32% to about 38% albumin, by weight.

In some embodiments, the nanoparticles in the pharmaceutical composition are about 50% to about 80% (such as about 50-52%, about 52-54%, about 54-56%, about 56-58%, about 58-60%, about 60-62%, about 62-64%, about 64-66%, about 66-68%, about 68-70%, about 70-72%, about 72-74%, about 74-76%, about 76-78%, or about 78-80%, or a combination of such ranges) rapamycin by weight. In some embodiments, the nanoparticles in the pharmaceutical composition are about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 59%, or 80% rapamycin by weight.

In some embodiments, the nanoparticles in the pharmaceutical composition comprise about 62% to about 68% rapamycin, by weight.

In some embodiments, the weight ratio of the albumin to the rapamycin in the nanoparticles of the pharmaceutical composition is about 1:1 to about 1:4 (such as about 1:1 to about 1:1.5, about 1:1.5 to about 1:2, about 1:2 to about 1:2.5, about 1.25 to about 1:3, about 1:3 to about 1:3.5, or about 1:3.5 to about 1:4, or any combination of such ranges). In some embodiments, the weight ratio of the albumin to the rapamycin in the pharmaceutical nanoparticle portion is about 1:1, about 1:1.5, about 1:2, about 1:2.5, about 1:3, about 1:3.5, or about 1:4.

In some embodiments, the weight ratio of the albumin to the rapamycin in the nanoparticles of the pharmaceutical composition is about 32:68 to about 38:62.

In some embodiments, the weight ratio of the total albumin to the total rapamycin in the pharmaceutical composition is about 1:1 to about 12:1 (such as about 1:1 to about 2:1, about 2:1 to about 3:1, about 3:1 to about 4:1, about 4:1 to about 5:1, about 5:1 to about 6:1, about 6:1 to about 7:1, about 7:1 to about 8:1, about 8:1 to about 9:1, or about 9:1 to about 10:1, or any combination of such ranges). In some embodiments, the weight ratio of the total albumin to the total rapamycin in the pharmaceutical composition is about 1:1, about 2:1, about 3:1, about 4:1, about 5:1, about 6:1, about 7:1, about 8:1, about 9:1, about 10:1, about 11:1, or about 12:1.

In some embodiments, the weight ratio of the total albumin to the total rapamycin in the pharmaceutical composition is about 7:1 to about 9:1. In some embodiments, the weight ratio of the total albumin to the total rapamycin in the pharmaceutical composition is about 8:1.

In some embodiments, the concentration of albumin in the pharmaceutical composition is about 30 mg/mL to about 100 mg/mL (for example, about 30-35 mg/mL, about 35-40 mg/mL, about 40-45 mg/mL, about 45-50 mg/mL, about 50-55 mg/mL, about 55-60 mg/mL, about 60-65 mg/mL, about 65-70 mg/mL, about 70-75 mg/mL, about 75-80 mg/mL, about 80-85 mg/mL, about 85-90 mg/mL, about 90-95 mg/mL, about or about 95-100 mg/mL, or any combination of such ranges). In some embodiments, the concentration of albumin in the pharmaceutical composition is about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL. In some embodiments, the pharmaceutical composition is in a dried form, such as a lyophilized form. In the case of a dried (such as lyophilized) form, the concentration is assessed by the volume that the dried composition is to be reconstituted in.

In some embodiments, the concentration of albumin in the pharmaceutical composition is about 35 mg/mL to about 45 mg/mL.

In some embodiments, the concentration of albumin in the non-nanoparticle portion of the pharmaceutical composition is about 30 mg/mL to about 100 mg/mL (for example, about 30-35 mg/mL, about 35-40 mg/mL, about 40-45 mg/mL, about 45-50 mg/mL, about 50-55 mg/mL, about 55-60 mg/mL, about 60-65 mg/mL, about 65-70 mg/mL, about 70-75 mg/mL, about 75-80 mg/mL, about 80-85 mg/mL, about 85-90 mg/mL, about 90-95 mg/mL, about or about 95-100 mg/mL, or any combination of such ranges). In some embodiments, the concentration of albumin in the non-nanoparticle portion of the pharmaceutical composition is about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL. In some embodiments, the pharmaceutical composition is in a dried form, such as a lyophilized form. In the case of a dried (such as lyophilized) form, the concentration is assessed by the volume that the dried composition is to be reconstituted in.

In some embodiments, the concentration of albumin in the non-nanoparticle portion of the pharmaceutical composition is about 35 mg/mL to about 45 mg/mL.

In some embodiments, the concentration of albumin in the pharmaceutical composition that is in the nanoparticles of the pharmaceutical composition is about 1 mg/mL to about 10 mg/mL (such as about 1-1.2 mg/mL, about 1.2-1.5 mg/mL, about 1.5-1.8 mg/mL, about 1.8-2 mg/L, about 2-2.5 mg/mL, about 2.5-3 mg/mL, about 3-3.5 mg/mL, about 3.5-4 mg/mL, about 4-4.5 mg/mL, about 4.5-5 mg/mL, about 5-6 mg/mL, about 6-7 mg/mL, about 7-8 mg/mL, about 8-9 mg/mL, or about 9-10 mg/mL, or any combination of such ranges). In some embodiments, the concentration of albumin in the pharmaceutical composition that is in the nanoparticles of the pharmaceutical composition is about 1 mg/mL, about 1.2 mg/mL, about 1.5 mg/mL, about 1.8 mg/mL, about 2 mg/mL, about 2.5 mg/mL, about 3 mg/mL, about 3.5 mg/mL, about 4 mg/mL, about 4.5 mg/mL, or about 5 mg/mL.

In some embodiments, the concentration of albumin in the pharmaceutical composition that is in the nanoparticles of the composition is about 2.2 mg/mL to about 2.6 mg/mL.

In some embodiments, the concentration of rapamycin in the pharmaceutical composition is about 1 mg/mL to about 15 mg/mL (such as about 1-2 mg/mL, about 2-3 mg/mL, about 3-4 mg/mL, about 4-5 mg/mL, about 5-6 mg/mL, about 6-7 mg/mL, about 7-8 mg/mL, about 8-9 mg/mL, about, about 9-10 mg/mL, about 10-11 mg/mL, about 11-12 mg/mL, about 13-14 mg/mL, or about 14-15 mg/mL, or any combination of these ranges). In some embodiments, the concentration of rapamycin in the pharmaceutical composition is about 1 mg/ml, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, or about 15 mg/mL.

In some embodiments, the concentration of rapamycin in the pharmaceutical composition is about 4 mg/mL to about 6 mg/mL, such as about 5 mg/mL. In some embodiments, the concentration of rapamycin in the pharmaceutical composition is about 9 mg/mL to about 11 mg/mL, such as about 10 mg/mL.

In some embodiments, the concentration of rapamycin in the pharmaceutical composition that is in the nanoparticles of the pharmaceutical composition is about 1 mg/mL to about 15 mg/mL (such as about 1-2 mg/mL, about 2-3 mg/mL, about 3-4 mg/mL, about 4-5 mg/mL, about 5-6 mg/mL, about 6-7 mg/mL, about 7-8 mg/mL, about 8-9 mg/mL, about, about 9-10 mg/mL, about 10-11 mg/mL, about 11-12 mg/mL, about 13-14 mg/mL, or about 14-15 mg/mL, or any combination of these ranges). In some embodiments, the concentration of rapamycin in the pharmaceutical composition that is in the nanoparticles of the composition is about 1 mg/ml, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, or about 15 mg/mL.

In some embodiments, the concentration of rapamycin in the pharmaceutical composition that is in the nanoparticles of the pharmaceutical composition is about 4 mg/mL to about 6 mg/mL, such as about 5 mg/mL. In some embodiments, the concentration of rapamycin in the pharmaceutical composition that is in the nanoparticles of the pharmaceutical composition is about 9 mg/mL to about 11 mg/mL, such as about 10 mg/mL.

In some embodiments, the concentration of rapamycin in the non-nanoparticle portion of the pharmaceutical composition is less than about 55 µg/mL, such as about 1-5 µg/mL, about 5-10 µg/mL, about 10-15 µg/mL, about 15-20 µg/mL, about 20-25 µg/mL, about 25-30 µg/mL, about 30-35 µg/mL, about 35-40 µg/mL, about 40-45 µg/mL, about 45-50 µg/mL, or about 50-55 µg/mL (or a combination of such ranges).

In some embodiments, the concentration of rapamycin in the non-nanoparticle portion of the pharmaceutical composition is about 33 µg/mL to about 39 µg/mL.

In some embodiments, about 85% or more (such as about 90% or more, about 95% or more, about 97% or more, about 97.5% or more, about 98% or more, about 98.5% or more, about 99% or more, or about 99.5% or more) of the total rapamycin in the pharmaceutical composition is in the nanoparticles. For example, in some embodiments, about 85-90%, about 90-95%, about 95-97%, about 97-97.5%, about 97.5-98%, about 98-98.5%, about 98.5-99%, about 99-99.5%, or about 99.5-99.9% (or any combination of such ranges) of the total rapamycin in the pharmaceutical composition is in the nanoparticles. The balance of rapamycin in the pharmaceutical composition that is not in the nanoparticles is in the non-nanoparticle portion of the pharmaceutical composition.

In some embodiments, more than about 98% of the total rapamycin in the pharmaceutical composition is in the nanoparticles.

In some embodiments, about 80% or more (such as about 85% or more, about 90% or more, about 95% or more, about 97% or more, about 97.5% or more, about 98% or more, about 98.5% or more, about 99% or more, or about 99.5% or more) of the total albumin in the pharmaceutical composition is in the non-nanoparticle portion of the pharmaceutical composition. For example, in some embodiments, about 80-90%, about 85-90%, about 90-95%, about 95-97%, about 97-97.5%, about 97.5-98%, about 98-98.5%, about 98.5-99%, about 99-99.5%, or about 99.5-99.9% (or any combination of such ranges) of the total albumin in the pharmaceutical composition is in the non-nanoparticle portion of the pharmaceutical composition. The balance of total albumin in the pharmaceutical composition that is not in the non-nanoparticle portion of the pharmaceutical composition is in the nanoparticles of the pharmaceutical composition.

In some embodiments, about 95% or more of the total albumin in the pharmaceutical composition is in the non-nanoparticle portion of the composition.

In some embodiments, about 5% or less (such as about 4% or less, about 3% or less, about 2.5% or less, about 2% or less, about 1.5% or less, about 1% or less, about 0.5% or less, about 0.2% or less, about 0.1% or less, or about 0.05% or less) of the total rapamycin in the pharmaceutical composition is free rapamycin. In some embodiments, about 0.01% to about 5% (such as 0.01-0.05%, about 0.05-0.1% about 0.1-0.2%, about 0.2-0.5%, about 0.5-1%, about 1-1.5%, about 1.5-2%, about 2-2.5%, about 2.5-3%, about 3-4%, or about 4-5%) of the total rapamycin in the pharmaceutical composition is free rapamycin.

In some embodiments, less than about 1% of the rapamycin in the pharmaceutical composition is free rapamycin.

In some embodiments, about 20% or more (such as about 20% or more, about 25% or more, about 30% or more, about 35% or more, about 40% or more, about 45% or more, about 50% or more, about 55% or more, or about 60% or more) of the nanoparticles in the pharmaceutical composition are non-spherical or irregularly shaped.

In some embodiments, the nanoparticles in the pharmaceutical composition have a zeta-potential of about −25 mV to about −50 mV (such as about −25 mV to about −30 mV, about −30 mV to about −35 mV, about −35 mV to about −40 mV, about −40 mV to about −45 mV, or about −45 mV to about −50 mV, or any combination of such ranges.

In some embodiments, the nanoparticles in the pharmaceutical composition have a zeta potential of about −33 mV to about −39 mV.

In some embodiments, the vinyl chain of the rapamycin in the nanoparticles of the pharmaceutical composition interacts with the albumin in the nanoparticles of the pharmaceutical composition, for example as determined by NMR spectroscopy.

In some embodiments, the rapamycin in the nanoparticles of the pharmaceutical composition is amorphous (i.e., non-crystalline).

In some embodiments, about 3% or less (such as about 2.5% or less, about 2% or less, about 1.5% or less, about 1% or less, or about 0.5% or less) of the sum of seco-rapamycin and rapamycin in the pharmaceutical composition is seco-rapamycin. In some embodiments, about 0.1-3% (such as about 0.1-0.2%, about 0.2-0.3%, about 0.3-0.4%, about 0.4-0.5%, about 0.5-0.7%, about 0.7-1%, about 1-1.5%, about 1.5-2%, about 2-2.5%, or 2.5-3%, or any combination of such ranges) of the sum of seco-rapamycin and rapamycin in the pharmaceutical composition is seco-rapamycin.

In some embodiments, the sum of seco-rapamycin and rapamycin in the nanoparticles of the pharmaceutical composition is less than 1% seco-rapamycin, by weight. In some embodiments, the sum of seco-rapamycin and rapamycin in the nanoparticles of the pharmaceutical composition is about 0.5% to about 1% seco-rapamycin, by weight.

In some embodiments, the pharmaceutical composition has a rapamycin recovery of about 80% or more, about 81% or more, about 82% or more, about 83% or more, about 84% or more, about 85% or more, about 86% or more, about 87% or more, about 88% or more, about 89% or more, about 90% or more, about 91% or more, about 92% or more, about 93% or more, about 94% or more, about 95% or more, about 96% or more, about 97% or more, about 98% or more, about 99% or more, about 99.5% or more, about or more following a 0.2 micron filtration (for example, after formation of the nanoparticles or immediately after reconstitution). In some embodiments, the pharmaceutical composition has a rapamycin recovery of about 80-85%, about 85-90%, about 90-95%, about 95-98%, about 98-99%, about 99%-99.5%, or about 99.5%-100% following a 0.2 micron filtration (for example, after formation of the nanoparticles or immediately after reconstitution).

In some embodiments, the pharmaceutical composition has an osmolality of about 300 mOsm/kg to about 350 mOsm/kg (such as about 300-310 mOsm/kg, about 310-320 mOsm/kg, about 320-330 mOsm/kg, about 330-340 mOsm/kg, or about 340-350 mOsm/kg, or any combination of such ranges).

In some embodiments, the pharmaceutical composition has a viscosity of between about 1.20 centipoise (cP) to about 1.50 cP (such as about 1.20-1.25 cP, about 1.25-1.30 cP, about 1.30-1.35 cP, about 1.35-1.40 cP, about 1.40-1.45 cP, or about 1.45-1.50 cP, or any combination of such ranges).

In some embodiments, the osmolality of the pharmaceutical composition is about 325 mOsm/kg to about 340 mOsm/kg.

In some embodiments, the pharmaceutical composition has a viscosity of between about 1.20 centipoise (cP) to about 1.50 cP (such as about 1.20-1.25 cP, about 1.25-1.30 cP, about 1.30-1.35 cP, about 1.35-1.40 cP, about 1.40-1.45 cP, or about 1.45-1.50 cP, or any combination of such ranges). In some embodiments, the viscosity is assessed at room temperature, such as between about 20° C. and about 27° C. In some embodiments, the viscosity is assessed at room temperature, such as about 20° C., about 22° C., about 25° C., or about 27° C.

In some embodiments, the viscosity of the pharmaceutical composition is about 1.3 cP to about 1.35 cP. In some embodiments, the viscosity is assessed at room temperature, such as about 20° C., about 22° C., about 25° C., or about 27° C.

In some embodiments, the pharmaceutical is formulated to have a pH in the range of about 4.5 to about 9.0, for example pH ranges of any one of about 4.5-5.0, about 5.0-5.5, about 5.5-6.0, about 6.0-6.5, about 6.5-7.0, about 7.0-7.5, about 7.5-8.0, about 8.0-8.5, or about 8.5-9.0, or any combination of such ranges. In some embodiments, the pH of the pharmaceutical composition is formulated to no less than about 6, including for example no less than about any one of 6.5, 7, or 8. In some embodiments, the pH of the pharmaceutical composition is formulated to about 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0.

In some embodiments, the pH of the pharmaceutical composition is about 6.7 to about 6.8.

In some embodiments, the pharmaceutical composition comprises an albumin stabilizer. In some embodiments, the albumin stabilizer is selected from one or more of amino acids, salts of amino acids, derivatives of amino acids, fatty acids, salts of fatty acids, derivatives of fatty acids, sugars, polyols, and osmolytes. In some embodiments, the albumin stabilizer comprises caprylate, for example a caprylic acid derivative, e.g., sodium caprylate. In some embodiments, the albumin stabilizer comprises tryptophan derivative, e.g., N-acetyltryptophanate or tryptophan. In some embodiments, the albumin stabilizer comprises sodium caprylate and sodium acetyltryptophanate. In some embodiments, the pharmaceutical composition comprises about 0.05 mM to about 500 mM albumin stabilizer, such as about 0.05-0.1 mM, about 0.1-0.2 mM, about 0.2-0.5 mM, about 0.5-1 mM, about 1-2.5 mM, about 2.5-5 mM, about 5-10 mM, about 10-25 mM, about 25-50 mM, about 50-100 mM, about 100-150 mM, about 150-200 mM, about 200-250 mM, about 250 mM-300 mM, about 300-400 mM, or about 400-500 mM, or any combination of such ranges, of the albumin stabilizer. In some embodiments, the pharmaceutical composition comprises between about 0.05 mM and about 500 mM caprylic acid derivative, e.g., sodium caprylate (such as about 0.05-0.1 mM, about 0.1-0.2 mM, about 0.2-0.5 mM, about 0.5-1 mM, about 1-2.5 mM, about 2.5-5 mM, about 5-10 mM, about 10-25 mM, about 25-50 mM, about 50-100 mM, about 100-150 mM, about 150-200 mM, about 200-250 mM, about 250 mM-300 mM, about 300-400 mM, or about 400-500 mM caprylic acid derivative, e.g., sodium caprylate). In some embodiments, the pharmaceutical composition comprises between about 0.05 mM and about 500 mM tryptophan derivative, e.g., N-acetyltryptophanate (such as about 0.05-0.1 mM, about 0.1-0.2 mM, about 0.2-0.5 mM, about 0.5-1 mM, about 1-2.5 mM, about 2.5-5 mM, about 5-10 mM, about 10-25 mM, about 25-50 mM, about 50-100 mM, about 100-150 mM, about 150-200 mM, about 200-250 mM, about 250 mM-300 mM, about 300-400 mM, or about 400-500 mM tryptophan derivative, e.g., N-acetyltryptophanate).

In some embodiments, the pharmaceutical composition comprises less than about 20 µg/ml total organic solvent, such as any of less than about any of 20 µg/ml, 19 µg/ml, 18 µg/ml, 17 µg/ml, 16 µg/ml, 15 µg/ml, 14 µg/ml, 13 µg/ml, 12 µg/ml, 11 µg/ml, 10 µg/ml, 9 µg/ml, 8 µg/ml, 7 µg/ml, 6 µg/ml, 5 µg/ml, 4 µg/ml, 3 µg/ml, 2 µg/ml, or 1 µg/ml total organic solvent. In some embodiments, the pharmaceutical composition comprises about 1-5 µg/ml, about 5-10 µg/ml, about 10-15 µg/ml, about 15-20 µg/ml (or a combination of such ranges) of total organic solvent. In some embodiments, the pharmaceutical composition comprises less than about 20 ppm total organic solvent, such as any of less than about any of 20 ppm, 19 ppm, 18 ppm, 17 ppm, 16 ppm, 15 ppm, 14 ppm, 13 ppm, 12 ppm, 11 ppm, 10 ppm, 9 ppm, 8 ppm, 7 ppm, 6 ppm, 5 ppm, 4 ppm, 3 ppm, 2 ppm, or 1 ppm total organic solvent. In some embodiments, the pharmaceutical composition comprises about 1-5 ppm, about 5-10 ppm, about 10-15 ppm, about 15-20 ppm (or a combination of such ranges) of total organic solvent. In some embodiments, the pharmaceutical composition is substantially free of organic solvent.

In some embodiments, the pharmaceutical composition comprises less than about 10 µg/ml chloroform, such as less than about any of 10 µg/ml, 9 µg/ml, 8 µg/ml, 7 µg/ml, 6 µg/ml, 5 µg/ml, 4 µg/ml, 3 µg/ml, 2 µg/ml, or 1 µg/ml chloroform. In some embodiments, the pharmaceutical composition comprises any of about 1-2 µg/ml, about 2-5 µg/ml, or about 5-10 µg/ml chloroform. In some embodiments, the pharmaceutical composition comprises less than about 10 ppm chloroform, such as any of less than about 10 ppm, 9 ppm, 8 ppm, 7 ppm, 6 ppm, 5 ppm, 4 ppm, 3 ppm, 2 ppm, or 1 ppm chloroform. In some embodiments, the pharmaceutical composition comprises any of about 1-2 ppm, about 2-5 ppm, or about 5-10 ppm chloroform. In some embodiments, the pharmaceutical composition is substantially free of chloroform.

In some embodiments, the pharmaceutical composition comprises less than 5 µg/mL or less than 5 ppm chloroform.

In some embodiments, the pharmaceutical composition comprises less than about 10 µg/ml ethanol, such as less than about any of 10 µg/ml, 9 µg/ml, 8 µg/ml, 7 µg/ml, 6 µg/ml, 5 µg/ml, 4 µg/ml, 3 µg/ml, 2 µg/ml, or 1 µg/ml ethanol. In some embodiments, the pharmaceutical composition comprises any of about 1-2 µg/ml, about 2-5 µg/ml, or about 5-10 µg/ml ethanol. In some embodiments, the pharmaceutical composition comprises less than about 10 ppm ethanol, such as any of less than about 10 ppm, 9 ppm, 8 ppm, 7 ppm, 6 ppm, 5 ppm, 4 ppm, 3 ppm, 2 ppm, or 1 ppm ethanol. In some embodiments, the pharmaceutical composition comprises any of about 1-2 ppm, about 2-5 ppm, or about 5-10 ppm ethanol. In some embodiments, the pharmaceutical composition is substantially free of ethanol.

In some embodiments, the pharmaceutical composition comprises less than 5 µg/mL or less than 5 ppm ethanol.

In some embodiments, the pharmaceutical composition comprises less than about 10 µg/ml isopropanol, such as less than about any of 10 µg/ml, 9 µg/ml, 8 µg/ml, 7 µg/ml, 6 µg/ml, 5 µg/ml, 4 µg/ml, 3 µg/ml, 2 µg/ml, or 1 µg/ml isopropanol. In some embodiments, the pharmaceutical composition comprises any of about 1-2 µg/ml, about 2-5 µg/ml, or about 5-10 µg/ml isopropanol. In some embodiments, the pharmaceutical composition comprises less than about 10 ppm isopropanol, such as any of less than about 10 ppm, 9 ppm, 8 ppm, 7 ppm, 6 ppm, 5 ppm, 4 ppm, 3 ppm, 2 ppm, or 1 ppm isopropanol. In some embodiments, the pharmaceutical composition comprises any of about 1-2 ppm, about 2-5 ppm, or about 5-10 ppm isopropanol. In some embodiments, the pharmaceutical composition is substantially free of isopropanol.

In some embodiments, the pharmaceutical composition comprises less than 5 µg/mL or less than 5 ppm isopropanol.

In some embodiments, the pharmaceutical composition comprises less than about 10 µg/ml tert-butanol, such as less than about any of 10 µg/ml, 9 µg/ml, 8 µg/ml, 7 µg/ml, 6 µg/ml, 5 µg/ml, 4 µg/ml, 3 µg/ml, 2 µg/ml, or 1 µg/ml tert-butanol. In some embodiments, the pharmaceutical composition comprises any of about 1-2 µg/ml, about 2-5 µg/ml, or about 5-10 µg/ml tert-butanol. In some embodiments, the pharmaceutical composition comprises less than about 10 ppm tert-butanol, such as any of less than about 10 ppm, 9 ppm, 8 ppm, 7 ppm, 6 ppm, 5 ppm, 4 ppm, 3 ppm, 2 ppm, or 1 ppm tert-butanol. In some embodiments, the pharmaceutical composition comprises any of about 1-2 ppm, about 2-5 ppm, or about 5-10 ppm tert-butanol. In some embodiments, the pharmaceutical composition is substantially free of tert-butanol.

In some embodiments, the pharmaceutical composition comprises less than 10 µg/mL or less than 10 ppm tert-butanol.

In some embodiments, the pharmaceutical composition is suitable for administration to a human. In some embodiments, the pharmaceutical composition is suitable for administration to a human by parenteral administration. Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizing agents, and preservatives. The formulations can be presented in unit-dose or multi-dose sealed containers, such as ampules and vials, and can be stored in a freeze-dried (lyophilized) condition requiring only the addition of the sterile liquid excipient methods of treatment, methods of administration, and dosage regimens described herein (i.e., water) for injection, immediately prior to use. Extemporaneous injection solutions and suspensions can be prepared from sterile powders, granules, and tablets of the kind previously described. Injectable formulations are preferred. In some embodiments, the composition (such as a pharmaceutical composition) is contained in a single-use vial, such as a single-use sealed vial. In some embodiments, each single-use vial contains about 100 mg rapamycin. In some embodiments, the single-use vial contains about 900 mg albumin. In some embodiments, the composition (such as a pharmaceutical composition) is contained in a multi-use vial. In some embodiments, the composition (such as a pharmaceutical composition) is contained in bulk in a container.

Also provided are unit dosage forms comprising the compositions (such as pharmaceutical compositions) and formulations described herein. These unit dosage forms can be stored in a suitable packaging in single or multiple unit dosages and may also be further sterilized and sealed. In some embodiments, the composition (such as a pharmaceutical composition) also includes one or more other compounds (or pharmaceutically acceptable salts thereof) that are useful for treating cancer. In various variations, the amount of rapamycin in the pharmaceutical composition is included in any one of the following ranges: about 5 to about 50 mg, about 20 to about 50 mg, about 50 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of rapamycin in the pharmaceutical composition (e.g., a dosage or unit dosage form) is in the range of about 5 mg to about 500 mg, such as about 30 mg to about 300 mg or about 50 mg to about 200 mg. In some embodiments, the carrier is suitable for parental administration (e.g., intravenous administration). In some embodiments, the rapamycin is the only pharmaceutically active agent for the treatment of cancer that is contained in the composition.

The unit dosage form may be associated with a unit dosage label, which indicates the amount of rapamycin in the unit dosage form. The unit dosage label may be affixed to a container (e.g., vial, bag, or other packaging) containing the pharmaceutical composition of the unit dosage form. The unit dosage label may indicate, for example that the unit dosage form contains rapamycin in an amount of any one of 5 mg, 10 mg, 15 mg, 20 mg, 25 mg, 30 mg, 40 mg, 50 mg, 60 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, or 500 mg. The actual amount of rapamycin in the unit dosage form may differ slightly from the unit dosage label. In some embodiments, the amount of rapamycin in the unit dosage form differs by no more than about 20%, no more than about 15%, no more than about 10%, or no more than about 5% of the unit dosage label associated with the unit dosage form.

Content uniformity (i.e., the difference between the amount of rapamycin in the unit dosage form indicated on the unit dosage label and the amount of rapamycin in the unit dosage form) can be determined using a rapamycin reference standard. The reference standard can be prepared by mixing a measured amount of rapamycin in a solvent at a predetermined concentration. Optionally, two or more reference standards may be used at the same nominal rapamycin concentration, which can improve precision of the content uniformity measurement. The pharmaceutical composition is prepared, for example by reconstituting a dried composition or diluting a liquid composition. The reference standard (or reference standards, if multiple reference standards are used) and the prepared pharmaceutical composition are separately analyzed using HPLC (for example, RP-HPLC), and the peak area attributable to the rapamycin (e.g., the sum of the cis and trans rapamycin peaks) for the pharmaceutical composition is compared with the peak area attributable to the rapamycin for the reference standards (or average peak area, if multiple reference standards are used) to determine a ratio, which may be adjusted for differences in the volume or nominal concentration of the reference standard(s). In some embodiments, the unit dosage contains about 700 mg to about 1200 mg albumin, such as about 700 mg to about 800 mg, about 800 mg to about 900 mg, about 900 mg to about 1000 mg, about 1000 mg to about 1100 mg, or about 1100 mg to about 1200 mg albumin. In some embodiments, the unit dosage contains about 75 mg to about 125 mg (such as about 100 mg) rapamycin and about 700 mg to about 1200 mg albumin (such as about 700 mg to about 800 mg, about 800 mg to about 900 mg, about 900 mg to about 1000 mg, about 1000 mg to about 1100 mg, or about 1100 mg to about 1200 mg albumin).

In some embodiments, there is provided a dosage form (e.g., a unit dosage form) for the treatment of cancer comprising any one of the compositions (such as pharmaceutical compositions) described herein. In some embodiments, there are provided articles of manufacture comprising the compositions (such as pharmaceutical compositions), formulations, and unit dosages described herein in suitable packaging for use in the methods of treatment, methods of administration, and dosage regimens described herein. Suitable packaging for compositions (such as pharmaceutical compositions) described herein are known in the art, and include, for example, vials (such as sealed vials), vessels (such as sealed vessels), ampules, bottles, jars, flexible packaging (e.g., sealed Mylar or plastic bags), and the like. These articles of manufacture may further be sterilized and/or sealed.

In some embodiments, the pharmaceutical composition comprises (a) nanoparticles comprising rapamycin and albumin (such as human albumin), and (b) a non-nanoparticle portion comprising albumin (such as human albumin) and rapamycin. In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles comprising a coating comprising albumin (such as human albumin) and a core comprising rapamycin, and (b) a non-nanoparticle portion comprising albumin (such as human albumin) and rapamycin. In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles comprising rapamycin and albumin (such as human albumin), wherein about 70% to about 85% of the albumin in the nanoparticles is in the form of monomeric albumin; and (b) a non-nanoparticle portion comprising albumin (such as human albumin) and rapamycin. In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles comprising rapamycin and albumin (such as human albumin), wherein about 25% to about 50% of the albumin in the nanoparticles is in the form of monomeric albumin; and (b) a non-nanoparticle portion comprising albumin (such as human albumin) and rapamycin. In some embodiments, about 0.5% to about 7% of the albumin in the non-nanoparticle portion or the total albumin in the pharmaceutical composition is in the form of polymeric albumin (other than oligomeric albumin). In some embodiments, about 0.3% to about 4% of the albumin in the non-nanoparticle portion or the total albumin in the pharmaceutical composition is in the form of oligomeric albumin. In some embodiments, about 4% to about 15% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles comprising a coating comprising albumin (such as human albumin) and a core comprising rapamycin, wherein about 70% to about 85% of the albumin in the nanoparticles is in the form of monomeric albumin; and (b) a non-nanoparticle portion comprising albumin (such as human albumin) and rapamycin. In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles comprising rapamycin and albumin (such as human albumin), wherein about 5% to about 15% of the albumin in the nanoparticles is in the form of polymeric albumin (or trimeric albumin); and (b) a non-nanoparticle portion comprising albumin (such as human albumin) and rapamycin. In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the pharmaceutical composition is about 1:1 to about 10:1. In some embodiments, about 90% or more of the albumin in the pharmaceutical composition is in the non-nanoparticle portion. In some embodiments, about 90% or more of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles comprising rapamycin and albumin (such as human albumin), wherein about 42% to about 60% of the albumin in the nanoparticles is in the form of polymeric albumin (other than oligomeric albumin); and (b) a non-nanoparticle portion comprising albumin (such as human albumin) and rapamycin. In some embodiments, about 0.5% to about 7% of the albumin in the non-nanoparticle portion or the total albumin in the pharmaceutical composition is in the form of polymeric albumin (other than oligomeric albumin). In some embodiments, about 0.3% to about 4% of the albumin in the non-nanoparticle portion or the total albumin in the pharmaceutical composition is in the form of oligomeric albumin. In some embodiments, about 4% to about 15% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the pharmaceutical composition is about 1:1 to about 10:1. In some embodiments, about 90% or more of the albumin in the pharmaceutical composition is in the non-nanoparticle portion. In some embodiments, about 90% or more of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles comprising a coating comprising albumin (such as human albumin) and a core comprising rapamycin, wherein about 5% to about 15% of the albumin in the nanoparticles is in the form of polymeric albumin (or trimeric albumin); and (b) a non-nanoparticle portion comprising albumin (such as human albumin) and rapamycin. In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the composition is about 300 mOsm/kg to about 350 mOsm/kg. In some embodiments, the viscosity of the composition is about 1.2 cP to about 1.5 cP. In some embodiments, the pH of the composition is about 6.0 to about 7.5. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, a pharmaceutical composition comprises (a) nanoparticles comprising rapamycin and albumin (such as human albumin), wherein about 9% to about 20% of the albumin in the nanoparticles is in the form of dimeric albumin; and (b) a non-nanoparticle portion comprising albumin (such as human albumin) and rapamycin. In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the pharmaceutical composition is about 1:1 to about 10:1. In some embodiments, about 90% or more of the albumin in the pharmaceutical composition is in the non-nanoparticle portion. In some embodiments, about 90% or more of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, a pharmaceutical composition comprises (a) nanoparticles comprising rapamycin and albumin (such as human albumin), wherein about 5% to about 16% of the albumin in the nanoparticles is in the form of dimeric albumin; and (b) a non-nanoparticle portion comprising albumin (such as human albumin) and rapamycin. In some embodiments, about 0.5% to about 7% of the albumin in the non-nanoparticle portion or the total albumin in the pharmaceutical composition is in the form of polymeric albumin (other than oligomeric albumin). In some embodiments, about 0.3% to about 4% of the albumin in the non-nanoparticle portion or the total albumin in the pharmaceutical composition is in the form of oligomeric albumin. In some embodiments, about 4% to about 15% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the pharmaceutical composition is about 1:1 to about 10:1. In some embodiments, about 90% or more of the albumin in the pharmaceutical composition is in the non-nanoparticle portion. In some embodiments, about 90% or more of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles comprising a coating comprising albumin (such as human albumin) and a core comprising rapamycin, wherein about 9% to about 20% of the albumin in the nanoparticles is in the form of dimeric albumin; and (b) a non-nanoparticle portion comprising albumin (such as human albumin) and rapamycin. In some embodiments, about 0.5% to about 5% of the albumin in the non-nanoparticle portion or the total albumin in the pharmaceutical composition is in the form of polymeric albumin (other than oligomeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles comprising rapamycin and albumin (such as human albumin), wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin. In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles comprising rapamycin and albumin (such as human albumin), wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 60% of the albumin in the nanoparticles is in the form of polymeric albumin (other than oligomeric albumin); and (b) a non-nanoparticle portion comprising albumin (such as human albumin) and rapamycin. In some embodiments, about 0.5% to about 7% of the albumin in the non-nanoparticle portion or the total albumin in the pharmaceutical composition is in the form of polymeric albumin (other than oligomeric albumin). In some embodiments, about 0.3% to about 4% of the albumin in the non-nanoparticle portion or the total albumin in the pharmaceutical composition is in the form of oligomeric albumin. In some embodiments, about 4% to about 15% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles comprising a coating comprising albumin (such as human albumin) and a core comprising rapamycin, wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin. In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the composition is about 1:1 to about 10:1. In some embodiments, about 90% or more of the albumin in the pharmaceutical composition is in the non-nanoparticle portion. In some embodiments, about 90% or more of the rapamycin in the composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles comprising a coating comprising albumin (such as human albumin) and a core comprising rapamycin, wherein about 25% to about 50% of the albumin in the nanoparticles is in the form of monomeric albumin, about 5% to about 16% of the albumin in the nanoparticles is in the form of dimeric albumin, and about 42% to about 60% of the albumin in the nanoparticles is in the form of polymeric albumin; and (b) a non-nanoparticle portion comprising albumin (such as human albumin) and rapamycin. In some embodiments, about 0.5% to about 7% of the albumin in the non-nanoparticle portion or the total albumin in the pharmaceutical composition is in the form of polymeric albumin (other than oligomeric albumin). In some embodiments, about 0.3% to about 4% of the albumin in the non-nanoparticle portion or the total albumin in the pharmaceutical composition is in the form of oligomeric albumin. In some embodiments, about 4% to about 15% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the composition is about 1:1 to about 10:1. In some embodiments, about 90% or more of the albumin in the pharmaceutical composition is in the non-nanoparticle portion. In some embodiments, about 90% or more of the rapamycin in the composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 200 nm or less (such as about 50 nm to about 200 nm), comprising rapamycin and albumin (such as human albumin), wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin. In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the composition is about 1:1 to about 10:1. In some embodiments, about 90% or more of the albumin in the pharmaceutical composition is in the non-nanoparticle portion. In some embodiments, about 90% or more of the rapamycin in the composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 200 nm or less (such as about 50 nm to about 200 nm), comprising rapamycin and albumin (such as human albumin), wherein about 25% to about 50% of the albumin in the nanoparticles is in the form of monomeric albumin, about 5% to about 16% of the albumin in the nanoparticles is in the form of dimeric albumin, about 1% to about 4.5% of the albumin in the nanoparticles is in the form of oligomeric albumin, and about 42% to about 62% of the albumin in the nanoparticles is in the form of polymeric albumin (other than oligomeric albumin); and (b) a non-nanoparticle portion comprising albumin (such as human albumin) and rapamycin. In some embodiments, about 0.5% to about 7% of the albumin in the non-nanoparticle portion or the total albumin in the pharmaceutical composition is in the form of polymeric albumin (other than oligomeric albumin). In some embodiments, about 0.3% to about 4% of the albumin in the non-nanoparticle portion or the total albumin in the pharmaceutical composition is in the form oligomeric albumin. In some embodiments, about 4% to about 15% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the composition is about 1:1 to about 10:1. In some embodiments, about 90% or more of the albumin in the pharmaceutical composition is in the non-nanoparticle portion. In some embodiments, about 90% or more of the rapamycin in the composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 μg/mL tert-butanol and/or comprises less than 5 μg/mL chloroform.

In some embodiments, the pharmaceutical composition comprises (a) nanoparticles having a Z-average particle size of about 200 nm or less (such as about 50 nm to about 200 nm), comprising a coating comprising albumin (such as human albumin) and a core comprising rapamycin, wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin. In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the composition is about 1:1 to about 10:1. In some embodiments, about 90% or more of the albumin in the composition is in the non-nanoparticle portion. In some embodiments, about 90% or more of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 μg/mL tert-butanol and/or comprises less than 5 μg/mL chloroform.

In some embodiments, the pharmaceutical composition comprises (a) nanoparticles having a Z-average particle size of about 200 nm or less (such as about 50 nm to about 200 nm), comprising about 55% to about 75% (by weight) rapamycin and about 25% to about 45% (by weight) albumin (such as human albumin), wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin. In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the pharmaceutical composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 μg/mL tert-butanol and/or comprises less than 5 μg/mL chloroform.

In some embodiments, the pharmaceutical composition comprises (a) nanoparticles having a Z-average particle size of about 200 nm or less (such as about 50 nm to about 200 nm), comprising about 55% to about 75% (by weight) rapamycin and about 25% to about 45% (by weight) albumin (such as human albumin), wherein about 25% to about 50% of the albumin in the nanoparticles is in the form of monomeric albumin, about 5% to about 16% of the albumin in the nanoparticles is in the form of dimeric albumin, and about 42% to about 60% of the albumin in the nanoparticles is in the form of polymeric albumin (other than oligomeric albumin); and (b) a non-nanoparticle portion comprising albumin (such as human albumin) and rapamycin. In some embodiments, about 0.5% to about 7% of the albumin in the non-nanoparticle portion or the total albumin in the pharmaceutical composition is in the form of polymeric albumin (other than oligomeric albumin). In some embodiments, about 0.3% to about 4% of the albumin in the non-nanoparticle portion or the total albumin in the pharmaceutical composition is in the form of oligomeric albumin. In some embodiments, about 4% to about 15% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the pharmaceutical composition is about 1:1 to about 10:1. In some embodiments, about 90% or more of the albumin in the composition is in the non-nanoparticle portion. In some embodiments, about 90% or more of the rapamycin in the composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 200 nm or less (such as about 50 nm to about 200 nm), comprising a coating comprising albumin (such as human albumin) and a core comprising rapamycin, wherein the albumin comprises about 25% to about 45% of the nanoparticles by weight and the rapamycin comprises about 55% to about 75% of the nanoparticles by weight, wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin. In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the pharmaceutical composition is about 1:1 to about 10:1. In some embodiments, about 90% or more of the albumin in the pharmaceutical composition is in the non-nanoparticle portion. In some embodiments, about 90% or more of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 200 nm or less (such as about 50 nm to about 200 nm), comprising about 55% to about 75% (by weight) rapamycin and about 25% to about 45% (by weight) albumin (such as human albumin), wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin; wherein the concentration of the rapamycin in the pharmaceutical composition is about 1 mg/mL to about 100 mg/mL (such as about 1 mg/mL to about 15 mg/mL). In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the pharmaceutical composition is about 1:1 to about 10:1. In some embodiments, about 90% or more of the albumin in the pharmaceutical composition is in the non-nanoparticle portion. In some embodiments, about 90% or more of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 200 nm or less (such as about 50 nm to about 200 nm), comprising a coating comprising albumin (such as human albumin) and a core comprising rapamycin, wherein the albumin comprises about 25% to about 45% of the nanoparticles by weight and the rapamycin comprises about 55% to about 75% of the nanoparticles by weight, wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin; wherein the concentration of the rapamycin in the pharmaceutical composition is about 1 mg/mL to about 100 mg/mL (such as about 1 mg/mL to about 15 mg/mL). In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the pharmaceutical composition is about 1:1 to about 10:1. In some embodiments, about 90% or more of the albumin in the pharmaceutical composition is in the non-nanoparticle portion. In some embodiments, about 90% or more of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 200 nm or less (such as about 50 nm to about 200 nm) and a zeta potential of about −25 mV to about −50 mV, comprising about 55% to about 75% (by weight) rapamycin and about 25% to about 45% (by weight) albumin (such as human albumin), wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin; wherein the concentration of the rapamycin in the pharmaceutical composition is about 1 mg/mL to about 100 mg/mL (such as about 1 mg/mL to about 15 mg/mL). In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the pharmaceutical composition is about 1:1 to about 10:1. In some embodiments, about 90% or more of the albumin in the pharmaceutical composition is in the non-nanoparticle portion. In some embodiments, about 90% or more of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 200 nm or less (such as about 50 nm to about 200 nm) and a zeta potential of about −25 mV to about −50 mV, comprising a coating comprising albumin (such as human albumin) and a core comprising rapamycin, wherein the albumin comprises about 25% to about 45% of the nanoparticles by weight and the rapamycin comprises about 55% to about 75% of the nanoparticles by weight, wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin; wherein the concentration of the rapamycin in the pharmaceutical composition is about 1 mg/mL to about 100 mg/mL (such as about 1 mg/mL to about 15 mg/mL). In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in pharmaceutical composition is in the form of monomeric albumin. In some embodiments, the weight ratio of the albumin to the rapamycin in the composition is about 1:1 to about 10:1. In some embodiments, about 90% or more of the albumin in the pharmaceutical composition is in the non-nanoparticle portion. In some embodiments, about 90% or more of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 200 nm or less (such as about 50 nm to about 200 nm) and a zeta potential of about −25 mV to about −50 mV, comprising about 55% to about 75% (by weight) rapamycin and about 25% to about 45% (by weight) albumin (such as human albumin), wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin; wherein the concentration of the rapamycin in the pharmaceutical composition is about 1 mg/mL to about 100 mg/mL (such as about 1 mg/mL to about 15 mg/mL); and wherein about 3% or less of the rapamycin in the pharmaceutical composition is free rapamycin. In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the composition is about 1:1 to about 10:1. In some embodiments, about 90% or more of the albumin in the pharmaceutical composition is in the non-nanoparticle portion. In some embodiments, about 90% or more of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 200 nm or less (such as about 50 nm to about 200 nm) and a zeta potential of about −25 mV to about −50 mV, comprising a coating comprising albumin (such as human albumin) and a core comprising rapamycin, wherein the albumin comprises about 25% to about 45% of the nanoparticles by weight and the rapamycin comprises about 55% to about 75% of the nanoparticles by weight, wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin; wherein the concentration of the rapamycin in the pharmaceutical composition is about 1 mg/mL to about 100 mg/mL (such as about 1 mg/mL to about 15 mg/mL); and wherein about 3% or less of the rapamycin in the pharmaceutical composition is free rapamycin. In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the pharmaceutical composition is about 1:1 to about 10:1. In some embodiments, about 90% or more of the albumin in the pharmaceutical composition is in the non-nanoparticle portion. In some embodiments, about 90% or more of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 200 nm or less (such as about 50 nm to about 200 nm) and a zeta potential of about −25 mV to about −50 mV, comprising about 55% to about 75% (by weight) rapamycin and about 25% to about 45% (by weight) albumin (such as human albumin), wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin; wherein the concentration of the rapamycin in the pharmaceutical composition is about 1 mg/mL to about 100 mg/mL (such as about 1 mg/mL to about 15 mg/mL); and wherein the sum of seco-rapamycin and rapamycin in the nanoparticles is less than 3% (such as about 0.2% to about 3%) seco-rapamycin, by weight. In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the pharmaceutical composition is about 1:1 to about 10:1. In some embodiments, about 90% or more of the albumin in the pharmaceutical composition is in the non-nanoparticle portion. In some embodiments, about 90% or more of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 200 nm or less (such as about 50 nm to about 200 nm) and a zeta potential of about −25 mV to about −50 mV, comprising a coating comprising albumin (such as human albumin) and a core comprising rapamycin, wherein the albumin comprises about 25% to about 45% of the nanoparticles by weight and the rapamycin comprises about 55% to about 75% of the nanoparticles by weight, wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin (or trimeric albumin); and (b) a non-nanoparticle portion comprising albumin (such as human albumin) and rapamycin; wherein the concentration of the rapamycin in the pharmaceutical composition is about 1 mg/mL to about 100 mg/mL (such as about 1 mg/mL to about 15 mg/mL); and wherein the sum of seco-rapamycin and rapamycin in the nanoparticles is less than 3% (such as about 0.2% to about 3%) seco-rapamycin, by weight. In some embodiments, about 0.5% to about 5% of the albumin in the non-nanoparticle portion or the total albumin in the pharmaceutical composition is in the form of polymeric albumin (or trimeric albumin). In some embodiments, about 4% to about 14% of the albumin in the non-nanoparticle portion or the total albumin in the pharmaceutical composition is in the form of dimeric albumin. In some embodiments, about 80% to about 95% of the albumin in the non-nanoparticle portion or the total albumin in the pharmaceutical composition is in the form of monomeric albumin. In some embodiments, the weight ratio of the albumin to the rapamycin in the pharmaceutical composition is about 1:1 to about 10:1. In some embodiments, about 90% or more of the albumin in the composition is in the non-nanoparticle portion. In some embodiments, about 90% or more of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 30 mg/mL to about 100 mg/mL. In some embodiments, the osmolality of the pharmaceutical composition is about 300 mOsm/kg to about 350 mOsm/kg. In some embodiments, the viscosity of the pharmaceutical composition is about 1.2 cP to about 1.5 cP. In some embodiments, the pH of the pharmaceutical composition is about 6.0 to about 7.5. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles comprising rapamycin and albumin (such as human albumin), wherein about 74% to about 80% of the albumin in the nanoparticles is in the form of monomeric albumin; and (b) a non-nanoparticle portion comprising albumin (such as human albumin) and rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles comprising a coating comprising albumin (such as human albumin) and a core comprising rapamycin, wherein about 74% to about 80% of the albumin in the nanoparticles is in the form of monomeric albumin; and (b) a non-nanoparticle portion comprising albumin (such as human albumin) and rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles comprising rapamycin and albumin (such as human albumin), wherein about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 μg/mL tert-butanol and/or comprises less than 5 μg/mL chloroform.

In some embodiments, the pharmaceutical composition comprises (a) nanoparticles comprising a coating comprising albumin (such as human albumin) and a core comprising rapamycin, wherein about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 μg/mL tert-butanol and/or comprises less than 5 μg/mL chloroform.

In some embodiments, the pharmaceutical composition comprises (a) nanoparticles comprising rapamycin and albumin (such as human albumin), wherein about 12% to about 17% of the albumin in the nanoparticles is in the form of dimeric albumin; and (b) a non-nanoparticle portion comprising albumin (such as human albumin) and rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 μg/mL tert-butanol and/or comprises less than 5 μg/mL chloroform.

In some embodiments, the pharmaceutical composition comprises (a) nanoparticles comprising a coating comprising albumin (such as human albumin) and a core comprising rapamycin, wherein about 12% to about 17% of the albumin in the nanoparticles is in the form of dimeric albumin; and (b) a non-nanoparticle portion comprising albumin (such as human albumin) and rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles comprising rapamycin and albumin (such as human albumin), wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 μg/mL tert-butanol and/or comprises less than 5 μg/mL chloroform.

In some embodiments, the pharmaceutical composition comprises (a) nanoparticles having a Z-average particle size of about 85 nm to about 95 nm, comprising rapamycin and albumin (such as human albumin); and (b) a non-nanoparticle portion comprising albumin (such as human albumin) and rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 μg/mL tert-butanol and/or comprises less than 5 μg/mL chloroform.

In some embodiments, the pharmaceutical composition comprises (a) nanoparticles having a Z-average particle size of about 85 nm to about 95 nm, comprising a coating comprising albumin (such as human albumin) and a core comprising rapamycin; and (b) a non-nanoparticle portion comprising albumin (such as human albumin) and rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 μg/mL tert-butanol and/or comprises less than 5 μg/mL chloroform.

In some embodiments, the pharmaceutical composition comprises (a) nanoparticles having a Z-average particle size of about 85 nm to about 95 nm, comprising rapamycin and albumin (such as human albumin), wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 μg/mL tert-butanol and/or comprises less than 5 μg/mL chloroform.

In some embodiments, the pharmaceutical composition comprises (a) nanoparticles having a Z-average particle size of about 85 nm to about 95 nm, comprising a coating comprising albumin (such as human albumin) and a core comprising rapamycin, wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 μg/mL tert-butanol and/or comprises less than 5 μg/mL chloroform.

In some embodiments, the pharmaceutical composition comprises (a) nanoparticles having a zeta potential of about −33 mV to about −39 mV, comprising rapamycin and albumin (such as human albumin); and (b) a non-nanoparticle portion comprising albumin (such as human albumin) and rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 μg/mL tert-butanol and/or comprises less than 5 μg/mL chloroform.

In some embodiments, the pharmaceutical composition comprises (a) nanoparticles having a zeta potential of about −33 mV to about −39 mV, comprising a coating comprising albumin (such as human albumin) and a core comprising rapamycin; and (b) a non-nanoparticle portion comprising albumin (such as human albumin) and rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a zeta potential of about −33 mV to about −39 mV, comprising rapamycin and albumin (such as human albumin), wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 85 nm to about 95 nm and a zeta potential of about −33 mV to about −39 mV, comprising rapamycin and albumin (such as human albumin); and (b) a non-nanoparticle portion comprising albumin (such as human albumin) and rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 85 nm to about 95 nm and a zeta potential of about −33 mV to about −39 mV, comprising a coating comprising albumin (such as human albumin) and a core comprising rapamycin; and (b) a non-nanoparticle portion comprising albumin (such as human albumin) and rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 85 nm to about 95 nm and a zeta potential of about −33 mV to about −39 mV, comprising rapamycin and albumin (such as human albumin), wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 μg/mL tert-butanol and/or comprises less than 5 μg/mL chloroform.

In some embodiments, the pharmaceutical composition comprises (a) nanoparticles having a Z-average particle size of about 85 nm to about 95 nm and a zeta potential of about −33 mV to about −39 mV, comprising a coating comprising albumin (such as human albumin) and a core comprising rapamycin, wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 μg/mL tert-butanol and/or comprises less than 5 μg/mL chloroform.

In some embodiments, the pharmaceutical composition comprises (a) nanoparticles having a Z-average particle size of about 85 nm to about 95 nm, comprising about 62% to about 68% (by weight) rapamycin and about 32% to about 38% (by weight) albumin (such as human albumin), wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 μg/mL tert-butanol and/or comprises less than 5 μg/mL chloroform.

In some embodiments, the pharmaceutical composition comprises (a) nanoparticles having a Z-average particle size of about 85 nm to about 95 nm, comprising a coating comprising albumin (such as human albumin) and a core comprising rapamycin, wherein the albumin comprises about 32% to about 38% of the nanoparticles by weight and the rapamycin comprises about 62% to about 68% of the nanoparticles by weight, wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 85 nm to about 95 nm, comprising about 62% to about 68% (by weight) rapamycin and about 32% to about 38% (by weight) albumin (such as human albumin), wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL). In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 85 nm to about 95 nm, comprising a coating comprising albumin (such as human albumin) and a core comprising rapamycin, wherein the albumin comprises about 32% to about 38% of the nanoparticles by weight and the rapamycin comprises about 62% to about 68% of the nanoparticles by weight, wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL). In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 85 nm to about 95 nm and a zeta potential of about −33 mV to about −39 mV, comprising about 62% to about 68% (by weight) rapamycin and about 32% to about 38% (by weight) albumin (such as human albumin), wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL). In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 85 nm to about 95 nm and a zeta potential of about −33 mV to about −39 mV, comprising a coating comprising albumin (such as human albumin) and a core comprising rapamycin, wherein the albumin comprises about 32% to about 38% of the nanoparticles by weight and the rapamycin comprises about 62% to about 68% of the nanoparticles by weight, wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 85 nm to about 95 nm and a zeta potential of about −33 mV to about −39 mV, comprising about 62% to about 68% (by weight) rapamycin and about 32% to about 38% (by weight) albumin (such as human albumin), wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL); and wherein about 1% or less of the rapamycin in the nanoparticle composition is free rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 85 nm to about 95 nm and a zeta potential of about −33 mV to about −39 mV, comprising a coating comprising albumin (such as human albumin) and a core comprising rapamycin, wherein the albumin comprises about 32% to about 38% of the nanoparticles by weight and the rapamycin comprises about 62% to about 68% of the nanoparticles by weight, wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL); and wherein about 1% or less of the rapamycin in the nanoparticle composition is free rapamycin. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 µg/mL tert-butanol and/or comprises less than 5 µg/mL chloroform.

In some embodiments, the pharmaceutical composition comprises (a) nanoparticles having a Z-average particle size of about 85 nm to about 95 nm and a zeta potential of about of about −33 mV to about −39 mV, comprising about 62% to about 68% (by weight) rapamycin and about 32% to about 38% (by weight) albumin (such as human albumin), wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL); and wherein the sum of seco-rapamycin and rapamycin in the nanoparticles is less than 1% (such as about 0.5% to about 1%) seco-rapamycin, by weight. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 μg/mL tert-butanol and/or comprises less than 5 μg/mL chloroform.

In some embodiments, the pharmaceutical composition comprises (a) nanoparticles having a Z-average particle size of about 85 nm to about 95 nm and a zeta potential of about −33 mV to about −39 mV, comprising a coating comprising albumin (such as human albumin) and a core comprising rapamycin, wherein the albumin comprises about 32% to about 38% of the nanoparticles by weight and the rapamycin comprises about 62% to about 68% of the nanoparticles by weight, wherein about 74% to about 80% of the albumin in the nanoparticles is in the form of monomeric albumin, about 12% to about 17% of the albumin in the nanoparticles is in the form of dimeric albumin, and about 7% to about 11% of the albumin in the nanoparticles is in the form of polymeric albumin (or trimeric albumin); and (b) a non-nanoparticle portion comprising albumin (such as human albumin) and rapamycin; wherein the concentration of the rapamycin in the nanoparticle composition is about 1 mg/mL to about 100 mg/mL (such as about 1 mg/mL to about 15 mg/mL); and wherein the sum of seco-rapamycin and rapamycin in the nanoparticles is less than 1% (such as about 0.5% to about 1%) seco-rapamycin, by weight. In some embodiments, about 1.5% to about 3% of the albumin in the non-nanoparticle portion or the total albumin in the pharmaceutical composition is in the form of polymeric albumin (or trimeric albumin). In some embodiments, about 7% to about 11% of the albumin in the non-nanoparticle portion in the pharmaceutical composition is in the form of dimeric albumin. In some embodiments, about 7% to about 11% of the total albumin in the pharmaceutical composition is in the form of dimeric albumin. In some embodiments, about 83% to about 92% of the albumin in the non-nanoparticle portion or the total albumin in the pharmaceutical composition is in the form of monomeric albumin. In some embodiments, the weight ratio of the albumin to the rapamycin in the pharmaceutical composition is about 7:1 to about 9:1. In some embodiments, about 95% or more of the albumin in the pharmaceutical composition is in the non-nanoparticle portion. In some embodiments, about 98% to about 99.5% of the rapamycin in the pharmaceutical composition is in the nanoparticles. In some embodiments, the concentration of albumin in the pharmaceutical composition that is in the non-nanoparticle portion or the concentration of total albumin in the pharmaceutical composition is about 35 mg/mL to about 45 mg/mL. In some embodiments, the osmolality of the pharmaceutical composition is about 325 mOsm/kg to about 340 mOsm/kg. In some embodiments, the viscosity of the composition is about 1.3 cP to about 1.35 cP. In some embodiments, the pH of the composition is about 6.7 to about 6.8. In some embodiments, the pharmaceutical composition is stable at 4° C. and/or 25° C. for at least 24 hours. In some embodiments, the rapamycin in the nanoparticles has an amorphous morphology. In some embodiment, the pharmaceutical composition is a nanoparticle suspension. In some embodiments, the pharmaceutical composition is a dried composition. In some embodiments, the pharmaceutical composition is sterile, for example by filtration. In some embodiments, the pharmaceutical composition is contained within a sealed container, such as a sealed vial or a sealed bag. In some embodiments, the pharmaceutical composition comprises less than 10 μg/mL tert-butanol and/or comprises less than 5 μg/mL chloroform.

Commercial Batches

Described herein in various embodiments are commercial batches of a nanoparticle composition or a pharmaceutical composition. "Commercial batch" used herein refers to a batch size that is at least about 20 grams (by amount of rapamycin). Commercial batches are produced at a larger scale than experimental or bench-scale batches. The increased scale is associated with longer production times, including longer steps (such as evaporation steps) or longer hold times between steps.

The commercial batches described herein, in some embodiments, comprise nanoparticle compositions (such as pharmaceutical compositions) that may have distinct characteristics for any one or more (in any combination) of the following: (1) the oligomeric status of the albumin associated with (such as in) the nanoparticles, such as the percentage of albumin monomers, dimers, oligomers, and/or polymers (or polymers other than oligomers) of the albumin associated with (such as in) the nanoparticles; (2) the oligomeric status of the albumin associated with (such as in) the non-nanoparticle portion of the composition, such as the percentage of albumin monomers, dimers, oligomers, and/or polymers (or polymers other than oligomers) of the albumin associated with (such as in) the non-nanoparticle portion of the composition; (3) the oligomeric status of the total albumin in the composition, such as the percentage of albumin monomers, dimers, oligomers, and/or polymers (or polymers other than oligomers) of the total albumin in the composition; (4) the particle size profile of the nanoparticles, such as the average particle size, polydispersity index, and/or size distribution; (5) the portion (e.g., weight percentage) of the nanoparticles that is albumin and/or the portion (e.g., weight percentage) of the nanoparticles that is rapamycin; (6) the weight ratio of the albumin to the rapamycin in the nanoparticles; (7) the weight ratio of the albumin to the rapamycin in the non-nanoparticle portion of the composition; (8) the weight ratio of the albumin to the rapamycin in the non-nanoparticle portion of the composition (9) the weight ratio of the total albumin to the total rapamycin in the composition; (10) the portion (e.g., weight percentage) of rapamycin that is in the nanoparticles (or the non-nanoparticle portion of the composition) compared to the total rapamycin in the composition; (11) the portion (e.g., weight percentage) of albumin that is in the non-nanoparticle portion (or in the nanoparticles) compared to the total albumin in the composition; (12) the concentration of albumin in the composition; (13) the concentration of albumin in the non-nanoparticle portion of the composition; (14) the concentration of albumin in the composition that is associated with (such as in) the nanoparticles; (15) the concentration of rapamycin in the composition; (16) the concentration of rapamycin in the non-nanoparticle portion of the composition; (17) the concentration of rapamycin in the composition that is associated with (such as in) the nanoparticles; (18) the osmolality of the composition; (19) the viscosity of the composition; (20) the pH of the composition; (21) the stability of the nanoparticles in the composition; (22) the amount of residual solvent in the composition; (23) the zeta potential of the nanoparticles in the composition; (24) the crystalline status of the rapamycin in the nanoparticles; (25) the particle morphology of the nanoparticles, such as the shape, sphericity, thickness of the coating, and/or surface-to-volume ratio; (26) the weight percentage of seco-rapamycin in the nanoparticles, as compared to the sum of seco-rapamycin and rapamycin, by weight; (27) the presence, percentage, or concentration of albumin stabilizer (such as a caprylic acid derivative e.g., sodium caprylate and/or a tryptophan derivative e.g., N-acetyltryptophanate) in the composition; (28) the recovery of rapamycin following filtration; (29) in vitro release kinetics of the nanoparticles; and/or (30) the portion of total rapamycin in the composition that is both in the non-nanoparticle portion of the composition and not bound to albumin. The physicochemical parameters discussed above can affect drug release and delivery of the albumin-based rapamycin nanoparticle compositions (such as pharmaceutical compositions), and thus constitute unique properties to the compositions in the commercial batches.

The commercial batches described herein, in some embodiments, comprise nanoparticle compositions (such as pharmaceutical compositions) that may have distinct characteristics for any one or more (in any combination) of the following: (1) the oligomeric status of the albumin associated with (such as in) the nanoparticles, such as the percentage of albumin monomers, dimers, and/or trimers of the albumin associated with (such as in) the nanoparticles; (2) the oligomeric status of the albumin associated with (such as in) the non-nanoparticle portion of the composition, such as the percentage of albumin monomers, dimers, and/or trimers of the albumin associated with (such as in) the non-nanoparticle portion of the composition; (3) the oligomeric status of the total albumin in the composition, such as the percentage of albumin monomers, dimers, and/or trimers of the total albumin in the composition; (4) the particle size profile of the nanoparticles, such as the average particle size, polydispersity index, and/or size distribution; (5) the portion (e.g., weight percentage) of the nanoparticles that is albumin and/or the portion (e.g., weight percentage) of the nanoparticles that is rapamycin; (6) the weight ratio of the albumin to the rapamycin in the nanoparticles; (7) the weight ratio of the albumin to the rapamycin in the non-nanoparticle portion of the composition; (8) the weight ratio of the albumin to the rapamycin in the non-nanoparticle portion of the composition (9) the weight ratio of the total albumin to the total rapamycin in the composition; (10) the portion (e.g., weight percentage) of rapamycin that is in the nanoparticles (or the non-nanoparticle portion of the composition) compared to the total rapamycin in the composition; (11) the portion (e.g., weight percentage) of albumin that is in the non-nanoparticle portion (or in the nanoparticles) compared to the total albumin in the composition; (12) the concentration of albumin in the composition; (13) the concentration of albumin in the non-nanoparticle portion of the composition; (14) the concentration of albumin in the composition that is associated with (such as in) the nanoparticles; (15) the concentration of rapamycin in the composition; (16) the concentration of rapamycin in the non-nanoparticle portion of the composition; (17) the concentration of rapamycin in the composition that is associated with (such as in) the nanoparticles; (18) the osmolality of the composition; (19) the viscosity of the composition; (20) the pH of the composition; (21) the stability of the nanoparticles in the composition; (22) the amount of residual solvent in the composition; (23) the zeta potential of the nanoparticles in the composition; (24) the crystalline status of the rapamycin in the nanoparticles; (25) the particle morphology of the nanoparticles, such as the shape, sphericity, thickness of the coating, and/or surface-to-volume ratio; (26) the weight percentage of seco-rapamycin in the nanoparticles, as compared to the sum of seco-rapamycin and rapamycin, by weight; (27) the presence, percentage, or concentration of albumin stabilizer (such as a caprylic acid derivative e.g., sodium caprylate and/or a tryptophan derivative e.g., N-acetyltryptophanate) in the composition; (28) the recovery of rapamycin following filtration; (29) in vitro release kinetics of the nanoparticles; and/or (30) the portion of total rapamycin in the composition that is both in the non-nanoparticle portion of the composition and not bound to albumin. The physicochemical parameters discussed above can affect drug release and delivery of the albumin-based rapamycin nanoparticle compositions (such as pharmaceutical compositions), and thus constitute unique properties to the compositions in the commercial batches.

In some embodiments, the commercial batch size is at least about any of 30 grams, 40 grams, 50 grams, 60 grams, 70 grams, 80 grams, 90 grams, 100 grams, 150 grams, 200 grams, 250 grams, 300 grams, 350 grams, 400 grams, 450 grams, 500 grams, 550 grams, 600 grams, 650 grams, 700 grams, 750 grams, 800 grams, 850 grams, 900 grams, 1000 grams, 1500 grams, 2000 grams, 2500 grams, 3000 grams, 3500 grams, 4000 grams, 4500 grams, 5000 grams, or 10000 grams (by amount of rapamycin). In some embodiments, the commercial batch comprises a plurality of containers, such as vials, comprising any of the compositions (such as pharmaceutical compositions) described herein. In some embodiments, the commercial batch comprises at least about any of 100 vials, 150 vials, 200 vials, 250 vials, 300 vials, 350 vials, 400 vials, 450 vials, 500 vials, 550 vials, 600 vials, 650 vials, 700 vials, 750 vials, 800 vials, 850 vials, 900 vials, 1000 vials, 1500 vials, 2000 vials, 2500 vials, 3000 vials, 3500 vials, 4000 vials, 4500 vials, 5000 vials, 10000 vials, 12000 vials, 14000 vials, 16000 vials, 18000 vials, 20000 vials, 22000 vials, 24000 vials, 26000 vials, 28000 vials, 30000 vials, 32000 vials, 34000 vials, 36000 vials, 38000 vials, 40000 vials, 42000 vials, 44000 vials, 46000 vials, 48000 vials, or 50000 vials. For example, each vial contains about any of 10 mg, 50 mg, 100 mg, 200 mg, 300 mg, 400 mg, 500 mg, 600 mg, 700 mg, 800 mg, 900 mg, or 1000 mg of the composition (such as a pharmaceutical composition). In some embodiments, each vial contains about any of 10 mg, 50 mg, 100 mg, 200 mg, 300 mg, 400 mg, 500 mg, 600 mg, 700 mg, 800 mg, 900 mg, or 1000 mg rapamycin. In some embodiments, the pharmaceutical composition in the commercial batch is a liquid suspension. In some embodiments, the pharmaceutical composition in the commercial batch is in a dried form, such as a lyophilized powder.

Thus, the present application in some embodiments provides a commercial batch of a composition (such as a pharmaceutical composition) comprising any one of the compositions or pharmaceutical compositions described herein (see more details in the sections above). For example, in some embodiments, there is provided a commercial batch of a pharmaceutical composition comprising: a) nanoparticles comprising rapamycin associated (such as coated) with albumin, and b) a non-nanoparticle portion comprising albumin and rapamycin. The characteristics and properties of the compositions contained with the commercial batch are described and defined throughout this application. Those characteristics and properties which are quality control parameters may be assessed for the commercial batch by assessment of a sample of the commercial batch.

Kits

The present application also provides kits comprising the compositions (such as pharmaceutical compositions), formulations, unit dosages, and articles of manufacture described herein for use in the methods of treatment, methods of administration, and dosage regimens described herein. Kits described herein include one or more containers comprising the rapamycin pharmaceutical compositions (formulations or unit dosage forms and/or articles of manufacture), and, in some embodiments, further comprise instructions for use in accordance with any of the methods of treatment described herein. In various embodiments, the amount of rapamycin in the kit is included in any one of the following ranges: about 5 mg to about 20 mg, about 20 mg to about 50 mg, about 50 mg to about 100 mg, about 100 mg to about 125 mg, about 125 mg to about 150 mg, about 150 mg to about 175 mg, about 175 mg to about 200 mg, about 200 mg to about 225 mg, about 225 mg to about 250 mg, about 250 mg to about 300 mg, about 300 mg to about 350 mg, about 350 mg to about 400 mg, about 400 mg to about 450 mg, or about 450 mg to about 500 mg. In some embodiments, the amount of rapamycin in the kit is in the range of about 5 mg to about 500 mg, such as about 30 mg to about 300 mg or about 50 mg to about 200 mg. In some embodiments, the kit includes one or more other compounds (e.g., one or more compounds other than rapamycin that are useful for cancer).

Instructions supplied in the kits described herein are typically written instructions on a label or package insert (e.g., a paper sheet included in the kit), but machine-readable instructions (e.g., instructions carried on a magnetic or optical storage disk) are also acceptable. The instructions relating to the use of the pharmaceutical compositions generally include information as to dosage, dosing schedule, and route of administration for the intended treatment. The kit may further comprise a description of selecting an individual suitable or treatment.

In some embodiments, the kit comprises a plurality of doses of the pharmaceutical composition. In some embodiments, the instructions supplied in the kit describe methods of assessing the suitability of the pharmaceutical composition for medical use in a human individual by measuring a quality control parameter for the pharmaceutical composition and assessing the suitability of the pharmaceutical composition for medical use in a human individual, wherein a measured quality control parameter within a quality control threshold is indicative of suitability of the pharmaceutical composition for medical use. In some embodiments, the kit comprises a plurality of doses of the pharmaceutical composition each from the same manufacturing lot, wherein assessment of a sample of the pharmaceutical composition in the kit for suitability for medical use in a human individual allows assessment of all of the pharmaceutical composition provided by the kit.

The present application also provides kits comprising compositions (such as pharmaceutical compositions) (or unit dosages forms and/or articles of manufacture) described herein and may further comprise instruction(s) on methods of using the composition, such as uses further described herein. In some embodiments, the kit described herein comprises the packaging described above. In other variations, the kit described herein comprises the packaging described above and a second packaging comprising a buffer. It may further include other materials desirable from a commercial and user standpoint, including other buffers, diluents, filters, needles, syringes, and package inserts with instructions for performing any methods described herein.

For combination therapies described herein, the kit may contain instructions for administering the first and second therapies simultaneously and/or sequentially for the effective treatment of cancer. The first and second therapies can be present in separate containers or in a single container. It is understood that the kit may comprise one distinct composition or two or more compositions (such as pharmaceutical compositions) wherein one composition comprises a first therapy and one composition comprises a second therapy.

Kits may also be provided that contain sufficient dosages of the rapamycin as disclosed herein to provide effective treatment for an individual for an extended period, such as any one of a week, 2 weeks, 3 weeks, 4 weeks, 6 weeks, 8 weeks, 3 months, 4 months, 5 months, 6 months, 7 months, 8 months, 9 months or more. Kits may also include multiple unit doses of the rapamycin, compositions (such as pharmaceutical compositions), and formulations described herein and instructions for use and packaged in quantities sufficient for storage and use in pharmacies, for example, hospital pharmacies and compounding pharmacies. In some embodiments, the kit comprises a dry (e.g., lyophilized) composition that can be reconstituted, resuspended, or rehydrated to form generally a stable aqueous suspension of nanoparticles comprising rapamycin and albumin. The kits described herein are in suitable packaging. Suitable packaging include, but is not limited to, vials, bottles, jars, flexible packaging (e.g., sealed Mylar or plastic bags), and the like. Kits may optionally provide additional components such as buffers and interpretative information.

Quality Control Methods for Assessing the Suitability of Pharmaceutical Compositions for Medical Use The compositions described herein, including the pharmaceutical compositions, may be assessed for their suitability for use in an individual (such as a human individual) using a quality control process. Subjecting the pharmaceutical composition to a quality control process ensures that the pharmaceutical composition is safe and effective for use in the individual. One or more quality control parameters can be measured and compared to a corresponding quality control threshold (which may be qualitative or quantitative). The measured quality control parameter falling within the predetermined quality control threshold indicates that the pharmaceutical composition is suitable for use in the individual (such as a human individual). Multiple quality control parameters may be used (with corresponding quality control thresholds), and the plurality of quality control parameters falling within the corresponding quality control thresholds is indicative of the suitability of the pharmaceutical composition for use in an individual (such as a human individual). In some embodiments, if the one or more quality control parameters falls outside of the one or more quality control thresholds, it is indicative that the pharmaceutical composition is not suitable for use in the individual.

In some embodiments, a method of assessing suitability of a pharmaceutical composition for medical use in a human individual includes measuring one or more quality control parameters for the pharmaceutical composition, and assessing the suitability of the pharmaceutical composition for medical use in a human individual, wherein one or more measured quality control parameters within a quality control threshold(s) is indicative of suitability of the pharmaceutical composition for medical use. In some embodiments, the quality control parameter comprises a quality control parameter for the pharmaceutical composition, the nanoparticles in the pharmaceutical composition and/or the non-nanoparticle portion of the pharmaceutical composition. In some embodiments, the determination of at least one quality control parameter comprises determination of one or more (such as any of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36) of the following quality control parameters (in any combination of quality control parameters if a plurality of quality control parameters are used): (1) the weight percentage of albumin in the form of monomeric albumin in the nanoparticles of the total albumin in the nanoparticles; (2) the weight percentage of albumin in the form of polymeric albumin (or trimeric albumin) in the nanoparticles of the total albumin in the nanoparticles; (3) the weight percentage of albumin in the form of dimeric albumin in the nanoparticles of the total albumin in the nanoparticles; (4) the weight percentage of albumin in the form of polymeric albumin (or trimeric albumin) in the non-nanoparticle portion of the total albumin in the non-nanoparticle portion; (5) the weight percentage of albumin in the form of monomeric albumin in the non-nanoparticle portion of the total albumin in the non-nanoparticle portion; (6) the weight percentage of albumin in the form of dimeric albumin in the non-nanoparticle portion of the total albumin in the non-nanoparticle portion; (7) the weight percentage of albumin in the form of polymeric albumin (or trimeric albumin) in the pharmaceutical composition of the total albumin in the pharmaceutical composition; (8) the weight percentage of albumin in the form of monomeric albumin in the pharmaceutical composition of the total albumin in the pharmaceutical composition; (9) the weight percentage of albumin in the form of dimeric albumin in the pharmaceutical composition of the total albumin in the pharmaceutical composition; (10) the volume weighted mean particle size of the nanoparticles; (11) the Z-average particle size of the nanoparticles; (12) the polydispersity index of the nanoparticles; (13) the span of particle size distribution ((Dv95–Dv5)/Dv50) of the nanoparticles; (14) the weight percentage of the nanoparticles that is albumin; (15) the weight percentage of the nanoparticles that is rapamycin; (16) the weight ratio of the albumin to the rapamycin in the nanoparticles; (17) the weight ratio of the total albumin to the total rapamycin in the pharmaceutical composition; (18) the percentage of total albumin in the pharmaceutical composition that is in the non-nanoparticle portion; (19) the percentage of total rapamycin in the pharmaceutical composition that is in the nanoparticles; (20) the concentration of albumin in the pharmaceutical composition; (21) the concentration of albumin in the non-nanoparticle portion of the pharmaceutical composition; (22) the concentration of albumin in the pharmaceutical composition that is in the nanoparticles; (23) the concentration of rapamycin in the pharmaceutical composition; (24) the concentration of rapamycin in the pharmaceutical composition that is in the non-nanoparticle portion; (25) the concentration of rapamycin in the pharmaceutical composition that is in the nanoparticles; (26) the osmolality of the composition; (27) the viscosity of the pharmaceutical composition; (28) the stability of the pharmaceutical composition; (29) the pH of the pharmaceutical composition; (30) the concentration of tert-butanol in the pharmaceutical composition; (31) the concentration of chloroform in the pharmaceutical composition; (32) the zeta potential of the nanoparticles; (33) the morphology of the pharmaceutical composition (such as the crystallinity of a lyophilized form of the pharmaceutical composition and/or of the rapamycin in the pharmaceutical composition); (34) the interaction of a vinyl chain of the rapamycin in the nanoparticles with the album in the nanoparticles; (35) the sphericity of the nanoparticles (such as the percentage of nanoparticles that are non-spherical vs spherical); (36) the percentage of seco-rapamycin compared to the sum of seco-rapamycin and rapamycin, by weight, in the nanoparticles; and/or (37) the portion of rapamycin in the pharmaceutical composition that is free rapamycin.

In some embodiments, a method of assessing suitability of a pharmaceutical composition for medical use in a human individual includes measuring one or more quality control parameters for the pharmaceutical composition, and assessing the suitability of the pharmaceutical composition for medical use in a human individual, wherein one or more measured quality control parameters within a quality control threshold(s) is indicative of suitability of the pharmaceutical composition for medical use. In some embodiments, the quality control parameter comprises a quality control parameter for the pharmaceutical composition, the nanoparticles in the pharmaceutical composition and/or the non-nanoparticle portion of the pharmaceutical composition. In some embodiments, the determination of at least one quality control parameter comprises determination of one or more (such as any of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36) of the following quality control parameters (in any combination of quality control parameters if a plurality of quality control parameters are used): (1) the weight percentage of albumin in the form of monomeric albumin in the nanoparticles of the total albumin in the nanoparticles; (2) the weight percentage of albumin in the form of polymeric albumin (other than oligomeric albumin) in the nanoparticles of the total albumin in the nanoparticles; (3) the weight percentage of albumin in the form of dimeric albumin in the nanoparticles of the total albumin in the nanoparticles; (4) the weight percentage of albumin in the form of oligomeric albumin in the nanoparticles of the total albumin in the nanoparticles; (5) the weight percentage of albumin in the form of polymeric albumin (other than oligomeric albumin) in the non-nanoparticle portion of the total albumin in the non-nanoparticle portion; (6) the weight percentage of albumin in the form of monomeric albumin in the non-nanoparticle portion of the total albumin in the non-nanoparticle portion; (7) the weight percentage of albumin in the form of dimeric albumin in the non-nanoparticle portion of the total albumin in the non-nanoparticle portion; (8) the weight percentage of albumin in the form of oligomeric albumin in the non-nanoparticle portion of the total albumin in the non-nanoparticle portion; (9) the weight percentage of albumin in the form of polymeric albumin (other than oligomeric albumin) in the pharmaceutical composition of the total albumin in the pharmaceutical composition; (10) the weight percentage of albumin in the form of oligomeric albumin in the pharmaceutical composition of the total albumin in the pharmaceutical composition; (11) the weight percentage of albumin in the form of monomeric albumin in the pharmaceutical composition of the total albumin in the pharmaceutical composition; (12) the weight percentage of albumin in the form of dimeric albumin in the pharmaceutical composition of the total albumin in the pharmaceutical composition; (13) the volume weighted mean particle size of the nanoparticles; (14) the Z-average particle size of the nanoparticles; (15) the polydispersity index of the nanoparticles; (16) the span of particle size distribution ((Dv95−Dv5)/Dv50) of the nanoparticles; (17) the weight percentage of the nanoparticles that is albumin; (18) the weight percentage of the nanoparticles that is rapamycin; (19) the weight ratio of the albumin to the rapamycin in the nanoparticles; (20) the weight ratio of the total albumin to the total rapamycin in the pharmaceutical composition; (21) the percentage of total albumin in the pharmaceutical composition that is in the non-nanoparticle portion; (22) the percentage of total rapamycin in the pharmaceutical composition that is in the nanoparticles; (23) the concentration of albumin in the pharmaceutical composition; (24) the concentration of albumin in the non-nanoparticle portion of the pharmaceutical composition; (25) the concentration of albumin in the pharmaceutical composition that is in the nanoparticles; (26) the concentration of rapamycin in the pharmaceutical composition; (27) the concentration of rapamycin in the pharmaceutical composition that is in the non-nanoparticle portion; (28) the concentration of rapamycin in the pharmaceutical composition that is in the nanoparticles; (29) the osmolality of the composition; (30) the viscosity of the pharmaceutical composition; (31) the stability of the pharmaceutical composition; (32) the pH of the pharmaceutical composition; (33) the concentration of tert-butanol in the pharmaceutical composition; (34) the concentration of chloroform in the pharmaceutical composition; (35) the zeta potential of the nanoparticles; (36) the morphology of the pharmaceutical composition (such as the crystallinity of a lyophilized form of the pharmaceutical composition and/or of the rapamycin in the pharmaceutical composition); (37) the interaction of a vinyl chain of the rapamycin in the nanoparticles with the album in the nanoparticles; (38) the sphericity of the nanoparticles (such as the percentage of nanoparticles that are non-spherical vs spherical); (39) the percentage of seco-rapamycin compared to the sum of seco-rapamycin and rapamycin, by weight, in the nanoparticles; and/or (40) the portion of rapamycin in the pharmaceutical composition that is free rapamycin.

A quality control parameter may be determined using a method described herein or any other known method. In some embodiments, the quality control process includes a step of determining the quality control parameter for the pharmaceutical composition, the nanoparticles in the pharmaceutical composition, and/or the non-nanoparticle portion of the pharmaceutical composition.

The pharmaceutical compositions assessed for suitability for medical use in a human individual can be in liquid or powder forms. For example, in some embodiments, the pharmaceutical composition is a liquid nanoparticle suspension (for example, prior to lyophilization). In some embodiments, the pharmaceutical composition is a reconstituted suspension (e.g., a composition that was lyophilized and reconstituted to form an aqueous solution, such as a saline solution). In some embodiments, the pharmaceutical composition s lyophilized. In some embodiments, the pharmaceutical composition is sterile. In some embodiments, the pharmaceutical composition is in a container, such as a sealed vial. In some embodiments, the method comprises separating the nanoparticles from the non-nanoparticle portion. In some embodiments, the quality control parameter comprises a quality control parameter for the nanoparticles. In some embodiments, the quality control parameter comprises a quality control parameter for the non-nanoparticle portion. In some embodiments, the nanoparticles comprise a core comprising rapamycin and a coating comprising albumin. In some embodiments, the albumin is human albumin.

In some embodiments, one of the one or more quality control parameters is the weight percentage of albumin in the form of monomeric albumin in the nanoparticles of the total albumin in the nanoparticles. For example, the quality control method for assessing the suitability of the pharmaceutical composition can include measuring the weight percentage of albumin in the form of monomeric albumin in the nanoparticles of the total albumin in the nanoparticles, and assessing the suitability of the pharmaceutical composition for medical use in a human individual, wherein the measured weight percentage of albumin in the form of monomeric albumin in the nanoparticles of the total albumin in the nanoparticles falling within a quality control threshold for the weight percentage of albumin in the form of monomeric albumin in the nanoparticles of the total albumin in the nanoparticles is indicative of suitability of the pharmaceutical composition for medical use in the individual. In some embodiments, the measured weight percentage of albumin in the form of monomeric albumin in the nanoparticles of the total albumin in the nanoparticles falling outside of the quality control threshold for the weight percentage of albumin in the form of monomeric albumin in the nanoparticles of the total albumin in the nanoparticles is indicative of non-suitability of the pharmaceutical composition for medical use in the individual. In some embodiments, the quality control threshold for the weight percentage of albumin in the form of monomeric albumin in the nanoparticles of the total albumin in the nanoparticles is about 70% to about 85% (such as any of about 70-72%, about 72-74%, about 74-76%, about 76-78%, about 78-80%, about 80-82%, or about 82-85%, or any combination of such ranges), or about 70%, 71%, 72%, 73%, 74%, 75%, 76%, 77%, 78%, 79%, 80%, 81%, 82%, 83%, 84%, or 85% of the albumin in the nanoparticles of the pharmaceutical composition being in the form of albumin monomers.

In some embodiments, one of the one or more quality control parameters is the weight percentage of albumin in the form of monomeric albumin in the nanoparticles of the total albumin in the nanoparticles. For example, the quality control method for assessing the suitability of the pharmaceutical composition can include measuring the weight percentage of albumin in the form of monomeric albumin in the nanoparticles of the total albumin in the nanoparticles, and assessing the suitability of the pharmaceutical composition for medical use in a human individual, wherein the measured weight percentage of albumin in the form of monomeric albumin in the nanoparticles of the total albumin in the nanoparticles falling within a quality control threshold for the weight percentage of albumin in the form of monomeric albumin in the nanoparticles of the total albumin in the nanoparticles is indicative of suitability of the pharmaceutical composition for medical use in the individual. In some embodiments, the measured weight percentage of albumin in the form of monomeric albumin in the nanoparticles of the total albumin in the nanoparticles falling outside of the quality control threshold for the weight percentage of albumin in the form of monomeric albumin in the nanoparticles of the total albumin in the nanoparticles is indicative of non-suitability of the pharmaceutical composition for medical use in the individual. In some embodiments, the quality control threshold for the weight percentage of albumin in the form of monomeric albumin in the nanoparticles of the total albumin in the nanoparticles is about 25% to about 50% (such as any of about 25-30%, about 30-35%, about 35-40%, about 40-45%, or about 45-50%, or any combination of such ranges) of the albumin in the nanoparticles of the pharmaceutical composition being in the form of albumin monomers.

In some embodiments, one of the one or more quality control parameters is the weight percentage of albumin in the form of polymeric albumin (or trimeric albumin) in the nanoparticles of the total albumin in the nanoparticles. For example, the quality control method for assessing the suitability of the pharmaceutical composition can include measuring the weight percentage of albumin in the form of polymeric albumin (or trimeric albumin) in the nanoparticles of the total albumin in the nanoparticles, and assessing the suitability of the pharmaceutical composition for medical use in a human individual, wherein the measured weight percentage of albumin in the form of polymeric albumin (or trimeric albumin) in the nanoparticles of the total albumin in the nanoparticles falling within a quality control threshold for the weight percentage of albumin in the form of polymeric albumin (or trimeric albumin) in the nanoparticles of the total albumin in the nanoparticles is indicative of suitability of the pharmaceutical composition for medical use in the individual. In some embodiments, the measured weight percentage of albumin in the form of polymeric albumin (or trimeric albumin) in the nanoparticles of the total albumin in the nanoparticles falling outside of the quality control threshold for the weight percentage of albumin in the form of polymeric albumin (or trimeric albumin) in the nanoparticles of the total albumin in the nanoparticles is indicative of non-suitability of the pharmaceutical composition for medical use in the individual. In some embodiments, the quality control threshold for the weight percentage of albumin in the form of polymeric albumin (or trimeric albumin) in the nanoparticles of the total albumin in the nanoparticles is about 5% to about 15% (such as any of about 5-7%, about 7-9%, about 9-11%, about 11-13%, or about 13-15%, or any combination of such ranges), or about 5%, 6%, 7%, 8%, 9%, 10%, 11%, 12%, 13%, 14%, or 15% of the albumin in the nanoparticles of the pharmaceutical composition being in the form of albumin polymers (or trimeric albumin).

In some embodiments, one of the one or more quality control parameters is the weight percentage of albumin in the form of polymeric albumin (other than oligomeric albumin) in the nanoparticles of the total albumin in the nanoparticles. For example, the quality control method for assessing the suitability of the pharmaceutical composition can include measuring the weight percentage of albumin in the form of polymeric albumin (other than oligomeric albumin) in the nanoparticles of the total albumin in the nanoparticles, and assessing the suitability of the pharmaceutical composition for medical use in a human individual, wherein the measured weight percentage of albumin in the form of polymeric albumin (other than oligomeric albumin) in the nanoparticles of the total albumin in the nanoparticles falling within a quality control threshold for the weight percentage of albumin in the form of polymeric albumin (other than oligomeric albumin) in the nanoparticles of the total albumin in the nanoparticles is indicative of suitability of the pharmaceutical composition for medical use in the individual. In some embodiments, the measured weight percentage of albumin in the form of polymeric albumin (other than oligomeric albumin) in the nanoparticles of the total albumin in the nanoparticles falling outside of the quality control threshold for the weight percentage of albumin in the form of polymeric albumin (other than oligomeric albumin) in the nanoparticles of the total albumin in the nanoparticles is indicative of non-suitability of the pharmaceutical composition for medical use in the individual. In some embodiments, the quality control threshold for the weight percentage of albumin in the form of polymeric albumin (other than oligomeric albumin) in the nanoparticles of the total albumin in the nanoparticles is about 42% to about 60% (such as any of about 42-45%, about 45-48%, about 48-51%, about 51-54%, about 54-57%, or about 57-60%, or a combination of such ranges) of the albumin in the nanoparticles of the pharmaceutical composition being in the form of albumin polymers (other than oligomeric albumin).

In some embodiments, one of the one or more quality control parameters is the weight percentage of albumin in the form of dimeric albumin in the nanoparticles of the total albumin in the nanoparticles. For example, the quality control method for assessing the suitability of the pharmaceutical composition can include measuring the weight percentage of albumin in the form of dimeric albumin in the nanoparticles of the total albumin in the nanoparticles, and assessing the suitability of the pharmaceutical composition for medical use in a human individual, wherein the measured weight percentage of albumin in the form of dimeric albumin in the nanoparticles of the total albumin in the nanoparticles falling within a quality control threshold for the weight percentage of albumin in the form of dimeric albumin in the nanoparticles of the total albumin in the nanoparticles is indicative of suitability of the pharmaceutical composition for medical use in the individual. In some embodiments, the measured weight percentage of albumin in the form of dimeric albumin in the nanoparticles of the total albumin in the nanoparticles falling outside of the quality control threshold for the weight percentage of albumin in the form of dimeric albumin in the nanoparticles of the total albumin in the nanoparticles is indicative of non-suitability of the pharmaceutical composition for medical use in the individual. In some embodiments, the quality control threshold for the weight percentage of albumin in the form of dimeric albumin in the nanoparticles of the total albumin in the nanoparticles is about 9% to about 20% (such as about 9-11%, about 11-13%, about 13-15%, about 15-17%, or about 17-20%, or any combination of such ranges), or about 9%, 10%, 11%, 12%, 13%, 14%, 15%, 16%, 17%, 18%, 19%, or 20% of the albumin in the nanoparticles of the pharmaceutical composition being in the form of albumin dimers.

In some embodiments, one of the one or more quality control parameters is the weight percentage of albumin in the form of dimeric albumin in the nanoparticles of the total albumin in the nanoparticles. For example, the quality control method for assessing the suitability of the pharmaceutical composition can include measuring the weight percentage of albumin in the form of dimeric albumin in the nanoparticles of the total albumin in the nanoparticles, and assessing the suitability of the pharmaceutical composition for medical use in a human individual, wherein the measured weight percentage of albumin in the form of dimeric albumin in the nanoparticles of the total albumin in the nanoparticles falling within a quality control threshold for the weight percentage of albumin in the form of dimeric albumin in the nanoparticles of the total albumin in the nanoparticles is indicative of suitability of the pharmaceutical composition for medical use in the individual. In some embodiments, the measured weight percentage of albumin in the form of dimeric albumin in the nanoparticles of the total albumin in the nanoparticles falling outside of the quality control threshold for the weight percentage of albumin in the form of dimeric albumin in the nanoparticles of the total albumin in the nanoparticles is indicative of non-suitability of the pharmaceutical composition for medical use in the individual. In some embodiments, the quality control threshold for the weight percentage of albumin in the form of dimeric albumin in the nanoparticles of the total albumin in the nanoparticles is about 5% to about 16% (such as about 5-7%, about 7-9%, about 9-11%, about 11-13%, or about 13-16%, or any combination of such ranges) of the albumin in the nanoparticles of the pharmaceutical composition being in the form of albumin dimers.

In some embodiments, one of the one or more quality control parameters is the weight percentage of albumin in the form of oligomeric albumin in the nanoparticles of the total albumin in the nanoparticles. For example, the quality control method for assessing the suitability of the pharmaceutical composition can include measuring the weight percentage of albumin in the form of oligomeric albumin in the nanoparticles of the total albumin in the nanoparticles, and assessing the suitability of the pharmaceutical composition for medical use in a human individual, wherein the measured weight percentage of albumin in the form of oligomeric albumin in the nanoparticles of the total albumin in the nanoparticles falling within a quality control threshold for the weight percentage of albumin in the form of dimeric albumin in the nanoparticles of the total albumin in the nanoparticles is indicative of suitability of the pharmaceutical composition for medical use in the individual. In some embodiments, the measured weight percentage of albumin in the form of oligomeric albumin in the nanoparticles of the total albumin in the nanoparticles falling outside of the quality control threshold for the weight percentage of albumin in the form of oligomeric albumin in the nanoparticles of the total albumin in the nanoparticles is indicative of non-suitability of the pharmaceutical composition for medical use in the individual. In some embodiments, the quality control threshold for the weight percentage of albumin in the form of oligomeric albumin in the nanoparticles of the total albumin in the nanoparticles is about 1% to about 4.5% (1-1.5%, about 1.5-2%, about 2-2.5%, about 2.5-3%, about 3-3.5%, about 3.5-4%, or about 4-4.5%, or any combination of such ranges) of the albumin in the nanoparticles of the pharmaceutical composition being in the form of oligomeric albumin.

In some embodiments, one of the one or more quality control parameters is the weight percentage of albumin in the form of polymeric albumin (or trimeric albumin) in the non-nanoparticle portion of the total albumin in the non-nanoparticle portion. For example, the quality control method for assessing the suitability of the pharmaceutical composition can include measuring the weight percentage of albumin in the form of polymeric albumin (or trimeric albumin) in the non-nanoparticle portion of the total albumin in the non-nanoparticle portion, and assessing the suitability of the pharmaceutical composition for medical use in a human individual, wherein the measured weight percentage of albumin in the form of polymeric albumin (or trimeric albumin) in the non-nanoparticle portion of the total albumin in the non-nanoparticle portion falling within a quality control threshold for the weight percentage of albumin in the form of polymeric albumin (or trimeric albumin) in the non-nanoparticle portion of the total albumin in the non-nanoparticle portion is indicative of suitability of the pharmaceutical composition for medical use in the individual. In some embodiments, the measured weight percentage of albumin in the form of polymeric albumin (or trimeric albumin) in the non-nanoparticle portion of the total albumin in the non-nanoparticle portion falling outside of the quality control threshold for the weight percentage of albumin in the form of polymeric albumin (or trimeric albumin) in the non-nanoparticle portion of the total albumin in the non-nanoparticle portion is indicative of non-suitability of the pharmaceutical composition for medical use in the individual. In some embodiments, the quality control threshold for the weight percentage of albumin in the form of polymeric albumin (or trimeric albumin) in the non-nanoparticle portion of the total albumin in the non-nanoparticle portion is about 0.5% to about 5% (such about 0.5-1%, about 1-1.5%, about 1.5-2%, about 2-2.5%, about 2.5-3%, about 3-3.5%, about 3.5-4%, about 4-4.5%, or about 4.5-5%, or a combination of such ranges), or about 0.5%, 1%, 1.5%, 2%, 2.5%, 3%, 3.5%, 4%, 4.5%, or 5% of the albumin in the non-nanoparticle portion of the pharmaceutical composition being in the form of albumin polymers (or trimeric albumin).

In some embodiments, one of the one or more quality control parameters is the weight percentage of albumin in the form of polymeric albumin (other than oligomeric albumin) in the non-nanoparticle portion of the total albumin in the non-nanoparticle portion. For example, the quality control method for assessing the suitability of the pharmaceutical composition can include measuring the weight percentage of albumin in the form of polymeric albumin (other than oligomeric albumin) in the non-nanoparticle portion of the total albumin in the non-nanoparticle portion, and assessing the suitability of the pharmaceutical composition for medical use in a human individual, wherein the measured weight percentage of albumin in the form of polymeric albumin (other than oligomeric albumin) in the non-nanoparticle portion of the total albumin in the non-nanoparticle portion falling within a quality control threshold for the weight percentage of albumin in the form of polymeric albumin (other than oligomeric albumin) in the non-nanoparticle portion of the total albumin in the non-nanoparticle portion is indicative of suitability of the pharmaceutical composition for medical use in the individual. In some embodiments, the measured weight percentage of albumin in the form of polymeric albumin (other than oligomeric albumin) in the non-nanoparticle portion of the total albumin in the non-nanoparticle portion falling outside of the quality control threshold for the weight percentage of albumin in the form of polymeric albumin (other than oligomeric albumin) in the non-nanoparticle portion of the total albumin in the non-nanoparticle portion is indicative of non-suitability of the pharmaceutical composition for medical use in the individual. In some embodiments, the quality control threshold for the weight percentage of albumin in the form of polymeric albumin (other than oligomeric albumin) in the non-nanoparticle portion of the total albumin in the non-nanoparticle portion is about 0.5% to about 3% (such about 0.5-1%, about 1-1.5%, about 1.5-2%, about 2-2.5%, or about 2.5-3%, or a combination of such ranges) of the albumin in the non-nanoparticle portion of the pharmaceutical composition being in the form of albumin polymers (other than oligomeric albumin).

In some embodiments, one of the one or more quality control parameters is the weight percentage of albumin in the form of monomeric albumin in the non-nanoparticle portion of the total albumin in the non-nanoparticle portion. For example, the quality control method for assessing the suitability of the pharmaceutical composition can include measuring the weight percentage of albumin in the form of monomeric albumin in the non-nanoparticle portion of the total albumin in the non-nanoparticle portion, and assessing the suitability of the pharmaceutical composition for medical use in a human individual, wherein the measured weight percentage of albumin in the form of monomeric albumin in the non-nanoparticle portion of the total albumin in the non-nanoparticle portion falling within a quality control threshold for the weight percentage of albumin in the form of monomeric albumin in the non-nanoparticle portion of the total albumin in the non-nanoparticle portion is indicative of suitability of the pharmaceutical composition for medical use in the individual. In some embodiments, the measured weight percentage of albumin in the form of monomeric albumin in the non-nanoparticle portion of the total albumin in the non-nanoparticle portion falling outside of the quality control threshold for the weight percentage of albumin in the form of monomeric albumin in the non-nanoparticle portion of the total albumin in the non-nanoparticle portion is indicative of non-suitability of the pharmaceutical composition for medical use in the individual. In some embodiments, the quality control threshold for the weight percentage of albumin in the form of monomeric albumin in the non-nanoparticle portion of the total albumin in the non-nanoparticle portion is about 80% to about 95% (such as any of about 80% to about 82%, about 82% to about 84%, about 84% to about 86%, about 86% to about 88%, about 88% to about 90%, about 90% to about 92%, or about 90% to about 93%, or a combination of such ranges), or about 80%, 81%, 82%, 83%, 84%, 85%, 86%, 87%, 88%, 89%, 90%, 91%, 92%, 93%, 94%, or 95% of the albumin in the non-nanoparticle portion of the pharmaceutical composition being in the form of albumin monomers.

In some embodiments, one of the one or more quality control parameters is the weight percentage of albumin in the form of dimeric albumin in the non-nanoparticle portion of the total albumin in the non-nanoparticle portion. For example, the quality control method for assessing the suitability of the pharmaceutical composition can include measuring the weight percentage of albumin in the form of dimeric albumin in the non-nanoparticle portion of the total albumin in the non-nanoparticle portion, and assessing the suitability of the pharmaceutical composition for medical use in a human individual, wherein the measured weight percentage of albumin in the form of dimeric albumin in the non-nanoparticle portion of the total albumin in the non-nanoparticle portion falling within a quality control threshold for the weight percentage of albumin in the form of dimeric albumin in the non-nanoparticle portion of the total albumin in the non-nanoparticle portion is indicative of suitability of the pharmaceutical composition for medical use in the individual. In some embodiments, the measured weight percentage of albumin in the form of dimeric albumin in the non-nanoparticle portion of the total albumin in the non-nanoparticle portion falling outside of the quality control threshold for the weight percentage of albumin in the form of dimeric albumin in the non-nanoparticle portion of the total albumin in the non-nanoparticle portion is indicative of non-suitability of the pharmaceutical composition for medical use in the individual. In some embodiments, the quality control threshold for the weight percentage of albumin in the form of dimeric albumin in the non-nanoparticle portion of the total albumin in the non-nanoparticle portion is about 4% to about 15% (such as about 4-6%, about 6-8%, about 8-10%, about 10-12%, or about 12-15%, or a combination of such ranges), or about 4%, 5%, 6%, 7%, 8%, 9%, 10%, 11%, 12%, 13%, or 14% of the albumin in the non-nanoparticle portion of the pharmaceutical composition being in the form of albumin dimers.

In some embodiments, one of the one or more quality control parameters is the weight percentage of albumin in the form of polymeric albumin (or trimeric albumin) in the pharmaceutical composition of the total albumin in the pharmaceutical composition. For example, the quality control method for assessing the suitability of the pharmaceutical composition can include measuring the weight percentage of albumin in the form of polymeric albumin (or trimeric albumin) in the pharmaceutical composition of the total albumin in the pharmaceutical composition, and assessing the suitability of the pharmaceutical composition for medical use in a human individual, wherein the measured weight percentage of albumin in the form of polymeric albumin (or trimeric albumin) in the pharmaceutical composition of the total albumin in the pharmaceutical composition falling within a quality control threshold for the weight percentage of albumin in the form of polymeric albumin (or trimeric albumin) in the pharmaceutical composition of the total albumin in the pharmaceutical composition is indicative of suitability of the pharmaceutical composition for medical use in the individual. In some embodiments, the measured weight percentage of albumin in the form of polymeric albumin (or trimeric albumin) in the pharmaceutical composition of the total albumin in the pharmaceutical composition falling outside of the quality control threshold for the weight percentage of albumin in the form of polymeric albumin (or trimeric albumin) in the pharmaceutical composition of the total albumin in the pharmaceutical composition is indicative of non-suitability of the pharmaceutical composition for medical use in the individual. In some embodiments, the quality control threshold for the weight percentage of albumin in the form of polymeric albumin (or trimeric albumin) in the pharmaceutical composition of the total albumin in the pharmaceutical composition is about 0.5% to about 5% (such about 0.5-1%, about 1-1.5%, about 1.5-2%, about 2-2.5%, about 2.5-3%, about 3-3.5%, about 3.5-4%, about 4-4.5%, or about 4.5-5%, or a combination of such ranges), or about 0.5%, 1%, 1.5%, 2%, 2.5%, 3%, 3.5%, 4%, 4.5%, or 5% of the total albumin in pharmaceutical composition being in the form of albumin polymers (or trimeric albumin).

In some embodiments, one of the one or more quality control parameters is the weight percentage of albumin in the form of polymeric albumin (other than oligomeric albumin) in the pharmaceutical composition of the total albumin in the pharmaceutical composition. For example, the quality control method for assessing the suitability of the pharmaceutical composition can include measuring the weight percentage of albumin in the form of polymeric albumin (other than oligomeric albumin) in the pharmaceutical composition of the total albumin in the pharmaceutical composition, and assessing the suitability of the pharmaceutical composition for medical use in a human individual, wherein the measured weight percentage of albumin in the form of polymeric albumin (other than oligomeric albumin) in the pharmaceutical composition of the total albumin in the pharmaceutical composition falling within a quality control threshold for the weight percentage of albumin in the form of polymeric albumin (other than oligomeric albumin) in the pharmaceutical composition of the total albumin in the pharmaceutical composition is indicative of suitability of the pharmaceutical composition for medical use in the individual. In some embodiments, the measured weight percentage of albumin in the form of polymeric albumin (other than oligomeric albumin) in the pharmaceutical composition of the total albumin in the pharmaceutical composition falling outside of the quality control threshold for the weight percentage of albumin in the form of polymeric albumin (other than oligomeric albumin) in the pharmaceutical composition of the total albumin in the pharmaceutical composition is indicative of non-suitability of the pharmaceutical composition for medical use in the individual. In some embodiments, the quality control threshold for the weight percentage of albumin in the form of polymeric albumin (other than oligomeric albumin) in the pharmaceutical composition of the total albumin in the pharmaceutical composition is about 2% to about 7% (such about 2-3%, about 3-4%, about 4-5%, about 5-6%, or about 6-7%, or a combination of such ranges) of the total albumin in pharmaceutical composition being in the form of albumin polymers (other than oligomeric albumin).

In some embodiments, one of the one or more quality control parameters is the weight percentage of albumin in the form of monomeric albumin in the pharmaceutical composition of the total albumin in the pharmaceutical composition. For example, the quality control method for assessing the suitability of the pharmaceutical composition can include measuring the weight percentage of albumin in the form of monomeric albumin in the pharmaceutical composition of the total albumin in the pharmaceutical composition, and assessing the suitability of the pharmaceutical composition for medical use in a human individual, wherein the measured weight percentage of albumin in the form of monomeric albumin in the pharmaceutical composition of the total albumin in the pharmaceutical composition falling within a quality control threshold for the weight percentage of albumin in the form of monomeric albumin in the pharmaceutical composition of the total albumin in the pharmaceutical composition is indicative of suitability of the pharmaceutical composition for medical use in the individual. In some embodiments, the measured weight percentage of albumin in the form of monomeric albumin in the pharmaceutical composition of the total albumin in the pharmaceutical composition falling outside of the quality control threshold for the weight percentage of albumin in the form of monomeric albumin in the pharmaceutical composition of the total albumin in the pharmaceutical composition is indicative of non-suitability of the pharmaceutical composition for medical use in the individual. In some embodiments, the quality control threshold for the weight percentage of albumin in the form of monomeric albumin in the pharmaceutical composition of the total albumin in the pharmaceutical composition is about 80% to about 95% (such about 80-83%, about 83-86%, about 86-89%, about 89-92%, or about 92-95%, or a combination of such ranges), or about 80%, 81%, 82%, 83%, 84%, 85%, 86%, 87%, 88%, 89%, 90%, 91%, 92%, 93%, 94% or 95% of the total albumin in pharmaceutical composition being in the form of albumin monomers.

In some embodiments, one of the one or more quality control parameters is the weight percentage of albumin in the form of dimeric albumin in the pharmaceutical composition of the total albumin in the pharmaceutical composition. For example, the quality control method for assessing the suitability of the pharmaceutical composition can include measuring the weight percentage of albumin in the form of dimeric albumin in the pharmaceutical composition of the total albumin in the pharmaceutical composition, and assessing the suitability of the pharmaceutical composition for medical use in a human individual, wherein the measured weight percentage of albumin in the form of dimeric albumin in the pharmaceutical composition of the total albumin in the pharmaceutical composition falling within a quality control threshold for the weight percentage of albumin in the form of dimeric albumin in the pharmaceutical composition of the total albumin in the pharmaceutical composition is indicative of suitability of the pharmaceutical composition for medical use in the individual. In some embodiments, the measured weight percentage of albumin in the form of dimeric albumin in the pharmaceutical composition of the total albumin in the pharmaceutical composition falling outside of the quality control threshold for the weight percentage of albumin in the form of dimeric albumin in the pharmaceutical composition of the total albumin in the pharmaceutical composition is indicative of non-suitability of the pharmaceutical composition for medical use in the individual. In some embodiments, the quality control threshold for the weight percentage of albumin in the form of dimeric albumin in the pharmaceutical composition of the total albumin in the pharmaceutical composition is about 4% to about 15% (such as about 4-6%, about 6-8%, about 8-10%, about 10-12%, or about 12-15%, or a combination of such ranges), or about 4%, 5%, 6%, 7%, 8%, 9%, 10%, 11%, 12%, 13%, 14%, or 15% of the total albumin in pharmaceutical composition being in the form of albumin dimers.

In some embodiments, one of the one or more quality control parameters is the volume-weighted mean particle size of the nanoparticles. For example, the quality control method for assessing the suitability of the pharmaceutical composition can include measuring the volume-weighted mean particle size of the nanoparticles, and assessing the suitability of the pharmaceutical composition for medical use in a human individual, wherein the measured volume-weighted mean particle size of the nanoparticles in the pharmaceutical composition falling within a quality control threshold for the volume-weighted mean particle size of the nanoparticles in the pharmaceutical composition is indicative of suitability of the pharmaceutical composition for medical use in the individual. In some embodiments, the measured volume-weighted mean particle size of the nanoparticles in the pharmaceutical composition falling outside of the quality control threshold for the volume-weighted mean particle size of the nanoparticles in the pharmaceutical composition is indicative of non-suitability of the pharmaceutical composition for medical use in the individual. In some embodiments, the quality control threshold for the volume-weighted mean particle size of the nanoparticles in the pharmaceutical composition is about 200 nm or less, about 180 nm or less, about 160 nm or less, about 140 nm or less, about 120 nm or less, about 50-200 nm, about 60-70 nm, about 70-80 nm, about 80-90 nm, about 90-100 nm, about 100-110 nm, about 110-120 nm, about 120-130 nm, about 130-140 nm, about 140-150 nm, about 150-160 nm, about 160-180 nm, about 180-190 nm, about 190-200 nm, or any combination of such ranges.

In some embodiments, one of the one or more quality control parameters is the Z-average particle size of the nanoparticles. For example, the quality control method for assessing the suitability of the pharmaceutical composition can include measuring the Z-average particle size of the nanoparticles, and assessing the suitability of the pharmaceutical composition for medical use in a human individual, wherein the measured Z-average particle size of the nanoparticles in the pharmaceutical composition falling within a quality control threshold for the Z-average particle size of the nanoparticles in the pharmaceutical composition is indicative of suitability of the pharmaceutical composition for medical use in the individual. In some embodiments, the measured Z-average particle size of the nanoparticles in the pharmaceutical composition falling outside of the quality control threshold for the Z-average particle size of the nanoparticles in the pharmaceutical composition is indicative of non-suitability of the pharmaceutical composition for medical use in the individual. In some embodiments, the quality control threshold for the Z-average particle size of the nanoparticles in the pharmaceutical composition is about 200 nm or less, about 180 nm or less, about 160 nm or less, about 140 nm or less, about 120 nm or less, about 50-200 nm, about 60-70 nm, about 70-80 nm, about 80-90 nm, about 90-100 nm, about 100-110 nm, about 110-120 nm, about 120-130 nm, about 130-140 nm, about 140-150 nm, about 150-160 nm, about 160-180 nm, about 180-190 nm, about 190-200 nm, or any combination of such ranges.

In some embodiments, one of the one or more quality control parameters is the polydispersity index of the nanoparticles. For example, the quality control method for assessing the suitability of the pharmaceutical composition can include measuring the polydispersity index of the nanoparticles, and assessing the suitability of the pharmaceutical composition for medical use in a human individual, wherein the measured polydispersity index of the nanoparticles in the pharmaceutical composition falling within a quality control threshold for the polydispersity index of the nanoparticles in the pharmaceutical composition is indicative of suitability of the pharmaceutical composition for medical use in the individual. In some embodiments, the measured polydispersity index of the nanoparticles in the pharmaceutical composition falling outside of the quality control threshold for the polydispersity index of the nanoparticles in the pharmaceutical composition is indicative of non-suitability of the pharmaceutical composition for medical use in the individual. In some embodiments, the quality control threshold for the polydispersity index of the nanoparticles in the pharmaceutical composition is about 0.3 or less, 0.25 or less, 0.2 or less, 0.15 or less, 0.15 or less, 0.1 or less, 0.05 or less, 0.03-0.05, 0.05-0.07, 0.07-0.09, 0.09-0.11, 0.11-0.13, 0.13-0.15, 0.15-0.17, 0.17-0.2, 0.2-0.25, 0.25-0.3, 0.05-0.09, 0.09-0.13, 0.13-0.17, 0.17-0.25, 0.06-0.08, 0.08-0.12, 0.12-0.16, 0.16-0.18, 0.18-0.22, 0.22-0.28, 0.28-0.3, 0.06-0.12, 0.12-0.18, 0.18-0.3, 0.05-0.1, 0.1-0.15, 0.15-0.2, or 0.2-0.3, or any combination of such ranges.

In some embodiments, one of the one or more quality control parameters is the span of particle size distribution ((Dv95−Dv5)/Dv50) of the nanoparticles. For example, the quality control method for assessing the suitability of the pharmaceutical composition can include measuring the span of particle size distribution ((Dv95−Dv5)/Dv50) of the nanoparticles, and assessing the suitability of the pharmaceutical composition for medical use in a human individual, wherein the measured span of particle size distribution ((Dv95−Dv5)/Dv50) of the nanoparticles in the pharmaceutical composition falling within a quality control threshold for the span of particle size distribution ((Dv95−Dv5)/Dv50) of the nanoparticles in the pharmaceutical composition is indicative of suitability of the pharmaceutical composition for medical use in the individual. In some embodiments, the measured span of particle size distribution ((Dv95−Dv5)/Dv50) of the nanoparticles in the pharmaceutical composition falling outside of the quality control threshold for the span of particle size distribution ((Dv95−Dv5)/Dv50) of the nanoparticles in the pharmaceutical composition is indicative of non-suitability of the pharmaceutical composition for medical use in the individual. In some embodiments, the quality control threshold for the span of particle size distribution ((Dv95−Dv5)/Dv50) of the nanoparticles in the pharmaceutical composition is about 1.5 or less, such as about 0.8 to about 1.5, 0.8-0.9, 0.9-1, 1-1.1, 1.1-1.2, 1.2-1.3, 1.3-1.4, or 0.2-0.3, or any combination of such ranges.

In some embodiments, one of the one or more quality control parameters is the weight percentage of the nanoparticles that is albumin. For example, the quality control method for assessing the suitability of the pharmaceutical composition can include measuring the weight percentage of the nanoparticles that is albumin, and assessing the suitability of the pharmaceutical composition for medical use in a human individual, wherein the measured weight percentage of the nanoparticles that is albumin falling within a quality control threshold for the weight percentage of the nanoparticles that is albumin is indicative of suitability of the pharmaceutical composition for medical use in the individual. In some embodiments, the measured weight percentage of the nanoparticles that is albumin falling outside of the quality control threshold for the weight percentage of the nanoparticles that is albumin is indicative of non-suitability of the pharmaceutical composition for medical use in the individual. In some embodiments, the quality control threshold for weight percentage of the nanoparticles that is albumin is about 25% to about 45% albumin by weight, such as about 25-26%, about 26-27%, about 27-28%, about 28-29%, about 29-30%, about 30-31%, about 31-32%, about 32-33%, about 33-34%, about 34-35%, about 35-36%, about 36-37%, about 37-38%, about 38-39%, about 39-40%, about 40-41%, about 41-42%, about 42-43%, about 43-44%, or about 44-45% (or any combination of such ranges) albumin by weight.

In some embodiments, one of the one or more quality control parameters is the weight percentage of the nanoparticles that is rapamycin. For example, the quality control method for assessing the suitability of the pharmaceutical composition can include measuring the weight percentage of the nanoparticles that is rapamycin, and assessing the suitability of the pharmaceutical composition for medical use in a human individual, wherein the measured weight percentage of the nanoparticles that is rapamycin falling within a quality control threshold for the weight percentage of the nanoparticles that is rapamycin is indicative of suitability of the pharmaceutical composition for medical use in the individual. In some embodiments, the measured weight percentage of the nanoparticles that is rapamycin falling outside of the quality control threshold for the weight percentage of the nanoparticles that is rapamycin is indicative of non-suitability of the pharmaceutical composition for medical use in the individual. In some embodiments, the quality control threshold for weight percentage of the nanoparticles that is rapamycin is about 50% to about 75% rapamycin by weight, such as about 50-52%, about 52-54%, about 54-56%, about 56-58%, about 58-60%, about 60-62%, about 62-64%, about 64-66%, about 66-68%, about 68-70%, about 70-72%, about 72-74%, about 74-76%, about 76-78%, or about 78-80% (or any combination of such ranges) rapamycin by weight.

In some embodiments, one of the one or more quality control parameters is the weight ratio of the albumin to the rapamycin in the nanoparticles. For example, the quality control method for assessing the suitability of the pharmaceutical composition can include measuring the weight ratio of the albumin to the rapamycin in the nanoparticles, and assessing the suitability of the pharmaceutical composition for medical use in a human individual, wherein the measured weight ratio of the albumin to the rapamycin in the nanoparticles falling within a quality control threshold for the weight ratio of the albumin to the rapamycin in the nanoparticles is indicative of suitability of the pharmaceutical composition for medical use in the individual. In some embodiments, the measured weight ratio of the albumin to the rapamycin in the nanoparticles falling outside of the quality control threshold for the weight ratio of the albumin to the rapamycin in the nanoparticles is indicative of non-suitability of the pharmaceutical composition for medical use in the individual. In some embodiments, the quality control threshold for weight ratio of the albumin to the rapamycin in the nanoparticles is about 1:1 to about 1:4 (such as about 1:1 to about 1:1.5, about 1:1.5 to about 1:2, about 1:2 to about 1:2.5, about 1.25 to about 1:3, about 1:3 to about 1:3.5, or about 1:3.5 to about 1:4, or any combination of such ranges), about 1:1, about 1:1.5, about 1:2, about 1:2.5, about 1:3, about 1:3.5, or about 1:4.

In some embodiments, one of the one or more quality control parameters is weight ratio of the albumin to the rapamycin in the pharmaceutical composition. For example, the quality control method for assessing the suitability of the pharmaceutical composition can include measuring the weight ratio of the albumin to the rapamycin in the pharmaceutical composition, and assessing the suitability of the pharmaceutical composition for medical use in a human individual, wherein the measured weight ratio of the albumin to the rapamycin in the pharmaceutical composition falling within a quality control threshold for the weight ratio of the albumin to the rapamycin in the pharmaceutical composition is indicative of suitability of the pharmaceutical composition for medical use in the individual. In some embodiments, the measured weight ratio of the albumin to the rapamycin in the pharmaceutical composition falling outside of the quality control threshold for the weight ratio of the albumin to the rapamycin in the pharmaceutical composition is indicative of non-suitability of the pharmaceutical composition for medical use in the individual. In some embodiments, the quality control threshold for the weight ratio of the albumin to the rapamycin in the pharmaceutical composition is about 1:1 to about 12:1 (such as about 1:1 to about 2:1, about 2:1 to about 3:1, about 3:1 to about 4:1, about 4:1 to about 5:1, about 5:1 to about 6:1, about 6:1 to about 7:1, about 7:1 to about 8:1, about 8:1 to about 9:1, or about 9:1 to about 10:1, or any combination of such ranges), about 1:1, about 2:1, about 3:1, about 4:1, about 5:1, about 6:1, about 7:1, about 8:1, about 9:1, about 10:1, about 11:1, or about 12:1.

In some embodiments, one of the one or more quality control parameters is the percentage of total albumin in the pharmaceutical composition that is in the non-nanoparticle portion. For example, the quality control method for assessing the suitability of the pharmaceutical composition can include measuring the percentage of total albumin in the pharmaceutical composition that is in the non-nanoparticle portion, and assessing the suitability of the pharmaceutical composition for medical use in a human individual, wherein the measured percentage of total albumin in the pharmaceutical composition that is in the non-nanoparticle portion falling within a quality control threshold for the percentage of total albumin in the pharmaceutical composition that is in the non-nanoparticle portion is indicative of suitability of the pharmaceutical composition for medical use in the individual. In some embodiments, the measured percentage of total albumin in the pharmaceutical composition that is in the non-nanoparticle portion falling outside of the quality control threshold for the percentage of total albumin in the pharmaceutical composition that is in the non-nanoparticle portion is indicative of non-suitability of the pharmaceutical composition for medical use in the individual. In some embodiments, the quality control threshold for the percentage of total albumin in the pharmaceutical composition that is in the non-nanoparticle portion is about 80% or more (such as about 85% or more, about 90% or more, about 95% or more, about 97% or more, about 97.5% or more, about 98% or more, about 98.5% or more, about 99% or more, or about 99.5% or more, about 80-90%, about 85-90%, about 90-95%, about 95-97%, about 97-97.5%, about 97.5-98%, about 98-98.5%, about 98.5-99%, about 99-99.5%, or about 99.5-99.9% (or any combination of such ranges)) of the total albumin in the pharmaceutical composition being in the non-nanoparticle portion of the pharmaceutical composition.

In some embodiments, one of the one or more quality control parameters is the percentage of total rapamycin in the pharmaceutical composition that is in the nanoparticles. For example, the quality control method for assessing the suitability of the pharmaceutical composition can include measuring the percentage of total rapamycin in the pharmaceutical composition that is in the nanoparticles, and assessing the suitability of the pharmaceutical composition for medical use in a human individual, wherein measured percentage of total rapamycin in the pharmaceutical composition that is in the nanoparticles falling within a quality control threshold for percentage of total rapamycin in the pharmaceutical composition that is in the nanoparticles is indicative of suitability of the pharmaceutical composition for medical use in the individual. In some embodiments, the measured percentage of total rapamycin in the pharmaceutical composition that is in the nanoparticles falling outside of the quality control threshold for the percentage of total rapamycin in the pharmaceutical composition that is in the nanoparticles is indicative of non-suitability of the pharmaceutical composition for medical use in the individual. In some embodiments, the quality control threshold for the percentage of total rapamycin in the pharmaceutical composition that is in the nanoparticles is about 85% or more (such as about 90% or more, about 95% or more, about 97% or more, about 97.5% or more, about 98% or more, about 98.5% or more, about 99% or more, or about 99.5% or more, about 85-90%, about 90-95%, about 95-97%, about 97-97.5%, about 97.5-98%, about 98-98.5%, about 98.5-99%, about 99-99.5%, or about 99.5-99.9% (or any combination of such ranges)) of the total rapamycin in the pharmaceutical composition being in the nanoparticles.

In some embodiments, one of the one or more quality control parameters is the concentration of total albumin in the pharmaceutical composition. For example, the quality control method for assessing the suitability of the pharmaceutical composition can include measuring the concentration of total albumin in the pharmaceutical composition, and assessing the suitability of the pharmaceutical composition for medical use in a human individual, wherein measured concentration of total albumin in the pharmaceutical composition falling within a quality control threshold for concentration of total albumin in the pharmaceutical composition is indicative of suitability of the pharmaceutical composition for medical use in the individual. In some embodiments, the measured concentration of total albumin in the pharmaceutical composition falling outside of the quality control threshold for the concentration of total albumin in the pharmaceutical composition is indicative of non-suitability of the pharmaceutical composition for medical use in the individual. In some embodiments, the quality control threshold for the concentration of total albumin in the pharmaceutical composition is about 30 mg/mL to about 100 mg/mL (for example, about 30-35 mg/mL, about 35-40 mg/mL, about 40-45 mg/mL, about 45-50 mg/mL, about 50-55 mg/mL, about 55-60 mg/mL, about 60-65 mg/mL, about 65-70 mg/mL, about 70-75 mg/mL, about 75-80 mg/mL, about 80-85 mg/mL, about 85-90 mg/mL, about 90-95 mg/mL, about or about 95-100 mg/mL, or any combination of such ranges).

In some embodiments, one of the one or more quality control parameters is the concentration of total albumin in the pharmaceutical composition. For example, the quality control method for assessing the suitability of the pharmaceutical composition can include measuring the concentration of total albumin in the pharmaceutical composition, and assessing the suitability of the pharmaceutical composition for medical use in a human individual, wherein the measured concentration of total albumin in the pharmaceutical composition falling within a quality control threshold for the concentration of total albumin in the pharmaceutical composition is indicative of suitability of the pharmaceutical composition for medical use in the individual. In some embodiments, the measured concentration of total albumin in the pharmaceutical composition falling outside of the quality control threshold for the concentration of total albumin in the pharmaceutical composition is indicative of non-suitability of the pharmaceutical composition for medical use in the individual. In some embodiments, the quality control threshold for the concentration of total albumin in the pharmaceutical composition is about 30 mg/mL to about 100 mg/mL (for example, about 30-35 mg/mL, about 35-40 mg/mL, about 40-45 mg/mL, about 45-50 mg/mL, about 50-55 mg/mL, about 55-60 mg/mL, about 60-65 mg/mL, about 65-70 mg/mL, about 70-75 mg/mL, about 75-80 mg/mL, about 80-85 mg/mL, about 85-90 mg/mL, about 90-95 mg/mL, about or about 95-100 mg/mL, or any combination of such ranges).

In some embodiments, one of the one or more quality control parameters is the concentration of albumin in the non-nanoparticle portion of the pharmaceutical composition. For example, the quality control method for assessing the suitability of the pharmaceutical composition can include measuring the concentration of albumin in the non-nanoparticle portion, and assessing the suitability of the pharmaceutical composition for medical use in a human individual, wherein concentration of albumin in the non-nanoparticle portion falling within a quality control threshold for the concentration of albumin in the non-nanoparticle portion is indicative of suitability of the pharmaceutical composition for medical use in the individual. In some embodiments, the concentration of albumin in the non-nanoparticle portion falling outside of the quality control threshold for the concentration of albumin in the non-nanoparticle portion is indicative of non-suitability of the pharmaceutical composition for medical use in the individual. In some embodiments, the quality control threshold for the concentration of albumin in the non-nanoparticle portion is about 30 mg/mL to about 100 mg/mL (for example, about 30-35 mg/mL, about 35-40 mg/mL, about 40-45 mg/mL, about 45-50 mg/mL, about 50-55 mg/mL, about 55-60 mg/mL, about 60-65 mg/mL, about 65-70 mg/mL, about 70-75 mg/mL, about 75-80 mg/mL, about 80-85 mg/mL, about 85-90 mg/mL, about 90-95 mg/mL, about or about 95-100 mg/mL, or any combination of such ranges).

In some embodiments, one of the one or more quality control parameters is the concentration of albumin in the pharmaceutical composition that is in the nanoparticles of the pharmaceutical composition. For example, the quality control method for assessing the suitability of the pharmaceutical composition can include measuring the concentration of albumin in the pharmaceutical composition that is in the nanoparticles, and assessing the suitability of the pharmaceutical composition for medical use in a human individual, wherein the measured concentration of albumin in the pharmaceutical composition that is in the nanoparticles falling within a quality control threshold for the concentration of albumin in the pharmaceutical composition that is in the nanoparticles is indicative of suitability of the pharmaceutical composition for medical use in the individual. In some embodiments, the measured concentration of albumin in the pharmaceutical composition that is in the nanoparticles falling outside of the quality control threshold for the concentration of albumin in the pharmaceutical composition that is in the nanoparticles is indicative of non-suitability of the pharmaceutical composition for medical use in the individual. In some embodiments, the quality control threshold for the concentration of albumin in the pharmaceutical composition that is in the nanoparticles is about 1 mg/mL to about 10 mg/mL (such as about 1-1.2 mg/mL, about 1.2-1.5 mg/mL, about 1.5-1.8 mg/mL, about 1.8-2 mg/L, about 2-2.5 mg/mL, about 2.5-3 mg/mL, about 3-3.5 mg/mL, about 3.5-4 mg/mL, about 4-4.5 mg/mL, or about 4.5-5 mg/mL, about 5-6 mg/mL, about 6-7 mg/mL, about 7-8 mg/mL, about 8-9 mg/mL or about 9-10 mg/mL, or any combination of such ranges).

In some embodiments, one of the one or more quality control parameters is the concentration of total rapamycin in the pharmaceutical composition. For example, the quality control method for assessing the suitability of the pharmaceutical composition can include measuring the concentration of total rapamycin in the pharmaceutical composition, and assessing the suitability of the pharmaceutical composition for medical use in a human individual, wherein the measured concentration of total rapamycin in the pharmaceutical composition that is in the nanoparticles falling within a quality control threshold for the concentration of total rapamycin in the pharmaceutical composition is indicative of suitability of the pharmaceutical composition for medical use in the individual. In some embodiments, the measured concentration of total rapamycin in the pharmaceutical composition falling outside of the quality control threshold for the concentration of total rapamycin in the pharmaceutical composition is indicative of non-suitability of the pharmaceutical composition for medical use in the individual. In some embodiments, the quality control threshold for the concentration of total rapamycin in the pharmaceutical composition is about 1 mg/mL to about 15 mg/mL (such as about 1-2 mg/mL, about 2-3 mg/mL, about 3-4 mg/mL, about 4-5 mg/mL, about 5-6 mg/mL, about 6-7 mg/mL, about 7-8 mg/mL, about 8-9 mg/mL, about, about 9-10 mg/mL, about 10-11 mg/mL, about 11-12 mg/mL, about 13-14 mg/mL, or about 14-15 mg/mL, or any combination of these ranges), about 1 mg/ml, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, or about 15 mg/mL.

In some embodiments, one of the one or more quality control parameters is the concentration of rapamycin in the pharmaceutical composition that is in the non-nanoparticle portion. For example, the quality control method for assessing the suitability of the pharmaceutical composition can include measuring the concentration of rapamycin in the pharmaceutical composition that is in the non-nanoparticle portion, and assessing the suitability of the pharmaceutical composition for medical use in a human individual, wherein the measured concentration of rapamycin in the pharmaceutical composition that is in the non-nanoparticle portion falling within a quality control threshold for the concentration of rapamycin in the pharmaceutical composition that is in the non-nanoparticle portion is indicative of suitability of the pharmaceutical composition for medical use in the individual. In some embodiments, the measured concentration of rapamycin in the pharmaceutical composition that is in the non-nanoparticle portion falling outside of the quality control threshold for the concentration of rapamycin in the pharmaceutical composition that is in the non-nanoparticle portion is indicative of non-suitability of the pharmaceutical composition for medical use in the individual. In some embodiments, the quality control threshold for the concentration of rapamycin in the pharmaceutical composition that is in the non-nanoparticle portion is less than about 55 µg/mL, such as about 1-5 µg/mL, about 5-10 µg/mL, about 10-15 µg/mL, about 15-20 µg/mL, about 20-25 µg/mL, about 25-30 µg/mL, about 30-35 µg/mL, about 35-40 µg/mL, about 40-45 µg/mL, about 45-50 µg/mL, or about 50-55 µg/mL (or a combination of such ranges).

In some embodiments, one of the one or more quality control parameters is the concentration of rapamycin in the pharmaceutical composition that is in the nanoparticles. For example, the quality control method for assessing the suitability of the pharmaceutical composition can include measuring the concentration of rapamycin in the pharmaceutical composition that is in the nanoparticles, and assessing the suitability of the pharmaceutical composition for medical use in a human individual, wherein the measured concentration of rapamycin in the pharmaceutical composition that is in the nanoparticles falling within a quality control threshold for the concentration of rapamycin in the pharmaceutical composition that is in the nanoparticles is indicative of suitability of the pharmaceutical composition for medical use in the individual. In some embodiments, the measured concentration of rapamycin in the pharmaceutical composition that is in the nanoparticles falling outside of the quality control threshold for the concentration of rapamycin in the pharmaceutical composition that is in the nanoparticles is indicative of non-suitability of the pharmaceutical composition for medical use in the individual. In some embodiments, the quality control threshold for the concentration of rapamycin in the pharmaceutical composition that is in the nanoparticles is about 1 mg/mL to about 15 mg/mL (such as about 1-2 mg/mL, about 2-3 mg/mL, about 3-4 mg/mL, about 4-5 mg/mL, about 5-6 mg/mL, about 6-7 mg/mL, about 7-8 mg/mL, about 8-9 mg/mL, about, about 9-10 mg/mL, about 10-11 mg/mL, about 11-12 mg/mL, about 13-14 mg/mL, or about 14-15 mg/mL, or any combination of these ranges).

In some embodiments, one of the one or more quality control parameters is the osmolality of the pharmaceutical composition. For example, the quality control method for assessing the suitability of the pharmaceutical composition can include measuring the osmolality of the pharmaceutical composition, and assessing the suitability of the pharmaceutical composition for medical use in a human individual, wherein the measured osmolality of the pharmaceutical composition falling within a quality control threshold for the osmolality of the pharmaceutical composition is indicative of suitability of the pharmaceutical composition for medical use in the individual. In some embodiments, the measured osmolality of the pharmaceutical composition falling outside of the quality control threshold for the osmolality of the pharmaceutical composition is indicative of non-suitability of the pharmaceutical composition for medical use in the individual. In some embodiments, the quality control threshold for the osmolality of the pharmaceutical composition is about 300 mOsm/kg to about 350 mOsm/kg (such as about 300-310 mOsm/kg, about 310-320 mOsm/kg, about 320-330 mOsm/kg, about 330-340 mOsm/kg, or about 340-350 mOsm/kg, or any combination of such ranges). In some embodiments, the osmolality of the pharmaceutical composition is adjusted to fall within the quality control threshold.

In some embodiments, one of the one or more quality control parameters is the viscosity of the pharmaceutical composition. For example, the quality control method for assessing the suitability of the pharmaceutical composition can include measuring the viscosity of the pharmaceutical composition, and assessing the suitability of the pharmaceutical composition for medical use in a human individual, wherein the measured viscosity of the pharmaceutical composition falling within a quality control threshold for the viscosity of the pharmaceutical composition is indicative of suitability of the pharmaceutical composition for medical use in the individual. In some embodiments, the measured viscosity of the pharmaceutical composition falling outside of the quality control threshold for the viscosity of the pharmaceutical composition is indicative of non-suitability of the pharmaceutical composition for medical use in the individual. In some embodiments, the quality control threshold for the viscosity of the pharmaceutical composition is between about 1.20 centipoise (cP) to about 1.50 cP (such as about 1.20-1.25 cP, about 1.25-1.30 cP, about 1.30-1.35 cP, about 1.35-1.40 cP, about 1.40-1.45 cP, or about 1.45-1.50 cP, or any combination of such ranges). In some embodiments, the viscosity of the pharmaceutical composition is adjusted to fall within the quality control threshold.

In some embodiments, one of the one or more quality control parameters is the stability of the pharmaceutical composition. Stability of the pharmaceutical composition can be determined by storing the pharmaceutical composition for a period of time at a set temperature, and observing one or more of the quality control parameters before and after the storage period. A change of that quality control parameter by about 20% or less, about 15% or less, about 10% or less, about 5% or less, or about 2% or less during the storage period indicates that the pharmaceutical composition is stable. The set temperature may be, for example, about 2° C. to about 8° C., about 15° C. to about 25°, or about 25° C. to about 40° C., or about 2° C., about 4° C., about 8° C., about 15° C., about 25° C., about 30° C., or about 40° C. For example, the quality control method for assessing the suitability of the pharmaceutical composition can include measuring the stability of the pharmaceutical composition, and assessing the suitability of the pharmaceutical composition for medical use in a human individual, wherein the measured quality control parameter of the pharmaceutical composition changing by about 20% or less, about 15% or less, about 10% or less, about 5% or less, or about 2% or less during the storage period is indicative of suitability of the pharmaceutical composition for medical use in the individual. In some embodiments, the measured quality control parameter changes by about 2% or more, about 5% or more, about 10% or more, about 15% or more, or about 20% or more, which is indicative of non-suitability of the pharmaceutical composition for medical use in the individual.

In some embodiments, one of the one or more quality control parameters is the pH of the pharmaceutical composition. For example, the quality control method for assessing the suitability of the pharmaceutical composition can include measuring the pH of the pharmaceutical composition, and assessing the suitability of the pharmaceutical composition for medical use in a human individual, wherein the measured pH of the pharmaceutical composition falling within a quality control threshold for the pH of the pharmaceutical composition is indicative of suitability of the pharmaceutical composition for medical use in the individual. In some embodiments, the measured pH of the pharmaceutical composition falling outside of the quality control threshold for the pH of the pharmaceutical composition is indicative of non-suitability of the pharmaceutical composition for medical use in the individual. In some embodiments, the quality control threshold for the pH of the pharmaceutical composition is about 4.5 to about 9.0, for example pH ranges of any one of about 4.5-5.0, about 5.0-5.5, about 5.5-6.0, about 6.0-6.5, about 6.5-7.0, about 7.0-7.5, about 7.5-8.0, about 8.0-8.5, or about 8.5-9.0 (or any combination of such ranges), or about 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0. In some embodiments, the pH of the pharmaceutical composition is adjusted to fall within the quality control threshold.

In some embodiments, one of the one or more quality control parameters is the concentration of organic solvent in the pharmaceutical composition. For example, the quality control method for assessing the suitability of the pharmaceutical composition can include measuring concentration of organic solvent in the pharmaceutical composition, and assessing the suitability of the pharmaceutical composition for medical use in a human individual, wherein the measured concentration of organic solvent in the pharmaceutical composition falling within a quality control threshold for the concentration of organic solvent in the pharmaceutical composition is indicative of suitability of the pharmaceutical composition for medical use in the individual. In some embodiments, the measured concentration of organic solvent in the pharmaceutical composition falling outside of the quality control threshold for the concentration of organic solvent in the pharmaceutical composition is indicative of non-suitability of the pharmaceutical composition for medical use in the individual. In some embodiments, the quality control threshold for concentration of organic solvent in the pharmaceutical composition is less than about any of 20 µg/ml, 19 µg/ml, 18 µg/ml, 17 µg/ml, 16 µg/ml, 15 µg/ml, 14 µg/ml, 13 µg/ml, 12 µg/ml, 11 µg/ml, 10 µg/ml, 9 µg/ml, 8 µg/ml, 7 µg/ml, 6 µg/ml, 5 µg/ml, 4 µg/ml, 3 µg/ml, 2 µg/ml, or 1 µg/ml total organic solvent, or less than about any of 20 ppm, 19 ppm, 18 ppm, 17 ppm, 16 ppm, 15 ppm, 14 ppm, 13 ppm, 12 ppm, 11 ppm, 10 ppm, 9 ppm, 8 ppm, 7 ppm, 6 ppm, 5 ppm, 4 ppm, 3 ppm, 2 ppm, or 1 ppm total organic solvent.

In some embodiments, one of the one or more quality control parameters is the concentration of chloroform in the pharmaceutical composition. For example, the quality control method for assessing the suitability of the pharmaceutical composition can include measuring concentration of chloroform in the pharmaceutical composition, and assessing the suitability of the pharmaceutical composition for medical use in a human individual, wherein the measured concentration of chloroform in the pharmaceutical composition falling within a quality control threshold for the concentration of chloroform in the pharmaceutical composition is indicative of suitability of the pharmaceutical composition for medical use in the individual. In some embodiments, the measured concentration of chloroform in the pharmaceutical composition falling outside of the quality control threshold for the concentration of chloroform in the pharmaceutical composition is indicative of non-suitability of the pharmaceutical composition for medical use in the individual. In some embodiments, the quality control threshold for concentration of chloroform in the pharmaceutical composition is less than any of about 10 µg/ml, 9 µg/ml, 8 µg/ml, 7 µg/ml, 6 µg/ml, 5 µg/ml, 4 µg/ml, 3 µg/ml, 2 µg/ml, or 1 µg/ml chloroform, or less than about any of 10 ppm, 9 ppm, 8 ppm, 7 ppm, 6 ppm, 5 ppm, 4 ppm, 3 ppm, 2 ppm, or 1 ppm chloroform.

In some embodiments, one of the one or more quality control parameters is the concentration of ethanol in the pharmaceutical composition. For example, the quality control method for assessing the suitability of the pharmaceutical composition can include measuring concentration of ethanol in the pharmaceutical composition, and assessing the suitability of the pharmaceutical composition for medical use in a human individual, wherein the measured concentration of ethanol in the pharmaceutical composition falling within a quality control threshold for the concentration of ethanol in the pharmaceutical composition is indicative of suitability of the pharmaceutical composition for medical use in the individual. In some embodiments, the measured concentration of ethanol in the pharmaceutical composition falling outside of the quality control threshold for the concentration of ethanol in the pharmaceutical composition is indicative of non-suitability of the pharmaceutical composition for medical use in the individual. In some embodiments, the quality control threshold for concentration of ethanol in the pharmaceutical composition is less than any of about 10 µg/ml, 9 µg/ml, 8 µg/ml, 7 µg/ml, 6 µg/ml, 5 µg/ml, 4 µg/ml, 3 µg/ml, 2 µg/ml, or 1 µg/ml ethanol, or less than about any of 10 ppm, 9 ppm, 8 ppm, 7 ppm, 6 ppm, 5 ppm, 4 ppm, 3 ppm, 2 ppm, or 1 ppm ethanol.

In some embodiments, one of the one or more quality control parameters is the concentration of isopropanol in the pharmaceutical composition. For example, the quality control method for assessing the suitability of the pharmaceutical composition can include measuring concentration of isopropanol in the pharmaceutical composition, and assessing the suitability of the pharmaceutical composition for medical use in a human individual, wherein the measured concentration of isopropanol in the pharmaceutical composition falling within a quality control threshold for the concentration of isopropanol in the pharmaceutical composition is indicative of suitability of the pharmaceutical composition for medical use in the individual. In some embodiments, the measured concentration of isopropanol in the pharmaceutical composition falling outside of the quality control threshold for the concentration of isopropanol in the pharmaceutical composition is indicative of non-suitability of the pharmaceutical composition for medical use in the individual. In some embodiments, the quality control threshold for concentration of isopropanol in the pharmaceutical composition is less than any of about 10 µg/ml, 9 µg/ml, 8 µg/ml, 7 µg/ml, 6 µg/ml, 5 µg/ml, 4 µg/ml, 3 µg/ml, 2 µg/ml, or 1 µg/ml isopropanol, or less than about any of 10 ppm, 9 ppm, 8 ppm, 7 ppm, 6 ppm, 5 ppm, 4 ppm, 3 ppm, 2 ppm, or 1 ppm isopropanol.

In some embodiments, one of the one or more quality control parameters is the concentration of tert-butanol in the pharmaceutical composition. For example, the quality control method for assessing the suitability of the pharmaceutical composition can include measuring concentration of tert-butanol in the pharmaceutical composition, and assessing the suitability of the pharmaceutical composition for medical use in a human individual, wherein the measured concentration of tert-butanol in the pharmaceutical composition falling within a quality control threshold for the concentration of tert-butanol in the pharmaceutical composition is indicative of suitability of the pharmaceutical composition for medical use in the individual. In some embodiments, the measured concentration of tert-butanol in the pharmaceutical composition falling outside of the quality control threshold for the concentration of tert-butanol in the pharmaceutical composition is indicative of non-suitability of the pharmaceutical composition for medical use in the individual. In some embodiments, the quality control threshold for concentration of tert-butanol in the pharmaceutical composition is less than any of about 10 µg/ml, 9 µg/ml, 8 µg/ml, 7 µg/ml, 6 µg/ml, 5 µg/ml, 4 µg/ml, 3 µg/ml, 2 µg/ml, or 1 µg/ml tert-butanol, or less than about any of 10 ppm, 9 ppm, 8 ppm, 7 ppm, 6 ppm, 5 ppm, 4 ppm, 3 ppm, 2 ppm, or 1 ppm tert-butanol.

In some embodiments, one of the one or more quality control parameters is the zeta potential of the nanoparticles. For example, the quality control method for assessing the suitability of the pharmaceutical composition can include measuring zeta potential of the nanoparticles in the pharmaceutical composition, and assessing the suitability of the pharmaceutical composition for medical use in a human individual, wherein the measured zeta potential of the nanoparticles falling within a quality control threshold for the zeta potential of the nanoparticles is indicative of suitability of the pharmaceutical composition for medical use in the individual. In some embodiments, the measured zeta potential of the nanoparticles falling outside of the quality control threshold for the zeta potential of the nanoparticles is indicative of non-suitability of the pharmaceutical composition for medical use in the individual. In some embodiments, the quality control threshold for the zeta potential of the nanoparticles in the pharmaceutical composition is about −25 mV to about −50 mV (such as about −25 mV to about −30 mV, about −30 mV to about −35 mV, about −35 mV to about −40 mV, about −40 mV to about −45 mV, or about −45 mV to about −50 mV, or any combination of such ranges.

In some embodiments, one of the one or more quality control parameters is the crystalline status of a dried form of the pharmaceutical composition. For example, the quality control method for assessing the suitability of the pharmaceutical composition can include determining the crystalline status of a dried form of the pharmaceutical composition, and assessing the suitability of the pharmaceutical composition for medical use in a human individual, wherein the crystalline status of a dried form of the pharmaceutical composition being amorphous is indicative of suitability of the pharmaceutical composition for medical use in the individual. In some embodiments, the determined crystalline status of a dried form of the pharmaceutical composition being crystalline is indicative of non-suitability of the pharmaceutical composition for medical use in the individual.

In some embodiments, one of the one or more quality control parameters is the crystalline status of the rapamycin in the nanoparticles of the pharmaceutical composition. For example, the quality control method for assessing the suitability of the pharmaceutical composition can include determining the crystalline status of the rapamycin in the nanoparticles of the pharmaceutical composition, and assessing the suitability of the pharmaceutical composition for medical use in a human individual, wherein the crystalline status of the rapamycin in the nanoparticles of the pharmaceutical composition being amorphous is indicative of suitability of the pharmaceutical composition for medical use in the individual. In some embodiments, the determined crystalline status of the rapamycin in the nanoparticles of the pharmaceutical composition being crystalline is indicative of non-suitability of the pharmaceutical composition for medical use in the individual.

In some embodiments, one of the one or more quality control parameters is the interaction of the vinyl chain of the rapamycin in the nanoparticles with the albumin in the nanoparticles of the pharmaceutical composition. For example, the quality control method for assessing the suitability of the pharmaceutical composition can include determining the interaction of the vinyl chain of the rapamycin in the nanoparticles with the albumin in the nanoparticles of the pharmaceutical composition, and assessing the suitability of the pharmaceutical composition for medical use in a human individual, wherein and interaction of the vinyl chain of the rapamycin in the nanoparticles with the albumin in the nanoparticles of the pharmaceutical composition is indicative of suitability of the pharmaceutical composition for medical use in the individual. In some embodiments, an absence of interaction of the vinyl chain of the rapamycin in the nanoparticles with the albumin in the nanoparticles of the pharmaceutical composition is indicative of non-suitability of the pharmaceutical composition for medical use in the individual.

In some embodiments, one of the one or more quality control parameters is the portion of nanoparticles in the pharmaceutical composition that are non-spherical. For example, the quality control method for assessing the suitability of the pharmaceutical composition can include measuring portion of nanoparticles in the pharmaceutical composition that are non-spherical, and assessing the suitability of the pharmaceutical composition for medical use in a human individual, wherein the measured portion of nanoparticles in the pharmaceutical composition that are non-spherical falling within a quality control threshold for the portion of nanoparticles in the pharmaceutical composition that are non-spherical is indicative of suitability of the pharmaceutical composition for medical use in the individual. In some embodiments, the measured portion of nanoparticles in the pharmaceutical composition that are non-spherical falling outside of the quality control threshold for the portion of nanoparticles in the pharmaceutical composition that are non-spherical is indicative of non-suitability of the pharmaceutical composition for medical use in the individual. In some embodiments, the quality control threshold for the portion of nanoparticles in the pharmaceutical composition that are non-spherical is about 20% or more (such as about 20% or more, about 25% or more, about 30% or more, about 35% or more, about 40% or more, about 45% or more, about 50% or more, about 55% or more, or about 60% or more).

In some embodiments, one of the one or more quality control parameters is the percentage of the sum of seco-rapamycin and rapamycin in the pharmaceutical composition that is seco-rapamycin. For example, the quality control method for assessing the suitability of the pharmaceutical composition can include measuring the percentage of the sum of seco-rapamycin and rapamycin in the pharmaceutical composition that is seco-rapamycin, and assessing the suitability of the pharmaceutical composition for medical use in a human individual, wherein the measured percentage of the sum of seco-rapamycin and rapamycin in the pharmaceutical composition that is seco-rapamycin falling within a quality control threshold for the percentage of the sum of seco-rapamycin and rapamycin in the pharmaceutical composition that is seco-rapamycin is indicative of suitability of the pharmaceutical composition for medical use in the individual. In some embodiments, the measured percentage of the sum of seco-rapamycin and rapamycin in the pharmaceutical composition that is seco-rapamycin falling outside of the quality control threshold for the percentage of the sum of seco-rapamycin and rapamycin in the pharmaceutical composition that is seco-rapamycin is indicative of non-suitability of the pharmaceutical composition for medical use in the individual. In some embodiments, the quality control threshold for the percentage of the sum of seco-rapamycin and rapamycin in the pharmaceutical composition that is seco-rapamycin is about 3% or less (such as about 2.5% or less, about 2% or less, about 1.5% or less, about 1% or less, or about 0.5% or less).

The quality control methods described herein are useful for assessing the suitability of the pharmaceutical composition for medical use in an individual, such as a human individual. As discussed above, the pharmaceutical composition can be identified as suitable for medical use in the individual, or in the alternative as not suitable for use in the individual.

A pharmaceutical composition identified as suitable for use in a human individual may be released, for example for commercial distribution. The pharmaceutical composition may be released or distributed, for example, to a wholesaler, a pharmacy, a physician or a patient. Commercial batches, such as the commercial batches described herein, of the pharmaceutical composition may be released when the pharmaceutical composition is identified as suitable for use in the individual. In some embodiments, a commercial batch of the pharmaceutical composition is released after assessing the suitability of the pharmaceutical composition for medical use in a human individual using one or more samples selected from the commercial batch. As the samples are representative of the commercial batch, it is presumed that the pharmaceutical composition in the in the commercial batch is suitable for use in an individual when the samples taken from the commercial batch are determined to be suitable for use in the individual.

In some embodiments, a record of the suitability of the pharmaceutical composition for use in an individual or human individual is generated. The record may be retained, for example, to monitor the manufacturing quality control over a period of time. A container containing the pharmaceutical composition is optionally labeled as suitable for use in a human individual, for example in preparation of release or distribution.

In some embodiments, the pharmaceutical composition may be prepared, for example for release and/or distribution, once the pharmaceutical composition has be identified as suitable for use in an individual. The pharmaceutical composition may be packaged, for example by filling the pharmaceutical composition into a container (such as a bag or vial), which is preferably sterile. In some embodiments, the pharmaceutical composition is lyophilized. In some embodiments, the pharmaceutical composition is filled into a container before lyophilizing the pharmaceutical composition. In some embodiments, the container, once filled with the pharmaceutical composition, is sealed. The containers having the pharmaceutical composition suitable for use in an individual or human individual may be labeled to indicate its suitability.

If the pharmaceutical composition is assessed as not suitable for medical use in a human individual, it may be disposed of and/or used for research purposes. For example, the pharmaceutical composition may be disposed of by inactivating the pharmaceutical composition, such as by heat, chemical neutralization, or other suitable destruction. A record may be made indicating that the assessed pharmaceutical composition is not suitable for used in an individual or human individual, although the pharmaceutical composition may optionally be used for a non-medical use or use in a non-human individual. In some embodiments, the non-medical use comprises any of laboratory research, in vitro research, or animal research. In some embodiments, the pharmaceutical composition is in a container and a record associated with the container may be made to indicate the pharmaceutical composition is not suitable for medical use or suitable only for non-medical use. In some embodiments, the pharmaceutical composition is in a container, and the container may be labeled such that the pharmaceutical composition contents of the container are identified as not suitable for medical use in an individual.

Emulsions of Albumin and Rapamycin

The nanoparticle composition may be formed by removing organic solvent from an emulsion, for example in accordance with the methods further described herein. The emulsion includes an organic phase of nanodroplets comprising rapamycin dissolved in an organic solvent, and the nanodroplets are dispersed in a continuous aqueous phase comprising albumin. Other emulsions of organic phase nanodroplets dispersed in a continuous aqueous phase are generally unstable, as the nanodroplets coalesce over time resulting in larger nanodroplets. The emulsion provided herein that includes a dispersed organic phase comprising nanodroplets of rapamycin dissolved in an organic solvent dispersed in a continuous aqueous phase comprising albumin is surprisingly stable, which allows small solid nanoparticles to be formed from the emulsion by removing the organic solvent.

In some embodiments, the organic solvent is one or more of ethanol, methanol, isopropanol, butanol, tert-butanol, chloroform, or other suitable organic solvent. In some embodiments, the organic solvent is a mixture of two or more organic solvents, such as a mixture of chloroform and butanol, a mixture of chloroform and isopropanol, a mixture of chloroform and tert-butanol, a mixture of methanol and isopropanol, a mixture of methanol and butanol, or a mixture of methanol and tert-butanol. In some embodiments, two or more organic solvents may be included at a ratio of about 1:1 to about 9:1 (such as about 1:1 to about 2:1, about 2:1 to about 3:1, about 3:1 to about 4:1, about 4:1 to about 5:1, about 5:1 to about 6:1, about 6:1 to about 7:1, about 7:1 to about 8:1, or about 8:1 to about 9:1, or any combination of such ranges). By way of example, in some embodiments, the organic solvent comprises chloroform and tert-butanol at a ratio of about 1:1 to about 9:1 (such as about 1:1 to about 2:1, about 2:1 to about 3:1, about 3:1 to about 4:1, about 4:1 to about 5:1, about 5:1 to about 6:1, about 6:1 to about 7:1, about 7:1 to about 8:1, or about 8:1 to about 9:1, or any combination of such ranges).

In some embodiments, the emulsion (such as a crude emulsion or a homogenized emulsion) comprises about 1% to about 20% (such as about 1-2%, about 2-4%, about 4-6%, about 6-8%, about 8-10%, about 10-12%, about 12-15%, or about 15-20%, or any combination of such ranges) organic phase by total volume. In some embodiments, the emulsion comprises about 80% to about 99% (such as about 80-85%, about 85-88%, about 88-90%, about 90-92%, about 92-94%, about 94-96%, about 96-98%, or about 98-99%, or any combination of such ranges) aqueous phase by total volume.

In some embodiments, the organic solvent comprises between about 20 mg/ml and about 500 mg/ml rapamycin, such as any of about 20-50 mg/ml, 50-75 mg/ml, 75-100 mg/ml, 100-125 mg/ml, 125-150 mg/ml, 150-175 mg/ml, 175-200 mg/ml, 200-225 mg/ml, 225-250 mg/ml, 250-300 mg/ml, 300-350 mg/ml, 350-400 mg/ml, or 400-500 mg/ml (or any combination of such ranges) rapamycin. In some embodiments, the emulsion comprises between about 2 mg/ml and about 50 mg/ml rapamycin, such as any of about 2-5 mg/ml, 5-7.5 mg/ml, 7.5-10 mg/ml, 10-12.5 mg/ml, 12.5-15 mg/ml, 15-17.5 mg/ml, 17.5-20 mg/ml, 20-22.5 mg/ml, 22.5-25 mg/ml, 25-30 mg/ml, 30-35 mg/ml, 35-40 mg/ml, or 40-50 mg/ml (or any combination of such ranges) rapamycin.

In some embodiments, the aqueous phase comprises between about between 10 mg/ml and 200 mg/ml albumin, such as any of about 10-20 mg/ml, 20-30 mg/ml, 30-40 mg/ml, 40-50 mg/ml, 50-70 mg/ml, 70-90 mg/ml, 90-120 mg/ml 120-140 mg/ml, 140-160 mg/ml, 160-180 mg/ml, or 180-200 mg/ml albumin. In some embodiments, the emulsion comprises between about between 10 mg/ml and 200 mg/ml albumin, such as any of about 10-20 mg/ml, 20-30 mg/ml, 30-40 mg/ml, 40-50 mg/ml, 50-70 mg/ml, 70-90 mg/ml, 90-120 mg/ml 120-140 mg/ml, 140-160 mg/ml, 160-180 mg/ml, or 180-200 mg/ml albumin.

The organic phase nanodroplets in the emulsion can have a Z-average particle size of about 200 nm or less, such as about 50-200 nm (for example, about 50-60 nm, about 60-70 nm, about 70-80 nm, about 80-90 nm, about 90-100 nm, about 100-110 nm, about 110-120 nm, about 120-130 nm, about 130-140 nm, about 140-150 nm, about 150-160 nm, about 160-170 nm, about 170-180 nm, about 180-190 nm, or about 190-200 nm, or any combination of such ranges.

The emulsion is relatively stable, and can be stored for a period of time before being further processed to form nanoparticles. Stability of the emulsion refers to limited Z-average particle size increase of the nanodroplets over a period of time. For example, in some embodiments, the Z-average of the particle size of the nanodroplets increases by less than 5%, less than 10%, less than 15%, less than 20%, less than 25%, or less than 30% after 4 hour storage at 4° C. In some embodiments, the Z-average of the particle size of the nanodroplets increases by less than 5%, less than 10%, less than 15%, less than 20%, less than 25%, or less than 30% after 8 hour storage at 4° C. In some embodiments, the Z-average of the particle size of the nanodroplets increases by less than 5%, less than 10%, less than 15%, less than 20%, less than 25%, or less than 30% after 12 hour storage at 4° C. In some embodiments, the Z-average of the particle size of the nanodroplets increases by less than 5%, less than 10%, less than 15%, less than 20%, less than 25%, or less than 30% after 16 hour storage at 4° C. In some embodiments, the Z-average of the particle size of the nanodroplets increases by less than 5%, less than 10%, less than 15%, less than 20%, less than 25%, or less than 30% after 24 hour storage at 4° C. In some embodiments, the Z-average of the particle size of the nanodroplets increases by less than 5%, less than 10%, less than 15%, less than 20%, less than 25%, or less than 30% after 4 hour storage at 10° C. In some embodiments, the Z-average of the particle size of the nanodroplets increases by less than 5%, less than 10%, less than 15%, less than 20%, less than 25%, or less than 30% after 8 hour storage at 10° C. In some embodiments, the Z-average of the particle size of the nanodroplets increases by less than 5%, less than 10%, less than 15%, less than 20%, less than 25%, or less than 30% after 12 hour storage at 10° C. In some embodiments, the Z-average of the particle size of the nanodroplets increases by less than 5%, less than 10%, less than 15%, less than 20%, less than 25%, or less than 30% after 16 hour storage at 10° C. In some embodiments, the Z-average of the particle size of the nanodroplets increases by less than 5%, less than 10%, less than 15%, less than 20%, less than 25%, or less than 30% after 24 hour storage at 10° C.

In some embodiments, the emulsion comprises a dispersed organic phase comprising nanodroplets comprising rapamycin dissolved in an organic solvent comprising chloroform and tert-butanol, and a continuous aqueous phase comprising albumin (such as human albumin). In some embodiments, the phase fraction of the organic phase in the emulsion is about 1% to about 20%. In some embodiments, the Z-average particle size of the nanodroplets does not increase by more than 30% after storing the emulsion for about 4 hours, about 8 hours, about 12 hours, about 16 hours and/or 24 hours at about 4° C. and/or about 10° C.

In some embodiments, the emulsion comprises a dispersed organic phase comprising nanodroplets comprising rapamycin dissolved in an organic solvent comprising about 50% to about 90% chloroform and about 10% to about 50% tert-butanol, and a continuous aqueous phase comprising albumin (such as human albumin). In some embodiments, the phase fraction of the organic phase in the emulsion is about 1% to about 20%. In some embodiments, the Z-average particle size of the nanodroplets does not increase by more than 30% after storing the emulsion for about 4 hours, about 8 hours, about 12 hours, about 16 hours and/or 24 hours at about 4° C. and/or about 10° C.

In some embodiments, the emulsion comprises a dispersed organic phase comprising nanodroplets comprising about 20 mg/mL to about 500 mg/mL rapamycin dissolved in an organic solvent comprising about 50% to about 90% chloroform and about 10% to about 50% tert-butanol, and a continuous aqueous phase comprising about 10 mg/mL to about 200 mg/mL albumin (such as human albumin). In some embodiments, the phase fraction of the organic phase in the emulsion is about 1% to about 20%. In some embodiments, the Z-average particle size of the nanodroplets does not increase by more than 30% after storing the emulsion for about 4 hours, about 8 hours, about 12 hours, about 16 hours and/or 24 hours at about 4° C. and/or about 10° C.

In some embodiments, the emulsion comprises a dispersed organic phase comprising nanodroplets having a Z-average particle size of about 200 nm or less (such as about 50 nm to about 200 nm) comprising rapamycin dissolved in an organic solvent comprising chloroform and tert-butanol, and a continuous aqueous phase comprising albumin (such as human albumin). In some embodiments, the phase fraction of the organic phase in the emulsion is about 1% to about 20%. In some embodiments, the Z-average particle size of the nanodroplets does not increase by more than 30% after storing the emulsion for about 4 hours, about 8 hours, about 12 hours, about 16 hours and/or 24 hours at about 4° C. and/or about 10° C.

In some embodiments, the emulsion comprises a dispersed organic phase comprising nanodroplets having a Z-average particle size of about 200 nm or less (such as about 50 nm to about 200 nm) comprising rapamycin dissolved in an organic solvent comprising about 50% to about 90% chloroform and about 10% to about 50% tert-butanol, and a continuous aqueous phase comprising albumin (such as human albumin). In some embodiments, the phase fraction of the organic phase in the emulsion is about 1% to about 20%. In some embodiments, the Z-average particle size of the nanodroplets does not increase by more than 30% after storing the emulsion for about 4 hours, about 8 hours, about 12 hours, about 16 hours and/or 24 hours at about 4° C. and/or about 10° C.

In some embodiments, the emulsion comprises a dispersed organic phase comprising nanodroplets having a Z-average particle size of about 200 nm or less (such as about 50 nm to about 200 nm) comprising about 20 mg/mL to about 500 mg/mL rapamycin dissolved in an organic solvent comprising about 50% to about 90% chloroform and about 10% to about 50% tert-butanol, and a continuous aqueous phase comprising about 10 mg/mL to about 200 mg/mL albumin (such as human albumin). In some embodiments, the phase fraction of the organic phase in the emulsion is about 1% to about 20%. In some embodiments, the Z-average particle size of the nanodroplets does not increase by more than 30% after storing the emulsion for about 4 hours, about 8 hours, about 12 hours, about 16 hours and/or 24 hours at about 4° C. and/or about 10° C.

Methods of Making the Albumin-Rapamycin Compositions

Methods of making the rapamycin compositions (such as pharmaceutical compositions) are further described herein. Nanoparticles containing rapamycin and albumin can be prepared using high shear forces and high pressure homogenization, such as sonication, high pressure homogenization, or the like to form a fine emulsion, which is further processed to obtain the nanoparticles. Similar high pressure homogenization methods are disclosed in, for example, U.S. Pat. Nos. 5,916,596; 6,096,331; 6,749,868; 6,537,579; International Application Pub. No. WO 98/14174; International Application Pub. No. WO 99/00113; International Application Pub. No. WO 07/027941; and International Application Pub. No. WO 07/027819, with the exception that rapamycin is included in the emulsion. The contents of these publications, particularly with respect to the method of making compositions (such as pharmaceutical compositions) containing carrier proteins, are hereby incorporated by reference in their entireties.

Generally, to make the rapamycin pharmaceutical compositions described herein, rapamycin is dissolved in an organic solvent. Suitable organic solvents include, for example, ketones, esters, ethers, chlorinated solvents, and other solvents known in the art. For example, the organic solvent can be a mixture of methylene chloride/ethanol, chloroform/ethanol, or chloroform/tert-butanol (for example with a ratio of about any one of 1:9, 1:8, 1:7, 1:6, 1:5, 1:4, 1:3, 1:2, 1:1, 2:1, 3:1, 4:1, 5:1, 6:1, 7:1, 8:1, or 9:1 or with a ratio of about any one of 3:7, 5:7, 4:6, 5:5, 6:5, 8:5, 9:5, 9.5:5, 5:3, 7:3, 6:4, or 9.5:0.5). In some embodiments, the organic solvent comprises between about 10% and about 50% tert-butanol by volume. In some embodiments, the organic solvent comprises about any of 10%, 15%, 20%, 25%, 30%, 35%, 40%, 45%, or 50% tert-butanol by volume. In some embodiments, the organic solvent comprises about any of 10-15%, 15-20%, 20-25%, 25-30%, 30-35%, 35-40%, 40-45%, or 45-50%, or any combination of such ranges, of tert-butanol by volume. In some embodiments, the organic solvent comprises between about 50% and about 90% chloroform by volume. In some embodiments, the organic solvent comprises about any of 50%, 55%, 60%, 65%, 70%, 75%, 80%, 85%, or 90% chloroform by volume. In some embodiments, the organic solvent comprises about any of 50-55%, 55-60%, 60-65%, 65-70%, 70-75%, 75-80%, 80-85%, or 85-90%, or any combination of such ranges, of chloroform by volume. In some embodiments, the organic solvent comprises between about 10% and about 50% tert-butanol by volume and between about 50% and about 90% chloroform by volume. In some embodiments, the organic solvent comprises chloroform and tert-butanol at a volumetric ratio of about 1:1 to about 1:9, such as about any of 1:1, 2:1, 3:1, 4:1, 5:1, 6:1, 7:1, 8:1, and 9:1.

Albumin (such as recombinant albumin, for example NOVOZYME™ recombinant albumin or INTRIVIA™ recombinant albumin disclosed herein) is dissolved in an aqueous solution (such as water) and combined with the rapamycin solution to form a crude emulsion. The mixture is subjected to high pressure homogenization (e.g., using an Avestin, APV Gaulin, MICROFLUIDIZER™ such as a MICROFLUIDIZER™ Processor M-110EH from Microfluidics, Stansted, or Ultra Turrax homogenizer). The emulsion may be cycled through the high pressure homogenizer for between about 2 to about 100 cycles, such as about 5 to about 50 cycles or about 6 to about 20 cycles (e.g., about any one of 6, 8, 10, 12, 14, 16, 18 or 20 cycles). The organic solvent can then be removed by evaporation utilizing suitable equipment known for this purpose, including, but not limited to, rotary evaporators, falling film evaporators, wiped film evaporators, spray driers, and the like that can be operated in batch mode or in continuous operation. In some embodiments, the evaporator is a wiped film evaporator. The solvent may be removed at reduced pressure (such as at about any one of 25 mm Hg, 30 mm Hg, 40 mm Hg, 50 mm Hg, 100 mm Hg, 200 mm Hg, or 300 mm Hg). The amount of time used to remove the solvent under reduced pressure may be adjusted based on the volume of the formulation. For example, for a formulation produced on a 300 mL scale, the solvent can be removed at about 1 to about 300 mm Hg (e.g., about any one of 5-100 mm Hg, 10-50 mm Hg, 20-40 mm Hg, or 25 mm Hg) for about 5 to about 60 minutes (e.g., about any one of 7, 8, 9, 10, 11, 12, 13, 14, 15 16, 18, 20, 25, or 30 minutes). The dispersion obtained can be further lyophilized.

Thus, in some embodiments, a method of making a nanoparticle suspension is provided, the method comprising removing organic solvent from an emulsion to make the nanoparticle suspension. In some embodiments, the method further comprises forming the emulsion. In some embodiments, forming the emulsion comprises combining an organic phase and an aqueous phase to form an emulsion (such as a crude emulsion). In some embodiments, the method further comprises homogenizing an emulsion (such as a crude emulsion) to form an emulsion (such as a homogenized emulsion). In some embodiments, the emulsion comprises a dispersed organic phase comprising nanodroplets comprising rapamycin dissolved in an organic solvent and a continuous aqueous phase comprising water and albumin.

In some embodiments, the emulsion (such as a crude emulsion or a homogenized emulsion) comprises about 1% to about 20% organic phase by total volume. In some embodiments, the emulsion comprises about 80% to about 99% aqueous phase by total volume. In some embodiments, the organic phase comprises an organic solvent comprising chloroform and tert-butanol. In some embodiments, the organic solvent comprises between about 20 mg/ml and about 500 mg/ml rapamycin, such as any of about 20-50 mg/ml, 50-100 mg/ml, 100-150 mg/ml, 150-200 mg/ml, 175-200 mg/ml, 175-225 mg/ml, 200-225 mg/ml, 225-250 mg/ml, 250-300 mg/ml, 300-350 mg/ml, or 350-500 mg/ml rapamycin. In some embodiments, the aqueous phase comprises between about between about 10 mg/ml and 200 mg/ml albumin, such as any of about 10-20 mg/ml, 20-40 mg/ml, 40-60 mg/ml, 60-80 mg/ml, 80-100 mg/ml, 100-120 mg/ml, 120-140 mg/ml, 140-160 mg/ml, 160-180 mg/ml, or 180-200 mg/ml albumin.

In some embodiments, the method comprises removing the organic solvent using an evaporator. In some embodiments, the evaporator is a wiped film evaporator. In some embodiments, the organic and aqueous phases are homogenized using a high pressure homogenizer before removing the organic solvent. In some embodiments, the organic and aqueous phases are homogenized using a high pressure homogenizer in a continuous process with the evaporator.

In some embodiments, the method further comprises storing the emulsion, for example, at a temperature below room temperature such as between about 2° C. and about 20° C., including between about 2° C. and about 8° C. In some embodiments, the method further comprises filtering the organic phase prior to forming the emulsion. In some embodiments, the method further comprises filtering the aqueous phase prior to forming the emulsion. In some embodiments, the method further comprises filtering both the organic and aqueous phases prior to forming the emulsion.

In some embodiments, combining the organic phase comprising an organic solvent and rapamycin and an aqueous phase comprising albumin forms an emulsion comprising nanodroplets that have a Z-average particle size of about 50 nm to about 200 nm, such as about any of 50-70 nm, 70-90 nm, 90-110 nm, 110-130 nm, 130-150 nm, 150-170 nm, 170-190 nm, 180-200 nm, 50-80 nm, 60-90 nm, 70-100 nm, 80-110 nm, 110-140 nm, 140-170 nm, 170-200 nm, 50-90 nm, 60-100 nm, 70-110 nm, 80-120 nm, 90-130 nm, 100-140 nm, 110-150 nm, 120-160 nm, 130-170 nm, 140-180 nm, 150-190 nm, or 160-200 nm. In some embodiments, combining the organic phase comprising an organic solvent and rapamycin and an aqueous phase comprising albumin forms an emulsion comprising nanodroplets that have a Z-average particle size of less than about 200 nm, such as about any of less than 180 nm, 160 nm, 140 nm, 120 nm, 100 nm, 80 nm, or 60 nm.

If desired, additional albumin solution may be added to the dispersion to adjust the albumin to rapamycin ratio, or to adjust the concentration of rapamycin in the dispersion. For example, albumin solution (e.g., 25% w/v) can be added to adjust the albumin to rapamycin ratio to about any one of 18:1, 15:1 14:1, 13:1, 12:1, 11:1, 10:1, 9:1, 8:1, 7.5:1, 7:1, 6:1, 5:1, 4:1, 3.5:1, 3:1, or 2.5:1. In another example, albumin solution (e.g., 25% w/v) or another solution is added to adjust the concentration of rapamycin to less than 15 mg/ml, such as about any of 0.5 mg/ml, 1.0 mg/ml, 1.5 mg/ml, 2 mg/ml, 3 mg/ml, 4 mg/ml, 5 mg/ml, 5.5 mg/ml, 6 mg/ml, 6.5 mg/ml, 7 mg/ml, 7.5 mg/ml, 8 mg/ml, 9 mg/ml, 10 mg/ml, or 15 mg/ml. In some embodiments, albumin solution or another solution is added to adjust the concentration of rapamycin to any of about 1-2 mg/ml, 2-3 mg/ml, 3-4 mg/ml, 4-5 mg/ml, 5-6 mg/ml, 6-7 mg/ml, 7-8 mg/ml, 8-9 mg/ml, 9-10 mg/ml, 10-11 mg/ml, 11-12 mg/ml, 12-13 mg/ml, 13-14 mg/ml, 14-15 mg/ml, 1-4 mg/ml, 4-6 mg/ml, 6-8 mg/ml, 8-10 mg/ml, 10-12 mg/ml, 12-14 mg/ml, 13-15 mg/ml, 1-5 mg/ml, 5-9 mg/ml, 9-13 mg/ml, 11-15 mg/ml, 1-8 mg/ml, or 8-15 mg/ml. The dispersion may be filtered, such as through one or more of a 1.2 µm, 0.8 µm, and 0.2 µm filter, or any other filter known in the art. The dispersion obtained can be further lyophilized. The pharmaceutical compositions may be made using a batch process or a continuous process (e.g., the production of a composition (such as a pharmaceutical composition) on a large scale).

If desired, a second therapy (e.g., one or more compounds useful for treating cancer), an antimicrobial agent, sugar, and/or stabilizing agent can also be included in the composition. For example, this additional agent can either be admixed with rapamycin and/or the albumin during the preparation of the rapamycin pharmaceutical composition, or added after the rapamycin pharmaceutical composition is prepared. In some embodiments, the agent is admixed with the rapamycin pharmaceutical composition prior to lyophilization. In some embodiments, the agent is added to the lyophilized rapamycin pharmaceutical composition. In some embodiments when the addition of the agent changes the pH of the composition, the pH in the composition (such as a pharmaceutical composition) are generally (but not necessarily) adjusted to a desired pH. Exemplary pH values of the compositions (such as pharmaceutical compositions) include, for example, in the range of about 5 to about 8.5. In some embodiments, the pH of the composition (such as a pharmaceutical composition) is adjusted to no less than about 6, including for example no less than any one of about 6.5, 7, or 8 (e.g., about 8).

Methods of Treating Diseases

The pharmaceutical compositions of the present invention may be used to treat diseases associated with cellular proliferation or hyperproliferation, such as cancers.

Examples of cancers that may be treated by the methods described herein include, but are not limited to, breast cancer (such as metastatic breast cancer), lung cancer (such as non-small cell lung cancer), pancreatic cancer (such as metastatic pancreatic cancer or locally advanced unresectable pancreatic cancer), multiple myeloma, renal cell carcinoma, prostate cancer, melanoma (such as metastatic melanoma), colon cancer, colorectal cancer, ovarian cancer, liver cancer, renal cancer, and gastric cancer. In some embodiments, the cancer is breast cancer after failure of combination chemotherapy for metastatic disease or relapse within 6 months of adjuvant chemotherapy. In some embodiments, the prior therapy includes an anthracycline treatment.

Cancers to be treated by compositions (such as pharmaceutical compositions) described herein include, but are not limited to, carcinoma, lymphoma, blastoma, sarcoma, and leukemia. Examples of cancers that can be treated by compositions (such as pharmaceutical compositions) described herein include, but are not limited to, squamous cell cancer, lung cancer (including small cell lung cancer, non-small cell lung cancer, adenocarcinoma of the lung, and squamous carcinoma of the lung, including squamous NSCLC), cancer of the peritoneum, hepatocellular cancer, gastric or stomach cancer (including gastrointestinal cancer), pancreatic cancer (such as advanced pancreatic cancer), glioblastoma, cervical cancer, ovarian cancer, liver cancer (such as hepatocellular carcinoma), bladder cancer, hepatoma, breast cancer, colon cancer, melanoma, endometrial or uterine carcinoma, salivary gland carcinoma, kidney or renal cancer, prostate cancer (such as advanced prostate cancer), vulval cancer, thyroid cancer, hepatic carcinoma, head and neck cancer, colorectal cancer, rectal cancer, soft-tissue sarcoma, Kaposi's sarcoma, B-cell lymphoma (including low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's macroglobulinemia), chronic lymphocytic leukemia (CLL), acute lymphoblastic leukemia (ALL), myeloma, Hairy cell leukemia, chronic myeloblastic leukemia, and post-transplant lymphoproliferative disorder (PTLD), as well as abnormal vascular proliferation associated with phakomatoses, edema (such as that associated with brain tumors), and Meigs' syndrome. In some embodiments, there is provided a method of treating metastatic cancer (that is, cancer that has metastasized from the primary tumor). In some embodiments, there is provided a method of reducing cell proliferation and/or cell migration. In some embodiments, there is provided a method of treating hyperplasia, for example hyperplasia in the vascular system that can result in restenosis or hyperplasia that can result in arterial or venous hypertension.

In some embodiments, there are provided methods of treating cancer at advanced stage(s). In some embodiments, there are provided methods of treating breast cancer (which may be HER2 positive or HER2 negative), including, for example, advanced breast cancer, stage IV breast cancer, locally advanced breast cancer, and metastatic breast cancer. In some embodiments, the cancer is lung cancer, including, for example, non-small cell lung cancer (NSCLC, such as advanced NSCLC), small cell lung cancer (SCLC, such as advanced SCLC), and advanced solid tumor malignancy in the lung. In some embodiments, the cancer is ovarian cancer, head and neck cancer, gastric malignancies, melanoma (including metastatic melanoma), colorectal cancer, pancreatic cancer, and solid tumors (such as advanced solid tumors). In some embodiments, the cancer is any of (and in some embodiments selected from the group consisting of) breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, gliomas, glioblastomas, neuroblastomas, and multiple myeloma. In some embodiments, the cancer is a solid tumor.

In some embodiments, the cancer to be treated is breast cancer, such as metastatic breast cancer. In some embodiments, the cancer to be treated is lung cancer, such as non-small cell lung cancer, including advanced stage non-small cell lung cancer. In some embodiments, the cancer to be treated is pancreatic cancer, such as early stage pancreatic cancer or advanced or metastatic pancreatic cancer. In some embodiments, the cancer to be treated is melanoma, such as stage III or IV melanoma.

In some embodiments, the individual being treated for a proliferative disease has been identified as having one or more of the conditions described herein. Identification of the conditions as described herein by a skilled physician is routine in the art (e.g., via blood tests, X-rays, CT scans, endoscopy, biopsy, angiography, CT-angiography, etc.) and may also be suspected by the individual or others, for example, due to tumor growth, hemorrhage, ulceration, pain, enlarged lymph nodes, cough, jaundice, swelling, weight loss, cachexia, sweating, anemia, paraneoplastic phenomena, thrombosis, etc. In some embodiments, the individual has been identified as susceptible to one or more of the conditions as described herein. The susceptibility of an individual may be based on any one or more of a number of risk factors and/or diagnostic approaches appreciated by the skilled artisan, including, but not limited to, genetic profiling, family history, medical history (e.g., appearance of related conditions), lifestyle or habits.

In some embodiments, the cancer is breast cancer (such as metastatic breast cancer). In some embodiments, the cancer is lung cancer (such as non-small cell lung cancer ("NSCLC"), for example locally advanced or metastatic NSCLC). In some embodiments, the cancer is pancreatic cancer (such as metastatic adenocarcinoma of the pancreas).

In some embodiments, the methods and/or compositions (such as pharmaceutical compositions) used herein reduce the severity of one or more symptoms associated with proliferative disease (e.g., cancer) by at least about any one of 10%, 20%, 30%, 40%, 50%, 60%, 70%, 80%, 90%, 95%, or 100% compared to the corresponding symptom in the same individual prior to treatment or compared to the corresponding symptom in other individuals not receiving the methods and/or compositions (such as pharmaceutical compositions).

In some embodiments, the composition (such as a pharmaceutical composition) described herein is used in combination with another administration modality or treatment. For example, in some embodiments, the composition (such as a pharmaceutical composition) is used in combination with gemcitabine (for example for treating pancreatic cancer). In some embodiments, the composition (such as a pharmaceutical composition) is used in combination with carboplatin (for example for treating lung cancer).

Dosing and Method of Administration

The amount of the pharmaceutical composition administered to an individual (such as a human) may vary with the particular composition, the method of administration, and the particular type of recurrent cancer being treated. The amount should be sufficient to produce a desirable beneficial effect. For example, in some embodiments, the amount of the composition (such as a pharmaceutical composition) is effective to result in an objective response (such as a partial response or a complete response). In some embodiments, the amount of pharmaceutical composition is sufficient to result in a complete response in the individual. In some embodiments, the amount of the composition (such as a pharmaceutical composition) is sufficient to result in a partial response in the individual. In some embodiments, the amount of the composition (such as a pharmaceutical composition) administered alone is sufficient to produce an overall response rate of more than about any one of 40%, 50%, 60%, or 64% among a population of individuals treated with the composition. Responses of an individual to the treatment of the methods described herein can be determined, for example, based on RECIST or CA-125 level. For example, when CA-125 is used, a complete response can be defined as a return to a normal range value of at least 28 days from the pretreatment value. A partial response can be defined as a sustained over 50% reduction from the pretreatment value.

In some embodiments, the amount of pharmaceutical composition is sufficient to prolong progress-free survival of the individual (for example as measured by RECIST or CA-125 changes). In some embodiments, the amount of the pharmaceutical composition is sufficient to prolong overall survival of the individual. In some embodiments, the amount of the composition (such as a pharmaceutical composition) is sufficient to produce clinical benefit of more than about any one of 50%, 60%, 70%, or 77% among a population of individuals treated with the composition.

In some embodiments, the amount of rapamycin in the pharmaceutical composition is below the level that induces a toxicological effect (i.e., an effect above a clinically acceptable level of toxicity) or is at a level where a potential side effect can be controlled or tolerated when the composition (such as a pharmaceutical composition) is administered to the individual. In some embodiments, the amount of the composition (such as a pharmaceutical composition) is close to a maximum tolerated dose (MTD) of the composition (such as a pharmaceutical composition) following the same dosing regimen. In some embodiments, the amount of the composition (such as a pharmaceutical composition) is more than about any one of 80%, 90%, 95%, or 98% of the MTD.

In some embodiments, the amount of rapamycin and/or composition is an amount sufficient to decrease the size of a tumor, decrease the number of cancer cells, or decrease the growth rate of a tumor by at least about any one of 10%, 20%, 30%, 40%, 50%, 60%, 70%, 80%, 90%, 95% or 100% compared to the corresponding tumor size, number of cancer cells, or tumor growth rate in the same subject prior to treatment or compared to the corresponding activity in other subjects not receiving the treatment. Standard methods can be used to measure the magnitude of this effect, such as in vitro assays with purified enzyme, cell-based assays, animal models, or human testing.

In some embodiments, the amount of rapamycin in the pharmaceutical composition is included in any one of the following ranges: about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of rapamycin in the pharmaceutical composition (e.g., a unit dosage form) is in the range of about 5 mg to about 500 mg, such as about 30 mg to about 300 mg or about 50 mg to about 200 mg. In some embodiments, the concentration of the rapamycin in the pharmaceutical composition is dilute (about 0.1 mg/ml) or concentrated (about 100 mg/ml), including for example any one of about 0.1 to about 50 mg/ml, about 0.1 to about 20 mg/ml, about 1 to about 10 mg/ml, about 2 mg/ml to about 8 mg/ml, about 4 to about 6 mg/ml, or about 5 mg/ml. In some embodiments, the concentration of the rapamycin is at least about any one of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml.

Exemplary doses of rapamycin in the pharmaceutical composition include, but are not limited to, about any one of 25 mg/m$^2$, 30 mg/m$^2$, 50 mg/m$^2$, 60 mg/m$^2$, 75 mg/m$^2$, 80 mg/m$^2$, 90 mg/m$^2$, 100 mg/m$^2$, 120 mg/m$^2$, 160 mg/m$^2$, 175 mg/m$^2$, 180 mg/m$^2$, 200 mg/m$^2$, 210 mg/m$^2$, 220 mg/m$^2$, 250 mg/m$^2$, 260 mg/m$^2$, 300 mg/m$^2$, 350 mg/m$^2$, 400 mg/m$^2$, 500 mg/m$^2$, 540 mg/m$^2$, 750 mg/m$^2$, 1000 mg/m$^2$, or 1080 mg/m$^2$ of rapamycin. In various embodiments, the composition (such as a pharmaceutical composition) includes less than about any one of 350 mg/m$^2$, 300 mg/m$^2$, 250 mg/m$^2$, 200 mg/m$^2$, 150 mg/m$^2$, 120 mg/m$^2$, 100 mg/m$^2$, 90 mg/m$^2$, 50 mg/m$^2$, or 30 mg/m$^2$ of rapamycin. In some embodiments, the amount of rapamycin per administration is less than about any one of 25 mg/m$^2$, 22 mg/m$^2$, 20 mg/m$^2$, 18 mg/m$^2$, 15 mg/m$^2$, 14 mg/m$^2$, 13 mg/m$^2$, 12 mg/m$^2$, 11 mg/m$^2$, 10 mg/m$^2$, 9 mg/m$^2$, 8 mg/m$^2$, 7 mg/m$^2$, 6 mg/m$^2$, 5 mg/m$^2$, 4 mg/m$^2$, 3 mg/m$^2$, 2 mg/m$^2$, or 1 mg/m$^2$. In some embodiments, the dose of rapamycin in the pharmaceutical composition is included in any one of the following ranges: about 1 to about 5 mg/m$^2$, about 5 to about 10 mg/m$^2$, about 10 to about 25 mg/m$^2$, about 25 to about 50 mg/m$^2$, about 50 to about 75 mg/m$^2$, about 75 to about 100 mg/m$^2$, about 100 to about 125 mg/m$^2$, about 125 to about 150 mg/m$^2$, about 150 to about 175 mg/m$^2$, about 175 to about 200 mg/m$^2$, about 200 to about 225 mg/m$^2$, about 225 to about 250 mg/m$^2$, about 250 to about 300 mg/m$^2$, about 300 to about 350 mg/m$^2$, or about 350 to about 400 mg/m$^2$. Preferably, the dose of rapamycin in the pharmaceutical composition is about 5 to about 300 mg/m$^2$, such as about 100 to about 150 mg/m$^2$, about 120 mg/m$^2$, about 130 mg/m$^2$, or about 140 mg/m$^2$.

In some embodiments of any of the above aspects, the dose of rapamycin in the pharmaceutical composition includes at least about any one of 1 mg/kg, 2.5 mg/kg, 3.5 mg/kg, 5 mg/kg, 6.5 mg/kg, 7.5 mg/kg, 10 mg/kg, 15 mg/kg, or 20 mg/kg. In various variations, the dose of rapamycin in the pharmaceutical composition includes less than about any one of 350 mg/kg, 300 mg/kg, 250 mg/kg, 200 mg/kg, 150 mg/kg, 100 mg/kg, 50 mg/kg, 25 mg/kg, 20 mg/kg, 10 mg/kg, 7.5 mg/kg, 6.5 mg/kg, 5 mg/kg, 3.5 mg/kg, 2.5 mg/kg, 2 mg/kg, 1.5 mg/kg, or 1 mg/kg of rapamycin. In some embodiments, the dose of rapamycin in the pharmaceutical composition includes less than about any one of 500 µg/kg, 350 µg/kg, 300 µg/kg, 250 µg/kg, 200 µg/kg, 150 µg/kg, 100 µg/kg, 50 µg/kg, 25 µg/kg, 20 µg/kg, 10 µg/kg, 7.5 µg/kg, 6.5 µg/kg, 5 µg/kg, 3.5 µg/kg, 2.5 µg/kg, 2 µg/kg, 1.5 µg/kg, 1 µg/kg, or 0.5 µg/kg of rapamycin.

Exemplary dosing frequencies include, but are not limited to, any one of weekly without break; weekly, three out of four weeks; once every three weeks; once every two weeks; weekly, two out of three weeks. In some embodiments, the composition (such as a pharmaceutical composition) is administered about once every 2 weeks, once every 3 weeks, once every 4 weeks, once every 6 weeks, or once every 8 weeks. In some embodiments, the composition (such as a pharmaceutical composition) is administered at least about any one of 1×, 2×, 3×, 4×, 5×, 6×, or 7× (i.e., daily) a week. In some embodiments, the intervals between each administration are less than about any one of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any one of 1 month, 2 months, 3 months, 4 months, 5 months, 6 months, 8 months, or 12 months. In some embodiments, there is no break in the dosing schedule. In some embodiments, the interval between each administration is no more than about a week.

The administration of the composition (such as a pharmaceutical composition) can be over an extended period of time, such as from about a month up to about seven years. In some embodiments, the composition (such as a pharmaceutical composition) is administered over a period of at least about any one of 2, 3, 4, 5, 6, 7, 8, 9, 10, 11, 12, 18, 24, 30, 36, 48, 60, 72, or 84 months. In some embodiments, the composition (such as a pharmaceutical composition) is administered over a period of at least one month, wherein the interval between each administration is no more than about a week, and wherein the dose of rapamycin at each administration is about 0.25 mg/m$^2$ to about 75 mg/m$^2$, such as about 0.25 mg/m$^2$ to about 25 mg/m$^2$ or about 25 mg/m$^2$ to about 50 mg/m$^2$.

In some embodiments, the dosage of rapamycin in a pharmaceutical composition can be in the range of 5-400 mg/m$^2$ when given on a 3 week schedule, or 5-250 mg/m$^2$ when given on a weekly schedule. For example, the amount of a rapamycin is about 60 to about 300 mg/m$^2$ (e.g., about 260 mg/m$^2$).

Other exemplary dosing schedules for the administration of the pharmaceutical composition include, but are not limited to, any one of 100 mg/m$^2$, weekly, without break; 75 mg/m² weekly, 3 out of four weeks; 100 mg/m², weekly, 3 out of 4 weeks; 125 mg/m², weekly, 3 out of 4 weeks; 125 mg/m², weekly, 2 out of 3 weeks; 130 mg/m², weekly, without break; 175 mg/m², once every 2 weeks; 260 mg/m², once every 2 weeks; 260 mg/m², once every 3 weeks; 180-300 mg/m², every three weeks; 60-175 mg/m², weekly, without break; 20-150 mg/m² twice a week; and 150-250 mg/m² twice a week. The dosing frequency of the composition (such as a pharmaceutical composition) may be adjusted over the course of the treatment based on the judgment of the administering physician.

In some embodiments, the composition (such as a pharmaceutical composition) is administered (e.g., intravenously) at 260 mg/m2 every three weeks. In some embodiments, the composition (such as a pharmaceutical composition) is administered (e.g., intravenously) at 220 mg/m², every three weeks. In some embodiments, the composition (such as a pharmaceutical composition) is administered (e.g., intravenously) at 180 mg/m², every three weeks. In some embodiments, the composition (such as a pharmaceutical composition) is administered (e.g., intravenously) at 200 mg/m², every three weeks. In some embodiments, the composition (such as a pharmaceutical composition) is administered (e.g., intravenously) at 130 mg/m², every three weeks.

In some embodiments, the composition (such as a pharmaceutical composition) is administered (e.g., intravenously) at 150 mg/m² on days 1, 8, and 15 every 4 weeks. In some embodiments, the composition (such as a pharmaceutical composition) is administered (e.g., intravenously) at 125 mg/m2 on days 1, 8, and 15 every 4 weeks. In some embodiments, the composition (such as a pharmaceutical composition) is administered (e.g., intravenously) at 100 mg/m² on days 1, 8, and 15 every 4 weeks. In some embodiments, the composition (such as a pharmaceutical composition) is administered (e.g., intravenously) at 75 mg/m2 on days 1, 8, and 15 every 4 weeks. In some embodiments, the composition (such as a pharmaceutical composition) is administered (e.g., intravenously) at 50 mg/m² on days 1, 8, and 15 every 4 weeks.

The compositions (such as pharmaceutical compositions) described herein allow infusion of the composition (such as a pharmaceutical composition) to an individual over an infusion time that is shorter than about 24 hours. For example, in some embodiments, the composition (such as a pharmaceutical composition) is administered over an infusion period of less than about any one of 24 hours, 12 hours, 8 hours, 5 hours, 3 hours, 2 hours, 1 hour, 30 minutes, 20 minutes, or 10 minutes. In some embodiments, the composition (such as a pharmaceutical composition) is administered over an infusion period of about 30 minutes. In some embodiments, the composition (such as a pharmaceutical composition) is administered over an infusion period between about 30 minutes to about 40 minutes.

In some embodiments, the present application provides a method of treating cancer in an individual by parenterally administering to the individual (e.g., a human) an effective amount of a composition (such as a pharmaceutical composition) described herein. The present application also provides a method of treating cancer in an individual by intravenous, intra-arterial, intramuscular, subcutaneous, inhalation, oral, intraperitoneal, nasally, or intra-tracheal administering to the individual (e.g., a human) an effective amount of a rapamycin pharmaceutical composition. In some embodiments, the route of administration is intraperitoneal. In some embodiments, the route of administration is intravenous, intra-arterial, intramuscular, or subcutaneous.

In various variations, about 5 mg to about 500 mg, such as about 30 mg to about 300 mg or about 50 to about 500 mg, of the rapamycin is administered per dose. In some embodiments, the rapamycin is the only pharmaceutically active agent for the treatment of cancer that is contained in the composition.

Any of the compositions (such as pharmaceutical compositions) described herein can be administered to an individual (such as human) via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, transdermal, intratumoral, direct injection into the blood vessel wall, intracranial, or intra-cavity. In some embodiments, sustained continuous release formulation of the composition (such as a pharmaceutical composition) may be used. In one variation described herein, nanoparticles (such as albumin nanoparticles) of the inventive compositions (such as pharmaceutical compositions) can be administered by any acceptable route including, but not limited to, orally, intramuscularly, transdermally, intravenously, through an inhaler or other air borne delivery systems and the like.

In some embodiments, the albumin-based rapamycin pharmaceutical compositions may be administered with a second therapeutic compound and/or a second therapy. The dosing frequency of the composition (such as a pharmaceutical composition) and the second compound may be adjusted over the course of the treatment based on the judgment of the administering physician. In some embodiments, the first and second therapies are administered simultaneously, sequentially, or concurrently. When administered separately, the pharmaceutical composition and the second compound can be administered at different dosing frequency or intervals. For example, the composition (such as a pharmaceutical composition) can be administered weekly, while a second compound can be administered more or less frequently. In some embodiments, sustained continuous release formulation of rapamycin-containing nanoparticle and/or second compound may be used. Various formulations and devices for achieving sustained release are known in the art. A combination of the administration configurations described herein can be used.

In some embodiments, the cancer is breast cancer (for example metastatic breast cancer), and the composition (such as a pharmaceutical composition) is administered at 260 mg/m² once every three weeks.

In some embodiments, the cancer is pancreatic cancer (for example advanced pancreatic cancer, or adenocarcinoma of the pancreas), and the composition (such as a pharmaceutical composition) is administered at 125 mg/m² weekly, three out of four weeks. In some embodiments, the cancer is pancreatic cancer (for example advanced pancreatic cancer), and the composition (such as a pharmaceutical composition) is administered at 125 mg/m² weekly, three out of four weeks in combination with gemcitabine at 1000 mg/m².

In some embodiments, the cancer is lung cancer (for example non-small cell lung cancer), and the composition (such as a pharmaceutical composition) is administered at 100 mg/m² weekly. In some embodiments, the cancer is lung cancer (for example non-small cell lung cancer), and the composition (such as a pharmaceutical composition) is administered at 100 mg/m² weekly, such as on Days 1, 8, 15 of each three weeks cycle, in combination with carboplatin at AUC=6 mg·min/mL once every three weeks, such as on Day 1 of each three weeks cycle.

Metronomic Therapy Regimens

The present invention also provides metronomic therapy regimens for any of the methods of treatment and methods of administration described herein. Exemplary metronomic therapy regimens and variations for the use of metronomic therapy regimens are discussed below and disclosed in US 2006/0263434 A1 (such as those described in paragraphs [0138] to [0157] therein), which is hereby incorporated by reference in its entirety. In some embodiments, the pharmaceutical composition is administered over a period of at least one month, wherein the interval between each administration is no more than about a week, and wherein the dose of the rapamycin at each administration is about 0.25% to about 25% of its maximum tolerated dose following a traditional dosing regimen. In some embodiments, the pharmaceutical composition is administered over a period of at least two months, wherein the interval between each administration is no more than about a week, and wherein the dose of the rapamycin at each administration is about 1% to about 20% of its maximum tolerated dose following a traditional dosing regimen. In some embodiments, the dose of rapamycin per administration is less than about any one of 25%, 24%, 23%, 22%, 20%, 18%, 15%, 14%, 13%, 12%, 11%, 10%, 9%, 8%, 7%, 6%, 5%, 4%, 3%, 2%, or 1% of the maximum tolerated dose. In some embodiments, any pharmaceutical composition is administered at least about any one of 1×, 2×, 3×, 4×, 5×, 6×, or 7× (i.e., daily) a week. In some embodiments, the intervals between each administration are less than about any one of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any one of 1 month, 2 months, 3 months, 4 months, 5 months, 6 months, 8 months, or 12 months. In some embodiments, the composition (such as a pharmaceutical composition) is administered over a period of at least about any one of 2, 3, 4, 5, 6, 7, 8, 9, 10, 11, 12, 18, 24, 30, 36, 48, 60, 72, or 84 months.

EXEMPLARY EMBODIMENTS

Embodiment 1. A nanoparticle composition comprising: (a) nanoparticles comprising rapamycin and albumin, and (b) a non-nanoparticle portion comprising albumin and rapamycin.

Embodiment 2. The nanoparticle composition of embodiment 1, wherein the nanoparticles comprise a core comprising rapamycin and a coating comprising albumin.

Embodiment 3. The nanoparticle composition of embodiment 1 or 2, wherein about 70% to about 85% of the albumin in the nanoparticles is in the form of monomeric albumin.

Embodiment 4. The nanoparticle composition of any one of embodiments 1-3, wherein about 5% to about 15% of the albumin in the nanoparticles is in the form of polymeric albumin.

Embodiment 5. The nanoparticle composition of embodiment 4, wherein about 5% to about 15% of the albumin in the nanoparticles is in the form of trimeric albumin.

Embodiment 6. The nanoparticle composition of any one of embodiments 1-5, wherein about 9% to about 20% of the albumin in the nanoparticles is in the form of dimeric albumin.

Embodiment 7. The nanoparticle composition of any one of embodiments 1-6, wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of trimeric albumin; the percentage of each of the monomeric albumin, the dimeric albumin, and the trimeric albumin in the nanoparticles is determined as a percentage of the sum of monomeric albumin, dimeric albumin, and trimeric albumin in the nanoparticles; and the percentage of monomeric albumin, dimeric albumin, and trimeric albumin in the nanoparticles is determined by separating the nanoparticles from the non-nanoparticle portion, re-suspending the nanoparticles in saline, and subjecting the re-suspended nanoparticles to size-exclusion chromatography (SEC) using a saline mobile phase coupled with a multiple angle light scattering (MALS) detector.

Embodiment 8. The nanoparticle composition of any one of embodiments 1-7, wherein about 0.5% to about 5% of the albumin in the non-nanoparticle portion is in the form of polymeric albumin.

Embodiment 9. The nanoparticle composition of embodiment 8, wherein about 0.5% to about 5% of the albumin in the non-nanoparticle portion is in the form of trimeric albumin.

Embodiment 10. The nanoparticle composition of any one of embodiments 1-9, wherein about 80% to about 95% of the albumin in the non-nanoparticle portion is in the form of monomeric albumin.

Embodiment 11. The nanoparticle composition of any one of embodiments 1-10, wherein about 4% to about 14% of the albumin in the non-nanoparticle portion is in the form of dimeric albumin.

Embodiment 12. The nanoparticle composition of any one of embodiments 8-11, wherein about 80% to about 95% of the albumin in the non-nanoparticle portion is in the form of monomeric albumin, about 4% to about 14% of the albumin in the non-nanoparticle portion is in the form of dimeric albumin, and about 0.5% to about 5% of the albumin in the non-nanoparticle portion is in the form of trimeric albumin; the percentage of each of the monomeric albumin, the dimeric albumin, and the trimeric albumin in the non-nanoparticle portion is determined as a percentage of the sum of monomeric albumin, dimeric albumin, and trimeric albumin in the non-nanoparticle portion; and the percentage of monomeric albumin, dimeric albumin, and trimeric albumin in the non-nanoparticle portion is determined by separating the nanoparticles from the non-nanoparticle portion, and subjecting the non-nanoparticle portion to size-exclusion chromatography (SEC) using a saline mobile phase coupled with a multiple angle light scattering (MALS) detector.

Embodiment 13. The nanoparticle composition of any one of embodiments 1-12, wherein about 0.5% to about 5% of total albumin in the composition is in the form of polymeric albumin.

Embodiment 14. The nanoparticle composition of any one of embodiments 1-13, wherein about 0.5% to about 5% of total albumin in the composition is in the form of trimeric albumin.

Embodiment 15. The nanoparticle composition of any one of embodiments 1-14, wherein about 80% to about 95% of total albumin in the composition is in the form of monomeric albumin.

Embodiment 16. The nanoparticle composition of any one of embodiments 1-15, wherein about 4% to about 15% of total albumin in the composition is in the form of dimeric albumin.

Embodiment 17. The nanoparticle composition of any one of embodiments 13-16, wherein about 80% to about 95% of the albumin in the composition is in the form of monomeric albumin, about 4% to about 15% of the albumin in the composition is in the form of dimeric albumin, and about 0.5% to about 5% of the albumin in the composition is in the form of trimeric albumin; the percentage of each of the monomeric albumin, the dimeric albumin, and the trimeric albumin in the composition is determined as a percentage of the sum of monomeric albumin, dimeric albumin, and trimeric albumin in the composition; and the percentage of monomeric albumin, dimeric albumin, and trimeric albumin in the composition is determined by subjecting the composition to size-exclusion chromatography (SEC) using a saline mobile phase coupled with a multiple angle light scattering (MALS) detector.

Embodiment 18. The nanoparticle composition of embodiment 1 or 2, wherein about 25% to about 50% of the albumin in the nanoparticles is in the form of monomeric albumin.

Embodiment 19. The nanoparticle composition of any one of embodiments 1, 2, and 18, wherein about 5% to about 16% of the albumin in the nanoparticles is in the form of dimeric albumin.

Embodiment 20. The nanoparticle composition of any one of embodiments 1, 2, 18, and 19, wherein about 1% to about 4.5% of the albumin in the nanoparticles is in the form of oligomeric albumin.

Embodiment 21. The nanoparticle composition of any one of embodiments 1, 2, and 18-20, wherein about 42% to about 60% of the albumin in the nanoparticles is in the form of polymeric albumin other than oligomeric albumin.

Embodiment 22. The nanoparticle composition of any one of embodiments 18-21, wherein the percentage of monomeric albumin, dimeric albumin, oligomeric albumin, or polymeric albumin other than oligomeric albumin is determined by separating the nanoparticles from the non-nanoparticle portion, dissolving the nanoparticles, and subjecting the dissolved nanoparticles to size-exclusion chromatography.

Embodiment 23. A nanoparticle composition comprising: (a) nanoparticles comprising rapamycin and albumin, and (b) a non-nanoparticle portion comprising albumin and rapamycin, about 42% to about 60% of the albumin in the nanoparticles is in the form of polymeric albumin other than oligomeric albumin as determined by separating the nanoparticles from the non-nanoparticle portion, dissolving the nanoparticles, and subjecting the dissolved nanoparticles to size-exclusion chromatography.

Embodiment 24. The nanoparticle composition of embodiment 23, wherein about 1% to about 4.5% of the albumin in the nanoparticles is in the form of oligomeric albumin as determined by separating the nanoparticles from the non-nanoparticle portion, dissolving the nanoparticles, and subjecting the dissolved nanoparticles to size-exclusion chromatography.

Embodiment 25. The nanoparticle composition of embodiment 23 or 24, wherein about 25% to about 50% of the albumin in the nanoparticles is in the form of monomeric albumin and about 5% to about 16% of the albumin in the nanoparticles is in the form of dimeric albumin as determined by separating the nanoparticles from the non-nanoparticle portion, dissolving the nanoparticles, and subjecting the dissolved nanoparticles to size-exclusion chromatography.

Embodiment 26. The nanoparticle composition of any one of embodiments 1, 2, and 18-25, wherein about 80% to about 95% of the albumin in the non-nanoparticle portion is in the form of monomeric albumin.

Embodiment 27. The nanoparticle composition of any one of embodiments 1, 2, and 18-26, wherein about 4% to about 14% of the albumin in the non-nanoparticle portion is in the form of dimeric albumin.

Embodiment 28. The nanoparticle composition of any one of embodiments 1, 2, and 18-27, wherein about 0.5% to about 4% of the albumin in the non-nanoparticle portion is in the form of oligomeric albumin.

Embodiment 29. The nanoparticle composition of any one of embodiments 1, 2, and 18-28, wherein about 0.5% to about 3% of the albumin in the non-nanoparticle portion is in the form of polymeric albumin other than oligomeric albumin.

Embodiment 30. The nanoparticle composition of any one of embodiments 26-29, wherein the percentage of monomeric albumin, dimeric albumin, oligomeric albumin, or polymeric albumin other than oligomeric albumin is determined by separating the nanoparticles from the non-nanoparticle portion, and subjecting the non-nanoparticle portion to size-exclusion chromatography.

Embodiment 31. The nanoparticle composition of any one of embodiments 1, 2, and 18-30, wherein about 80% to about 95% of the total albumin composition is in the form of monomeric albumin.

Embodiment 32. The nanoparticle composition of any one of embodiments 1, 2, and 18-31, wherein about 4% to about 15% of the total albumin in the composition is in the form of dimeric albumin.

Embodiment 33. The nanoparticle composition of any one of embodiments 1, 2, and 18-32, wherein about 0.3% to about 3% of the total albumin in the composition is in the form of oligomeric albumin.

Embodiment 34. The nanoparticle composition of any one of embodiments 1, 2, and 18-33, wherein about 2% to about 7% of the total albumin in the composition is in the form of polymeric albumin other than oligomeric albumin.

Embodiment 35. The nanoparticle composition of any one of embodiments 31-34, wherein the percentage of monomeric albumin, dimeric albumin, oligomeric albumin, or polymeric albumin other than oligomeric albumin in the composition is determined by subjecting the composition to size-exclusion chromatography.

Embodiment 36. A nanoparticle composition comprising: (a) nanoparticles comprising rapamycin and albumin, and (b) a non-nanoparticle portion comprising albumin and rapamycin, wherein: about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin; wherein the percentage of each of the monomeric albumin, the dimeric albumin, and the trimeric albumin in the nanoparticles is determined as a percentage of the sum of monomeric albumin, dimeric albumin, and trimeric albumin in the nanoparticles; and the percentage of monomeric albumin, dimeric albumin, and trimeric albumin in the nanoparticles is determined by separating the nanoparticles from the non-nanoparticle portion, re-suspending the nanoparticles in saline, and subjecting the re-suspended nanoparticles to size-exclusion chromatography (SEC) using a saline mobile phase coupled with a multiple angle light scattering (MALS) detector; and about 80% to about 95% of the albumin in the non-nanoparticle portion is in the form of monomeric albumin, about 4% to about 14% of the albumin in the non-nanoparticle portion is in the form of dimeric albumin, and about 0.5% to about 5% of the albumin in the non-nanoparticle portion is in the form of polymeric albumin; the percentage of each of the monomeric albumin, the dimeric albumin, and the trimeric albumin in the non-nanoparticle portion is determined as a percentage of the sum of monomeric albumin, dimeric albumin, and trimeric albumin in the non-nanoparticle portion; and the percentage of monomeric albumin, dimeric albumin, and trimeric albumin in the non-nanoparticle portion is determined by separating the nanoparticles from the non-nanoparticle portion, and subjecting the non-nanoparticle portion to size-exclusion chromatography (SEC) using a saline mobile phase coupled with a multiple angle light scattering (MALS) detector.

Embodiment 37. The nanoparticle composition of embodiment 36, wherein about 80% to about 95% of total albumin in the composition is in the form of monomeric albumin, about 4% to about 15% of total albumin in the composition is in the form of dimeric albumin, and about 0.5% to about 5% of total albumin in the composition is in the form of polymeric albumin; the percentage of each of the monomeric albumin, the dimeric albumin, and the trimeric albumin in the composition is determined as a percentage of the sum of monomeric albumin, dimeric albumin, and trimeric albumin in the composition; and the percentage of monomeric albumin, dimeric albumin, and trimeric albumin in the composition is determined by subjecting the composition to size-exclusion chromatography (SEC) using a saline mobile phase coupled with a multiple angle light scattering (MALS) detector.

Embodiment 38. The nanoparticle composition of any one of embodiments 1-37, wherein the volume weighted mean particle size of the nanoparticles is about 200 nm or less.

Embodiment 39. The nanoparticle composition of any one of embodiments 1-38, wherein the volume weighted mean particle size of the nanoparticles is about 50 nm to about 200 nm.

Embodiment 40. The nanoparticle composition of any one of embodiments 1-39, wherein the Z-average particle size of the nanoparticles is about 200 nm or less.

Embodiment 41. The nanoparticle composition of any one of embodiments 1-40, wherein the Z-average particle size of the nanoparticles is about 50 nm to about 200 nm.

Embodiment 42. The nanoparticle composition of any one of embodiments 1-41, wherein the polydispersity index of the nanoparticles is less than 0.2.

Embodiment 43. The nanoparticle composition of any one of embodiments 1-42, wherein the polydispersity index of the nanoparticles is about 0.03 to about 0.2.

Embodiment 44. The nanoparticle composition of any one of embodiments 1-43, wherein the span of particle size distribution $((D_v95-D_v5)/D_v50)$ of the nanoparticles is about 0.8 to about 1.2.

Embodiment 45. The nanoparticle composition of any one of embodiments 1-44, wherein the weight percentage of the albumin in the nanoparticles is about 25% to about 45%.

Embodiment 46. The nanoparticle composition of any one of embodiments 1-44, wherein the weight percentage of rapamycin in the nanoparticles is about 55% to about 75%.

Embodiment 47. The nanoparticle composition of any one of embodiments 1-46, wherein the weight ratio of the albumin to the rapamycin in the nanoparticles is about 1:1 to about 1:4.

Embodiment 48. The nanoparticle composition of any one of embodiments 1-47, wherein the weight ratio of the albumin to the rapamycin in the composition is about 1:1 to about 10:1.

Embodiment 49. The nanoparticle composition of any one of embodiments 1-48, wherein about 90% or more of the albumin in the composition is in the non-nanoparticle portion.

Embodiment 50. The nanoparticle composition of any one of embodiments 1-49, wherein about 90% or more of the rapamycin in the composition is in the nanoparticles.

Embodiment 51. The nanoparticle composition of any one of embodiments 1-50, wherein about 99% or more of the rapamycin in the composition is in the nanoparticles.

Embodiment 52. The nanoparticle composition of any one of embodiments 1-51, wherein about 99.9% or more of the rapamycin in the composition is in the nanoparticles.

Embodiment 53. The nanoparticle composition of any one of embodiments 1-52, wherein about 99.95% or more of the rapamycin in the composition is in the nanoparticles.

Embodiment 54. The nanoparticle composition of any one of embodiments 1-53, wherein about 3% or less of the rapamycin in the nanoparticle composition is free rapamycin.

Embodiment 55. The nanoparticle composition of any one of embodiments 1-54, wherein about 1% or less of the rapamycin in the nanoparticle composition is free rapamycin.

Embodiment 56. The nanoparticle composition of any one of embodiments 1-55, wherein about 0.1% or less of the rapamycin in the nanoparticle composition is free rapamycin.

Embodiment 57. The nanoparticle composition of any one of embodiments 1-56, wherein about 0.05% or less of the rapamycin in the nanoparticle composition is free rapamycin.

Embodiment 58. The nanoparticle composition of any one of embodiments 1-57, wherein the nanoparticle composition is a nanoparticle suspension.

Embodiment 59. The nanoparticle composition of embodiment 58, wherein the concentration of albumin in the composition is about 30 mg/mL to about 100 mg/mL.

Embodiment 60. The nanoparticle composition of embodiment 58 or 59, wherein the concentration of albumin in the composition that is in the non-nanoparticle portion is about 30 mg/mL to about 100 mg/mL.

Embodiment 61. The nanoparticle composition of any one of embodiments 58-60, wherein the concentration of albumin in the nanoparticle composition that is in the nanoparticles is about 1 mg/mL to about 5 mg/mL.

Embodiment 62. The nanoparticle composition of any one of embodiments 58-61, wherein the concentration of rapamycin in the nanoparticle composition is about 1 mg/mL to about 100 mg/mL.

Embodiment 63. The nanoparticle composition of any one of embodiments 58-62, wherein the concentration of rapamycin in the composition that is in the non-nanoparticle portion is about 20 µg/mL to about 55 µg/mL.

Embodiment 64. The nanoparticle composition of any one of embodiments 58-63, wherein the concentration of rapamycin in the composition that is in the nanoparticles is about 1 mg/mL to about 15 mg/mL.

Embodiment 65. The nanoparticle composition of any one of embodiments 58-64, wherein the osmolality of the composition is about 300 mOsm/kg to about 350 mOsm/kg.

Embodiment 66. The nanoparticle composition of any one of embodiments 58-65, wherein the viscosity of the composition is about 1.2 cP to about 1.5 cP.

Embodiment 67. The nanoparticle composition of any one of embodiments 58-66, wherein the composition is stable at 25° C. for at least 24 hours.

Embodiment 68. The nanoparticle composition of any one of embodiments 58-67, wherein the composition is stable at 4° C. for at least 24 hours.

Embodiment 69. The nanoparticle composition of any one of embodiments 58-68, wherein the nanoparticles had been resuspended from a dried composition.

Embodiment 70. The nanoparticle composition of any one of embodiments 58-69, wherein the pH of the composition is about 6.0 to about 7.5.

Embodiment 71. The nanoparticle composition of any one of embodiments 58-70, wherein the composition comprises less than 10 μg/mL tert-butanol.

Embodiment 72. The nanoparticle composition of any one of embodiments 58-71, wherein the composition comprises tert-butanol.

Embodiment 73. The nanoparticle composition of any one of embodiments 58-72, wherein the composition comprises less than 5 μg/mL chloroform.

Embodiment 74. The nanoparticle composition of any one of embodiments 58-73, wherein the composition comprises chloroform.

Embodiment 75. The nanoparticle composition of any one of embodiments 1-57, wherein the composition is a dried composition.

Embodiment 76. The nanoparticle composition of any one of embodiments 1-75, wherein the zeta potential of the nanoparticles is about −25 mV to about −50 mV.

Embodiment 77. The nanoparticle composition of any one of embodiments 1-76, wherein the composition has an amorphous morphology as determined by measuring crystallinity of a lyophilized form of the composition by X-ray diffraction.

Embodiment 78. The nanoparticle composition of any one of embodiments 1-77, wherein the nanoparticles have an amorphous morphology as determined by separating the nanoparticles from the composition, lyophilizing the separated nanoparticles, and measuring crystallinity of the separated and lyophilized nanoparticles by X-ray diffraction.

Embodiment 79. The nanoparticle composition of any one of embodiments 1-77, wherein the rapamycin in nanoparticles has an amorphous morphology as determined by Raman spectroscopy, polarized light microscopy, differential scanning calorimetry (DSC), modulated differential scanning calorimetry (mDSC), Fourier transform infrared (FTIR) spectroscopy, or nuclear magnetic resonance (NMR) spectroscopy.

Embodiment 80. The nanoparticle composition of any one of embodiments 1-79, wherein the vinyl chain of the rapamycin in the nanoparticles interacts with the albumin in the nanoparticles.

Embodiment 81. The nanoparticle composition of any one of embodiments 1-80, wherein at least a portion of the nanoparticles are non-spherical.

Embodiment 82. The nanoparticle composition of any one of embodiments 1-81, wherein at least 20% of the nanoparticles in the composition are non-spherical.

Embodiment 83. The nanoparticle composition of any one of embodiments 1-82, wherein the nanoparticles have a non-smooth surface.

Embodiment 84. The nanoparticle composition of any one of embodiments 1-83, wherein seco-rapamycin is less than 3% by weight of the sum of seco-rapamycin and rapamycin in the nanoparticles.

Embodiment 85. The nanoparticle composition of any one of embodiments 1-84, wherein seco-rapamycin is more than 0.2% by weight of the sum of seco-rapamycin and rapamycin in the nanoparticles.

Embodiment 86. The nanoparticle composition of any one of embodiments 1-85, wherein the albumin is human albumin.

Embodiment 87. The nanoparticle composition of any one of embodiments 1-86, wherein the nanoparticle composition is sterile.

Embodiment 88. The nanoparticle composition of embodiment 87, wherein the nanoparticle composition has been sterilized by filtration.

Embodiment 89. The nanoparticle composition of any one of embodiments 1-88, wherein the nanoparticle composition is contained within a sealed container.

Embodiment 90. The nanoparticle composition of embodiment 89, wherein the sealed container is a sealed vial or a sealed bag.

Embodiment 91. The nanoparticle composition of any one of embodiments 1-90, wherein the nanoparticle composition is a pharmaceutical composition.

Embodiment 92. An emulsion, comprising: a dispersed organic phase comprising nanodroplets comprising rapamycin dissolved in an organic solvent comprising chloroform and tert-butanol, and a continuous aqueous phase comprising albumin.

Embodiment 93. The emulsion of embodiment 92, wherein the organic solvent comprises about 10% to about 50% tert-butanol by volume.

Embodiment 94. The emulsion of embodiment 92 or 93, wherein the organic solvent comprises about 50% to about 90% chloroform by volume.

Embodiment 95. The emulsion of any one of embodiments 92-94, wherein the organic solvent comprises chloroform and tert-butanol at a volumetric ratio of about 1:1 to about 9:1.

Embodiment 96. The emulsion of any one of embodiments 92-95, wherein the concentration of rapamycin in the organic phase is about 20 mg/mL to about 500 mg/mL.

Embodiment 97. The emulsion of any one of embodiments 92-96, wherein the concentration of rapamycin in the emulsion is about 2 mg/mL to about 50 mg/mL.

Embodiment 98. The emulsion of any one of embodiments 92-97, wherein the concentration of albumin in the aqueous phase is about 10 mg/mL to about 200 mg/mL.

Embodiment 99. The emulsion of any one of embodiments 92-98, wherein the concentration of albumin in the emulsion is about 8 mg/mL to about 200 mg/mL.

Embodiment 100. The emulsion of any one of embodiments 92-99, wherein the phase fraction of the organic phase in the emulsion is about 1% to about 20%.

Embodiment 101. The emulsion of any one of embodiments 92-100, wherein the nanodroplets have a Z-average particle size of about 200 nm or less.

Embodiment 102. The emulsion of any one of embodiments 92-101, wherein the nanodroplets have a Z-average particle size of about 50 nm to about 200 nm.

Embodiment 103. The emulsion of any one of embodiments 92-102, wherein the Z-average particle size of the nanodroplets does not increase by more than 30% after storing the emulsion for about 4 hours at 4° C.

Embodiment 103. The emulsion of any one of embodiments 92-102, wherein the Z-average particle size of the nanodroplets does not increase by more than 30% after storing the emulsion for about 4 hours at 4° C.

Embodiment 104. The emulsion of any one of embodiments 92-103, wherein the Z-average particle size of the nanodroplets does not increase by more than 30% after storing the emulsion for about 24 hours at 4° C.

Embodiment 105. The emulsion of any one of embodiments 92-104, wherein the albumin is human albumin.

Embodiment 106. A method of making a nanoparticle suspension, comprising: removing organic solvent from an emulsion to make the nanoparticle suspension, the emulsion comprising: a dispersed organic phase comprising nanodroplets comprising rapamycin dissolved in an organic solvent comprising chloroform and tert-butanol, and a continuous aqueous phase comprising albumin.

Embodiment 107. The method of embodiment 106, wherein the organic solvent is removed using a wiped film evaporator.

Embodiment 108. The method of embodiment 106, wherein the organic solvent is removed using a rotary evaporator.

Embodiment 109. The method of any one of embodiments 106-108, further comprising forming the emulsion by homogenizing the organic phase and the aqueous phase.

Embodiment 110. The method of any one of embodiments 106-109, wherein the emulsion is stored between about 2° C. and about 8° C. before removing the organic solvent.

Embodiment 111. The method of embodiment 110, wherein the emulsion is stored for about 4 hours or for about 24 hours.

Embodiment 112. The method of any one of embodiments 106-111, further comprising filtering the organic phase, the aqueous phase, or both, prior to forming the emulsion.

Embodiment 113. The method of any one of embodiments 106-112, wherein the organic phase and the aqueous phase are homogenized using a high pressure homogenizer.

Embodiment 114. The method of any one of embodiments 106-113, further comprising adding a solution comprising albumin to the nanoparticle suspension.

Embodiment 115. The method of embodiment 114, wherein adding the solution comprising albumin adjusts the weight ratio of albumin to rapamycin in the nanoparticle suspension to between about 1:1 and about 10:1.

Embodiment 116. The method of any one of embodiments 106-115, further comprising filtering the nanoparticle suspension.

Embodiment 117. The method of any one of embodiments 106-116, further comprising lyophilizing the nanoparticle suspension.

Embodiment 118. The method of any one of embodiments 106-117, further comprising adding the nanoparticle suspension into one or more vials.

Embodiment 119. The method of embodiment 118, further comprising lyophilizing the nanoparticle suspension after adding the nanoparticle suspension into the one or more vials.

Embodiment 120. The method of any one of embodiments 106-119, wherein the organic solvent comprises about 10% to about 50% tert-butanol by volume.

Embodiment 121. The method of any one of embodiments 106-120, wherein the organic solvent comprises about 50% to about 90% chloroform by volume.

Embodiment 122. The method of any one of embodiments 106-121, wherein the organic solvent comprises chloroform and tert-butanol at a volumetric ratio of about 1:1 to about 9:1.

Embodiment 123. The method of any one of embodiments 106-122, wherein the concentration of rapamycin in the organic phase is about 20 mg/mL to about 500 mg/mL.

Embodiment 124. The method of any one of embodiments 106-123, wherein the concentration of rapamycin in the emulsion is about 2 mg/mL to about 50 mg/mL.

Embodiment 125. The method of any one of embodiments 106-124, wherein the concentration of albumin in the aqueous phase is about 10 mg/mL to about 200 mg/mL.

Embodiment 126. The method of any one of embodiments 106-112526, wherein the concentration of albumin in the emulsion is about 8 mg/mL to about 200 mg/mL.

Embodiment 127. The method of any one of embodiments 106-126, wherein the phase fraction of the organic phase in the emulsion is about 1% to about 20%.

Embodiment 128. The method of any one of embodiments 106-127, wherein the nanodroplets have a Z-average particle size of about 200 nm or less.

Embodiment 129. The method of any one of embodiments 106-128, wherein the nanodroplets have a Z-average particle size of about 50 nm to about 200 nm.

Embodiment 130. The method of any one of embodiments 106-129, wherein the albumin is human albumin.

Embodiment 131. A method of assessing suitability of a pharmaceutical composition for medical use in a human individual, wherein the pharmaceutical composition comprises (a) nanoparticles comprising rapamycin and albumin, and (b) a non-nanoparticle portion comprising albumin and rapamycin, the method comprising: measuring a quality control parameter for the pharmaceutical composition; and assessing the suitability of the pharmaceutical composition for medical use in a human individual, wherein a measured quality control parameter within a quality control threshold is indicative of suitability of the pharmaceutical composition for medical use.

Embodiment 132. The method of embodiment 131, further comprising separating the nanoparticles from the non-nanoparticle portion, wherein the quality control parameter comprises a quality control parameter for the nanoparticles or the non-nanoparticle portion.

Embodiment 133. The method of embodiment 131 or 132, wherein the nanoparticles comprise a core comprising rapamycin and a coating comprising albumin.

Embodiment 134. The method of any one of embodiments 131-133, wherein: the quality control parameter comprises a weight percentage of albumin in the form of monomeric albumin in the nanoparticles of the total albumin in the nanoparticles; and a weight percentage of albumin in the form of monomeric albumin in the nanoparticles of the total albumin in the nanoparticles being about 70% to about 85% is indicative of suitability of the pharmaceutical composition for medical use.

Embodiment 135. The method of any one of embodiments 131-134, wherein: the quality control parameter comprises a weight percentage of albumin in the form of polymeric albumin in the nanoparticles of the total albumin in the nanoparticles; and a weight percentage of albumin in the form of polymeric albumin in the nanoparticles of the total albumin in the nanoparticles being about 5% to about 15% is indicative of suitability of the pharmaceutical composition for medical use.

Embodiment 136. The method of any one of embodiments 131-135, wherein: the quality control parameter comprises a weight percentage of albumin in the form of dimeric albumin in the nanoparticles of the total albumin in the nanoparticles; and a weight percentage of albumin in the form of dimeric albumin in the nanoparticles of the total albumin in the nanoparticles being about 9% to about 20% is indicative of suitability of the pharmaceutical composition for medical use.

Embodiment 137. The method of any one of embodiments 131-136, wherein: the quality control parameter comprises a weight percentage of albumin in the form of polymeric albumin in the non-nanoparticle portion of the total albumin in the non-nanoparticle portion; and a weight percentage of albumin in the form of polymeric albumin in the non-nanoparticle portion of the total albumin in the non-nanoparticle portion being about 0.5% to about 5% is indicative of suitability of the pharmaceutical composition for medical use.

Embodiment 138. The method of any one of embodiments 131-137, wherein: the quality control parameter comprises a weight percentage of albumin in the form of monomeric albumin in the non-nanoparticle portion of the total albumin in the non-nanoparticle portion; and a weight percentage of albumin in the form of monomeric albumin in the non-nanoparticle portion of the total albumin in the non-nanoparticle portion being about 80% to about 95% is indicative of suitability of the pharmaceutical composition for medical use.

Embodiment 139. The method of any one of embodiments 131-138, wherein: the quality control parameter comprises a weight percentage of albumin in the form of dimeric albumin in the non-nanoparticle portion of the total albumin in the non-nanoparticle portion; and a weight percentage of albumin in the form of dimeric albumin in the non-nanoparticle portion of the total albumin in the non-nanoparticle portion being about 4% to about 15% is indicative of suitability of the pharmaceutical composition for medical use.

Embodiment 140. The method of any one of embodiments 131-138, wherein: the quality control parameter comprises a weight percentage of albumin in the form of polymeric albumin in the composition of the total albumin in the composition; and a weight percentage of albumin in the form of polymeric albumin in the composition of the total albumin in the composition being about 0.5% to about 5% is indicative of suitability of the pharmaceutical composition for medical use.

Embodiment 141. The method of any one of embodiments 131-140, wherein: the quality control parameter comprises a weight percentage of albumin in the form of monomeric albumin in the composition of the total albumin in the composition; and a weight percentage of albumin in the form of monomeric albumin in the composition of the total albumin in the composition being about 80% to about 95% is indicative of suitability of the pharmaceutical composition for medical use.

Embodiment 142. The method of any one of embodiments 131-141, wherein: the quality control parameter comprises a weight percentage of albumin in the form of dimeric albumin in the composition of the total albumin in the composition; and a weight percentage of albumin in the form of dimeric albumin in the composition of the total albumin in the composition being about 4% to about 15% is indicative of suitability of the pharmaceutical composition for medical use.

Embodiment 143. The method of any one of embodiments 131-142, wherein the percentage of polymeric albumin, dimeric albumin, or monomeric albumin is determined using size-exclusion chromatography.

Embodiment 144. The method of any one of embodiments 131-143, wherein: the quality control parameter comprises a volume weighted mean particle size of the nanoparticles; and a volume weighted mean particle size of the nanoparticles being about 200 nm or less is indicative of suitability of the pharmaceutical composition for medical use.

Embodiment 145. The method of any one of embodiments 131-144, wherein: the quality control parameter comprises a volume-weighted mean particle size of the nanoparticles; and a volume weighted mean particle size of the nanoparticles being about 50 nm to about 200 nm is indicative of suitability of the pharmaceutical composition for medical use.

Embodiment 146. The method of any one of embodiments 131-145, wherein: the quality control parameter comprises a Z-average particle size of the nanoparticles; and a Z-average particle size of the nanoparticles being about 200 nm or less is indicative of suitability of the pharmaceutical composition for medical use.

Embodiment 147. The method of any one of embodiments 131-146, wherein: the quality control parameter comprises a Z-average particle size of the nanoparticles; and a Z-average particle size being about 50 nm to about 200 nm is indicative of suitability of the pharmaceutical composition for medical use.

Embodiment 148. The method of any one of embodiments 131-147, wherein: the quality control parameter comprises a polydispersity index of the nanoparticles; and a polydispersity index of the nanoparticles being less than 0.3 is indicative of suitability of the pharmaceutical composition for medical use.

Embodiment 149. The method of any one of embodiments 131-148, wherein: the quality control parameter comprises a polydispersity index of the nanoparticles; and a polydispersity index of the nanoparticles being about 0.03 to about 0.3 is indicative of suitability of the pharmaceutical composition for medical use.

Embodiment 150. The method of any one of embodiments 131-149, wherein: the quality control parameter comprises a span of particle size distribution (($D_v95-D_v5)/D_v50$) of the nanoparticles; and a span of particle size distribution of the nanoparticles being about 1.2 or less is indicative of suitability of the pharmaceutical composition for medical use.

Embodiment 151. The method of any one of embodiments 131-150, wherein: the quality control parameter comprises a weight percentage of the albumin in the nanoparticles; and a weight percentage of the albumin in the nanoparticles being about 25% to about 45% is indicative of the suitability of the pharmaceutical composition for medical use.

Embodiment 152. The method of any one of embodiments 131-151, wherein: the quality control parameter comprises a weight percentage of the rapamycin in the nanoparticles; and a weight percentage of the rapamycin in the nanoparticles being about 55% to about 75% is indicative of the suitability of the pharmaceutical composition for medical use.

Embodiment 153. The method of any one of embodiments 131-152, wherein: the quality control parameter comprises a weight ratio of the albumin to the rapamycin in the nanoparticles; and a weight ratio of the albumin to the rapamycin in the nanoparticles being about 1:1 to about 1:4 is indicative of the suitability of the pharmaceutical composition for medical use.

Embodiment 154. The method of any one of embodiments 131-153, wherein: the quality control parameter comprises a weight ratio of the albumin to the rapamycin in the composition; and a weight ratio of the albumin to the rapamycin in the composition being about 1:1 to about 10:1 is indicative of the suitability of the pharmaceutical composition for medical use.

Embodiment 155. The method of any one of embodiments 131-154, wherein: the quality control parameter comprises a percentage of albumin in the composition that is in the non-nanoparticle portion; and a percentage of albumin in the composition that is in the non-nanoparticle portion being about 95% or more is indicative of the suitability of the pharmaceutical composition for medical use.

Embodiment 156. The method of any one of embodiments 131-155, wherein: the quality control parameter comprises a percentage of rapamycin in the composition that is in the nanoparticles; and a percentage of rapamycin in the composition that is in the nanoparticles being about 98% or more is indicative of the suitability of the pharmaceutical composition for medical use.

Embodiment 157. The method of any one of embodiments 131-156, wherein the pharmaceutical composition is a nanoparticle suspension.

Embodiment 158. The method of any one of embodiments 131-157, wherein the pharmaceutical composition is reconstituted from a dried nanoparticle composition.

Embodiment 159. The method of any one of embodiments 131-158, wherein: the quality control parameter comprises a concentration of albumin in the composition; and a concentration of albumin in the composition being about 30 mg/mL to about 100 mg/mL is indicative of the suitability of the pharmaceutical composition for medical use.

Embodiment 160. The method of any one of embodiments 131-159, wherein: the quality control parameter comprises a concentration of albumin in the composition that is in the non-nanoparticle portion; and a concentration of albumin in the composition that is in the non-nanoparticle portion being about 30 mg/mL to about 100 mg/mL is indicative of the suitability of the pharmaceutical composition for medical use.

Embodiment 161. The method of any one of embodiments 131-160, wherein: the quality control parameter comprises a concentration of albumin in the composition that is in the nanoparticles; and a concentration of albumin in the composition that is in the nanoparticles being about 1.8 mg/mL to about 15 mg/mL is indicative of the suitability of the pharmaceutical composition for medical use.

Embodiment 162. The method of any one of embodiments 131-161, wherein: the quality control parameter comprises a concentration of rapamycin in the composition; and a concentration of rapamycin in the composition being about 1 mg/mL to about 15 mg/mL is indicative of the suitability of the pharmaceutical composition for medical use.

Embodiment 163. The method of any one of embodiments 131-162, wherein: the quality control parameter comprises a concentration of rapamycin in the composition that is in the non-nanoparticle portion; and a concentration of rapamycin in the composition that is in the non-nanoparticle portion being about 20 µg/mL to about 55 µg/mL is indicative of the suitability of the pharmaceutical composition for medical use.

Embodiment 164. The method of any one of embodiments 131-163, wherein: the quality control parameter comprises a concentration of rapamycin in the composition that is in the nanoparticles; and a concentration of rapamycin in the composition that is in the nanoparticles being about 1 mg/mL to about 15 mg/mL is indicative of the suitability of the pharmaceutical composition for medical use.

Embodiment 165. The method of any one of embodiments 131-164, wherein: the quality control parameter comprises an osmolality of the composition; and an osmolality of the composition being about 300 mOsm/kg to about 350 mOsm/kg is indicative of the suitability of the pharmaceutical composition for medical use.

Embodiment 166. The method of any one of embodiments 131-165, wherein: the quality control parameter comprises a viscosity of the composition; and a viscosity of the composition being about 1.2 cP to about 1.5 cP is indicative of the suitability of the pharmaceutical composition for medical use.

Embodiment 167. The method of any one of embodiments 131-166, wherein: the quality control parameter comprises a stability of the composition; and the composition being stable at 25° C. for at least 24 hours is indicative of the suitability of the pharmaceutical composition for medical use.

Embodiment 168. The method of any one of embodiments 131-167, wherein: the quality control parameter comprises a stability of the composition; and the composition being stable at 4° C. for at least 24 hours is indicative of the suitability of the pharmaceutical composition for medical use.

Embodiment 169. The method of any one of embodiments 131-168, wherein: the quality control parameter comprises a pH of the composition; and a pH of the composition being about 6.0 to about 7.5 is indicative of the suitability of the pharmaceutical composition for medical use.

Embodiment 170. The method of any one of embodiments 131-169, wherein the composition is made using tert-butanol, and wherein: the quality control parameter comprises a concentration of tert-butanol; and a concentration of tert-butanol being less than 10 µg/mL tert-butanol is indicative of the suitability of the pharmaceutical composition for medical use.

Embodiment 171. The method of any one of embodiments 131-170, wherein the composition is made using chloroform, and wherein: the quality control parameter comprises a concentration of chloroform; and a concentration of tert-butanol being less than 5 µg/mL chloroform is indicative of the suitability of the pharmaceutical composition for medical use.

Embodiment 172. The method of any one of embodiments 131-171, wherein: the quality control parameter comprises a zeta potential of the nanoparticles; and a zeta potential of the nanoparticles being about −25 mV to about −50 mV is indicative of the suitability of the pharmaceutical composition for medical use.

Embodiment 173. The method of any one of embodiments 131-172, wherein: the quality control parameter comprises a morphology of the composition, wherein the morphology is measured by measuring crystallinity of a lyophilized form of the composition by X-ray diffraction; and an amorphous morphology of the composition is indicative of the suitability of the pharmaceutical composition for medical use.

Embodiment 174. The method of any one of embodiments 131-173, wherein: the quality control parameter comprises a morphology of the composition, wherein the morphology is measured by separating the nanoparticles from the composition, lyophilizing the separated nanoparticles, and measuring crystallinity of the separated and lyophilized nanoparticles by X-ray diffraction; and an amorphous morphology of the composition is indicative of the suitability of the pharmaceutical composition for medical use.

Embodiment 175. The method of any one of embodiments 131-174, wherein: the quality control parameter comprises a morphology of the composition, wherein the morphology is measured by Raman spectroscopy differential scanning calorimetry (DSC), modulated differential scanning calorimetry (mDSC), Fourier transform infrared (FTIR) spectroscopy, or nuclear magnetic resonance (NMR) spectroscopy; and an amorphous morphology of the composition is indicative of the suitability of the pharmaceutical composition for medical use.

Embodiment 176. The method of any one of embodiments 131-175, wherein: the quality control parameter comprises an interaction of the vinyl chain of the rapamycin in the nanoparticles with the albumin in the nanoparticles; and an identified interaction between the vinyl chain of the rapamycin in the nanoparticles with the albumin in the nanoparticles is indicative of the suitability of the pharmaceutical composition for medical use.

Embodiment 177. The method of any one of embodiments 131-176, wherein: the quality control parameter comprises a portion of the nanoparticles that are non-spherical; and identification of at least a portion of the nanoparticles as non-spherical is indicative of the suitability of the pharmaceutical composition for medical use.

Embodiment 178. The method of any one of embodiments 131-177, wherein: the quality control parameter comprises a portion of the nanoparticles that are non-spherical; and identification of at least 20% of the nanoparticles as non-spherical is indicative of the suitability of the pharmaceutical composition for medical use.

Embodiment 179. The method of any one of embodiments 131-178, wherein: the quality control parameter comprises a percentage of seco-rapamycin compared to the sum of seco-rapamycin and rapamycin, by weight, in the nanoparticles; and a percentage of seco-rapamycin compared to the sum of seco-rapamycin and rapamycin, by weight, in the nanoparticles being less than 2.5% seco-rapamycin is indicative of the suitability of the pharmaceutical composition for medical use.

Embodiment 180. The method of any one of embodiments 131-179, wherein: the quality control parameter comprises a percentage of rapamycin in the pharmaceutical composition that is free rapamycin; and a percentage of rapamycin in the pharmaceutical composition that is free rapamycin being less than 3% is indicative of the suitability of the pharmaceutical composition for medical use.

Embodiment 181. The method of any one of embodiments 131-180, wherein the albumin is human albumin.

Embodiment 182. The method of any one of embodiment 131-181, wherein the quality control parameter comprises an amount of rapamycin in a unit dosage form comprising the pharmaceutical composition, and wherein the amount of rapamycin being within 10% of an amount of rapamycin indicated on a unit dosage label associated with the unit dosage form is indicative of suitability of the pharmaceutical composition for medical use.

Embodiment 183. A method of releasing a commercial batch of a pharmaceutical composition comprising (a) nanoparticles comprising rapamycin and albumin, and (b) a non-nanoparticle portion comprising albumin and rapamycin, the method comprising: assessing the suitability of the pharmaceutical composition for medical use in a human individual using a sample of the commercial batch, wherein the suitability of the pharmaceutical composition is assessed according to the method of any one of embodiments 131-182; and releasing the commercial batch if the pharmaceutical composition is suitable for medical use.

Embodiment 184. A method of processing a sample of a pharmaceutical composition to validate the sample as suitable for medical use in a human individual, the pharmaceutical composition comprising (a) nanoparticles comprising rapamycin and albumin, and (b) a non-nanoparticle portion comprising albumin and rapamycin, the method comprising: obtaining the sample from a commercial batch; and assessing the suitability of the pharmaceutical composition for medical use in a human individual using a sample of the commercial batch, wherein the suitability of the pharmaceutical composition is assessed according to the method of any one of embodiments 131-182.

Embodiment 185. A method of preparing a pharmaceutical composition comprising (a) nanoparticles comprising rapamycin and albumin, and (b) a non-nanoparticle portion comprising albumin and rapamycin for release, the method comprising: assessing the suitability of the pharmaceutical composition for medical use in a human individual according to the method of any one of embodiments 131-182; identifying the pharmaceutical composition as suitable for medical use in a human individual; and packaging the pharmaceutical composition for release.

Embodiment 186. The method of embodiment 185, wherein packaging the pharmaceutical composition comprises lyophilizing the pharmaceutical composition.

Embodiment 187. The method of embodiment 185 or 186, wherein packaging the pharmaceutical composition comprises filling the pharmaceutical composition in a container.

Embodiment 188. The method of embodiment 187, comprising sealing the container.

Embodiment 189. The nanoparticle composition of embodiment 91, wherein the pharmaceutical composition is associated with a unit dosage label indicating an amount of rapamycin in the pharmaceutical composition, and wherein the amount of rapamycin in the pharmaceutical composition is within 10% of the amount of rapamycin indicated on the unit dosage label.

Embodiment 190. A nanoparticle composition comprising (a) nanoparticles comprising rapamycin and albumin, and (b) a non-nanoparticle portion comprising albumin and rapamycin; wherein about 80% to about 95% of the albumin in the composition is in the form of monomeric albumin, about 4% to about 15% of the albumin in the composition is in the form of dimeric albumin, and about 0.5% to about 5% of the albumin in the composition is in the form of polymeric albumin when the percentage of albumin in the composition that is in the form of monomeric albumin, dimeric albumin, or polymeric albumin is determined by subjecting the composition to size-exclusion chromatography (SEC) using a saline mobile phase coupled with a multiple angle light scattering (MALS) detector.

Embodiment 191. The nanoparticle composition of embodiment 190, wherein about 70% to about 85% of the albumin in the nanoparticles is in the form of monomeric albumin, about 9% to about 20% of the albumin in the nanoparticles is in the form of dimeric albumin, and about 5% to about 15% of the albumin in the nanoparticles is in the form of polymeric albumin when the percentage of albumin in the nanoparticles that is in the form of monomeric albumin, dimeric albumin, or polymeric albumin is determined by separating the nanoparticles from the non-nanoparticle portion, re-suspending the nanoparticles in saline, and subjecting the re-suspended nanoparticles to size-exclusion chromatography (SEC) using a saline mobile phase coupled with a multiple angle light scattering (MALS) detector.

Embodiment 192. The nanoparticle composition of embodiment 190 or 191, wherein about 80% to about 95% of the albumin in the non-nanoparticle portion is in the form of monomeric albumin, about 4% to about 14% of the albumin in the non-nanoparticle portion is in the form of dimeric albumin, and about 0.5% to about 5% of the albumin in the non-nanoparticle portion is in the form of polymeric albumin when the percentage of albumin in the non-nanoparticle portion that is in the form of monomeric albumin, dimeric albumin, or polymeric albumin is determined by separating the nanoparticles from the non-nanoparticle portion, and subjecting the non-nanoparticle portion to size-exclusion chromatography (SEC) using a saline mobile phase coupled with a multiple angle light scattering (MALS) detector.

Embodiment 193. A nanoparticle composition comprising: (a) nanoparticles comprising rapamycin and albumin, and (b) a non-nanoparticle portion comprising albumin and rapamycin; wherein about 42% to about 60% of the albumin in the nanoparticles is in the form of polymeric albumin other than oligomeric albumin when the percentage of albumin in the nanoparticles that is in the form of polymeric albumin other than oligomeric albumin is determined by separating the nanoparticles from the non-nanoparticle portion, dissolving the nanoparticles, and subjecting the dissolved nanoparticles to size-exclusion chromatography.

Embodiment 194. The nanoparticle composition of embodiment 193, wherein about 1% to about 4.5% of the albumin in the nanoparticles is in the form of oligomeric albumin when the percentage of albumin in the nanoparticles that is in the form of oligomeric albumin is determined by separating the nanoparticles from the non-nanoparticle portion, dissolving the nanoparticles, and subjecting the dissolved nanoparticles to size-exclusion chromatography.

Embodiment 195. The nanoparticle composition of embodiment 193 or 194, wherein about 25% to about 50% of the albumin in the nanoparticles is in the form of monomeric albumin or about 5% to about 16% of the albumin in the nanoparticles is in the form of dimeric albumin when the percentage of albumin in the nanoparticles that is in the form of monomeric albumin or dimeric albumin is determined by separating the nanoparticles from the non-nanoparticle portion, dissolving the nanoparticles, and subjecting the dissolved nanoparticles to size-exclusion chromatography.

Embodiment 196. The nanoparticle composition of any one of embodiments 193-195, wherein about 80% to about 95% of the albumin in the non-nanoparticle portion is in the form of monomeric albumin, about 4% to about 14% of the albumin in the non-nanoparticle portion is in the form of dimeric albumin, about 0.5% to about 4% of the albumin in the non-nanoparticle portion is in the form of oligomeric albumin, and/or about 0.5% to about 3% of the albumin in the non-nanoparticle portion is in the form of polymeric albumin other than oligomeric albumin when the percentage of albumin in the non-nanoparticle portion that is in the form of monomeric albumin, dimeric albumin, oligomeric albumin, and/or polymeric albumin other than oligomeric albumin is determined by separating the nanoparticles from the non-nanoparticle portion, and subjecting the non-nanoparticle portion to size-exclusion chromatography.

Embodiment 197. The nanoparticle composition of any one of embodiments 193-196, wherein about 80% to about 95% of the total albumin composition is in the form of monomeric albumin, about 4% to about 15% of the total albumin in the composition is in the form of dimeric albumin, about 0.3% to about 3% of the total albumin in the composition is in the form of oligomeric albumin, and/or about 2% to about 7% of the total albumin in the composition is in the form of polymeric albumin other than oligomeric albumin when the percentage of monomeric albumin, dimeric albumin, oligomeric albumin, and/or polymeric albumin other than oligomeric albumin in the composition is determined by subjecting the composition to size-exclusion chromatography.

Embodiment 198. The nanoparticle composition of any one of embodiments 190-197, wherein seco-rapamycin is less than 3% by weight of the sum of seco-rapamycin and rapamycin in the composition.

Embodiment 199. A nanoparticle composition comprising: (a) nanoparticles comprising rapamycin and albumin, and (b) a non-nanoparticle portion comprising albumin and rapamycin, wherein seco-rapamycin is less than 3% by weight of the sum of seco-rapamycin and rapamycin in the composition.

Embodiment 200. The nanoparticle composition of any one of embodiments 190-199, wherein less than 1% of rapamycin in the composition is free rapamycin.

Embodiment 201. A nanoparticle composition comprising: (a) nanoparticles comprising rapamycin and albumin, and (b) a non-nanoparticle portion comprising albumin and rapamycin, wherein less than 1% of the rapamycin in the composition is free rapamycin.

Embodiment 202. The nanoparticle composition of any one of embodiments 190-201, wherein the volume weighted mean particle size of the nanoparticles is about 200 nm or less.

Embodiment 203. The nanoparticle composition of any one of embodiments 190-202, wherein the Z-average particle size of the nanoparticles is about 200 nm or less.

Embodiment 204. The nanoparticle composition of any one of embodiments 190-203, wherein the polydispersity index of the nanoparticles is less than 0.3.

Embodiment 205. The nanoparticle composition of any one of embodiments 190-204, wherein the span of particle size distribution $((D_v95-D_v5)/D_v50)$ of the nanoparticles is about 0.8 to about 1.2.

Embodiment 206. The nanoparticle composition of any one of embodiments 190-205, wherein the nanoparticles are about 25% to about 45% albumin by weight.

Embodiment 207. The nanoparticle composition of any one of embodiments 190-206, wherein the nanoparticles are about 55% to about 75% rapamycin by weight.

Embodiment 208. The nanoparticle composition of any one of embodiments 190-207, wherein the weight ratio of the albumin to the rapamycin in the composition is about 1:1 to about 10:1.

Embodiment 209. The nanoparticle composition of any one of embodiments 190-208, wherein the nanoparticle composition is a nanoparticle suspension.

Embodiment 210. The nanoparticle composition of embodiment 209, wherein the concentration of albumin in the composition is about 30 mg/mL to about 100 mg/mL.

Embodiment 211. The nanoparticle composition of embodiment 209 or 210, wherein the concentration of rapamycin in the nanoparticle composition is about 1 mg/mL to about 100 mg/mL.

Embodiment 212. The nanoparticle composition of any one of embodiments 209-211, wherein the osmolality of the composition is about 280 mOsm/kg to about 400 mOsm/kg.

Embodiment 213. The nanoparticle composition of any one of embodiments 209-212, wherein the viscosity of the composition is about 1.2 cP to about 1.5 cP.

Embodiment 214. The nanoparticle composition of any one of embodiments 209-213, wherein the composition is stable at 25° C. for at least 24 hours.

Embodiment 215. The nanoparticle composition of any one of embodiments 209-214, wherein the composition is stable at 4° C. for at least 24 hours.

Embodiment 216. The nanoparticle composition of any one of embodiments 209-215, wherein the nanoparticles had been resuspended from a dried composition.

Embodiment 217. The nanoparticle composition of any one of embodiments 209-216, wherein the pH of the composition is about 6.0 to about 7.5.

Embodiment 218. The nanoparticle composition of any one of embodiments 190-217, wherein the composition is a dried composition.

Embodiment 219. The nanoparticle composition of any one of embodiments 190-218, wherein the composition comprises less than 250 ppm tert-butanol.

Embodiment 220. The nanoparticle composition of any one of embodiments 190-219, wherein the composition comprises less than 60 ppm chloroform.

Embodiment 221. The nanoparticle composition of any one of embodiments 190-220, wherein the zeta potential of the nanoparticles is about −25 mV to about −50 mV.

Embodiment 222. The nanoparticle composition of any one of embodiments 190-221, wherein less than 1% of the rapamycin in the composition is amorphous.

Embodiment 223. The nanoparticle composition of any one of embodiments 190-222, wherein the composition has an amorphous morphology as determined by measuring crystallinity of a lyophilized form of the composition by X-ray diffraction.

Embodiment 224. The nanoparticle composition of any one of embodiments 190-223, wherein the nanoparticles have an amorphous morphology as determined by separating the nanoparticles from the composition, lyophilizing the separated nanoparticles, and measuring crystallinity of the separated and lyophilized nanoparticles by X-ray diffraction.

Embodiment 225. The nanoparticle composition of any one of embodiments 190-224, wherein the rapamycin in nanoparticles has an amorphous morphology as determined by Raman spectroscopy, polarized light microscopy, differential scanning calorimetry (DSC), modulated differential scanning calorimetry (mDSC), Fourier transform infrared (FTIR) spectroscopy, or nuclear magnetic resonance (NMR) spectroscopy.

Embodiment 226. The nanoparticle composition of any one of embodiments 190-225, wherein the vinyl chain of the rapamycin in the nanoparticles interacts with the albumin in the nanoparticles.

Embodiment 227. The nanoparticle composition of any one of embodiments 190-226, wherein at least a portion of the nanoparticles are non-spherical as determined by cryogenic transmission electron microscopy (cryo-TEM).

Embodiment 228. The nanoparticle composition of any one of embodiments 190-227, wherein the nanoparticles have a non-smooth surface as determined by cryogenic transmission electron microscopy (cryo-TEM).

Embodiment 229. The nanoparticle composition of any one of embodiments 190-228, wherein the albumin is human albumin.

Embodiment 230. The nanoparticle composition of any one of embodiments 190-229, wherein 90% or more of the rapamycin in the composition is in the nanoparticles.

Embodiment 231. The nanoparticle composition of any one of embodiments 190-230, wherein the nanoparticle composition is sterile.

Embodiment 232. The nanoparticle composition of any one of embodiments 190-231, wherein the nanoparticle composition comprises sodium caprylate.

Embodiment 233. The nanoparticle composition of any one of embodiments 190-232, wherein the pharmaceutical composition is associated with a unit dosage label indicating an amount of rapamycin in the pharmaceutical composition, and wherein the amount of rapamycin in the pharmaceutical composition is within 10% of the amount of rapamycin indicated on the unit dosage label.

Embodiment 234. The nanoparticle composition of any one of embodiments 190-233, wherein the nanoparticle composition is contained within a sealed container.

Embodiment 235. The nanoparticle composition of embodiment 234, wherein the sealed container is a sealed vial or a sealed bag.

Embodiment 236. The nanoparticle composition of any one of embodiments 190-235, wherein the nanoparticle composition is a pharmaceutical composition.

Embodiment 237. A commercial batch of the nanoparticle composition according to any one of embodiments 190-236.

Embodiment 238. A commercial batch of an emulsion, comprising: a dispersed organic phase comprising nanodroplets comprising rapamycin dissolved in an organic solvent comprising chloroform and tert-butanol, and a continuous aqueous phase comprising albumin.

Embodiment 239. The emulsion of embodiment 238, wherein the organic solvent comprises about 10% to about 50% tert-butanol by volume.

Embodiment 240. The emulsion of embodiment 238 or 239, wherein the organic solvent comprises about 50% to about 90% chloroform by volume.

Embodiment 241. The emulsion of any one of embodiments 238-240, wherein the organic solvent comprises chloroform and tert-butanol at a volumetric ratio of about 1:1 to about 9:1.

Embodiment 242. The emulsion of any one of embodiments 238-241, wherein the concentration of rapamycin in the organic phase is about 20 mg/mL to about 500 mg/mL.

Embodiment 243. The emulsion of any one of embodiments 238-242, wherein the concentration of rapamycin in the emulsion is about 2 mg/mL to about 50 mg/mL.

Embodiment 244. The emulsion of any one of embodiments 238-243, wherein the concentration of albumin in the aqueous phase is about 10 mg/mL to about 200 mg/mL.

Embodiment 245. The emulsion of any one of embodiments 238-244, wherein the concentration of albumin in the emulsion is about 8 mg/mL to about 200 mg/mL.

Embodiment 246. The emulsion of any one of embodiments 238-245, wherein the phase fraction of the organic phase in the emulsion is about 1% to about 20%.

Embodiment 247. The emulsion of any one of embodiments 238-246, wherein the nanodroplets have a Z-average particle size of about 200 nm or less.

Embodiment 248. The emulsion of any one of embodiments 238-247, wherein the Z-average particle size of the nanodroplets does not increase by more than 30% after storing the emulsion for about 4 hours at 4° C.

Embodiment 249. The emulsion of any one of embodiments 238-24, wherein the Z-average particle size of the nanodroplets does not increase by more than 30% after storing the emulsion for about 24 hours at 4° C.

Embodiment 250. The emulsion of any one of embodiments 238-249, wherein the albumin is human albumin.

Embodiment 251. A method of making a commercial batch of a nanoparticle suspension, comprising removing organic solvent from the commercial batch of the emulsion according to any one of embodiments 48-60 to make the nanoparticle suspension.

Embodiment 252. The method of embodiment 251, wherein the organic solvent is removed using a wiped film evaporator.

Embodiment 253. The method of embodiment 251, wherein the organic solvent is removed using a rotary evaporator.

Embodiment 254. The method of any one of embodiments 251-253, further comprising forming the emulsion by homogenizing the organic phase and the aqueous phase.

Embodiment 255. The method of any one of embodiments 251-254, wherein the emulsion is stored between about 2° C. and about 8° C. before removing the organic solvent.

Embodiment 256. The method of embodiment 255, wherein the emulsion is stored for about 4 hours or for about 24 hours.

Embodiment 257. A method of assessing suitability of a pharmaceutical composition for medical use in a human individual, wherein the pharmaceutical composition comprises (a) nanoparticles comprising rapamycin and albumin, and (b) a non-nanoparticle portion comprising albumin and rapamycin, the method comprising: measuring a quality control parameter for the pharmaceutical composition; and assessing the suitability of the pharmaceutical composition for medical use in a human individual, wherein a measured quality control parameter within a quality control threshold is indicative of suitability of the pharmaceutical composition for medical use.

Embodiment 258. The method of embodiment 257, wherein the quality control parameter for the pharmaceutical composition comprises a percentage of albumin in the composition in the form of polymeric albumin other than oligomeric albumin; and the quality control threshold comprises a range set within about 42% and about 60% monomeric albumin when the percentage of albumin in the composition that is in the form of monomeric albumin is determined by separating the nanoparticles from the non-nanoparticle portion, dissolving the nanoparticles, and subjecting the dissolved nanoparticles to size-exclusion chromatography.

Embodiment 259. The method of embodiment 257, wherein the quality control parameter for the pharmaceutical composition comprises a percentage of albumin in the composition in the form of monomeric albumin, dimeric albumin, and polymeric albumin; and the quality control threshold comprises a range set within about 80% and about 95% monomeric albumin, a range set within about 4% and about 15% dimeric albumin, and a range set within about 0.5% and about 5% polymeric albumin when the percentage of albumin in the composition that is in the form of monomeric albumin, dimeric albumin, or polymeric albumin is determined by subjecting the composition to size-exclusion chromatography (SEC) using a saline mobile phase coupled with a multiple angle light scattering (MALS) detector.

Embodiment 260. The method of embodiment 257, wherein the quality control parameter for the pharmaceutical composition comprises a weight percentage of the sum of sec-rapamycin and rapamycin in the composition that is in the form of seco-rapamycin; and the quality control threshold is set at 3% seco-rapamycin by weight or less.

Embodiment 261. The method of embodiment 257, wherein the quality control parameter for the pharmaceutical composition comprises a percentage of rapamycin in the composition that is free rapamycin; and the quality control threshold is set at 1% of the rapamycin in the composition or less.

Embodiment 262. A method of releasing a commercial batch of a pharmaceutical composition comprising (a) nanoparticles comprising rapamycin and albumin, and (b) a non-nanoparticle portion comprising albumin and rapamycin, the method comprising: assessing the suitability of the pharmaceutical composition for medical use in a human individual using a sample of the commercial batch, wherein the suitability of the pharmaceutical composition is assessed according to the method of embodiment 257; and releasing the commercial batch if the pharmaceutical composition is suitable for medical use.

Embodiment 263. A method of processing a sample of a pharmaceutical composition to validate the sample as suitable for medical use in a human individual, the pharmaceutical composition comprising (a) nanoparticles comprising rapamycin and albumin, and (b) a non-nanoparticle portion comprising albumin and rapamycin, the method comprising: obtaining the sample from a commercial batch; and assessing the suitability of the pharmaceutical composition for medical use in a human individual using a sample of the commercial batch, wherein the suitability of the pharmaceutical composition is assessed according to the method embodiment 257.

Embodiment 264. A method of preparing a pharmaceutical composition comprising (a) nanoparticles comprising rapamycin and albumin, and (b) a non-nanoparticle portion comprising albumin and rapamycin for release, the method comprising: assessing the suitability of the pharmaceutical composition for medical use in a human individual according to the method of embodiment 257; identifying the pharmaceutical composition as suitable for medical use in a human individual; and packaging the pharmaceutical composition for release.

Embodiment 265. A commercial batch of a pharmaceutical composition comprising (a) nanoparticles comprising rapamycin and albumin, and (b) a non-nanoparticle portion comprising albumin and rapamycin; wherein about 42% to about 60% of the albumin in the nanoparticles is in the form of polymeric albumin other than oligomeric albumin when the percentage of albumin in the nanoparticles that is in the form of polymeric albumin other than oligomeric albumin is determined by separating the nanoparticles from the non-nanoparticle portion, dissolving the nanoparticles, and subjecting the dissolved nanoparticles to size-exclusion chromatography.

Embodiment 266. The commercial batch of embodiment 265, wherein about 1% to about 4.5% of the albumin in the nanoparticles is in the form of oligomeric albumin when the percentage of albumin in the nanoparticles that is in the form of oligomeric albumin is determined by separating the nanoparticles from the non-nanoparticle portion, dissolving the nanoparticles, and subjecting the dissolved nanoparticles to size-exclusion chromatography.

Embodiment 267. The commercial batch of embodiment 265 or 266, wherein about 25% to about 50% of the albumin in the nanoparticles is in the form of monomeric albumin and about 5% to about 16% of the albumin in the nanoparticles is in the form of dimeric albumin when the percentage of albumin in the nanoparticles that is in the form of monomeric albumin and dimeric albumin is determined by separating the nanoparticles from the non-nanoparticle portion, dissolving the nanoparticles, and subjecting the dissolved nanoparticles to size-exclusion chromatography.

Embodiment 268. The commercial batch of any one of embodiments 265-267, wherein about 80% to about 95% of the total albumin composition is in the form of monomeric albumin, about 4% to about 15% of the total albumin in the composition is in the form of dimeric albumin, about 0.3% to about 3% of the total albumin in the composition is in the form of oligomeric albumin, and about 2% to about 7% of the total albumin in the composition is in the form of polymeric albumin other than oligomeric albumin when the percentage of monomeric albumin, dimeric albumin, oligomeric albumin, and polymeric albumin other than oligomeric albumin in the composition is determined by subjecting the composition to size-exclusion chromatography.

Embodiment 269. The commercial batch of any one of embodiments 265-268, wherein about 80% to about 95% of the albumin in the non-nanoparticle portion is in the form of monomeric albumin, about 4% to about 14% of the albumin in the non-nanoparticle portion is in the form of dimeric albumin, about 0.5% to about 4% of the albumin in the non-nanoparticle portion is in the form of oligomeric albumin, and about 0.5% to about 3% of the albumin in the non-nanoparticle portion is in the form of polymeric albumin other than oligomeric albumin when the percentage of albumin in the non-nanoparticle portion that is in the form of monomeric albumin, dimeric albumin, oligomeric albumin, and polymeric albumin other than oligomeric albumin is determined by separating the nanoparticles from the non-nanoparticle portion, and subjecting the non-nanoparticle portion to size-exclusion chromatography.

Embodiment 270. The commercial batch of any one of embodiments 265-269, wherein seco-rapamycin is less than 3% by weight of the sum of seco-rapamycin and rapamycin in the composition.

Embodiment 271. The commercial batch of any one of embodiments 265-270, wherein the volume weighted mean particle size of the nanoparticles is about 200 nm or less.

Embodiment 272. T The commercial batch of any one of embodiments 265-271, wherein the Z-average particle size of the nanoparticles is about 200 nm or less.

Embodiment 273. The commercial batch of any one of embodiments 265-272, wherein the polydispersity index of the nanoparticles is less than 0.3.

Embodiment 274. The commercial batch of any one of embodiments 265-273, wherein the span of particle size distribution $((D_v95-D_v5)/D_v50)$ of the nanoparticles is about 0.8 to about 1.2.

Embodiment 275. The commercial batch of any one of embodiments 265-274, wherein the nanoparticles are about 25% to about 45% albumin by weight and about 55% to about 75% rapamycin by weight.

Embodiment 276. The commercial batch of any one of embodiments 265-275, wherein the nanoparticle composition is a nanoparticle suspension.

Embodiment 277. The commercial batch of any one of embodiments 265-276, wherein the concentration of albumin in the composition is about 30 mg/mL to about 100 mg/mL.

Embodiment 278. The commercial batch of any one of embodiments 265-277, wherein the concentration of rapamycin in the nanoparticle composition is about 1 mg/mL to about 100 mg/mL.

Embodiment 279. The commercial batch of any one of embodiments 265-278, wherein the osmolality of the composition is about 280 mOsm/kg to about 400 mOsm/kg.

Embodiment 280. The commercial batch of any one of embodiments 265-279, wherein the nanoparticles had been resuspended from a dried composition.

Embodiment 281. The commercial batch of any one of embodiments 265-280, wherein the composition is a dried composition.

Embodiment 282. The commercial batch of any one of embodiments 265-281, wherein the composition comprises less than 250 ppm tert-butanol or less than 60 ppm chloroform.

Embodiment 283. The commercial batch of any one of embodiments 265-282, wherein the zeta potential of the nanoparticles is about −25 mV to about −50 mV.

Embodiment 284. The commercial batch of any one of embodiments 265-283, wherein the nanoparticles have an amorphous morphology as determined by separating the nanoparticles from the composition, lyophilizing the separated nanoparticles, and measuring crystallinity of the separated and lyophilized nanoparticles by X-ray diffraction.

Embodiment 285. The commercial batch of any one of embodiments 265-284, wherein the rapamycin in nanoparticles has an amorphous morphology as determined by Raman spectroscopy, polarized light microscopy, differential scanning calorimetry (DSC), modulated differential scanning calorimetry (mDSC), Fourier transform infrared (FTIR) spectroscopy, or nuclear magnetic resonance (NMR) spectroscopy.

Embodiment 286. The commercial batch of any one of embodiments 265-285, wherein at least a portion of the nanoparticles are non-spherical as determined by cryogenic transmission electron microscopy (cryo-TEM).

Embodiment 287. The commercial batch of any one of embodiments 265-286, wherein the nanoparticles have a non-smooth surface as determined by cryogenic transmission electron microscopy (cryo-TEM).

Embodiment 288. The commercial batch of any one of embodiments 265-288, wherein the albumin is human albumin.

Embodiment 289. The commercial batch of any one of embodiments 265-288, wherein 90% or more of the rapamycin in the composition is in the nanoparticles.

Embodiment 290. The commercial batch of any one of embodiments 265-289, wherein the nanoparticle composition is sterile.

Embodiment 291. The commercial batch of any one of embodiments 265-290, wherein the nanoparticle composition comprises sodium caprylate.

Embodiment 292. The commercial batch of any one of embodiments 265-291, wherein the pharmaceutical composition is contained within a plurality of vials associated with a unit dosage label indicating an amount of rapamycin in each vial, and wherein the amount of rapamycin in the vials is within 10% of the amount of rapamycin indicated on the unit dosage label.

EXAMPLES

The examples below are intended to be purely exemplary of the invention and should therefore not be considered to limit the invention in any way. The following examples are presented in order to more fully illustrate embodiments and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art without departing from the spirit and scope of the invention. It should be understood that various alternatives to the embodiments described herein may be employed in practicing the methods described herein.

For the following examples, a pharmaceutical composition of rapamycin albumin-bound nanoparticles for injectable suspension was developed. The pharmaceutical composition, a drug product, comprises nanoparticles comprising the mTOR inhibitor rapamycin complexed with human albumin and is termed any of nab-sirolimus, nab-rapamycin, and ABI-009 (i.e., "the composition," or "the pharmaceutical composition"). Unless otherwise specified, the pharmaceutical composition was provided for most of the following examples in the form of lyophilized powder (i.e., lyophilized cake) from indicated manufacturing lots. Samples from various lots of the pharmaceutical composition were characterized and assayed in some of the following examples, either shortly after production (clinical samples) or after an indicated storage period (stability samples). Unless otherwise specified, a composition or pharmaceutical composition hereafter refers to a sample from one of these production lots.

Example 1. X-Ray Diffraction (XRD) of Rapamycin Nanoparticles

X-ray diffraction (XRD) analysis was performed on the pharmaceutical composition. The assessment was performed using lyophilized cake from several lots of the pharmaceutical composition stored under 5° C. and 25° C./60% relative humidity (RH) after storage between 0 to 24 months and beyond 36 months.

XRD analysis was also performed on the reconstituted pharmaceutical composition immediately after reconstitution (time zero; T0) and after storage for 24 hours after reconstitution at 5° C. (time 24 hours; T24 hrs). The pharmaceutical composition was reconstituted with a 0.9% sodium chloride solution to produce a 5 mg/ml stock solution of the pharmaceutical composition, as measured by the concentration of rapamycin. For example, starting from a vial of the lyophilized pharmaceutical composition containing 100 mg, as measured by the amount of rapamycin, 20 ml of 0.9% sodium chloride was slowly injected into the vial over a minimum of 1 minute using a sterile syringe. The flow of 0.9% sodium chloride was directed onto the inside wall of the vial. Subsequently, the lyophilized pharmaceutical composition was allowed to rest for 5 minutes and then the vial was gently swirled or slowly inverted for at least 2 minutes until complete dissolution of the pharmaceutical composition occurred. The lyophilized pharmaceutical composition was reconstituted in a manner to avoid the formation of foam. A spectrophotometer was set up with a 295 nm longwave pass filter placed between the UV light source and the cuvette. A 10-mm quartz cuvette was placed into an Agilent Cary 8454 UV-Vis spectrophotometer pre-equilibrated to 20° C. while stirring at 2000 rpm. An appropriate volume of water was transferred to the cuvette. A magnetic stirrer bar was added to the bottom of cuvette. The spectrophotometer was equilibrated over an hour (or longer) until the 340 nm signal was stabilized. An appropriate volume of the stock reconstituted pharmaceutical composition suspension was then added to the cuvette to achieve a target rapamycin concentration of 100 µg/ml. The suspension was immediately mixed and the cuvette was capped.

In addition, XRD analysis was performed on controls which are comprised of lyophilized human albumin, crystalline rapamycin, amorphous rapamycin, and physical mixtures containing 1 to 10% (w/w) of crystalline rapamycin in lyophilized human albumin.

The samples and controls used in the XRD analysis are summarized in Table 1 below.

TABLE 1

| Samples and Controls for XRD Characterization | | |
|---|---|---|
| Sample description | Lot number | Stability interval/Storage conditions/ Material information |
| Control 1, lyophilized human albumin | HA-1 | Albumin from human serum, lyophilized powder, fatty acid and globulin free |
| Control 2, crystalline rapamycin | R-A | Rapamycin drug substance |
| Control 3, amorphous rapamycin | R-B | Rapamycin drug substance dissolved in suitable organic solvent and mixed with a dilute acid to form an insoluble precipitate; the precipitate is purified and dried to generate amorphous rapamycin |
| Physical mixture of lyophilized human albumin and crystalline rapamycin | N/A | Physical mixture containing 1 to 10% (w/w) of crystalline rapamycin in lyophilized human albumin. Note: the percent rapamycin in the pharmaceutical composition is approximately 10% (w/w) |
| Pharmaceutical composition lyophilized cake | #11 | 24 months at 5° C. |
| Pharmaceutical composition lyophilized cake | #2 | 24 months at 25° C./60% RH and more than 36 months at 5° C. |
| Pharmaceutical composition lyophilized cake | #11 and #3 | T0; 3 months at 5° C.; 3 months at 25° C./60% RH; 6 months at 5° C.; and 6 months at 25° C./60% RH |
| Isolated nanoparticles of pharmaceutical composition | #12 | Nanoparticles isolated by ultracentrifugation performed at speeds and durations that allow the sedimentation of the nanoparticles without significant sedimentation of albumin and/or rapamycin not associated with the nanoparticles |

The crystallinity of the crystalline rapamycin (control 2) was confirmed by the presence of numerous sharp scattering peaks in the XRD pattern, while the amorphous rapamycin (control 3) exhibited a broad halo in its profile. The lyophilized human albumin (control 1) also has an amorphous structure as indicated by two broad scattering peaks in the XRD pattern. The XRD patterns of the physical mixture of lyophilized human albumin and crystalline rapamycin containing from 1 to 10% (w/w) of rapamycin in the mixture can be described as amorphous with distinct crystalline peaks. The diffused scattering is due to the amorphous human albumin and the sharp diffraction peaks are due to the crystalline rapamycin. Crystallinity down to 1% w/w of crystalline rapamycin in lyophilized human albumin was detectable using the current XRD method.

The typical XRD patterns of the pharmaceutical composition (lyophilized cake, initial time point) and controls demonstrates that the pharmaceutical composition is amorphous in nature as indicated by two broad scattering peaks.

The XRD patterns of the pharmaceutical composition (lyophilized cake) after storage for up to 3 months and for 24 months at 5° C. and 25° C./60% RH had similar patterns to the XRD patterns obtained at the initial time point, indicating that the drug product remains amorphous in nature during storage and during shelf life.

The XRD pattern of the isolated nanoparticles was determined. The nanoparticles were isolated by ultracentrifugation immediately after reconstitution (T0) and after storage of the reconstituted suspension for 24 hours at 5° C. (T24 hrs). The ultracentrifugation was performed at speeds and durations that allow the sedimentation of the nanoparticles without significant sedimentation of any albumin and/or rapamycin not associated with the nanoparticles. The sedimented nanoparticles were separated from the supernatant and lyophilized.

The X-ray diffractograms of the isolated nanoparticles exhibit broad scattering halos indicative of an amorphous material and confirmed that the pharmaceutical composition nanoparticles are amorphous and remain amorphous after storage of reconstituted suspension for 24 hours at 5° C.

Example 2. Raman Spectroscopy of Rapamycin Nanoparticles

Raman spectroscopy analysis was performed on controls and selected samples of the pharmaceutical composition (see Table 1 of Example 1). Raman spectroscopy detects the vibrational and rotational modes within molecules that result in changes in polarizability of intramolecular bonds. As the vibrational and rotational states and frequencies are altered by the physical state of the molecules, the Raman spectrum is different depending on the physical form of the sample.

The Raman spectra of the crystalline rapamycin, amorphous rapamycin, and lyophilized human albumin were significantly different. A distinct peak at 1630.4 cm$^{-1}$ in the crystalline form was shifted significantly to 1634.7 cm$^{-1}$ in the amorphous form, and many of the peaks observed in the crystalline forms are absent, for example, peaks at 1159.8 cm$^{-1}$, 1115.9 cm$^{-1}$, and 1000.2 cm$^{-1}$. These differences between the Raman spectra of the crystalline and amorphous rapamycin allow for differentiation between their physical states by Raman spectroscopy. The Raman spectrum of lyophilized human albumin contains several peaks characteristic of proteins, including a major peak at 1003 cm$^{-1}$ due to the aromatic ring in the phenylalanine side chain.

The Raman spectra of the pharmaceutical composition (lyophilized cake) in comparison with the controls was analyzed. A distinct peak at 1630 cm$^{-1}$ in the crystalline rapamycin was not observed in the pharmaceutical composition sample. Instead, the characteristic peak at 1634 cm$^{-1}$ attributed to amorphous rapamycin and at 1003 cm$^{-1}$ attributed to the lyophilized human albumin were present in all pharmaceutical composition samples. These results demonstrate that the rapamycin in the drug product is amorphous in nature and the pharmaceutical composition (lyophilized cake) is therefore not a physical mixture of albumin and rapamycin.

The Raman spectra of the pharmaceutical composition (lyophilized cake) stored at 5° C. and at 25° C./60% RH for up to 24 months showed similar patterns to that of the pharmaceutical composition (lyophilized cake) at initial time (T0) indicating that the amorphous nature of rapamycin remains unchanged during the storage.

The Raman spectra of the isolated nanoparticles was also determined. The nanoparticles were isolated by ultracentrifugation immediately after reconstitution (T0) and after storage of the reconstituted suspension for 24 hours at 5° C. (T24 hrs). The ultracentrifugation was performed at speeds and durations that allow the sedimentation of the nanoparticles without significant sedimentation of any albumin and/or rapamycin not associated with the nanoparticles. The sedimented nanoparticles were separated from the supernatant (designated as wet pellets at T0) and lyophilized (designated as dried pellets). The results demonstrate that rapamycin in isolated nanoparticles (both in wet pellets prior to being dried by lyophilization and in dried pellets after lyophilization) is amorphous in nature and remains amorphous after storage of reconstituted suspension for 24 hours at 5° C.

Example 3. Differential Scanning Calorimetry (DSC) and Thermal Gravimetric Analysis of Rapamycin Nanoparticles Thermal analysis was performed on controls and selected samples of the pharmaceutical composition (see Table 1 of Example 1) to determine the thermal stability and decomposition temperature of the pharmaceutical composition lyophilized product using differential scanning calorimetry (DSC) and thermal gravimetric analysis (TGA). Modulated differential scanning calorimetry (mDSC) was performed to determine the physical state of rapamycin in isolated pharmaceutical composition nanoparticles.

The DSC of crystalline rapamycin showed a strong endothermic peak at 179.0° C. (data obtained at 2° C./min) followed by the decomposition. The decomposition temperature for crystalline rapamycin measured by TGA was 178° C., similar to the DSC result. This indicated that the drug melt and degradation is observed within the same endotherm. Also, the lack of any weight loss in the TGA at lower temperatures indicated that the rapamycin is anhydrous.

The DSC of lyophilized human albumin showed a broad endothermic peak at about 80° C. (peak point), followed by another broad endothermic peak start at a temperature between 180-190° C. The TGA thermogram showed that the initial endotherm in the DSC is most likely due to a loss of adsorbed water (indicated by the weight loss of around 6% w/w) while the second broad endotherm beginning at temperature between 180-190° C. was due to decomposition of lyophilized human albumin.

The DSC of the pharmaceutical composition (lyophilized cake), stored at 5° C. and 25° C./60% RH for 3 months and 24 months, had thermal profiles that mimicked pure lyophilized human albumin showing a broad endothermic peak at about 80° C. (peak point), followed by another broad endothermic peak starting at about 180-190° C. The physical mixture of 10% crystalline rapamycin (w/w) in lyophilized human albumin exhibited the endothermic peak at about 80° C. and the broad endothermic peak at about 180-190° C., due to human albumin, but also exhibited a melting peak at about 166° C. due to crystalline rapamycin. Since the behavior of the pharmaceutical composition observed is similar to the thermal behavior of lyophilized human albumin by itself (i.e., a lack of melting endotherm of crystalline rapamycin), this acts as supportive evidence that the rapamycin in the pharmaceutical composition is amorphous.

Modulated DSC (mDSC) was used to study the thermal behavior and physical state of isolated nanoparticles from reconstituted drug product in comparison with amorphous rapamycin control. mDSC analysis of amorphous rapamycin resulted in a thermal event at around 84 to 87° C., which when separated into reversible and irreversible components indicated that the event was a glass transition with a $T_g$ mid-point of 84° C. The TGA also showed very little loss of water for the amorphous rapamycin (i.e., less than 1%).

mDSC was performed on isolated nanoparticles from lots #11 and #3 (see Table 1 of Example 1). The pharmaceutical composition was reconstituted with 0.9% sodium chloride injection. The nanoparticles were isolated by ultracentrifugation immediately after reconstitution (T0) and after storage of the reconstituted suspension for 24 hours at 5° C. (T24 hrs). The ultracentrifugation was performed at speeds and durations that allowed the sedimentation of the nanoparticles without significant sedimentation of any albumin and/or rapamycin not associated with the nanoparticles. The sedimented nanoparticles were separated from the supernatant and lyophilized. The mDSC scan (ramped at 5° C./min) showed a clear glass transition temperature ($T_g$) at around 92° C., followed by recrystallization, melting, and finally degradation. The presence of the $T_g$ supports that the rapamycin is amorphous in isolated nanoparticles. The temperature, however, is higher than that observed for pure amorphous rapamycin, which was between 84-87° C. There are two likely explanations for this observation. First, the presence of some amount of human albumin in the pellet could be acting as an anti-plasticizer. Second, the structural relaxation of the amorphous form in the presence of water (which increases the molecular mobility) could result in increased viscosity of the subsequently dried amorphous drug which leads to a higher $T_g$.

Example 4. Fourier Transform Infrared Spectroscopy of Rapamycin Nanoparticles

Fourier Transform Infrared Spectroscopy (FTIR) was used to study the interactions between human albumin and rapamycin. Controls and selected samples of the pharmaceutical composition (see Table 1 of Example 1) were used in the study. The rapamycin in the pharmaceutical composition was approximately 10% w/w. This allowed comparison of the absorbance of the pharmaceutical composition with a physical mixture of the same percentage of rapamycin.

The FTIR spectrum of crystalline rapamycin showed two sharp peaks between 1600-1750 $cm^{-1}$ occurring at 1632 $cm^{-1}$ and 1716 $cm^{-1}$. The first peak corresponds to C=C stretch band of the drug while the second peak represents the carbonyl group stretches. A peak was also observed at 2930 $cm^{-1}$ due to the presence of alkyl CH stretch in the macrocyclic group. In the amorphous form the peaks shifted to higher wavenumbers indicating slightly weaker interactions relative to the crystalline form. The peaks were also considerably broadened due to the availability of greater degrees of freedom in the disordered state. FTIR spectra of pure lyophilized human albumin showed only a few broad peaks with the main peaks being at 1643 $cm^{-1}$ and 1528 $cm^{-1}$.

The FTIR spectrum of the pharmaceutical composition (lyophilized cake, containing approximately 10% of rapamycin) had no additional peaks as compared to that of a physical mixture of 10% (w/w) of crystalline rapamycin in lyophilized human albumin. However, even though the physical mixture still exhibited the characteristic peak of rapamycin at 1716 $cm^{-1}$, this peak was absent from the from the pharmaceutical composition spectrum. Since at least a broad peak at 1717 $cm^{-1}$ of the amorphous form can be expected to be present in the drug product spectrum, the complete absence of this peak indicates hydrogen bonding of the drug CO group with the acidic groups of the human albumin which shifts the stretching peak to lower wavenumbers and overlap with the human albumin peaks in the region. There were also peak shifts in the human albumin spectrum that occurred towards higher wavenumbers. The lack of the characteristic peak at 1717 $cm^{-1}$ of the amorphous rapamycin and the shift in the stretching peaks of the human albumin were indicative of a molecular level interaction between the two compounds resulting in a change in the conformation of the protein. The peaks at 1643 $cm^{-1}$ and 1528 $cm^{-1}$ in human albumin represent the amide 1 and the amide II bands, respectively, with the amide I group being more sensitive to secondary structure changes. Shifts in these peaks generally represent molecular level interaction of the drug with the CO and CN groups of the polypeptide. Therefore, the peak shift from 1643 $cm^{-1}$ to 1648 $cm^{-1}$ would represent interaction between the rapamycin and human albumin in the lyophilized drug product which was not observed in the physical mixture.

The FTIR spectrum of nanoparticles isolated from reconstituted pharmaceutical composition showed the characteristic peak of amorphous rapamycin as well as peaks matching that of lyophilized human albumin. The ratio of peaks at 1644 $cm^{-1}$ and 1717 $cm^{-1}$ is much higher in the isolated nanoparticles as compared to the amorphous rapamycin control, indicating that this sample still had considerable amount of human albumin interacting with the drug nanoparticles.

Example 5. Nuclear Magnetic Resonance Spectroscopy of Rapamycin Nanoparticles

A $^{13}C$ solid state NMR study was performed on controls and selected samples of the pharmaceutical composition (see Table 1 of Example 1) to understand the physical state of rapamycin and human albumin in the pharmaceutical composition drug product.

The chemical shifts between crystalline and amorphous rapamycin were generally consistent with each other; except that the downfield carbonyl signals were broadened out beyond 220 ppm which was mostly due to the large chemical shielding anisotropy of carbonyl groups. The broad linewidth of carbon resonances observed from the spectrum of amorphous rapamycin is characteristic of rapamycin in amorphous form and can be used as reference in analysis of the physical form of rapamycin in the pharmaceutical composition.

The spectrum of the pharmaceutical composition (lot #2, containing approximately 10% w/w of rapamycin) showed no additional peaks as compared to the sum of the spectra of amorphous rapamycin and lyophilized human albumin. The observation indicates that there are no additional covalent bonds formed in the pharmaceutical composition drug product, and there is no chemical interaction occurred between rapamycin and human albumin in the pharmaceutical composition drug product. By comparing the spectrum of amorphous rapamycin, which is used as a control, and the pharmaceutical composition, the line shape and the chemical shifts of drug signals (i.e., amorphous rapamycin) in the pharmaceutical composition remain unchanged as compared with the control. The physical state of rapamycin in the pharmaceutical composition drug product is confirmed as amorphous form.

A series of stability samples of the pharmaceutical composition drug products (from initial time point, 24 months, and more than 36 months of storage between 5° C. and under 25° C./60% RH) were analyzed by solid state NMR. The NMR data indicated that spectral features in each spectrum, such as peak shape, and chemical shifts, are consistent, and the rapamycin in the pharmaceutical composition drug products remains as amorphous form under various stability storage, within shelf life (such as 24 months), and beyond (more than 36 months).

Comparison of the NMR spectra of the pharmaceutical composition (lot #2) and amorphous rapamycin showed a down-field shift of carbonyl carbons and an up-field shift of vinyl carbons in rapamycin. In the spectrum of amorphous rapamycin, two of the carbonyl carbons appear at 169 ppm; however, they are not observed in the spectrum of the pharmaceutical composition. It is believed that the carbonyl carbons are shifted downfield and are overlapped with the carbonyl signal of human albumin at 175 ppm. This is proven by measuring and comparing the intensity of three carbonyl signals from human albumin, rapamycin, and the pharmaceutical composition. The down-field shift from 169 to 175 ppm is mostly due to the hydrogen bonding between the carbonyl groups in rapamycin and the N-terminus of amino acids in human albumin. A similar outcome was seen in the FTIR spectra as well with the drug carbonyl stretch not being observed in the pharmaceutical composition drug product due to a shift to lower wavenumbers from 1717 cm$^{-1}$ to 1649 cm$^{-1}$ and being obscured by the albumin carbonyl peak (which was shifted to slightly higher wavenumbers from 1643 cm$^{-1}$ to 1649 cm$^{-1}$). On the other hand, the up-field shift in the $^{13}$C NMR spectrum (about 2-3 ppm) of vinyl carbons in rapamycin suggests a different molecular environment of rapamycin vinyl chain in the pharmaceutical composition compared to the drug substance itself; and indicates that the interaction also exists between the rapamycin vinyl chain and the human albumin. The interaction may be resulting from lipophilic interactions through the rapamycin vinyl chain and the aromatic rings on human albumin, or electrostatic interactions between both molecules. Shifts in the amide I and amide II peaks in the FTIR spectrum also show that there is molecular level interaction of the drug with the CO and CN groups of the protein.

Example 6. Cryogenic Transmission Electron Microscopy of Rapamycin Nanoparticles Cryogenic transmission electron microscopy (Cryo-TEM) was used to characterize the morphology, size, shape, and internal structure of the nanoparticles in the pharmaceutical composition drug product. The main advantage of Cryo-TEM, compared to other electron microscopy methods such as Transmission Electron Microscopy (TEM) and Scanning electron Microscopy (SEM), is that the nanoparticles can be studied in their native environment, at cryogenic temperatures, which minimizes perturbation of the reconstituted drug product during sample preparation.

Four lots of the pharmaceutical composition drug product was studied: lot #1, lot #2, lot #3, and lot #11. In addition, lyophilized human albumin was studied for comparison.

Each sample (i.e., each drug product sample and lyophilized human albumin comparison) was reconstituted at the study site using 20 mL of normal saline (0.9% w/v NaCl). The samples were imaged undiluted within 24 hours of reconstitution.

Each sample was preserved in vitrified ice supported by holey carbon films on 400-mesh copper grids. Each sample was prepared by applying a 3 μl drop of sample suspension to a cleaned grid, blotting away with filter paper, and immediately proceeding with vitrification in liquid ethane. Grids were stored under liquid nitrogen until transferred to the electron microscope for imaging.

Electron microscopy was performed using a FEI Tecnai T12 electron microscope (serial number D1100), operating at 120 keV equipped with an FEI Eagle 4 k×4 k CCD camera. Vitreous ice grids were transferred into the electron microscope using a cryostage that maintains the grids at a temperature below −170° C.

Images of each grid were acquired at multiple scales to assess the overall distribution of the specimen. After identifying potentially suitable target areas for imaging at lower magnifications, high magnification images were acquired at nominal magnifications of 110,000× (0.10 nm/pixel), 52,000× (0.21 nm/pixel), and 21,000× (0.50 nm/pixel). The images were acquired at a nominal underfocus of −5 μm to −0.6 μm and electron doses of about 10-25 e$^-$/Å$^2$.

Images at each level of magnification for all four lots of the pharmaceutical composition were comparable. All images of the pharmaceutical composition have a high background of very small particles, similar to those observed in reconstituted human albumin, which is consistent with what would be expected for albumin.

More detailed image analysis was performed on lots #11 (selected image with annotations in FIG. 2) and #1 (selected image with annotations in FIG. 3), and was compared to human albumin alone. In the selected images, representative irregularly shaped particles with nonuniform internal density (IS), spherical particles with uniform density (SP), and small round particles (SRP) are indicated. The small round particles observed in the images of lots #11 and #1 were similar to the small round particles throughout the albumin-only sample.

In general, the Cryo-TEM studies revealed that all four lots of the pharmaceutical composition are similar in terms of their nanoparticles despite differences in the age of the drug products.

Visible in the samples and the human albumin-only sample were very small, round, dense particles that were widespread and were smaller than about 6 nm in diameter (see, e.g., FIGS. 2 and 3); these particles are consistent with what is expected for human albumin.

Visible in the lot #11 sample of the pharmaceutical composition were irregularly shaped particles displaying uneven internal densities. There were also spherical to oblong particles whose internal densities appeared uniform (see FIGS. 1 and 2). The variation in internal density observed for the irregular particles could be due to their particular shape. Particles ranged in size from about 20 to 120 nm in their longest dimension.

Figure 2:
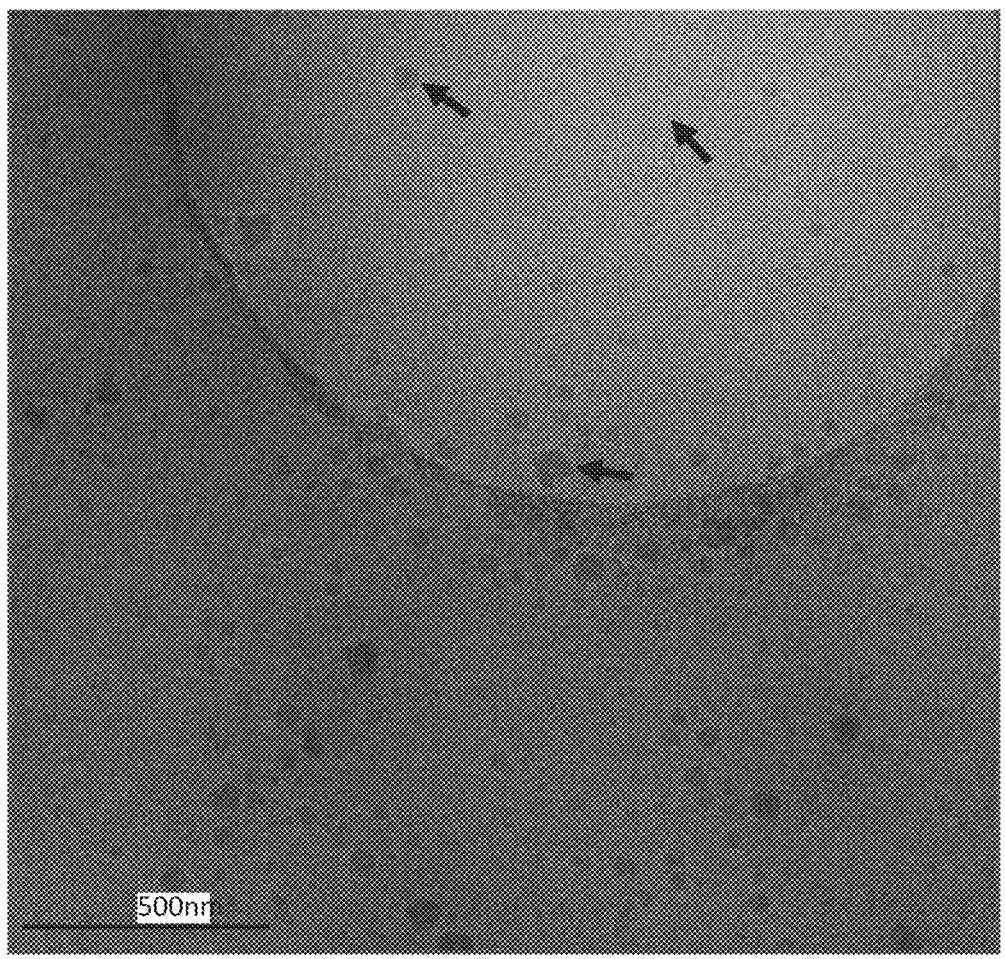
FIG. 2 depicts a Cryo-TEM image at 21,000× magnification of lot #11 with an observed irregularly shaped particles with nonuniform internal density (bottom arrow), a spherical particle with uniform density (top left arrow), and a small, round particle (top right arrow).

The sample also contained an abundance of very small, round, dense particles that were widespread and less than about 6 nm in diameter (see FIG. 2). The small particles are similar to those observed in a sample of lyophilized human albumin alone (reconstituted). These particles are likely human albumin.

Lot #1 contained similar types of particles as lot #11 (compare FIGS. 2 and 3). The particle size ranges of both samples were similar, as well: about 20 to 100 nm for lot #1 and about 20 to 120 nm for sample lot #11, in their longest dimensions. Both lot samples contained an abundance of very small, round particles that were widespread and similar to those observed in the lyophilized human albumin-only sample. These particles are likely human albumin (see FIGS. 2 and 3). There were no obvious differences in particle morphology when comparing images of both samples. Both lots contained a percentage of irregularly shaped/non-spherical particles.

Example 7. Particle Size of Rapamycin Nanoparticles

Mean particle size and size distribution of a pharmaceutical composition of nanoparticles comprising rapamycin coated with albumin was evaluated by Polarization Intensity Differential Scattering combined with Laser Diffraction (PIDS-LD). Lots of the pharmaceutical composition, samples tested, as well as testing results are summarized in Table 2, below.

TABLE 2

Summary of Rapamycin Nanoparticle Particle Size Measured by PIDS-LD

| | Particle Size volume Distribution (nm) | | |
|---|---|---|---|
| Lot number/Sample | Mean | <5% | <95% |
| #2, Release | 99 | 58 | 161 |
| #2, 6M, 25° C./60% RH | 101 | 58 | 163 |

TABLE 2-continued

Summary of Rapamycin Nanoparticle Particle Size Measured by PIDS-LD

| Lot number/Sample | Particle Size volume Distribution (nm) | | |
|---|---|---|---|
| | Mean | <5% | <95% |
| #2, 36M, 5° C. | 98 | 58 | 158 |
| #1, Release | 100 | 58 | 161 |
| #1, 6M, 25° C./60% RH | 102 | 58 | 169 |
| #1, 36M, 5° C. | 98 | 57 | 157 |
| #11, Release | 96 | 57 | 151 |
| #3, Release | 95 | 57 | 149 |
| #11, 6M, 25° C./60% RH | 99 | 60 | 146 |
| #3, 6M, 25° C./60% RH | 98 | 58 | 157 |
| Range (nm) | 95-102 | 57-60 | 146-169 |

The testing revealed that the fifth percentile (5%) and ninety-fifth percentile (95%) width of the volume particle size distribution of all clinical and stability lots tested is from 57 nm to 169 nm. These particle sizes are consistent with the U.S. Food and Drug Administration definition of nanoparticles (see U.S. FDA Office of Policy, "*Considering Whether an FDA-Regulated Product Involves the Application of Nanotechnology—Guidance for Industry*," FDA-2010-D-0530 (June 2014); and U.S. FDA Center for Drug Evaluation and Research, "*Drug Products, Including Biological Products, that Contain Nanomaterials—Guidance for Industry*," FDA-2013-S-0610 (December 2017)).

The mean of the volume particle size distribution was from 95 nm to 100 nm. The 5% and 95% of the volume distribution was from 57 nm to 60 nm and from 146 nm to 169 nm, respectively. The nanoparticles of the pharmaceutical composition maintained their mean size and size distribution after storage for up to 36 months at 5° C. and up to 6 months at 25° C./60% RH. There is no significant difference in particle size and size distribution between the lots tested, indicating the manufacturing process is highly reproducible.

An alternative method was also developed, utilizing Dynamic Light Scattering (DLS). DLS technique may be more suitable for measuring the size and distribution of nanoparticles. Mean particle size and size distribution of two recent lots of the pharmaceutical composition were evaluated by DLS. Mean particle size (intensity weighted) is reported as Z Average (nm) and size distribution is measured by Polydispersity Index (PDI). The DLS results are summarize in Table 3, below. The PIDS-LD results are included for comparison.

TABLE 3

Rapamycin Nanoparticle Particle Size Distribution Measured by DLS

| Lot Number/Storage | Z Average | PDI | Corresponding sample mean particle size (nm) measured by PIDS-LD |
|---|---|---|---|
| #11, Release | 90 | 0.15 | 96 |
| #11, 1M, 5° C. | 89 | 0.15 | 95 |
| #11, 3M, 5° C. | 93 | 0.16 | 96 |
| #11, 6M, 5° C. | 88 | 0.14 | 97 |
| #11, 1M, 25° C./60% RH | 89 | 0.14 | 95 |
| #11, 3M, 25° C./60% RH | 88 | 0.15 | 97 |
| #11, 6M, 25° C./60% RH | 89 | 0.15 | 99 |
| #3, Release | 89 | 0.15 | 95 |
| #3, 1M, 5° C. | 90 | 0.15 | 95 |
| #3, 3M, 5° C. | 89 | 0.14 | 95 |
| #3, 6M, 5° C. | 89 | 0.15 | 98 |
| #3, 1M, 25° C./60% RH | 90 | 0.15 | 97 |

TABLE 3-continued

Rapamycin Nanoparticle Particle Size Distribution Measured by DLS

| Lot Number/Storage | Z Average | PDI | Corresponding sample mean particle size (nm) measured by PIDS-LD |
|---|---|---|---|
| #3, 3M, 25° C./60% RH | 89 | 0.15 | 95 |
| #3, 6M, 25° C./60% RH | 87 | 0.14 | 98 |
| Range (nm) | 87 to 93 | 0.14 to 0.16 | 95 to 99 |

The mean of the intensity weighted particle size distribution reported as Z-average by DLS is from 87 nm to 93 nm. The particle size distribution measured by PDI is from 0.14 to 0.16. There is no significant difference in particle size and size distribution between the lots tested and stability samples (different time points and storage conditions) tested.

Example 8. Zeta Potential of Rapamycin Nanoparticles

Zeta potential testing was performed to evaluate the surface charge of nanoparticles of a pharmaceutical composition of nanoparticles comprising rapamycin and human albumin. Selected samples from lots #1, #2, #3, and #11 were tested for zeta potential. The samples tested and results are summarized below in Table 4.

TABLE 4

Zeta Potential of Rapamycin Nanoparticles

| Lot Number | Storage Conditions | Zeta potential (mV) |
|---|---|---|
| #2 | Over 36 months at 5° C. | −37.9 |
| #1 | Over 36 months at 5° C. | −35.1 |
| #11 | Initial | −38.3 |
| #11 | 6 months at 5° C. | −34.7 |
| #11 | 6 months at 25° C./60% RH | −34.1 |
| #3 | Initial | −36.4 |
| #3 | 6 months at 5° C. | −38.4 |
| #3 | 6 months at 25° C./60% RH | −35.0 |
| Range | | −34.1 to −38.4 |

The zeta potential of the pharmaceutical composition was approximately −36 mV. This may indicate that a human albumin layer on the nanoparticles of the pharmaceutical composition created a negative charge on the nanoparticles. The negative charge on the nanoparticles imparts electrostatic stabilization by creating a repulsion between the nanoparticles, thereby preventing aggregation. The zeta potential of the nanoparticles is maintained during storage.

Example 9. Osmolality of Rapamycin Nanoparticles

Osmotic pressure is fundamentally related to all biological processes that involve diffusion of solutes or transfer of fluids through membranes. The difference between the osmolalities of normal human plasma and parenterally administered fluids should be minimized to reduce any discomfort upon administration. The osmolality of normal human plasma is approximately 285 mOsm/kg. The osmolality of selected samples of lots of the pharmaceutical composition, after reconstitution in 0.9% sodium chloride, were evaluated. The osmolality values of the reconstituted pharmaceutical composition ranged from 325 to 337 mOsm/kg with no significant difference observed among the lots and storage conditions evaluated. The samples tested and corresponding osmolality data are provided in Table 5 below.

TABLE 5

Osmolality of Rapamycin Nanoparticles

| Lot Number | Storage Conditions | Osmolality (mOsm/kg) |
|---|---|---|
| #13 | Initial | 329 |
| #13 | 6 months at 5° C. | 328 |
| #13 | 6 months at 25° C./60% RH | 325 |
| #13 | 36 months at 5° C. | 327 |
| #13 | 36 months at 25° C./60% RH | 325 |
| #2 | Initial | 337 |
| #1 | Initial | 333 |
| #11 | Initial | 333 |
| #3 | Initial | 337 |
| | Range (mOsm/kg) | 325 to 337 |

Example 10. Viscosity of Rapamycin Nanoparticles

The rheological property dynamic viscosity of the pharmaceutical composition drug product was determined. Selected samples from lots of the pharmaceutical composition were tested. The samples tested and corresponding viscosity data are provided in Table 6 below.

TABLE 6

Viscosity of Rapamycin Nanoparticles

| Lot Number | Storage Conditions | Viscosity |
|---|---|---|
| #2 | Over 36 months at 5° C. | 1.30 |
| #1 | 36 months at 5° C. | 1.34 |
| #11 | Initial | 1.31 |
| #3 | Initial | 1.30 |
| #11 | 6 months at 5° C. | 1.31 |
| #3 | 6 months at 5° C. | 1.33 |
| #11 | 6 months at 25° C./60% RH | 1.33 |
| #3 | 6 months at 25° C./60% RH | 1.33 |
| | Range | 1.30 to 1.34 |

The dynamic viscosity of the reconstituted drug product was 1.30 to 1.34 centipoise (cP) at 25° C. The dynamic viscosity of the reconstituted drug product is similar to the dynamic viscosity of water (0.89 cP at 25° C.). The similarity in the dynamic viscosity minimizes the possibility of any adverse effects related to fluidity of the product that may be caused upon intravenous (IV) administration of the pharmaceutical composition. No significant change in viscosity was observed among the lots and storage conditions evaluated.

Example 11. Oligomer Composition of Human Albumin in Rapamycin Nanoparticle Drug Product The total oligomer composition of human albumin in the pharmaceutical composition drug product was assayed using size exclusion chromatography (SEC) coupled with a UV detector. Lyophilized samples were reconstituted in saline and diluted in saline to 0.18 mg/mL rapamycin. The diluted samples were injected on the SEC column with a 0.10 M $K_2HPO_4$ in 7.5% methanol mobile phase. The samples and composition data are summarized below in Table 7.

TABLE 7

Composition of Human Albumin in Rapamycin Nanoparticle Drug Product

| Lot Number/ Storage Conditions | Human Albumin Composition (%) | | | |
|---|---|---|---|---|
| | Monomer | Dimer | Oligomer | Polymer |
| #13, Release | 91.40 | 4.58 | 0.62 | 3.47 |
| #2, Release | 90.06 | 4.94 | 0.63 | 4.37 |
| #2, 24M, 5° C. | 89.41 | 5.84 | 0.74 | 4.01 |
| #2, 36M, 5° C. | 88.02 | 6.99 | 0.91 | 4.08 |
| #1, Release | 90.88 | 4.08 | 0.52 | 4.53 |
| #1, 24M, 5° C. | 87.62 | 6.87 | 1.01 | 4.51 |
| #11, Release | 89.27 | 5.58 | 0.83 | 4.32 |
| #11, 6M, 5° C. | 88.81 | 6.11 | 0.63 | 4.45 |
| #3, Release | 89.97 | 4.96 | 0.82 | 4.25 |
| #3, 6M, 5° C. | 88.60 | 6.21 | 0.58 | 4.60 |
| #11, 6M, 25° C./60% RH | 83.89 | 10.14 | 1.42 | 4.55 |
| #3, 6M, 25° C./60% RH | 84.04 | 10.04 | 1.40 | 4.52 |

Figure 4:
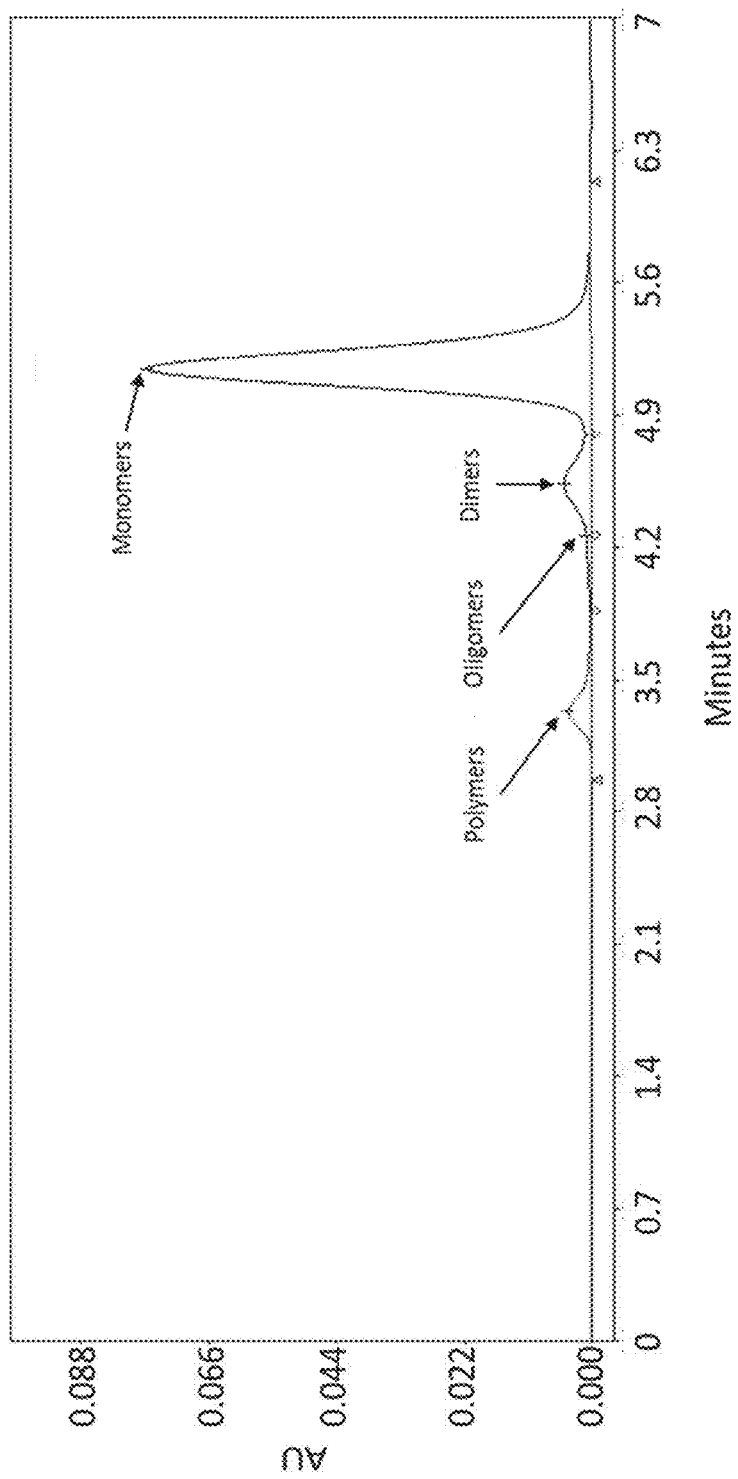
FIG. 4 depicts a representative chromatograph of the pharmaceutical composition comprising rapamycin and albumin (lot #1 after 12 months of storage at 5° C.) as measured by size exclusion chromatography (SEC). Peaks corresponding to monomer, dimer, polymer, and oligomers (which can be identified by suitable techniques such as mass spectrometry) are indicated on the chromatograph.

A sample chromatograph from lot #1 is depicted in FIG. 4. Monomers, dimers, and polymers of albumin were identified as distinct peaks (the apex of each peak is identified by hash mark in FIG. 4). The molecular weight identity of the albumin in the oligomers peak may be determined by any suitable means well-known in the art, including mass spectrometry such as MALDI-TOF-MS. There were no significant differences in the manufacturing process for the tested lots. The data confirm that the manufacturing process produces drug product with consistent total oligomer composition profile of human albumin. There is no significant change in oligomer profiles resulting from long-term 5° C. storage. It can be observed, however, a shift towards less monomers in the 25° C./60% RH stressed condition.

Example 12. Analysis of Rapamycin Associated with Nanoparticles in Rapamycin Nanoparticle Drug Product Ultracentrifugation was coupled with HPLC assays to determine the rapamycin and human albumin composition of supernatant and isolated nanoparticles from a reconstituted suspension of the pharmaceutical composition.

The ultracentrifugation technique coupled with HPLC methods allows for the determination of the concentration of rapamycin and human albumin in both solution (supernatant) and nanoparticle (pellet) fractions of the reconstituted suspension. The technique selectively sediments or pellets the rapamycin nanoparticles at a centrifugation speed and duration (50,000 rpm for 41 minutes) that only the rapamycin nanoparticles to sediment as a pellet.

Following ultracentrifugation of the reconstituted suspension, the supernatant and nanoparticle fractions were removed and assayed for rapamycin and human albumin using HPLC methods. A 4% human albumin solution was ultracentrifuged at the same time to serve as a system suitability check which met all result requirements for each ultracentrifugation experiment.

Greater than 98% of the total rapamycin resides in the nanoparticles (pellet) and less than 2% resides in the solution (supernatant). On the other hand, greater than 95% of the albumin resides in the solution (supernatant) and less than 5% in the nanoparticles (pellet). The human albumin to rapamycin ratio in the nanoparticles in the nanoparticle fraction was approximately 35:65 (w/w). The samples of the pharmaceutical composition tested and the results of the analysis are summarized in Table 8 below.

TABLE 8

Composition of Human Albumin in Rapamycin Nanoparticle Drug Product

| Sample Lot | Rapamycin in supernatant (µg/ml) | Rapamycin in pellet (µg/ml) | Human Albumin in supernatant (mg/ml) | Human Albumin in pellet (mg/ml) | Human Albumin:Rapamycin Ratio in Nanoparticles (w %/w %) |
|---|---|---|---|---|---|
| #2, 32M/° C. | 33.0 | 4452 | 38.0 | 2.4 | 35:65 |
| #2, 32M, 25° C./60% RH | 38.2 | 4394 | 37.9 | 2.6 | 37:63 |
| #1, 16M/5° C. (Clinical Material) | 34.7 | 4551 | 37.8 | 2.5 | 35:65 |
| #1, 16M/5° C. | 34.0 | 4719 | 38.4 | 2.4 | 33:67 |
| #11, Release | 46.9 | 4376 | 38.5 | 2.4 | 36:64 |
| #3, Release | 44.3 | 4407 | 37.3 | 2.3 | 35:65 |
| #11, 6M/5° C. | 42.4 | 4386 | 38.9 | 2.5 | 36:64 |
| #3, 6M/5° C. | 44.0 | 4364 | 37.2 | 2.3 | 34:66 |
| #11, 6M/25° C./60% RH | 33.0 | 4356 | 39.4 | 2.4 | 36:64 |
| #3, 6M/25° C./60% RH | 46.5 | 4361 | 37.4 | 2.2 | 34:66 |

Example 13. Solubility and Dissolution Kinetics in Rapamycin Nanoparticle Drug Product The change in intensity of light scattering in diluted samples of the reconstituted suspension of the pharmaceutical composition was used as a measure to determine the in vitro dissolution or disintegration of the nanoparticles, which implicates the release of rapamycin from the nanoparticles of the pharmaceutical composition. The percent of rapamycin released at any given time was determined using the light scattering intensity at zero time and at time t. The intensity of light scattering, measured by the Malvern Zetasizer Nano, is relative to the number of nanoparticles present in the pharmaceutical composition. If there are no nanoparticles in the diluted samples of the reconstituted suspension of the pharmaceutical composition, or if the percent release of rapamycin from the nanoparticles into the solution is 100%, then the light scattering intensity approaches zero. If the release of rapamycin from the nanoparticles is controlled by the solubility limit and the reconstituted suspension is diluted to a concentration within the solubility range, then the nanoparticles should rapidly dissolve, causing the rapamycin to be readily released from the nanoparticles of the pharmaceutical composition, and the light scattering intensity will approach zero.

Figure 5:
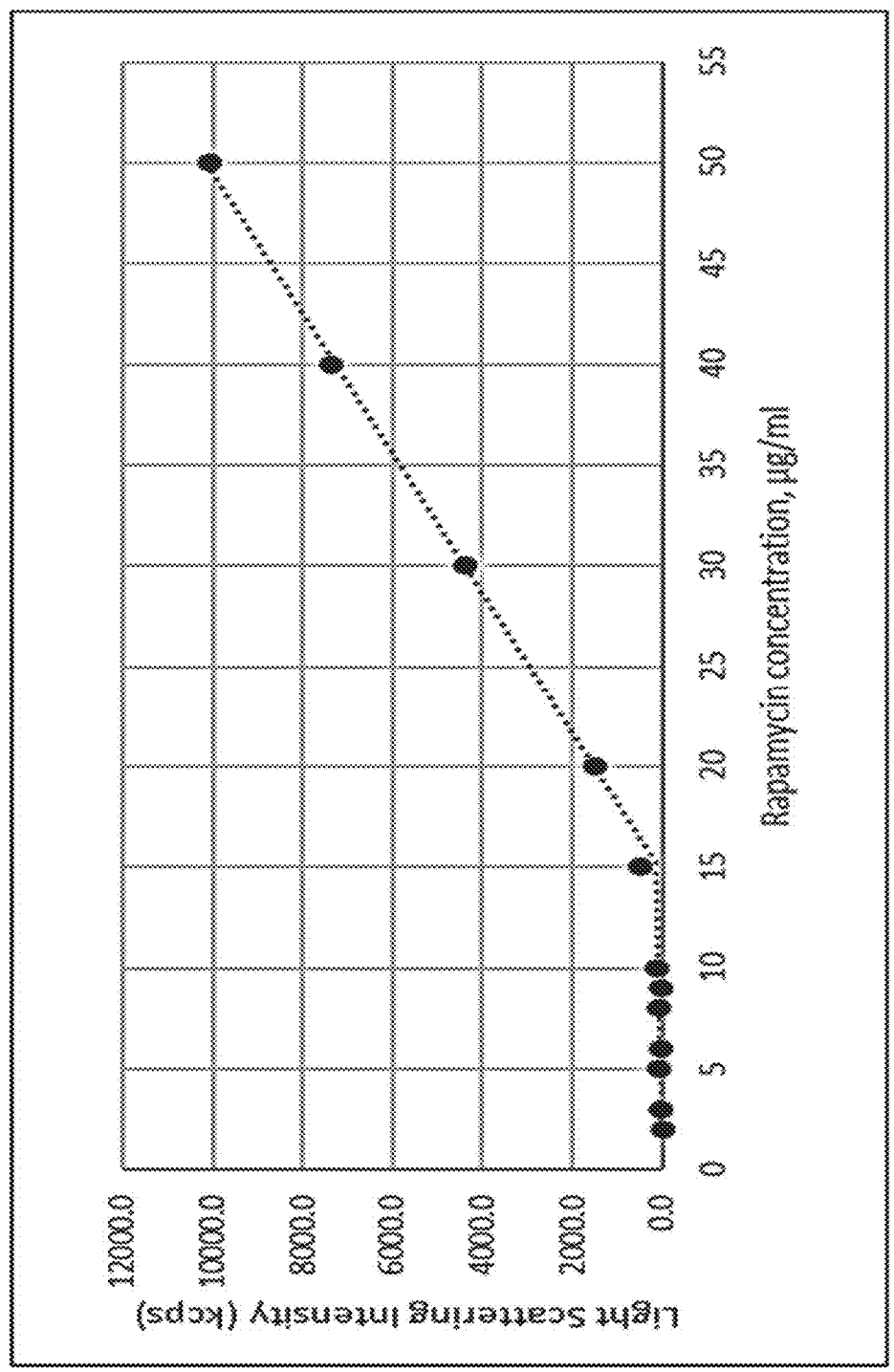
FIG. 5 depicts light scattering intensity (kcps) as a function of rapamycin concentration from a reconstituted suspension of the pharmaceutical composition comprising nanoparticles comprising rapamycin and albumin. When the suspensions were diluted to concentrations below the rapamycin solubility, the nanoparticles completely disintegrated and dissolved (see left 7-8 data points on graph). However, when the suspensions were diluted to concentrations above the rapamycin solubility, the nanoparticles only partially disintegrated and dissolved, and light scattering was observed (see right 4-5 data points on graph). The light scattering intensity increases linearly with increasing rapamycin concentration above the solubility point of rapamycin (calculated to be 16.1±1.8 µg/ml in 0.9% saline solution).

Prior to in vitro release test, the solubility of rapamycin in reconstituted suspension of the pharmaceutical composition in 0.9% saline was evaluated by measuring the scattered light intensity due to nanoparticles. As illustrated in FIG. 5, when the reconstituted suspensions of the pharmaceutical composition were diluted to concentrations below the rapamycin solubility, the nanoparticles completely disintegrated and dissolved, and showed no concentration dependent light scattering. When the suspensions were diluted to concentrations above the rapamycin solubility, the nanoparticles only partially disintegrated and dissolved, and light scattering was observed. The light scattering intensity increases linearly with increasing rapamycin concentration as indicated by the four rightmost data points of FIG. 5. The solubility of rapamycin was determined as the concentration at which the intensity of the scattered light begins to increase linearly. The solubility of rapamycin in the reconstituted suspension in 0.9% saline was determined to be 16.1±1.8 µg/ml (mean±95% CI).

Based on the solubility of rapamycin in the reconstituted suspension, the suspension was diluted in 0.9% saline solution to achieve two concentrations of rapamycin: approximately 5 µg/ml (below the solubility) and 25 µg/ml (above the solubility).

Figure 6:
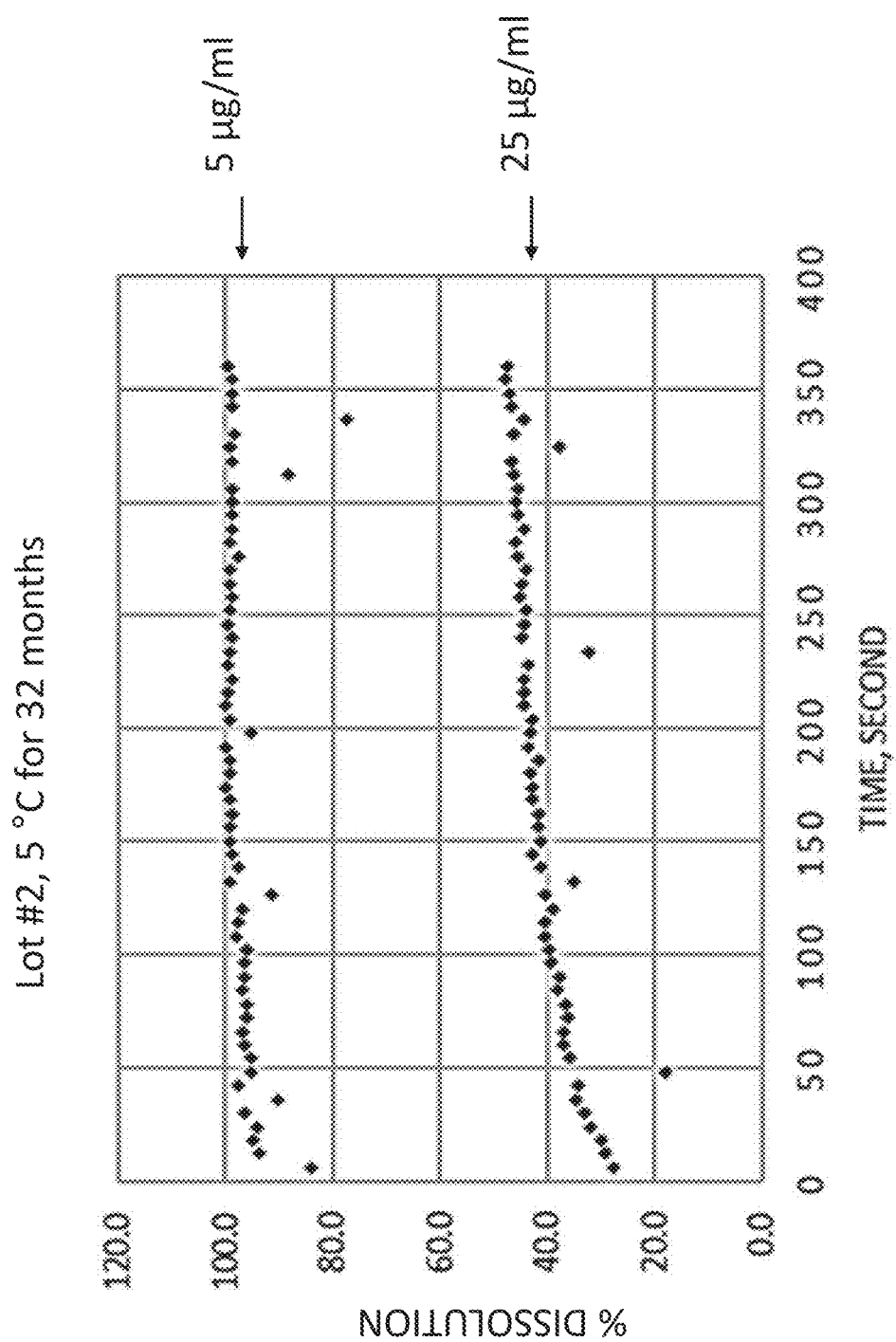
FIG. 6 depicts the dissolution profile of a reconstituted suspension of the pharmaceutical composition comprising nanoparticles comprising rapamycin and albumin (lot #2; stored for 32 months at 5° C. before reconstitution) at 5 µg/ml (top line) or 25 µg/ml (bottom line) rapamycin concentration.
Figure 7:
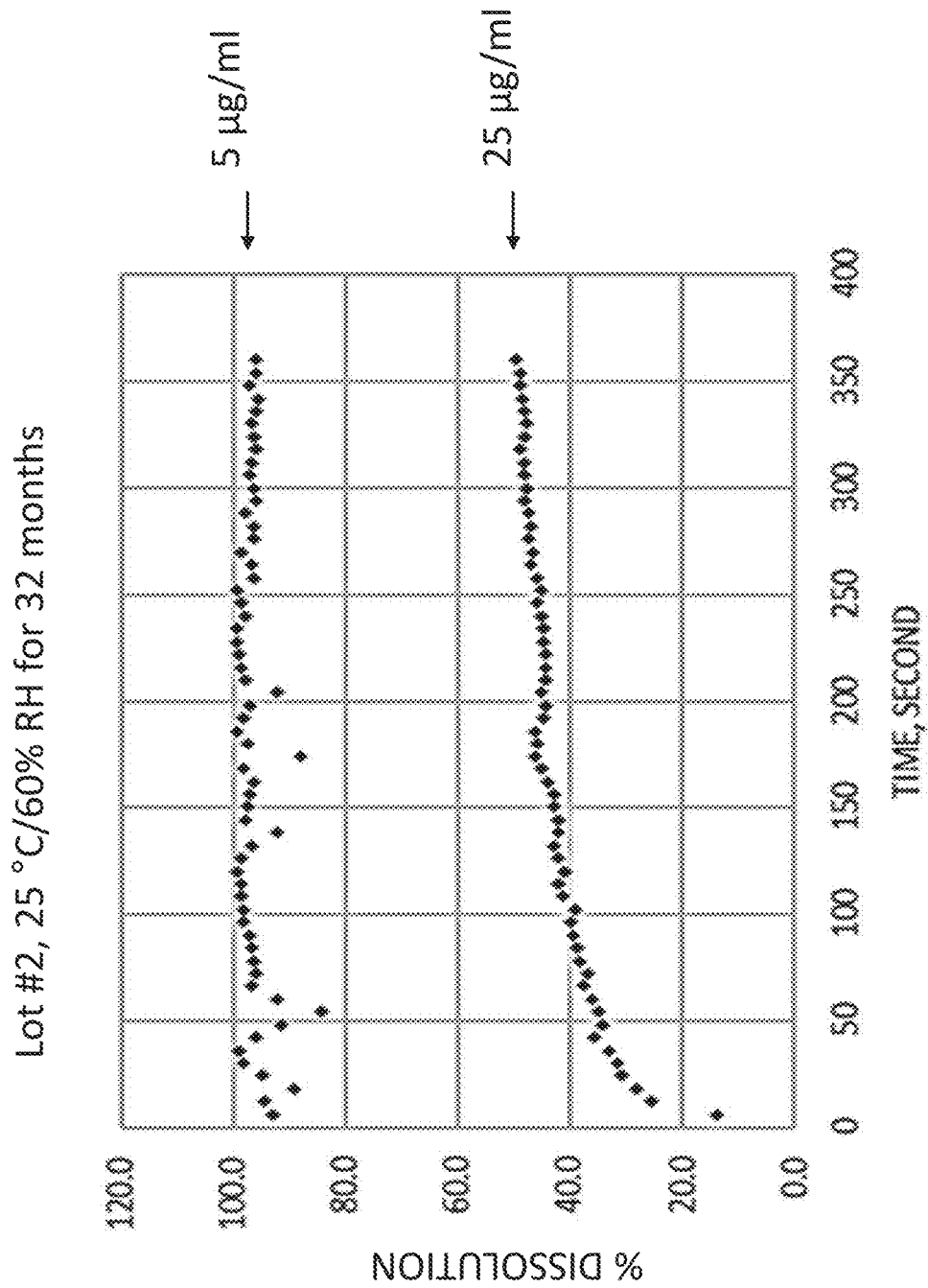
FIG. 7 depicts the dissolution profile of a reconstituted suspension of the pharmaceutical composition comprising nanoparticles comprising rapamycin and albumin (lot #2; stored for 32 months at 25° C./60% RH before reconstitution) at 5 µg/ml (top line) or 25 µg/ml (bottom line) rapamycin concentration.
Figure 8:
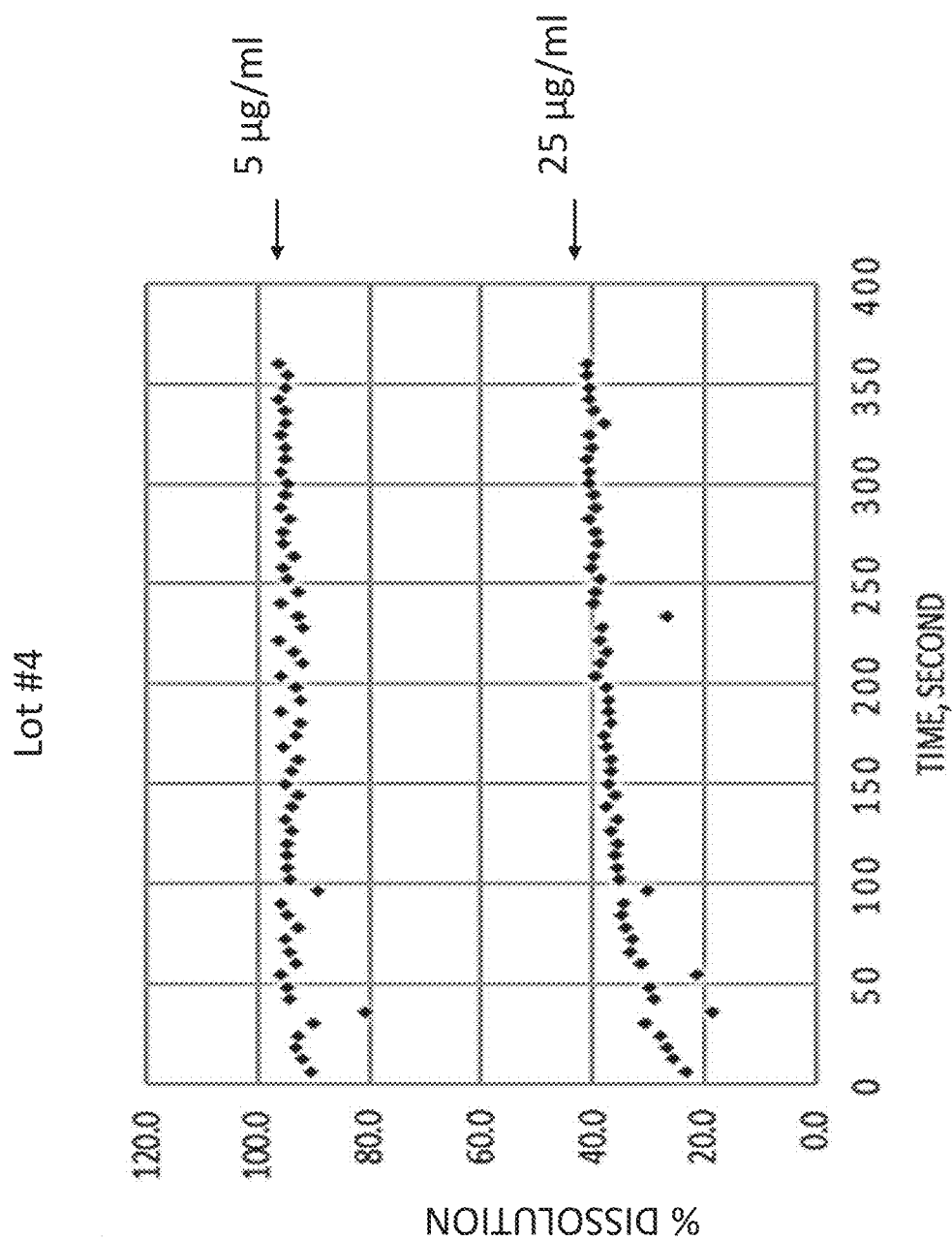
FIG. 8 depicts the dissolution profile of a reconstituted suspension of the pharmaceutical composition comprising nanoparticles comprising rapamycin and albumin (lot #4) at 5 µg/ml (top line) or 25 µg/ml (bottom line) rapamycin concentration.

In vitro nanoparticle dissolution for these diluted suspensions was determined using Dynamic Light Scattering (DLS), which measures the change of light scattering intensity caused by changes in rapamycin nanoparticle concentration. The percent of rapamycin nanoparticles that remain undissolved at any given time was determined by dividing the experimentally measured value of the light scattering intensity of the sample by the theoretical light scattering intensity predicted from the solubility plot. The percent of rapamycin nanoparticles dissolved at any given time was then derived by subtracting the percent of rapamycin nanoparticles undissolved from 100%. Representative dissolution profiles are depicted in FIGS. 6 and 7 for Lot #2 after storage at 5° C. for 32 months or after storage at 25° C./60% RH for 32 months, and for Lot #4 after reconstitution (FIG. 8). No significant differences were observed between lots or between storage conditions.

The results from the in vitro release profiles of the pharmaceutical composition demonstrate that rapamycin nanoparticle dissolution from the reconstituted suspension of the pharmaceutical composition is solubility dependent with each dissolution profile showing a similar trend. When the concentration of rapamycin in the reconstituted suspension is greater than the reported solubility range, rapamycin is liberated from the nanoparticles by a burst followed by a slow release until the solubility limit is reached after which the dissolution stops. However, when the concentration of rapamycin is within the solubility, the dissolution is instantaneous.

Approximately 80% of the nanoparticles are dissolved and hence rapamycin is dissolved before the first measurement is obtained. Due to the very rapid kinetics, a determination of the percent of nanoparticles dissolved and therefore rapamycin dissolved at the time of sample dilution (of the reconstituted suspension) cannot be measured accurately.

Example 14. Albumin Oligomerization Study

A study was undertaken using size exclusion chromatography with multi-angle light scattering and refractive index detection (SEC-MALS-RI) to further characterize the albumin oligomer status of albumin in the final albumin-based rapamycin nanoparticle product. Manufactured lots of lyophilized product (vials comprising 100 mg of rapamycin in rapamycin protein-bound particles) were reconstituted with 20 ml saline to yield 5 mg/ml rapamycin. Samples were centrifuged at 14,000 rpm in a Beckman Coulter Microfuge 22R centrifuge for 1 hour at 24° C. Samples could be aliquoted and frozen, but only one freeze/thaw cycle was allowed. Normalization constants were determined with U.S.P. Albutein® 25% (Lot No. B3ALC00082) standard at 4 mg/ml concentration in saline. 100 µl of each sample was injected in a BioSep-53000 (<7×10$^5$ Da; 5 µm) column with a saline mobile phase at a flow rate of 1 ml/min. Wyatt DAWN HELEOS II and Wyatt Optilab T-rEX detectors were used. Nanoparticle samples were diluted 10-fold in saline before injection. Reconstituted stock samples, pellets from centrifugation, and supernatants from centrifugation were tested. As a control for centrifugation, samples were also resuspended without separating supernatant to test stability of the oligomer profile from centrifugation.

The following lots of rapamycin protein-bound product were tested: lot #1, lot #2, lot #3, lot #8, lot #10, lot #14, and lot #16. Samples were tested without centrifugation (stock) or after centrifugation (pellet and supernatant). As a control, samples were also resuspended after pelleting, to demonstrate the pelleting did not substantially alter the oligomer profile.

TABLE 9

SEC-MALS-RI Oligomer study

| Sample | Monomer (%) | Dimer (%) | Trimer (%) |
|---|---|---|---|
| Lot #1 before centrifugation | 89.0 | 9.2 | 1.8 |
| Lot #1 after centrifugation | 88.3 | 9.6 | 2.3 |
| Lot #1 pellet | 77.0 | 13.5 | 9.5 |
| Lot #1 supernatant | 89.3 | 9.2 | 1.5 |
| Lot #2 before centrifugation | 87.7 | 9.9 | 2.4 |
| Lot #2 after centrifugation | 87.8 | 9.9 | 2.3 |
| Lot #2 pellet | 74.1 | 15.2 | 10.6 |
| Lot #2 supernatant | 88.9 | 9.3 | 1.7 |
| Lot #3 before centrifugation | 89.1 | 8.9 | 2.0 |
| Lot #3 after centrifugation | 89.2 | 8.8 | 2.0 |
| Lot #3 pellet | 80.0 | 12.4 | 7.6 |
| Lot #3 supernatant | 90.1 | 8.4 | 1.5 |
| Lot #8 before centrifugation | 86.3 | 10.9 | 2.9 |
| Lot #8 after centrifugation | ND | ND | ND |
| Lot #8 pellet | 77.7 | 13.9 | 8.4 |
| Lot #8 supernatant | 87.3 | 10.3 | 2.3 |
| Lot #10 before centrifugation | 89.1 | 8.8 | 2.1 |
| Lot #10 after centrifugation | ND | ND | ND |
| Lot #10 pellet | 74.0 | 15.5 | 10.5 |
| Lot #10 supernatant | 89.9 | 8.4 | 1.7 |
| Lot #14 before centrifugation | 90.7 | 7.9 | 1.4 |
| Lot #14 after centrifugation | ND | ND | ND |
| Lot #14 pellet | 78.5 | 12.9 | 8.6 |
| Lot #14 supernatant | 89.6 | 8.7 | 1.7 |
| Lot #16 before centrifugation | 89.1 | 8.8 | 2.1 |
| Lot #16 after centrifugation | 89.2 | 8.8 | 2.0 |
| Lot #16 pellet | 74.2 | 16.2 | 9.6 |
| Lot #16 supernatant | 90.0 | 8.4 | 1.6 |

Example 15. Drug Release Study

A study was undertaken to analyze rapamycin drug release from 12 lots of a batch of the pharmaceutical composition (Lots #1-10 and Lots 14-15) using a stable isotope tracer ultrafiltration assay (SITUA) (see Skoczen et al., *Stable Isotope Method to Measure Drug Release from Nanomedicines*, J. Control Release, 220(A):169-174 (2015). Drug release was examined at 10 µg/ml and 500 µg/ml of rapamycin following 10 minutes of incubation. Briefly, stable, isotope-labeled rapamycin was spiked into 4.5% human serum albumin (25% Albutein HSA diluted in 0.9% saline). MeOH-solvent rapamycin (as a control) or fresh reconstituted samples of each lot at 10 µg/ml or 500 µg/ml were added. After 10 minutes of equilibration at 29° C., a portion of the sample is taken and filtered using Vivacon® 10 kDa MWCO centrifuge devices prewarmed to 29° C. The sample and the ultrafiltrate are analyzed by LC-MS to determine the concentrations of normal rapamycin and isotope-labelled rapamycin. The ultrafilterable fraction of isotope-labeled rapamycin represents a measurement of free unbound fraction. The encapsulated and unencapsulated nanoparticle fractions can also be calculated.

TABLE 10

Lot comparison of drug release

| | 10 µg/ml | | 500 µg/ml | |
|---|---|---|---|---|
| Lot | Avg. Release (%) | SD/% CV | Avg. Release (%) | SD/% CV |
| Free rapamycin | 97.2 | 5.0/5.1 | 18.3 | 2.1/11.8 |
| Lot #1 | 94.7 | 2.0/2.2 | 16.7 | 1.2/7.5 |
| Lot #2 | 89.8 | 3.4/3.8 | 15.6 | 0.6/3.8 |
| Lot #3 | 89.7 | 3.2/3.5 | 15.1 | 0.7/4.6 |
| Lot #4 | 107.5 | 1.5/1.4 | 23.3 | 1.0/4.3 |
| Lot #5 | 107.7 | 3.1/2.9 | 24.7 | 0.7/2.8 |
| Lot #6 | 104.5 | 3.4/3.3 | 23.2 | 2.0/8.7 |
| Lot #7 | 99.9 | 4.3/4.3 | 19.5 | 1.0/5.3 |
| Lot #8 | 96.0 | 2.2/2.3 | 18.5 | 0.8/4.6 |
| Lot #9 | 99.1 | 2.3/2.3 | 19.3 | 1.5/7.8 |
| Lot #10 | 100.6 | 9.0/8.9 | 15.4 | 2.1/13.6 |
| Lot #14 | 100.7 | 5.2/5.2 | 16.1 | 0.9/5.4 |
| Lot #15 | 106.3 | 2.5/2.4 | 17.7 | 1.1/5.9 |

As summarized in Table 10, all lots displayed 89-106% calculated release at 10 µg/ml and 15-25% release at 500 µg/ml, similar to a free drug control, supporting solubility-dependent drug release and indicating a consistent formulation. Standard deviations and coefficients of variation are also indicated.

Example 16. Albumin-Bound Rapamycin Study

Rapamycin is present in both the nanoparticle and non-nanoparticle portion of the albumin-based rapamycin nanoparticle compositions. A study was undertaken to determine the levels of free and unbound rapamycin and albumin in several manufactured batches of the pharmaceutical composition. The pharmaceutical compositions from lots #1, #2, and #3 were reconstituted at a concentration of 5 mg/ml rapamycin.

Briefly, the nanoparticle portion of the composition was separated by centrifugation in a Microfuge 22R centrifuge at 14,000 rpm for 1 hour at 24° C. for each batch. The supernatant was separated and centrifuged at 14,000 rpm at 24° C. for 1 hour using a Microcon 10 kDa centrifugal device (Millpore, MRCPRT010, RC). The retentate in the device and the filtrate from the device was then analyzed for rapamycin content.

TABLE 11

Free Rapamycin Study

| Sample | Total Rapamycin mg/ml | Rapamycin in nanoparticle portion (%) | Protein-bound rapamycin in non-nanoparticle portion (%) | Unbound Rapamycin (%) | Filter-bound |
|---|---|---|---|---|---|
| Lot #1 | 4.62 ± 0.07 (n = 3) | 87 ± 2 (n = 5) | 9.7 ± 0.7 (n = 5) | 0.02 ± 0.01 (n = 5) | 3.3 ± 1.1 (n = 5) |

TABLE 11-continued

Free Rapamycin Study

| Sample | Total Rapamycin mg/ml | Rapamycin in nanoparticle portion (%) | Protein-bound rapamycin in non-nanoparticle portion (%) | Unbound Rapamycin (%) | Filter-bound |
|---|---|---|---|---|---|
| Lot #2 | 4.68 ± 0.09 (n = 5) | 86 ± 1 (n = 5) | 11.0 ± 0.5 (n = 5) | 0.02 ± 0.01 (n = 5) | 3.2 ± 0.3 (n = 5) |
| Lot #3 | 4.83 ± 0.09 (n 3) | 92 ± 6 (n = 5) | 8.5 ± 1.1 (n = 5) | 0.02 ± 0.01 (n = 5) | 2.7 ± 0.6 (n = 5) |

As summarized in Table 11, the majority of rapamycin was in the nanoparticle portion of the composition. Of the rapamycin in the non-nanoparticle portion, the majority was protein-bound, i.e., associated with albumin, and therefore found in the retentate of a 10 kDa centrifuge device. A proportion of rapamycin from the supernatant (between about 2.7% and about 3.3%) bound to the filter of the centrifuge device. No substantial differences were observed between different samples of each manufactured lot nor between each manufactured lot, indicating the manufacturing process is consistent.

Example 17. Manufacturing of Nanoparticle Composition

This example demonstrates a method of making an albumin/rapamycin nanoparticle composition (such as a pharmaceutical composition).

Emulsions were prepared to form albumin-rapamycin nanoparticles. The emulsions were optimized by testing different organic solvents at different ratios. An organic phase comprising chloroform and alcohol was tested at a 6:4 ratio of chloroform:ethanol or chloroform:isopropanol. An organic phase comprising chloroform and tert-butanol was tested at ratios of 6:4, 9:1, and 7:3 chloform:tert-butanol. Samples were also tested in the presence or absence of 0.6 M NaCl or 10% sucrose. An aqueous solution comprising 30 mg/ml human albumin (HA) was prepared. The albumin contained the stabilizers sodium caprylate (0.08 mM/g) and N-acetyltryptophanate (0.08 mM/g). The aqueous solution and various organic solutions were mixed at a 96:4 ratio of aqueous solution:organic solution in a high-shear homogenizer to form the crude emulsion. Crude emulsions were fed into a high-pressure homogenizer coupled to a wiped film evaporator. The post-evaporate (PE) suspension was pooled and held at about 2° C. to about 8° C. After holding and pooling, the PE was assayed for rapamycin (by RP-HPLC) and HA (by SEC-UV). Based on assay values, the PE suspension was diluted with a 20% HA solution to yield a rapamycin concentration of about 7 mg/ml rapamycin and 56 mg/ml albumin. The different preparation conditions were assayed for particle size (before and after 0.2 μm filtration) and for filterability through a 0.2 μm filter. The results are summarized in Table 10, below.

TABLE 10

Bench scale manufacturing experiments.

| Sample ID | Solvents | Z-average (nm) (unfiltered) | Z-average (nm) (filtered) | 0.2 μm Filterability (ml per filter) |
|---|---|---|---|---|
| Sample 1 | CHCl3:EtOH | 193.5 | 175.8 | 7 |
| Sample 2 | CHCl3:EtPH | 195.9 | 171.2 | 4-5 |
| Sample 3 | CHCl3:EtOH | 178.6 | 159.9 | 7 |
| Sample 4 | CHCl3:EtOH | 154.7 | 135.9 | 10 |
| Sample 5 | CHCl3:EtOH | 183.6 | 169.1 | 10 |
| Sample 6 | CHCl3:EtOH | 194.9 | 179.1 | 7 |
| Sample 7 | CHCl3:tBa | 191.4 | 175.6 | 10 |
| Sample 8 | CHCl3:IPA | 199.7 | 178.8 | 7-8 |
| Sample 9 | CHCl3:EtOH | 212.5 | 189.5 | 7.5 |
| Sample 10 | CHCl3:tBa | 134.6 | 83.3 | 10 |
| Sample 11 | CHCl3:tBa | 155.1 | 138.2 | 12-15 |
| Sample 12 | CHCl3:tBa | 224.0 | 153.9 | 2-3 |
| Sample 13 | CHCl3:EtOH | 174.1 | 148.2 | 5-7 |

Sample 11 demonstrated the best filterability based on volume per filter and low average particle size. Further, Sample 11 had reduced fibers as determined by light microscope, compared to the other samples.

The optimized conditions of Sample 11 are used to prepare commercial batches of the pharmaceutical composition. Diluted PE of the commercial batch are filtered through a 0.2 μm filter. Filtered product are aliquoted into approximately 5000-6000 depyrogenated vials and plugged with sterilized stoppers to yield sealed vials of the final product comprising lyophilized cake of about 100 mg rapamycin and about 800 mg albumin each. The atmosphere of each vile is replaced with nitrogen NF before stoppering. Each vial contains about 0.068 mM/vial of each of sodium caprylate and N-acetyltryptophanate and only trace or undetectable amounts of chloroform and tert-butanol. Each vial may be reconstituted with 20 ml of 0.9% NaCl to yield an injection of 5 mg/ml rapamycin.

Example 18. HPLC Assay of Content Uniformity and Identification of Rapamycin in the Pharmaceutical Composition An HPLC assay was developed to assess content uniformity and identification of rapamycin in the pharmaceutical composition. The assay uses reverse phase, isocratic HPLC with UV detection. Assay and identification of rapamycin by Retention Time Ratio (RTR) is accomplished by comparison to an external rapamycin standard. In general, if the pharmaceutical composition is provided in a dried form, it is first reconstituted (to about 5 mg/ml nominal rapamycin concentration) to form a suspension and then diluted (to about 100 μg/ml nominal rapamycin concentration) to form a working suspension. If the pharmaceutical composition is provided as a suspension, then it is diluted (to about 100 μg/ml nominal rapamycin concentration) to form the working suspension. The diluted working suspension of the pharmaceutical composition is then dissolved in an organic solvent to form a stable sample solution (at about 20 μg/ml nominal rapamycin concentration) immediately before assay.

Specifically, to assay the final lyophilized cake of the pharmaceutical composition, a nominal amount of rapamycin (such as a vial containing a nominal amount of 100 mg by mass rapamycin) of lyophilized cake of the pharmaceutical composition is reconstituted with 20 ml of water with a needle by directing the water onto the inside wall of a vial (to avoid foaming). After the water injection is complete, the vial sits for 5 minutes and the vial is then swirled and/or inverted for at least 2 minutes until complete dissolution of the lyophilized cake. The composition is then diluted in acetonitrile and water to a nominal concentration of 20 μg/ml of rapamycin for the assay.

To assay the pharmaceutical composition during the manufacturing process as described in Example 17, a sample of the post-evaporate (PE) suspension is prepared by diluting the PE to a nominal concentration of 20 μg/ml (by rapamycin) in water and acetonitrile.

As also described in Example 17, the PE suspension is adjusted to a nominal concentration of 7 mg/ml rapamycin by the addition of 20% HA. This adjusted suspension is then filtered to form the final filtration (FF) version of the pharmaceutical composition. To assay the FF, a sample is prepared by diluting the FF to a nominal concentration of 20 μg/ml (by rapamycin) in water and acetonitrile.

A working reference standard solution of rapamycin is prepared at a nominal concentration of 20 μg/ml rapamycin in 80:20 acetonitrile:water (v:v) from a stock reference standard of 1000 μg/ml rapamycin in acetonitrile.

A Waters Atlantis dC-18, 150×4.6 mm, 3 μm column (USP L1) is used at a column temperature of 45±3° C. Flow rate is 1.0 ml/min, injection volume is 10 μl, with a 80:20 methanol:water (v:v) mobile phase. The run time is 14 minutes. Acetonitrile is used as the wash solvent. 277 nm UV detection is used. The minor isomer of rapamycin, cis-rapamycin, has a longer retention time than the major isomer, trans-rapamycin.

The retention time ratio is calculated by comparing the retention time of the trans-rapamycin isomer peak of each sample divided by the retention time of the trans-rapamycin isomer peak of the reference standard of rapamycin. The RTR is deemed acceptable if it falls within an acceptance range, such as 0.98-1.02. The content uniformity of each sample is determined by comparing the total rapamycin peak area (sum of cis and trans rapamycin peak area) from each sample divided by the total rapamycin peak area of the reference standard of rapamycin, with the percent purity of the rapamycin standard known. The content uniformity of each sample is deemed acceptable if it falls within an acceptance range.

Example 19. HPLC Assay of Rapamycin Degradants

A method to specifically identify the degradation product seco-rapamycin was desired. Seco-rapamycin is the only degradation product detected in the pharmaceutical composition at both long term storage (e.g., at 5° C.) and accelerated storage (e.g., at 25° C./60% RH) for all tested batches of the pharmaceutical composition during the development process. Other rapamycin-like species are known, however, and are likely formed from the fermentation process during rapamycin production. Previous HPLC methods used for the pharmaceutical composition coeluted the fermentation process impurity, rapamycin dialdehyde, with seco-rapamycin. Thus, an RP-HPLC assay was developed to assess the major rapamycin degradation product, seco-rapamycin, in the pharmaceutical composition, and to resolve the seco-rapamycin from rapamycin dialdehyde.

The improved method is a reverse phase, gradient HPLC with UV detection. Identification of rapamycin by Retention Time Ratio (RTR) is accomplished by comparison to an external rapamycin standard. Seco-rapamycin, the only degradation product of rapamycin historically detected, is calculated by Area % on the chromatograph.

Rapamycin standards and samples are prepared as discussed in Example 18 to give sample solutions and reference standards at 20 μg/ml nominal rapamycin concentration each.

An Agilent Eclipse Plus C18, 100×3 mm, 1.8 μm column (USP L1) is used at a column temperature of 50±2° C. Flow rate is 0.5 ml/min, and the injection volume is 10 μl. The first mobile phase is 45% of 10 mM ammonium formate (0.05% formic acid, pH 3.5) and 55% acetonitrile. The second mobile phase is acetonitrile. The run time is 42 minutes. The gradient of the two mobile phases is summarized in table 11, below.

TABLE 11

HPLC assay gradient.

| Time (min) | Mobile Phase 1 (%) | Mobile Phase 2 (%) |
|---|---|---|
| 0 | 100 | 0 |
| 25 | 100 | 0 |
| 35 | 65 | 35 |
| 37 | 65 | 35 |
| 37.1 | 100 | 0 |
| 42 | 100 | 0 |

Using this method, seco-rapamycin (approximate RRT: 0.53), cis-rapamycin (approximate RRT: 1.15), and trans-rapamycin (standard RRT set to 1.0) are resolved. Human albumin has a short retention time and is fully resolved from all rapamycin peaks. Diluent-related peaks were not found to interfere with resolution of the rapamycin peaks.

Example 20. Stability Study of the Pharmaceutical Composition

A stability study was undertaken on lot #1 of the pharmaceutical composition over the course of 36 months. Lot #1 was supplied as a lyophilized cake in clear vials each containing nominal quantities of 100 mg rapamycin and 800 mg human albumin. Rapamycin was identified and quantified (rapamycin assay) by the HPLC method described in Example 18. Rapamycin impurities were initially (months 0-18 of the stability study) identified by a previous HPLC method. However, it was found that seco-rapamycin and rapamycin dialdehyde (a fermentation process impurity of rapamycin) coeluted, thus giving higher levels for seco-rapamycin. The improved HPLC method described in Example 19 was used to resolve seco-rapamycin for months 24 and 36 of the stability study of lot #1.

Vials of lot #1 stored at 5° C. were tested at 0, 1, 3, 6, 9, 12, 18, 24, and 36 months. Vials of lot #1 stored at 25° C./60% RH were tested at 0, 1, 3, and 6 months.

To test the appearance of the lyophilized cake, the cake was inspected visually and deemed passing if a white-to-yellow cake was observed. The completeness of suspension and appearance/visual color of the suspension was deemed acceptable if the lyophilized cake completely reconstituted into a white-to-yellow translucent suspension, leaving no lyophilized cake residue as undissolved matter. At various time points, pH, particulate matter (visual inspection), particulate matter (microscopic counting of total particles≥10 μm and ≥25 μm per vial), particle size (mean (volume distribution), <5% (volume distribution), and <95% (volume distribution)), color of the suspension by instrument measure (using a Hunter Labs Spectrocolorimeter with EasyMatchQC-ER Software to measure transmitted color of the reconstituted suspension; yellowness index D-1925 reported), osmolality, rapamycin content (% of target value), impurities (including seco-rapamycin as compared to the sum of seco-rapamycin and cis/trans-rapamycin), human albumin (mg/vial, by size exclusion method with a TosoHass, QC-PAK GFC 300, 150 mm×7.8 mm column and UV detection at 228 nm), water content of the lyophilized cake (by coulometric Karl Fischer Titrator Hydranal Coulomat AG coulometric titration reagent), container-closure integrity (by immersion of vials in solution containing yttrium and measurement of infused yttrium by Inductively Coupled Plasma Optical Emission Spectroscopy (ICP-OES)), sterility (by USP <71> method), and bacterial endotoxins (by USP <85> method) were assayed.

The appearance of the lyophilized cake, the suspension completeness (i.e., completeness of reconstitution), the appearance of the suspension (off-white translucent appearance), and the particulate matter (visual; essentially free from visible particulates) for lot #1 were all deemed acceptable after storage at 5° C. for 0 months (release test), 1 month, 3 months, 6 months, 9 months, 12 months, 18 months, 24 months, and 36 months.

The remaining assays for lot #1 after storage at 5° C. for 0 months (release test), 1 month, 3 months, 6 months, 9 months, 12 months, and 18 months are summarized in Table 12, below. Impurities below the quantification limit (0.05%) are reported as "ND." Assays that were not performed at a particular time point are reported as "NT." Meeting the acceptance criteria for sterility is reported as "Pass." Rapamycin is reported as the percent of expected (expected value is 100 mg trans/cis-rapamycin per vial).

TABLE 12

Stability study for lot #1 after 5° C. storage.

| Test | | 0 Mo | 1 Mo | 3 Mo | 6 Mo | 9 Mo | 12 Mo | 18 Mo |
|---|---|---|---|---|---|---|---|---|
| Reconstitution Time (min:sec) | | 7:20 | 6:35 | 6:14 | 6:48 | 9:28 | 6:42 | 15:45 |
| pH | | 6.7 | 6.8 | 6.7 | 6.8 | 6.8 | 6.8 | 6.9 |
| Instrument color | | 21 | 21 | 20 | 23 | 24 | 24 | NT |
| Osmolality (mOsm/kg) | | 333 | NT | NT | NT | NT | NT | NT |
| Rapamycin assay (%) | | 95.7 | 97.0 | 99.1 | 101.3 | 96.3 | 96.1 | 99.5 |
| Albumin assay (mg/vial) | | 765 | 858 | 872 | 871 | 874 | 881 | 853 |
| Water (%) | | 0.3 | NT | NT | NT | NT | 0.5 | NT |
| Particle Size (nm; volume distribution) | <5% | 58 | 58 | 58 | 57 | 57 | 57 | 58 |
| | <95% | 161 | 160 | 161 | 157 | 153 | 155 | 159 |
| | Mean | 100 | 99 | 99 | 98 | 96 | 97 | 99 |
| Particulate matter/vial (microscopy) | ≥10 μm | 20 | 27 | 21 | 51 | 22 | 16 | 21 |
| | ≥25 μm | 6 | 9 | 6 | 11 | 8 | 7 | 8 |
| Impurities (%) | Seco-rapamycin | 0.78 | 0.80 | 0.81 | 0.85 | 0.84 | 0.89 | 0.95 |
| | Prolylrapamycin | ND | ND | ND | ND | ND | ND | ND |
| | 14-epi rapamycin | ND | ND | ND | ND | ND | ND | ND |
| | Rapamycin aldehyde | ND | ND | ND | ND | ND | ND | ND |
| | RRT 0.68 | 0.05 | 0.06 | 0.06 | 0.08 | 0.05 | 0.07 | 0.06 |
| | RRT 1.30 | 0.06 | 0.06 | 0.06 | 0.05 | 0.06 | 0.06 | 0.06 |
| | Total | 0.89 | 0.92 | 0.94 | 0.99 | 0.95 | 1.02 | 1.07 |
| Sterility | | Pass | NT | NT | NT | NT | Pass | NT |
| Bacterial endotoxins (EU/mg) | | <0.24 | NT | NT | NT | NT | <0.24 | NT |

The remaining assays for lot #1 at months 24 and 36, including the HPLC assay to fully resolve seco-rapamycin, are summarized in Table 13, below.

TABLE 13

Stability results for lot #1 after 5° C. storage.

| Test | | 24 mo | 36 mo |
|---|---|---|---|
| Reconstitution time (min:sec) | | 5:56 | 7:59 |
| pH | | 6.9 | 6.8 |
| Rapamycin assay (%) | | 100.3 | 98.4 |
| Albumin assay (mg/vial) | | 837 | 847 |
| Water (%) | | 0.9 | 0.6 |
| Particle Size (nm; volume distribution) | <5% | 57 | 57 |
| | <95% | 156 | 157 |
| | Mean | 97 | 98 |
| Particulate matter/vial (microscopy) | ≥10 μm | 10 | 11 |
| | ≥25 μm | 3 | 5 |
| Impurities (%) | Seco-rapamycin | 0.77 | 0.79 |
| | Unspecified other degradation products | ND | ND |
| | Total degradation products | 0.77 | 0.79 |
| Sterility | | Pass | Pass |
| Bacterial endotoxins (EU/mg) | | <0.24 | Conforms |

The appearance of the lyophilized cake, the suspension completeness (i.e., completeness of reconstitution), the appearance of the suspension (off-white translucent appearance), and the particulate matter (visual; essentially free from visible particulates) for lot #1 were all deemed acceptable for lot #1 stored at 25° C./60% RH for 0 months (release test), 1 month, 3 months, and 6 months.

The remaining assays for lot #1 after storage at 25° C./60% for 0 months (release test), 1 month, 3 months, and 6 months are summarized in Table 14, below. Impurities below the quantification limit (0.05%) are reported as "ND." Assays that were not performed at a particular time point are reported as "NT." Meeting the acceptance criteria for sterility is reported as "Pass." The HPLC method used to detect impurities for the 25° C./60% storage condition did not resolve seco-rapamycin from rapamycin dialdehyde. Thus, the reported seco-rapamycin values are likely slightly higher than the actual values.

TABLE 14

Stability results for lot #1 after 25° C./60% RH storage.

| Test | | 0 Mo | 1 Mo | 3 Mo | 6 Mo |
|---|---|---|---|---|---|
| Reconstitution Time (min:sec) | | 7:20 | 6:59 | 4:43 | 7:07 |
| pH | | 6.7 | 6.8 | 6.7 | 6.8 |
| Instrument color | | 21 | 21 | 21 | 25 |
| Osmolality (mOsm/kg) | | 333 | NT | NT | NT |
| Rapamycin assay (%) | | 95.7 | 99.2 | 99.4 | 97.2 |
| Albumin assay (mg/vial) | | 765 | 859 | 880 | 860 |
| Water (%) | | 0.3 | NT | NT | 0.5 |
| Particle Size | <5% | 58 | 58 | 58 | 58 |
| (nm; volume | <95% | 161 | 161 | 160 | 169 |
| distribution) | Mean | 100 | 99 | 99 | 102 |
| Particulate | ≥10 μm | 20 | 27 | 18 | 52 |
| matter/vial | ≥25 μm | 6 | 8 | 1 | 16 |
| (microscopy) | | | | | |
| Impurities (%) | Seco-rapamycin | 0.78 | 0.98 | 1.09 | 1.21 |
| | Prolylrapamycin | ND | ND | ND | ND |
| | 14-epi rapamycin | ND | ND | ND | ND |
| | Rapamycin aldehyde | ND | ND | ND | ND |
| | RRT 0.68 | 0.05 | 0.06 | 0.06 | 0.08 |
| | RRT 1.30 | 0.06 | 0.07 | 0.06 | 0.06 |
| | Total | 0.89 | 1.10 | 1.21 | 1.35 |
| Sterility | | Pass | NT | NT | Pass |
| Bacterial endotoxins (EU/mg) | | <0.24 | NT | NT | <0.24 |

Lot #1 consistently met acceptance criteria for stability at all measured time points up to 36 months in clear glass vials stored at 5° C. and 6 months at 25° C./60% RH. Following FDA ICH Q1E guidelines and acceptance criteria for the assays the projected shelf life of lot #1 when stored at 5° C. was calculated at 66 months based on data obtained over the 36 month stability study. No significant changes were noted in the appearance of the lyophilized cake or the subsequently reconstituted suspensions after up to 36 months of storage at 5° C.

Example 21. Crystallinity Stress Test of Pharmaceutical Composition

A stress test of commercial samples of the pharmaceutical composition was developed to assess the likelihood of the pharmaceutical composition to form crystalline rapamycin due to the presence of organic solvents used during the manufacturing process (i.e., organic solvents used to prepare the emulsion of rapamycin). It was not considered possible to inject the solvents directly into the lyophilized product, since the solvents would not be distributed homogenously throughout the lyophilized cake. Instead, vials of the commercial product were opened in a nitrogen rich environment, and micro cuvettes containing chloroform and tert-butanol were suspended in the vials above the cake. The vials were then resealed. After a period of time, the vials were opened, and the lyophilized cakes were reconstituted. Quantifiable levels of chloroform and tert-butanol were detected in the samples. Using the USP35 Crystallinity Microscopy Test <776>, the results demonstrated that under accelerated conditions designed to promote the formation of crystalline rapamycin, the solvent-exposed samples did not show the presence of crystalline rapamycin.

In addition, samples from Lots #1, 2, 3, and 11 were tested using the USP test for crystallinity after storage at about 5° C. at ambient humidity for 32 months or about 25° C. at about 60% relative humidity for 32 months. There was no evidence of crystalline rapamycin above the limit of detection in the stored samples of the lots after reconstitution. These data indicate that the manufacturing method used to prepare the rapamycin nanoparticle composition produces a composition which maintains rapamycin in an amorphous state.

Example 22. Dynamic Light Scattering (DLS) Analysis of In Vitro Release Study Samples Test samples (from Lot #1) from Example 15 were analyzed by DLS for particle size to understand the physical state of rapamycin in the samples. Samples were diluted to 5 μg/mL, 10 μg/mL, 100 μg/mL, or 500 μg/mL rapamycin. Samples were analyzed at time zero, 30 minutes, and 2 hours after preparation. Only the 30 minute results are shown in the following tables, as results did not change over time.

Visual inspection and DLS analysis of the 100 μg/mL and 500 μg/mL concentrations of rapamycin in solvent and 4.5% human serum albumin indicated that these solutions precipitated immediately. The 100 μg/mL and 500 μg/mL concentrations of rapamycin in solvent and 4.5% human serum albumin appeared opaque, and the DLS analysis showed micron size particle populations typical of precipitated drug (Table 17 and Table 18).

By contrast, although the 500 μg/mL concentration of Lot #1 in 4.5% HSA appeared opaque, the DLS analysis showed a uniform particle size of ~150 nm (Table 18). At 100 μg/mL Lot #1 in 4.5% HSA solution appeared clear, and both ~110 nm and 7 nm DLS populations were observed, suggesting the Lot #1 particles were partially dissociated (Table 17). At concentrations below 100 μg/mL, Lot #1 solutions in 4.5% HSA were clear and the nanoparticles dissociated immediately into a DLS population of 7 nm consistent with non-nanoparticle associated albumin (Table 15 and Table 16). These data suggest that the nanoparticles are stable in 4.5% HSA at concentrations between 100 and 500 μg/mL. The pharmaceutical composition nanoparticles were stable at concentrations of 100 and 500 μg/mL, with a single DLS population of ~120 nm, while solvent rapamycin in saline precipitated at the same 100 and 500 μg/mL concentrations, with micron-sized DLS populations observed (Table 17 and Table 18).

Results from the 5 µg/mL rapamycin in vitro release experiment is shown below in Table 15 (NR, not reported).

TABLE 15

DLS Size Results for In Vitro Release at 5 µg/mL rapamycin.

| | Sample (Appearance) | | | |
|---|---|---|---|---|
| | 5-15 nm (Integrated intensity) | 60-170 nm (Integrated intensity) | 200-500 nm (Integrated intensity) | >1000 nm (integrated intensity) |
| Pharmaceutical composition in saline | 13 ± 3 (72 ± 6) | 139 ± 55 (26 ± 8) | NR | NR |
| HSA blank | 7.43 ± 0.09 (48.9 ± 0.4) | 85 ± 2 (51.1 ± 0.4) | NR | NR |
| Pharmaceutical composition in HSA at 30 minutes | 7.0 ± 0.1 (53.0 ± 0.6) | 71 ± 1 (47.0 ± 0.6) | NR | NR |
| Rapamycin in saline | NR | 115 ± 9 (97 ± 3) | NR | 4438 ± 751 (5 ± 2) |
| Rapamycin in HSA | 7.7 ± 0.01 (53.0 ± 0.2) | 76.3 ± 0.8 (47.0 ± 0.2) | NR | NR |

Results from the 10 µg/mL rapamycin in vitro release experiment is shown in Table 16 (NR, not reported).

TABLE 16

DLS Size Results for In Vitro Release at 10 µg/mL rapamycin.

| | Sample (Appearance) | | | |
|---|---|---|---|---|
| | 5-15 nm (Integrated intensity) | 60-170 nm (Integrated intensity) | 200-500 nm (Integrated intensity) | >1000 nm (integrated intensity) |
| Pharmaceutical composition in saline | 10 ± 1 (64 ± 2) | 93 ± 3 (36 ± 2) | NR | NR |
| HSA blank | 7.43 ± 0.09 (48.9 ± 0.4) | 85 ± 2 (51.1 ± 0.4) | NR | NR |
| Pharmaceutical composition in HSA at 30 minutes | 7.0 ± 0.03 (52.3 ± 0.3) | 68.1 ± 0.7 (47.7 ± 0.3) | NR | NR |
| Rapamycin in saline | NR | NR | 214 ± 22 (95 ± 7) | 2905 ± 2516 (5 ± 7) |
| Rapamycin in HSA | 7.0 ± 0.03 (51.9 ± 0.06) | 69 ± 1 (48.1 ± 0.06) | NR | NR |

Results from the 100 µg/mL rapamycin in vitro release experiment is shown in Table 17 (NR, not reported).

TABLE 17

DLS Size Results for In Vitro Release at 100 µg/mL rapamycin.

| | Sample (Appearance) | | | |
|---|---|---|---|---|
| | 5-15 nm (Integrated intensity) | 60-170 nm (Integrated intensity) | 200-500 nm (Integrated intensity) | >1000 nm (integrated intensity) |
| Pharmaceutical composition in saline | NR | 115 ± 3 (100 ± 0) | NR | NR |
| HSA blank | 7.43 ± 0.09 (48.9 ± 0.4) | 85 ± 2 (51.1 ± 0.4) | NR | NR |
| Pharmaceutical composition in HSA at 30 minutes | NR | NR | NR | 1378 ± 106 (100 ± 0) |
| Rapamycin in saline | NR | NR | NR | 1378 ± 106 (100 ± 0) |
| Rapamycin in HSA | 8.5 ± 0.1 (27.9 ± 0.9) | 166 ± 4 (66 ± 1) | NR | NR |

Results from the 500 µg/mL rapamycin in vitro release experiment is shown in Table 18 (NR, not reported).

TABLE 18

DLS Size Results for In Vitro Release at 500 µg/mL rapamycin.

| | Sample (Appearance) | | | |
|---|---|---|---|---|
| | 5-15 nm (Integrated intensity) | 60-170 nm (Integrated intensity) | 200-500 nm (Integrated intensity) | >1000 nm (integrated intensity) |
| Pharmaceutical composition in saline | NR | 126 ± 2 (100 ± 0) | NR | NR |
| HSA blank | 7.43 ± 0.09 (48.9 ± 0.4) | 85 ± 2 (51.1 ± 0.4) | NR | NR |
| Pharmaceutical composition in HSA at 30 minutes | NR | 142 ± 1 (100 ± 0) | NR | NR |
| Rapamycin in saline | NR | NR | NR | 4346 ± 137 (100 ± 0) |
| Rapamycin in HSA | NR | NR | 471 ± 19 (95 ± 1) | 4867 ± 127 (5 ± 1) |

Example 23. Oligomer Composition of Human Albumin in Rapamycin Nanoparticle Drug Product Additional characterization of the oligomer profile of human albumin in the pharmaceutical composition drug product was performed. Samples from Lot #1, Lot #2, Lot #5, and Lot #15 were assessed. Lyophilized samples from each lot were reconstituted in saline to yield a reconstituted pharmaceutical suspension with approximately 5 mg/mL rapamycin.

To assess the total albumin oligomeric profile, a Stock Sample Suspension was prepared at a target concentration of 1.8 mg/mL rapamycin by quantitatively transferring each reconstituted sample suspension into a 500 mL volumetric flask using water and then diluting to volume with water. The Stock Sample Suspension was stored at 2-8° C. A Working Sample Suspension was prepared at a target concentration of 0.18 mg/mL by diluting 5.0 mL of the Stock Sample Suspension to 50 mL with water. The Working Sample Suspension was stored at 2-8° C. Size exclusion chromatography was used with a column of appropriate separation capability for albumin, with UV detection at 228 nm. The mobile phase comprised 0.10 M $K_2HPO_4$ in 7.5% methanol. The peaks in the chromatogram were integrated to determine the composition of the different oligomeric species and the total albumin in the composition.

To determine the albumin oligomeric profile of the nanoparticle portion and non-nanoparticle portion of the compositions, 4 mL of the 5 mg/mL rapamycin reconstituted suspensions were transferred into ultra-centrifugation tubes and centrifuged at 50,000 rpm for 41 minutes. The supernatants were separated using a micro-pipette without disturbing the pellet and analyzed by SEC with UV detector with a mobile phase comprising 0.10 M K2HPO4 in 7.5% methanol as above. The pellets (the nanoparticle portion) were washed carefully with 2-3 mL of purified water. The rinsate was decanted. 2 mL of ethanol was added to the pellet. The pellet in ethanol was then sonicated in a water bath until fully dispersed. The dispersed pellet was transferred by pipette to a new ultra-centrifugation tube. An additional 3 mL of ethanol was added and the tubes were centrifuged at 10,000 rpm for 20 minutes. Following centrifugation, the supernatant was decanted without disturbing the pellet. 3 mL of saline was added to the pellet and allowed to dissolve for 15 minutes. Using a glass Pasteur pipette, the mixtures were transferred into a 10 mL volumetric flask. Saline was used to transfer the remaining material into the 10 mL volumetric flask. The samples were diluted to 10 mL with saline and sonicated until completely dissolved. The samples were analyzed by SEC with UV detector with a mobile phase comprising 0.10 M K2HPO4 in 7.5% methanol to determine the oligomeric profile of the nanoparticle portion.

The oligomeric profiles for Lots #1, #2, #5, and #15 for the total composition, the non-nanoparticle portion, and the nanoparticle portions are summarized in Table 16, below. Representative chromatograms are provided for the total albumin oligomeric profile (FIG. 9), the non-nanoparticle oligomeric profile (FIG. 10), and the nanoparticle oligomeric profile (FIG. 11).

TABLE 16

Composition of Human Albumin in Rapamycin Nanoparticle Drug Product

| | Human Albumin Composition (%) | | | |
|---|---|---|---|---|
| Lot #/Portion | Monomer | Dimer | Oligomer | Polymer |
| Lot #1/Total | 85.06 | 8.53 | 2.14 | 4.27 |
| Lot #1/Non-nanoparticle | 89.23 | 8.16 | 1.77 | 0.83 |
| Lot #1/Nanoparticle | 36.99 | 10.96 | 3.47 | 48.58 |
| Lot #2/Total | 85.08 | 8.89 | 2.13 | 3.89 |
| Lot #2/Non-nanoparticle | 89.01 | 8.52 | 1.72 | 0.75 |
| Lot #2/Nanoparticle | 38.5 | 11.23 | 3.72 | 46.55 |
| Lot #5/Total | 86.94 | 7.41 | 1.6 | 4.05 |
| Lot #5/Non-nanoparticle | 90.38 | 6.99 | 1.59 | 1.04 |
| Lot #5/Nanoparticle | 39.13 | 10.34 | 2.93 | 47.60 |
| Lot #15/Total | 85.49 | 8.34 | 2.05 | 4.11 |
| Lot #15/Non-nanoparticle | 89.13 | 8.09 | 1.86 | 0.92 |
| Lot #15/Nanoparticle | 38.56 | 9.72 | 2.65 | 49.07 |

Example 24. Image Analysis of Cryo-TEM Images of Rapamycin Nanoparticle Drug Product Image processing of cryo-TEM images of Lot #1, Lot #2, Lot #3, and Lot #11 from Example 6 above. The MIPAR image processor was used. The images were loaded into the computer system and the scale was calibrated per the cryo-TEM scale detailed in each picture. The image was rendered with a Median and StDev Filter for coarse particle identification. The remainder of the recipe compared the original image with the filtered and rendered image to reject features that do not meet the criteria of an identified nanoparticle. After an acceptable image of separate particles was generated, the measurements application was applied for the "features" (identified particles). The Area, Caliper Diameter (i.e., the maximum diameter of a feature), and minimum diameter are selected. The ratio of the minimum and maximum diameters were calculated to generate the percentage of how spherical the particles are. Features that are easily recognized as a combination of several particles or void space were rejected to ensure the calculations were representative. A ratio of 1 indicated a perfect sphere or circle cross section. For the purpose of the analysis, particles with a ratio of 0.9 to less than 1.0 were considered mostly spherical. Particles with a ratio less than 0.9 were considered irregularly shaped or non-spherical.

For Lot #1, software analysis was conducted on 29 particles. 58.6% of the particles had a ratio equal to or greater than 0.9 and 41.4% of the particles had a ratio less than 0.9. The average ratio for all particles counted was 0.87.

For Lot #2, software analysis was conducted on 71 particles. 22.5% of the particles had a ratio greater than or equal to 0.9 and 78.9% of the particles had a ratio less than 0.9. The average ratio for all particles counted was 0.80.

For Lot #3, software analysis was conducted on 92 particles. 19.6% of the particles had a ratio greater than or equal to 0.9 and 80.4% of the particles had a ratio less than 0.9. The average ratio for all particles counted was 0.78.

For Lot #11, software analysis was conducted on 115 particles. 27.8% of the particles had a ratio greater than or equal to 0.9 and 72.2% of the particles had a ratio less than 0.9. The average ratio for all particles counted was 0.76.

Example 25. Reconstitution of Rapamycin Nanoparticle Drug Product at High Concentrations Stability of reconstituted suspensions of nanoparticles can be challenging due to settling of particles or agglomeration. Samples of a nanoparticle composition containing nanoparticles of rapamycin and albumin in a non-nanoparticle portion containing albumin (100 mg rapamycin/vial) were reconstituted in different volumes of diluent by reconstituting in order to obtain a range of final nominal concentrations of rapamycin of 5 mg/mL, 10 mg/mL, 15 mg/mL, 20 mg/mL, and 25 mg/mL. The time course for the lyophilized cake to go into solution, the presence of clumping, or any other issues were observed and recorded.

The results for the concentration study (reconstitution using different volumes of diluent) showed that the product was reconstitutable at high concentrations and resulted in a smooth suspension was stable. This result was surprising as high concentrations of nanoparticles can readily aggregate or agglomerate causing instability.

What is claimed is:

1. A commercial batch of a pharmaceutical composition comprising (a) nanoparticles comprising rapamycin and albumin, and (b) a non-nanoparticle portion comprising albumin and rapamycin; wherein 42% to about 60% of the albumin in the nanoparticles is in the form of polymeric albumin other than oligomeric albumin when the percentage of albumin in the nanoparticles that is in the form of polymeric albumin other than oligomeric albumin is determined by separating the nanoparticles from the non-nanoparticle portion, dissolving the nanoparticles, and subjecting the dissolved nanoparticles to size-exclusion chromatography.

2. The commercial batch of claim 1, wherein about 1% to about 4.5% of the albumin in the nanoparticles is in the form of oligomeric albumin when the percentage of albumin in the nanoparticles that is in the form of oligomeric albumin is determined by separating the nanoparticles from the non-nanoparticle portion, dissolving the nanoparticles, and subjecting the dissolved nanoparticles to size-exclusion chromatography.

3. The commercial batch of claim 2, wherein about 25% to about 50% of the albumin in the nanoparticles is in the form of monomeric albumin and about 5% to about 16% of the albumin in the nanoparticles is in the form of dimeric albumin when the percentage of albumin in the nanoparticles that is in the form of monomeric albumin and dimeric albumin is determined by separating the nanoparticles from the non-nanoparticle portion, dissolving the nanoparticles, and subjecting the dissolved nanoparticles to size-exclusion chromatography.

4. The commercial batch of claim 1, wherein about 80% to about 95% of the total albumin composition is in the form of monomeric albumin, about 4% to about 15% of the total albumin in the composition is in the form of dimeric albumin, about 0.3% to about 3% of the total albumin in the composition is in the form of oligomeric albumin, and about 2% to about 7% of the total albumin in the composition is in the form of polymeric albumin other than oligomeric albumin when the percentage of monomeric albumin, dimeric albumin, oligomeric albumin, and polymeric albumin other than oligomeric albumin in the composition is determined subjecting the composition to size-exclusion chromatography.

5. The commercial batch of claim 4, wherein about 80% to about 95% of the albumin in the non-nanoparticle portion is in the form of monomeric albumin, about 4% to about 14% of the albumin in the non-nanoparticle portion is in the form of dimeric albumin, about 0.5% to about 4% of the albumin in the non-nanoparticle portion is in the form of oligomeric albumin, and about 0.5% to about 3% of the albumin in the non-nanoparticle portion is in the form of polymeric albumin other than oligomeric albumin when the percentage of albumin in the non-nanoparticle portion that is in the form of monomeric albumin, dimeric albumin, oligomeric albumin, and polymeric albumin other than oligomeric albumin is determined by separating the nanoparticles from the non-nanoparticle portion, and subjecting the non-nanoparticle portion to size-exclusion chromatography.

6. The commercial batch of claim 1, wherein seco-rapamycin is less than 3% by weight of the sum of seco-rapamycin and rapamycin in the composition.

7. The commercial batch of claim 1, wherein the volume weighted mean particle size of the nanoparticles is about 200 nm or less.

8. The commercial batch of claim 1, wherein the Z-average particle size of the nanoparticles is about 200 nm or less.

9. The commercial batch of claim 1, wherein the polydispersity index of the nanoparticles is less than 0.3.

10. The commercial batch of claim 1, wherein the span of particle size distribution $((D_v 95 - D_v 5)/D_v 50)$ of the nanoparticles is about 0.8 to about 1.2.

11. The commercial batch of claim 1, wherein the nanoparticles are about 25% to about 45% albumin by weight and about 55% to about 75% rapamycin by weight.

12. The commercial batch of claim 1, wherein the nanoparticle composition is a nanoparticle suspension.

13. The commercial batch of claim 1, wherein the concentration of albumin in the composition is about 1 mg/mL to about 100 mg/mL.

14. The commercial batch of claim 1, wherein the concentration of albumin in the composition is about 30 mg/mL to about 100 mg/mL.

15. The commercial batch of claim 1, wherein the concentration of rapamycin in the nanoparticle composition is about 1 mg/mL to about 50 mg/mL.

16. The commercial batch of claim 1, wherein the osmolality of the composition is about 280 mOsm/kg to about 400 mOsm/kg.

17. The commercial batch of claim 1, wherein the nanoparticles had been resuspended from a dried composition.

18. The commercial batch of claim 1, wherein the composition is a dried composition.

19. The commercial batch of claim 1, wherein the composition comprises less than 250 ppm tert-butanol.

20. The commercial batch of claim 1, wherein the composition comprises less than 60 ppm chloroform.

21. The commercial batch of claim 1, wherein the zeta potential of the nanoparticles is about −25 mV to about −50 mV.

22. The commercial batch of claim 1, wherein the nanoparticles have an amorphous morphology as determined by separating the nanoparticles from the composition, lyophilizing the separated nanoparticles, and measuring crystallinity of the separated and lyophilized nanoparticles by X-ray diffraction.

23. The commercial batch of claim 1, wherein the rapamycin in nanoparticles has an amorphous morphology as determined by Raman spectroscopy, polarized light microscopy, differential scanning calorimetry (DSC), modulated differential scanning calorimetry (mDSC), Fourier transform infrared (FTIR) spectroscopy, or nuclear magnetic resonance (NMR) spectroscopy.

24. The commercial batch of claim 1, wherein at least 20% of the nanoparticles are non-spherical as determined by cryogenic transmission electron microscopy (cryo-TEM).

25. The commercial batch of claim 1, wherein at least 20% of the nanoparticles have a non-smooth surface as determined by cryogenic transmission electron microscopy (cryo-TEM).

26. The commercial batch of claim 1, wherein the albumin is human albumin.

27. The commercial batch of claim 1, wherein 90% or more of the rapamycin in the composition is in the nanoparticles.

28. The commercial batch of claim 1, wherein the nanoparticle composition is sterile.

29. The commercial batch of claim 1, wherein the nanoparticle composition comprises a caprylic acid derivative and/or a tryptophan derivative.

30. The commercial batch of claim 1, wherein the pharmaceutical composition is contained within a plurality of vials associated with a unit dosage label indicating an amount of rapamycin in each vial, and wherein the amount of rapamycin in the vials is within 10% of the amount of rapamycin indicated on the unit dosage label.

* * * * *